US010166273B2

(12) United States Patent
Wittrup et al.

(10) Patent No.: US 10,166,273 B2
(45) Date of Patent: Jan. 1, 2019

(54) SYNERGISTIC TUMOR TREATMENT WITH ANTIBODIES TARGETING PD-1, PD-L1 OR CTLA4 AND INTEGRIN-BINDING-FC-FUSION PROTEIN

(71) Applicants: Massachusetts Institute of Technology, Cambridge, MA (US); The Board of Trustees of the Leland Stanford Junior University, Stanford, CA (US)

(72) Inventors: Karl Dane Wittrup, Chestnut Hill, MA (US); Jennifer R. Cochran, Stanford, CA (US); Byron Hua Kwan, Boston, MA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/501,028

(22) PCT Filed: Aug. 12, 2015

(86) PCT No.: PCT/US2015/044920
§ 371 (c)(1),
(2) Date: Feb. 1, 2017

(87) PCT Pub. No.: WO2016/025642
PCT Pub. Date: Feb. 18, 2016

(65) Prior Publication Data
US 2017/0216402 A1 Aug. 3, 2017

Related U.S. Application Data

(60) Provisional application No. 62/036,554, filed on Aug. 12, 2014.

(51) Int. Cl.
| | |
|---|---|
| *A61K 38/20* | (2006.01) |
| *A61K 38/16* | (2006.01) |
| *A61K 38/17* | (2006.01) |
| *C07K 14/55* | (2006.01) |
| *A61K 39/395* | (2006.01) |
| *C07K 16/22* | (2006.01) |
| *C07K 16/28* | (2006.01) |
| *A61K 45/06* | (2006.01) |
| *C07K 16/24* | (2006.01) |
| *C07K 16/30* | (2006.01) |
| *A61K 38/38* | (2006.01) |
| *A61K 47/48* | (2006.01) |
| *C07K 16/40* | (2006.01) |
| *A61K 39/00* | (2006.01) |

(52) U.S. Cl.
CPC .......... *A61K 38/2013* (2013.01); *A61K 38/16* (2013.01); *A61K 38/179* (2013.01); *A61K 38/385* (2013.01); *A61K 39/39558* (2013.01); *A61K 45/06* (2013.01); *A61K 47/48215* (2013.01); *C07K 14/55* (2013.01); *C07K 16/22* (2013.01); *C07K 16/249* (2013.01); *C07K 16/28* (2013.01); *C07K 16/2803* (2013.01); *C07K 16/2812* (2013.01); *C07K 16/2815* (2013.01); *C07K 16/2818* (2013.01); *C07K 16/30* (2013.01); *C07K 16/3053* (2013.01); *C07K 16/40* (2013.01); *A61K 2039/505* (2013.01); *A61K 2039/507* (2013.01); *C07K 2317/52* (2013.01); *C07K 2317/71* (2013.01); *C07K 2317/76* (2013.01); *C07K 2319/30* (2013.01); *C07K 2319/31* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 6,682,736 B1 | 1/2004 | Hanson et al. | |
| 6,984,720 B1 | 1/2006 | Korman et al. | |
| 7,943,743 B2 | 5/2011 | Korman et al. | |
| 8,008,449 B2 | 8/2011 | Korman et al. | |
| 2002/0039581 A1 | 4/2002 | Carreno et al. | |
| 2002/0086014 A1 | 7/2002 | Korman et al. | |
| 2005/0201994 A1 | 9/2005 | Korman et al. | |
| 2005/0287153 A1 | 12/2005 | Dennis | |
| 2007/0003549 A1 | 1/2007 | Ignatovich et al. | |
| 2011/0150892 A1 | 6/2011 | Thudium et al. | |
| 2012/0094909 A1 | 4/2012 | Camphausen et al. | |
| 2013/0022623 A1 | 1/2013 | Karsunky et al. | |
| 2013/0042057 A1 | 2/2013 | Sinclair et al. | |

(Continued)

FOREIGN PATENT DOCUMENTS

| | | | | |
|---|---|---|---|---|
| WO | WO2008/045252 | * | 4/2008 | ............. C07K 16/28 |
| WO | WO 2008045252 | | 4/2008 | |

(Continued)

OTHER PUBLICATIONS

Pardoll et al., The blockade of immune checkpoints in cancer immunotherapy. Nature Reviews Cancer, 12, 252-264, 2012.*

(Continued)

*Primary Examiner* — Elly-Gerald Stoica

(74) *Attorney, Agent, or Firm* — Brian E. Davy; Bozicevic, Field & Francis LLP

(57) ABSTRACT

The present invention provides a method of treating cancer with a combination of IL-2 and an integrin-binding-Fc fusion protein. The methods of the invention can be applied to a broad range of cancer types.

20 Claims, 29 Drawing Sheets

Specification includes a Sequence Listing.

(56) References Cited

U.S. PATENT DOCUMENTS

2013/0149236 A1 6/2013 Johnson et al.
2017/0044236 A1* 2/2017 Arnaout .................. C07K 7/06

FOREIGN PATENT DOCUMENTS

| WO | WO 2009083804 | | 7/2009 | | |
|----|---------------|---|--------|---|---|
| WO | WO 2009133208 | | 11/2009 | | |
| WO | WO2012/064658 | * | 5/2012 | ............. | C12P 21/04 |
| WO | WO 2012064658 | | 5/2012 | | |
| WO | WO 2012120125 | | 9/2012 | | |
| WO | WO 2013177187 | | 11/2013 | | |

OTHER PUBLICATIONS

Leary et al., Cytokine therapy for renal cell cancer: the evolving role of immunomodulation, Therapy 8, 347-358, 2011.*
Alignment form NCBI—accessed Apr. 23, 2018.*
Konrad et al. (1990) "Pharmacokinetics of Recombinant Interleukin 2 in Humans" Cancer Res.; 50:2009-2017.
Moore et al. (2013) "Engineered knottin peptide enables noninvasive optical imaging of intracranial medulloblastoma" Proceedings of the National Academy of Sciences, 110(36):14598-14603.
Zhu et al. (2015) "Synergistic Innate and Adaptive Immune Response to Combination Immunotherapy with Anti-Tumor Antigen Antibodies and Extended Serum Half-Life IL-2" Cancer Cell; 27:489-501.

\* cited by examiner

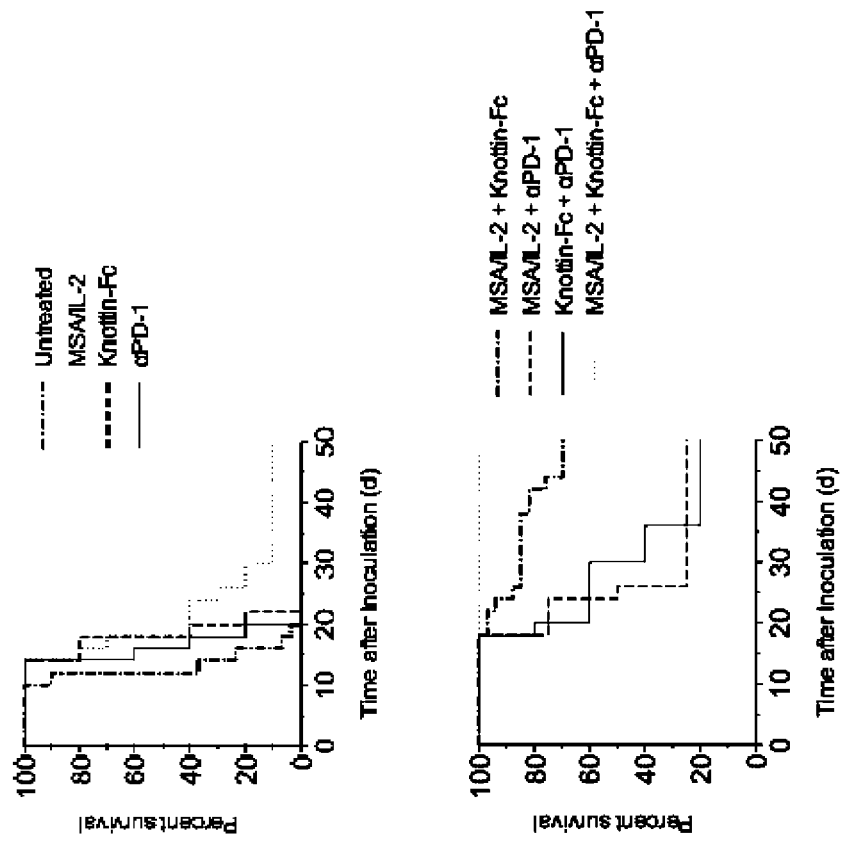

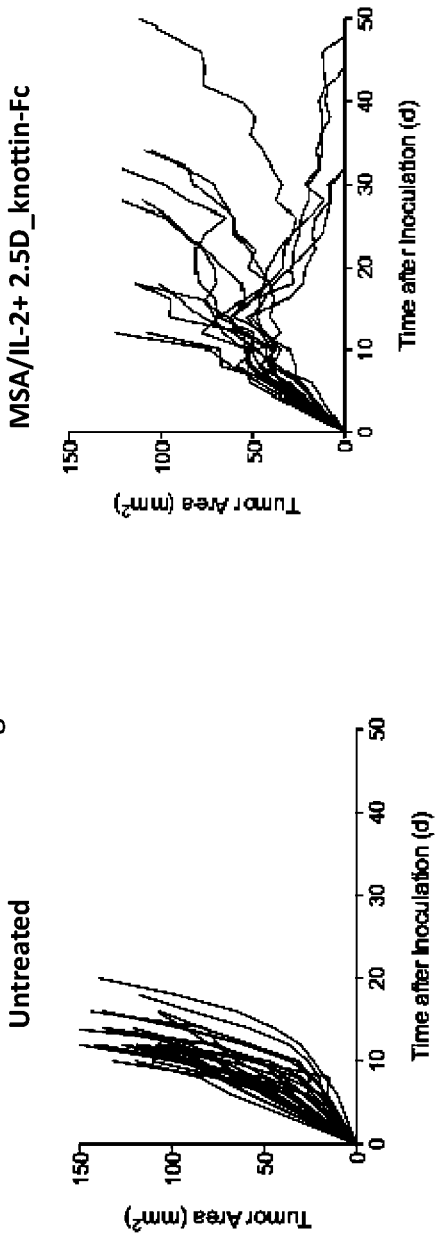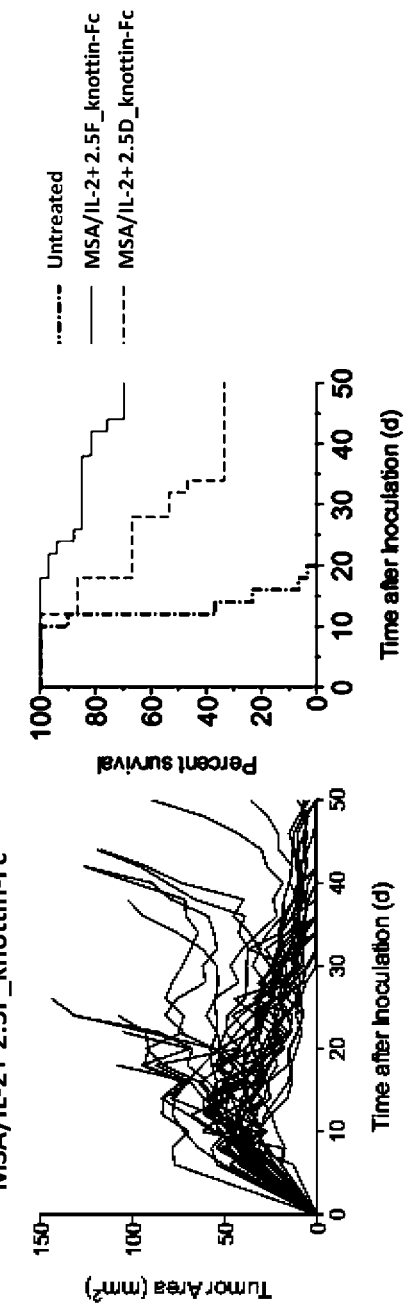
Figure 16A
Figure 16B

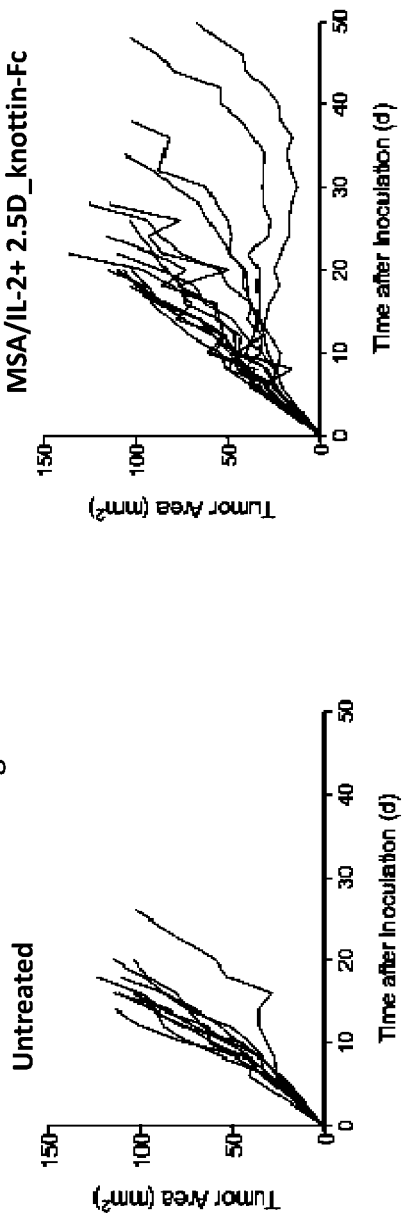
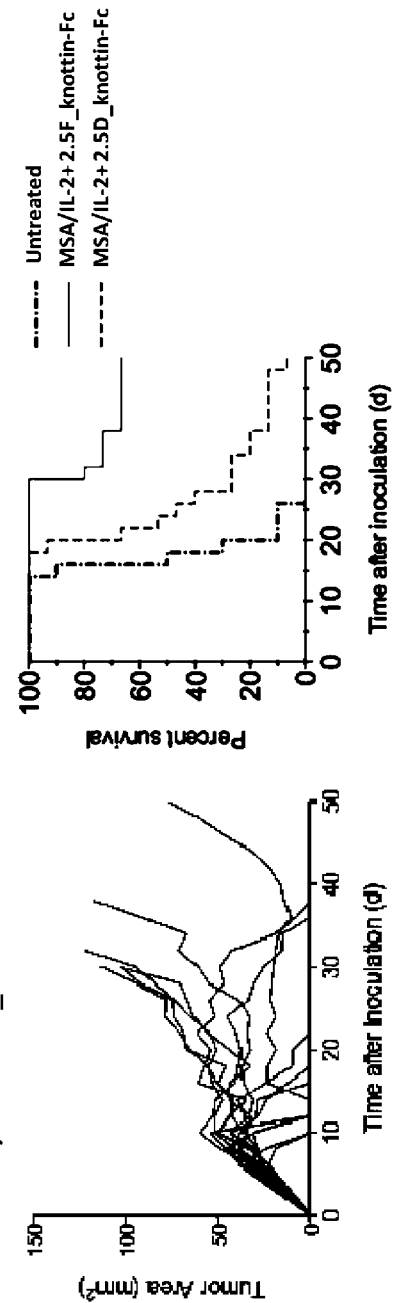
Figure 17A
Figure 17B

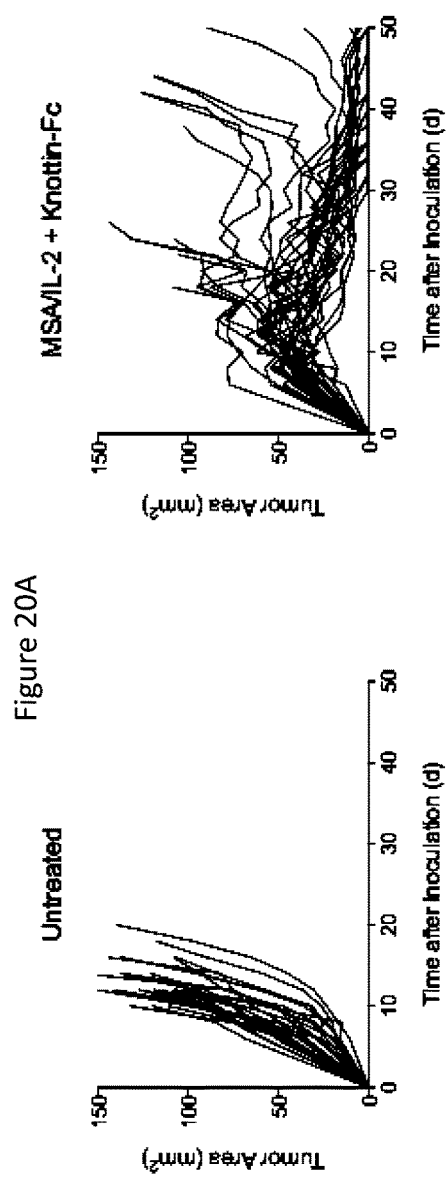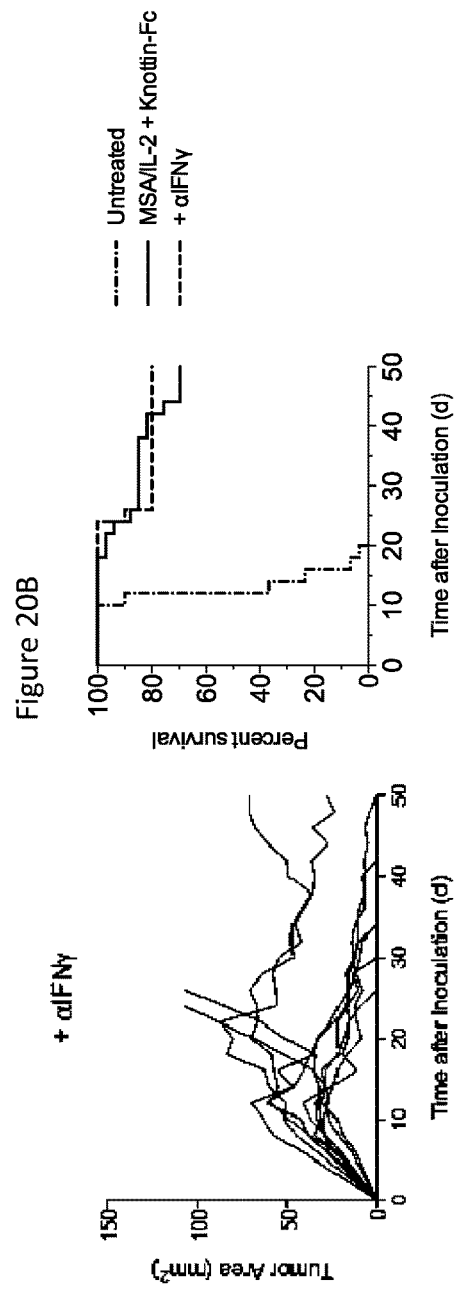
Figure 20A
Figure 20B

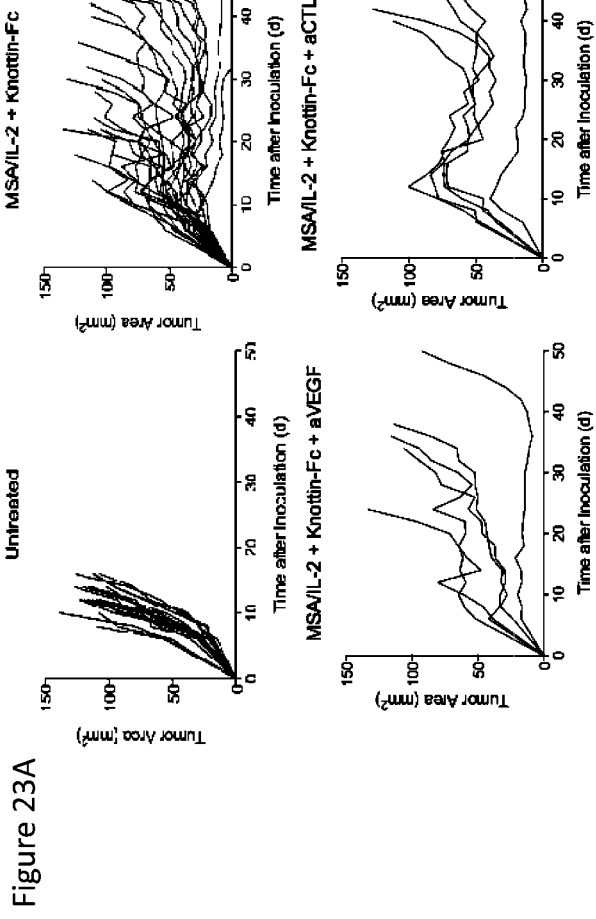
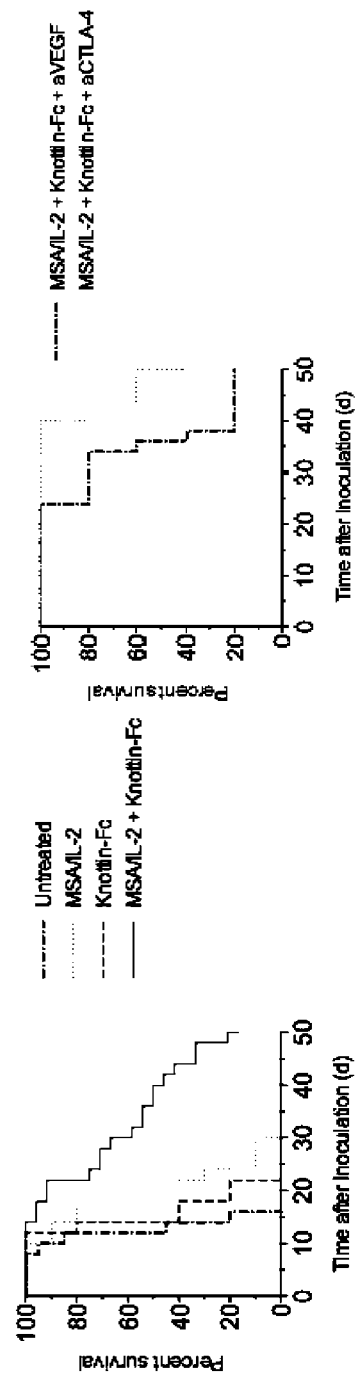
Figure 23A
Figure 23B

SEQUENCE LISTING

```
<160> NUMBER OF SEQ ID NOS: 138

<210> SEQ ID NO 1
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: Human IgG1 constant region (amino acid
      sequence)

<400> SEQUENCE: 1
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 232
<212> TYPE: PRT
<213> ORGANISM: Homo sapiens
<220> FEATURE:
<221> NAME/KEY: misc_feature
<222> LOCATION: (1)..(232)
<223> OTHER INFORMATION: Human IgG1 Fc domain (amino acid sequence)

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

-continued

```
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 3
<211> LENGTH: 227
<212> TYPE: PRT
<213> ORGANISM: Homo sapiens
<220> FEATURE:
<221> NAME/KEY: misc_feature
<222> LOCATION: (1)..(227)
<223> OTHER INFORMATION: Human IgG1 Fc domain (amino acid sequence)
      Deletion (delta-EPKSC) Upper Hinge

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220
```

Pro Gly Lys
225

<210> SEQ ID NO 4
<211> LENGTH: 447
<212> TYPE: DNA
<213> ORGANISM: Mouse
<220> FEATURE:
<221> NAME/KEY: misc_feature
<222> LOCATION: (1)..(447)
<223> OTHER INFORMATION: Mouse IL-2 (nucleic acid sequence)

<400> SEQUENCE: 4

```
gcacccactt caagctccac ttcaagctct acagcggaag cacagcagca gcagcagcag    60
cagcagcagc agcagcagca cctggagcag ctgttgatgg acctacagga gctcctgagc   120
aggatggaga attacaggaa cctgaaactc cccaggatgc tcaccttcaa attttacttg   180
cccaagcagg ccacagaatt gaaagatctt cagtgcctag aagatgaact tggacctctg   240
cggcatgttc tggatttgac tcaaagcaaa agctttcaat ggaagatgc tgagaatttc   300
atcagcaata tcagagtaac tgttgtaaaa ctaaagggct ctgacaacac atttgagtgc   360
caattcgatg atgagtcagc aactgtggtg gactttctga ggagatggat agccttctgt   420
caaagcatca tctcaacaag ccctcaa                                      447
```

<210> SEQ ID NO 5
<211> LENGTH: 149
<212> TYPE: PRT
<213> ORGANISM: Mouse
<220> FEATURE:
<221> NAME/KEY: misc_feature
<222> LOCATION: (1)..(149)
<223> OTHER INFORMATION: Mouse IL-2 (amino acid sequence)

<400> SEQUENCE: 5

Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
                20                  25                  30

Met Asp Leu Gln Glu Leu Leu Ser Arg Met Glu Asn Tyr Arg Asn Leu
                35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
                100                 105                 110

Gly Ser Asp Asn Thr Phe Glu Cys Gln Phe Asp Asp Glu Ser Ala Thr
            115                 120                 125

Val Val Asp Phe Leu Arg Arg Trp Ile Ala Phe Cys Gln Ser Ile Ile
        130                 135                 140

Ser Thr Ser Pro Gln
145

<210> SEQ ID NO 6
<211> LENGTH: 447
<212> TYPE: DNA
<213> ORGANISM: Artificial Sequence
<220> FEATURE:

<223> OTHER INFORMATION: Synthetic: QQ6210 (nucleic acid sequence)

<400> SEQUENCE: 6

```
gcacccactt caagctccac ttcaagctct acagcggaag cacaacagca gcagcagcag      60
cagcagcagc agcagcagca cctggagcag ctgttgatgg acctacagga actcctgagt     120
aggatggagg atcacaggaa cctgagactc cccaggatgc tcaccttcaa attttacttg     180
cccgagcagg ccacagaatt ggaagatctt cagtgcctag aagatgaact tgaaccactg     240
cggcaagttc tggatttgac tcaaagcaaa agctttcaat tggaagatgc tgagaatttc     300
atcagcaata tcagagtaac tgttgtaaaa ctaaagggct ctgacaacac atttgagtgc     360
caattcgacg atgagccagc aactgtggtg gactttctga ggagatggat agccttctgt     420
caaagcatca tctcaacaag ccctcaa                                         447
```

<210> SEQ ID NO 7
<211> LENGTH: 149
<212> TYPE: PRT
<213> ORGANISM: Artificial Sequence
<220> FEATURE:
<223> OTHER INFORMATION: Synthetic: QQ6210 (amino acid sequence)

<400> SEQUENCE: 7

```
Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asp His Arg Asn Leu
            35                  40                  45

Arg Leu Pro Arg Met Leu Thr Phe Lys Phe Tyr Leu Pro Glu Gln Ala
        50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145
```

<210> SEQ ID NO 8
<211> LENGTH: 447
<212> TYPE: DNA
<213> ORGANISM: Artificial Sequence
<220> FEATURE:
<223> OTHER INFORMATION: Synthetic: E76A (nucleic acid sequence)

<400> SEQUENCE: 8

```
gcacccactt caagctccac ttcaagctct acagcggaag cacagcagca gcagcagcag      60
cagcagcagc agcagcagca cctggagcag ctgttgatgg acctacagga gctcctgagc     120
aggatggaga attacaggaa cctgaaactc cccaggatgc tcaccttcaa attttacttg     180
cccaagcagg ccacagaatt gaagatctt cagtgcctag aagatgctct ggacctctg      240
cggcatgttc tggatttgac tcaaagcaaa agctttcaat tggaagatgc tgagaatttc     300
```

-continued

```
atcagcaata tcagagtaac tgttgtaaaa ctaaagggct ctgacaacac atttgagtgc      360
caattcgatg atgagtcagc aactgtggtg gactttctga ggagatggat agccttctgt      420
caaagcatca tctcaacaag ccctcaa                                          447
```

<210> SEQ ID NO 9
<211> LENGTH: 149
<212> TYPE: PRT
<213> ORGANISM: Artificial Sequence
<220> FEATURE:
<223> OTHER INFORMATION: Synthetic: E76A (amino acid sequence)

<400> SEQUENCE: 9

```
Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Ala Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145
```

<210> SEQ ID NO 10
<211> LENGTH: 447
<212> TYPE: DNA
<213> ORGANISM: Artificial Sequence
<220> FEATURE:
<223> OTHER INFORMATION: Synthetic: E76G (nucleic acid sequence)

<400> SEQUENCE: 10

```
gcacccactt caagctccac ttcaagctct acagcggaag cacagcagca gcagcagcag       60
cagcagcagc agcagcagca cctggagcag ctgttgatgg acctacagga gctcctgagc      120
aggatggaga attacaggaa cctgaaactc cccaggatgc tcaccttcaa attttacttg      180
cccaagcagg ccacagaatt gaaagatctt cagtgcctag aagatggtct tggacctctg      240
cggcatgttc tggatttgac tcaaagcaaa agctttcaat tggaagatgc tgagaatttc      300
atcagcaata tcagagtaac tgttgtaaaa ctaaagggct ctgacaacac atttgagtgc      360
caattcgatg atgagtcagc aactgtggtg gactttctga ggagatggat agccttctgt      420
caaagcatca tctcaacaag ccctcaa                                          447
```

<210> SEQ ID NO 11
<211> LENGTH: 149
<212> TYPE: PRT
<213> ORGANISM: Artificial Sequence
<220> FEATURE:

<223> OTHER INFORMATION: Synthetic: E76G (amino acid sequence)

<400> SEQUENCE: 11

```
Ala Pro Thr Ser Ser Thr Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Gly Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145
```

<210> SEQ ID NO 12
<211> LENGTH: 816
<212> TYPE: DNA
<213> ORGANISM: Artificial Sequence
<220> FEATURE:
<223> OTHER INFORMATION: Synthetic: D265A Fc/Flag (nucleic acid sequence)

<400> SEQUENCE: 12

```
atgagggtcc ccgctcagct cctggggctc ctgctgctct ggctcccagg tgcacgatgt      60
gagcccagag tgcccataac acagaacccc tgtcctccac tcaaagagtg tccccccatgc    120 gcagctccag acctcttggg tggaccatcc gtcttcatct ccctccaaa gatcaaggat     180 gtactcatga tctccctgag ccccatggtc acatgtgtgg tggtggccgt gagcgaggat    240
gacccagacg tccagatcag ctggtttgtg aacaacgtgg aagtacacac agctcagaca    300
caaacccata gagaggatta caacagtact ctccgggtgg tcagtgccct ccccatccag    360
caccaggact ggatgagtgg caaggagttc aaatgcaagg tcaacaacag agccctccca    420
tcccccatcg agaaaaccat ctcaaaaccc agagggccag taagagctcc acaggtatat    480
gtcttgcctc caccagcaga agagatgact aagaaagagt tcagtctgac ctgcatgatc    540
acaggcttct acctgccga aattgctgtg gactggacca gcaatgggcg tacagagcaa    600
aactacaaga caccgcaac agtcctggac tctgatggtt cttacttcat gtacagcaag    660
ctcagagtac aaaagagcac ttgggaaaga ggaagtcttt tcgcctgctc agtggtccac    720
gagggtctgc acaatcacct tacgactaag accatctccc ggtctctggg taaaggtggc    780
ggatctgact acaaggacga cgatgacaag tgataa                              816
```

<210> SEQ ID NO 13
<211> LENGTH: 270
<212> TYPE: PRT
<213> ORGANISM: Artificial Sequence
<220> FEATURE:

<223> OTHER INFORMATION: Synthetic: D265A Fc/Flag (amino acid sequence)

<400> SEQUENCE: 13

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Asp Tyr Lys Asp Asp Asp Asp Lys
            260                 265                 270
```

<210> SEQ ID NO 14
<211> LENGTH: 1257
<212> TYPE: DNA
<213> ORGANISM: Artificial Sequence
<220> FEATURE:
<223> OTHER INFORMATION: Synthetic: D265A Fc/wt mIL-2 (nucleic acid sequence)

<400> SEQUENCE: 14

```
atgagggtcc ccgctcagct cctggggctc ctgctgctct ggctcccagg tgcacgatgt     60
gagcccagag tgcccataac acagaacccc tgtcctccac tcaaagagtg tcccccatgc    120
gcagctccag acctcttggg tgaccatcc gtcttcatct ccctccaaa gatcaaggat      180 gtactcatga tctccctgag ccccatggtc acatgtgtgg tggtggccgt gagcgaggat    240
gacccagacg tccagatcag ctggtttgtg aacaacgtgg aagtacacac agctcagaca    300
caaacccata gagaggatta caacagtact ctccgggtgg tcagtgccct ccccatccag    360
caccaggact ggatgagtgg caaggagttc aaatgcaagg tcaacaacag agccctccca    420
```

```
tcccccatcg agaaaaccat ctcaaaaccc agagggccag taagagctcc acaggtatat    480
gtcttgcctc caccagcaga agagatgact aagaaagagt tcagtctgac ctgcatgatc    540
acaggcttct tacctgccga aattgctgtg gactggacca gcaatgggcg tacagagcaa    600
aactacaaga acaccgcaac agtcctggac tctgatggtt cttacttcat gtacagcaag    660
ctcagagtac aaaagagcac ttgggaagga ggaagtcttt tcgcctgctc agtggtccac    720
gagggtctgc acaatcacct tacgactaag accatctccc ggtctctggg taaaggaggg    780
ggctccgcac ccacttcaag ctccacttca agctctacag cggaagcaca gcagcagcag    840
cagcagcagc agcagcagca gcagcacctg gagcagctgt tgatggacct acaggagctc    900
ctgagcagga tggagaatta caggaacctg aaactcccca ggatgctcac cttcaaattt    960
tacttgccca gcaggccac agaattgaaa gatcttcagt gcctagaaga tgaacttgga   1020
cctctgcggc atgttctgga tttgactcaa agcaaaagct ttcaattgga agatgctgag   1080
aatttcatca gcaatatcag agtaactgtt gtaaaactaa agggctctga caacacattt   1140
gagtgccaat tcgatgatga gtcagcaact gtggtggact ttctgaggag atggatagcc   1200
ttctgtcaaa gcatcatctc aacaagccct caacaccatc accaccatca ctgataa      1257
```

<210> SEQ ID NO 15
<211> LENGTH: 417
<212> TYPE: PRT
<213> ORGANISM: Artificial Sequence
<220> FEATURE:
<223> OTHER INFORMATION: Synthetic: D265A Fc/wt mIL-2 (amino acid sequence)

<400> SEQUENCE: 15

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205
```

```
Leu Asp Ser Asp Gly Ser Tyr Phe Met Tyr Ser Lys Leu Arg Val Gln
            210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Thr Ser Ser Ser
                260                 265                 270

Thr Ala Glu Ala Gln Gln Gln Gln Gln Gln Gln Gln Gln Gln
            275                 280                 285

His Leu Glu Gln Leu Leu Met Asp Leu Gln Glu Leu Leu Ser Arg Met
            290                 295                 300

Glu Asn Tyr Arg Asn Leu Lys Leu Pro Arg Met Leu Thr Phe Lys Phe
305                 310                 315                 320

Tyr Leu Pro Lys Gln Ala Thr Glu Leu Lys Asp Leu Gln Cys Leu Glu
                325                 330                 335

Asp Glu Leu Gly Pro Leu Arg His Val Leu Asp Leu Thr Gln Ser Lys
                340                 345                 350

Ser Phe Gln Leu Glu Asp Ala Glu Asn Phe Ile Ser Asn Ile Arg Val
            355                 360                 365

Thr Val Val Lys Leu Lys Gly Ser Asp Asn Thr Phe Glu Cys Gln Phe
370                 375                 380

Asp Asp Glu Ser Ala Thr Val Val Asp Phe Leu Arg Arg Trp Ile Ala
385                 390                 395                 400

Phe Cys Gln Ser Ile Ile Ser Thr Ser Pro Gln His His His His
                405                 410                 415

His
```

```
<210> SEQ ID NO 16
<211> LENGTH: 1257
<212> TYPE: DNA
<213> ORGANISM: Artificial Sequence
<220> FEATURE:
<223> OTHER INFORMATION: Synthetic: D265A Fc /QQ6210 (nucleic acid
      sequence)

<400> SEQUENCE: 16
atgagggtcc ccgctcagct cctggggctc ctgctgctct ggctcccagg tgcacgatgt     60
gagcccagag tgcccataac acagaacccc tgtcctccac tcaaagagtg tccccatgc    120 gcagctccag acctcttggg tggaccatcc gtcttcatct ccctccaaa gatcaaggat    180 gtactcatga tctccctgag ccccatggtc acatgtgtgg tggtggccgt gagcgaggat    240
gacccagacg tccagatcag ctggtttgtg aacaacgtgg aagtacacac agctcagaca    300
caaacccata gagaggatta aacagtact ctccgggtgg tcagtgccct ccccatccag    360
caccaggact ggatgagtgg caaggagttc aaatgcaagg tcaacaacag agccctccca    420
tcccccatcg agaaaaccat ctcaaaaccc agagggccag taagagctcc acaggtatat    480
gtcttgcctc caccagcaga agagatgact aagaaagagt tcagtctgac ctgcatgatc    540
acaggcttct acctgccga aattgctgtg gactggacca gcaatgggcg tacagagcaa    600
aactacaaga acaccgcaac agtcctggac tctgatggtt cttacttcat gtacagcaag    660
ctcagagtac aaaagagcac ttgggaaaga ggaagtcttt tcgcctgctc agtggtccac    720
gagggtctgc acaatcacct tacgactaag accatctccc ggtctctggg taaaggaggg    780
ggctccgcac ccacttcaag ctccacttca agctctacag cggaagcaca acagcagcag    840
```

```
cagcagcagc agcagcagca gcagcacctg gagcagctgt tgatggacct acaggaactc      900
ctgagtagga tggaggatca caggaacctg agactcccca ggatgctcac cttcaaattt      960
tacttgcccg agcaggccac agaattggaa gatcttcagt gcctagaaga tgaacttgaa     1020
ccactgcggc aagttctgga tttgactcaa agcaaaagct ttcaattgga agatgctgag     1080
aatttcatca gcaatatcag agtaactgtt gtaaaactaa agggctctga caacacattt     1140
gagtgccaat tcgacgatga ccagcaact gtggtggact ttctgaggag atggatagcc      1200
ttctgtcaaa gcatcatctc aacaagccct caacaccatc accaccatca ctgataa       1257
```

<210> SEQ ID NO 17
<211> LENGTH: 417
<212> TYPE: PRT
<213> ORGANISM: Artificial Sequence
<220> FEATURE:
<223> OTHER INFORMATION: Synthetic: D265A Fc /QQ6210 (amino acid sequence)

<400> SEQUENCE: 17

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65              70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145             150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225             230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285
```

```
His Leu Glu Gln Leu Leu Met Asp Leu Gln Glu Leu Leu Ser Arg Met
    290                 295                 300

Glu Asp His Arg Asn Leu Arg Leu Pro Arg Met Leu Thr Phe Lys Phe
305                 310                 315                 320

Tyr Leu Pro Glu Gln Ala Thr Glu Leu Glu Asp Leu Gln Cys Leu Glu
                325                 330                 335

Asp Glu Leu Glu Pro Leu Arg Gln Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
    370                 375                 380

Asp Asp Glu Pro Ala Thr Val Val Asp Phe Leu Arg Arg Trp Ile Ala
385                 390                 395                 400

Phe Cys Gln Ser Ile Ile Ser Thr Ser Pro Gln His His His His His
                405                 410                 415

His
```

<210> SEQ ID NO 18
<211> LENGTH: 1257
<212> TYPE: DNA
<213> ORGANISM: Artificial Sequence
<220> FEATURE:
<223> OTHER INFORMATION: Synthetic: D265A Fc / E76A (nucleic acid sequence)

<400> SEQUENCE: 18

```
atgagggtcc ccgctcagct cctggggctc ctgctgctct ggctcccagg tgcacgatgt      60
gagcccagag tgcccataac acagaacccc tgtcctccac tcaaagagtg tccccccatgc    120
gcagctccag acctcttggg tggaccatcc gtcttcatct ccctccaaa gatcaaggat      180
gtactcatga tctccctgag ccccatggtc acatgtgtgg tggtggccgt gagcgaggat     240
gacccagacg tccagatcag ctggtttgtg aacaacgtgg aagtacacac agctcagaca    300
caaacccata gagaggatta acagtact ctccgggtgg tcagtgccct ccccatccag       360
caccaggact ggatgagtgg caaggagttc aaatgcaagg tcaacaacag agccctccca    420
tcccccatcg agaaaaccat ctcaaaaccc agagggccag taagagctcc acaggtatat    480
gtcttgcctc caccagcaga gagatgact aagaaagagt tcagtctgac ctgcatgatc     540
acaggcttct tacctgccga aattgctgtg gactggacca gcaatgggcg tacagagcaa    600
aactacaaga cacccgcaac agtcctggac tctgatggtt cttacttcat gtacagcaag    660
ctcagagtac aaaagagcac ttgggaaaga ggaagtcttt tcgcctgctc agtggtccac    720
gagggtctgc acaatcacct tacgactaag accatctccc ggtctctggg taaaggaggg    780
ggctccgcac ccacttcaag ctccacttca agctctacag cggaagcaca gcagcagcag    840
cagcagcagc agcagcagca gcagcacctg gagcagctgt tgatggacct acaggagctc    900
ctgagcagga tggagaatta caggaacctg aaactcccca ggatgctcac cttcaaattt    960
tacttgccca gcaggccac agaattgaaa gatcttcagt gcctagaaga tgctcttgga   1020
cctctgcggc atgttctgga tttgactcaa agcaaaagct tcaattgga agatgctgag    1080
aatttcatca gcaatatcag agtaactgtt gtaaaactaa agggctctga caacacattt    1140
gagtgccaat tcgatgatga gtcagcaact gtggtggact tctgaggag atggatagcc    1200
ttctgtcaaa gcatcatctc aacaagcct caacaccatc accaccatca ctgataa       1257
```

<210> SEQ ID NO 19
<211> LENGTH: 417
<212> TYPE: PRT
<213> ORGANISM: Artificial Sequence
<220> FEATURE:
<223> OTHER INFORMATION: Synthetic: D265A Fc / E76A (amino acid sequence)

<400> SEQUENCE: 19

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asn Tyr Arg Asn Leu Lys Leu Pro Arg Met Leu Thr Phe Lys Phe
305                 310                 315                 320

Tyr Leu Pro Lys Gln Ala Thr Glu Leu Lys Asp Leu Gln Cys Leu Glu
                325                 330                 335

Asp Ala Leu Gly Pro Leu Arg His Val Leu Asp Leu Thr Gln Ser Lys
            340                 345                 350

Ser Phe Gln Leu Glu Asp Ala Glu Asn Phe Ile Ser Asn Ile Arg Val
```

355                 360                 365
Thr Val Val Lys Leu Lys Gly Ser Asp Asn Thr Phe Glu Cys Gln Phe
        370                 375                 380

Asp Asp Glu Ser Ala Thr Val Val Asp Phe Leu Arg Arg Trp Ile Ala
385                 390                 395                 400

Phe Cys Gln Ser Ile Ile Ser Thr Ser Pro Gln His His His His His
                405                 410                 415

His

<210> SEQ ID NO 20
<211> LENGTH: 1257
<212> TYPE: DNA
<213> ORGANISM: Artificial Sequence
<220> FEATURE:
<223> OTHER INFORMATION: Synthetic:  D265A Fc / E76G (nucleic acid sequence)

<400> SEQUENCE: 20

```
atgagggtcc ccgctcagct cctggggctc ctgctgctct ggctcccagg tgcacgatgt      60
gagcccagag tgcccataac acagaacccc tgtcctccac tcaaagagtg tcccccatgc     120
gcagctccag acctcttggg tggaccatcc gtcttcatct ccctccaaa gatcaaggat      180
gtactcatga tctccctgag ccccatggtc acatgtgtgg tggtggccgt gagcgaggat     240
gacccagacg tccagatcag ctggtttgtg aacaacgtgg aagtacacac agctcagaca     300
caaacccata gagaggatta caacagtact ctccgggtgg tcagtgccct ccccatccag     360
caccaggact ggatgagtgg caaggagttc aaatgcaagg tcaacaacag agccctccca     420
tcccccatcg agaaaaccat ctcaaaaccc agagggccag taagagctcc acaggtatat     480
gtcttgcctc caccagcaga agagatgact aagaaagagt tcagtctgac ctgcatgatc     540
acaggcttct acctgccga aattgctgtg actggaccaa gcaatgggcg tacagagcaa     600
aactacaaga acaccgcaac agtcctggac tctgatggtt cttacttcat gtacagcaag     660
ctcagagtac aaaagagcac ttgggaaaga ggaagtcttt tcgcctgctc agtggtccac     720
gagggtctgc acaatcacct tacgactaag accatctccc cgtctctggg taaaggaggg     780
ggctccgcac ccacttcaag ctccacttca agctctacag cggaagcaca gcagcagcag     840
cagcagcagc agcagcagca gcagcacctg gagcagctgt tgatggacct acaggagctc     900
ctgagcagga tggagaatta caggaacctg aaactcccca ggatgctcac cttcaaattt     960
tacttgccca gcaggccac agaattgaaa gatcttcagt gcctagaaga tggtcttgga    1020
cctctgcggc atgttctgga tttgactcaa gcaaaagct tcaattgga agatgctgag    1080
aatttcatca gcaatatcag agtaactgtt gtaaaactaa agggctctga caacacattt    1140
gagtgccaat cgatgatga gtcagcaact gtggtggact ttctgaggag atggatagcc    1200
ttctgtcaaa gcatcatctc aacaagccct caacaccatc accaccatca ctgataa      1257
```

<210> SEQ ID NO 21
<211> LENGTH: 417
<212> TYPE: PRT
<213> ORGANISM: Artificial Sequence
<220> FEATURE:
<223> OTHER INFORMATION: Synthetic:  D265A Fc / E76G (amino acid sequence)

<400> SEQUENCE: 21

Met Arg Val Pro Ala Gln Leu Leu Gly Leu Leu Leu Leu Trp Leu Pro
1               5                   10                  15

```
Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asn Tyr Arg Asn Leu Lys Leu Pro Arg Met Leu Thr Phe Lys Phe
305                 310                 315                 320

Tyr Leu Pro Lys Gln Ala Thr Glu Leu Lys Asp Leu Gln Cys Leu Glu
                325                 330                 335

Asp Gly Leu Gly Pro Leu Arg His Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
    370                 375                 380

Asp Asp Glu Ser Ala Thr Val Val Asp Phe Leu Arg Arg Trp Ile Ala
385                 390                 395                 400

Phe Cys Gln Ser Ile Ile Ser Thr Ser Pro Gln His His His His His
                405                 410                 415

His
```

<210> SEQ ID NO 22
<211> LENGTH: 447
<212> TYPE: DNA
<213> ORGANISM: Artificial Sequence
<220> FEATURE:
<223> OTHER INFORMATION: Synthetic: mIL-2 QQ 6.2-4 (nucleic acid sequence)

<400> SEQUENCE: 22

```
gcacccacct caagctccac ttcaagctct acagcggaag cacaacagca gcagcagcag      60
cagcagcagc agcagcagca cctggagcag ctgttgatgg acctacagga gctcctgagc     120
aggatggagg attccaggaa cctgagactc cccaggatgc tcaccttcaa attttacttg     180
cccaagcagg ccacagaatt ggaagatctt cagtgcctag aagatgaact tgaacctctg     240
cggcaagttc tggatttgac tcaaagcaaa agctttcaat ggaagatgc tgagaatttc      300
atcagcaata tcagagtaac tgttgtaaaa ctaaagggct ctgacaacac atttgagtgc     360
caattcgatg atgagccagc aactgtggtg ggctttctga ggagatggat agccttctgt     420
caaagcatca tctcaacgag ccctcaa                                         447
```

<210> SEQ ID NO 23
<211> LENGTH: 149
<212> TYPE: PRT
<213> ORGANISM: Artificial Sequence
<220> FEATURE:
<223> OTHER INFORMATION: Synthetic: mIL-2 QQ 6.2-4 (amino acid sequence)

<400> SEQUENCE: 23

```
Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asp Ser Arg Asn Leu
        35                  40                  45

Arg Leu Pro Arg Met Leu Thr Phe Lys Phe Tyr Leu Pro Lys Gln Ala
    50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125

Val Val Gly Phe Leu Arg Arg Trp Ile Ala Phe Cys Gln Ser Ile Ile
    130                 135                 140

Ser Thr Ser Pro Gln
145
```

<210> SEQ ID NO 24
<211> LENGTH: 435
<212> TYPE: DNA
<213> ORGANISM: Artificial Sequence
<220> FEATURE:
<223> OTHER INFORMATION: Synthetic: mIL-2 QQ 6.2-8 (nucleic acid sequence)

<400> SEQUENCE: 24

```
gcacccacct caagctccac ttcaagctct acagcggaag cacaacagca gcagcagcag      60
```

| | |
|---|---|
| cagcagcacc tggagcagct gttgatggac ctacaggagc tcctgagtag gatggaggat | 120 |
| cacaggaacc tgagactccc caggatgctc accttcaaat tttacttgcc caagcaggcc | 180 |
| acagaattgg aagatcttca gtgcctagaa gatgaacttg aacctctgcg gcaagttctg | 240 |
| gatttgactc aaagcaaaag ctttcaattg gaagatgctg agaatttcat cagcaatatc | 300 |
| agagtaactg ttgtaaaact aaagggctct gacaacacat ttgagtgcca attcgatgat | 360 |
| gagccagcaa ctgtggtgga ctttctgagg agatggatag ccttctgtca agcatcatc | 420 |
| tcaacaagcc ctcga | 435 |

```
<210> SEQ ID NO 25
<211> LENGTH: 145
<212> TYPE: PRT
<213> ORGANISM: Artificial Sequence
<220> FEATURE:
<223> OTHER INFORMATION: Synthetic: mIL-2 QQ 6.2-8 (amino acid
      sequence)

<400> SEQUENCE: 25

Ala Pro Thr Ser Ser Thr Ser Ser Ser Thr Ala Glu Ala Gln Gln
1               5                   10                  15

Gln Gln Gln Gln Gln Gln His Leu Glu Gln Leu Leu Met Asp Leu Gln
            20                  25                  30

Glu Leu Leu Ser Arg Met Glu Asp His Arg Asn Leu Arg Leu Pro Arg
        35                  40                  45

Met Leu Thr Phe Lys Phe Tyr Leu Pro Lys Gln Ala Thr Glu Leu Glu
    50                  55                  60

Asp Leu Gln Cys Leu Glu Asp Glu Leu Glu Pro Leu Arg Gln Val Leu
65                  70                  75                  80

Asp Leu Thr Gln Ser Lys Ser Phe Gln Leu Glu Asp Ala Glu Asn Phe
                85                  90                  95

Ile Ser Asn Ile Arg Val Thr Val Val Lys Leu Lys Gly Ser Asp Asn
            100                 105                 110

Thr Phe Glu Cys Gln Phe Asp Asp Glu Pro Ala Thr Val Val Asp Phe
        115                 120                 125

Leu Arg Arg Trp Ile Ala Phe Cys Gln Ser Ile Ile Ser Thr Ser Pro
    130                 135                 140

Arg
145

<210> SEQ ID NO 26
<211> LENGTH: 447
<212> TYPE: DNA
<213> ORGANISM: Artificial Sequence
<220> FEATURE:
<223> OTHER INFORMATION: Synthetic: mIL-2 QQ 6.2-10 (nucleic acid
      sequence)

<400> SEQUENCE: 26
```

| | |
|---|---|
| gcacccacct caagctccac ttcaagctct acagcggaag cacaacagca gcagcagcag | 60 |
| cagcagcagc agcagcagca cctggagcag ctgttgatgg acctacagga actcctgagt | 120 |
| aggatggagg atcacaggaa cctgagactc cccaggatgc tcaccttcaa attttacttg | 180 |
| cccgagcagg ccacagaatt ggaagatctt cagtgcctag aagatgaact tgaaccactg | 240 |
| cggcaagttc tggatttgac tcaaagcaaa agctttcaat tggaagatgc tgagaatttc | 300 |
| atcagcaata tcagagtaac tgttgtaaaa ctaaagggct ctgacaacac atttgagtgc | 360 | caattcgacg atgagccagc aactgtggtg gactttctga ggagatggat agccttctgt    420 caaagcatca tctcaacaag ccctcag    447

```
<210> SEQ ID NO 27
<211> LENGTH: 149
<212> TYPE: PRT
<213> ORGANISM: Artificial Sequence
<220> FEATURE:
<223> OTHER INFORMATION: Synthetic: mIL-2 QQ 6.2-10 (amino acid
      sequence)
```

<400> SEQUENCE: 27

Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asp His Arg Asn Leu
        35                  40                  45

Arg Leu Pro Arg Met Leu Thr Phe Lys Phe Tyr Leu Pro Glu Gln Ala
    50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145

```
<210> SEQ ID NO 28
<211> LENGTH: 438
<212> TYPE: DNA
<213> ORGANISM: Artificial Sequence
<220> FEATURE:
<223> OTHER INFORMATION: Synthetic: mIL-2 QQ 6.2-11 (nucleic acid
      sequence)
```

<400> SEQUENCE: 28
gcacccacct caagctccac ttcaagctct acagcggaag cacaacagca gcagcagcag    60
cagcagcagc acctggagca gctgttgatg gacctacagg agctcctgag caggatggag    120
gattccagga acctgagact ccccagaatg ctcaccttca aatttactt gcccgagcag    180 gccacagaat tgaaagatct ccagtgccta gaagatgaac ttgaacctct gcggcaagtt    240
ctggatttga ctcaaagcaa aagctttcaa ttggaagatg ctgagaattt catcagcaat    300
atcagagtaa ctgttgtaaa actaaagggc tctgacaaca catttgagtg ccaattcgac    360
gatgagccag caactgtggt ggactttctg aggagatgga tagccttctg tcaaagcatc    420
atctcaacaa gccctcag    438

```
<210> SEQ ID NO 29
<211> LENGTH: 146
<212> TYPE: PRT
<213> ORGANISM: Artificial Sequence
<220> FEATURE:
<223> OTHER INFORMATION: Synthetic: mIL-2 QQ 6.2-11 (amino acid
``` sequence)

<400> SEQUENCE: 29

Ala Pro Thr Ser Ser Ser Thr Ser Ser Ser Thr Ala Glu Ala Gln Gln
1               5                   10                  15

Gln Gln Gln Gln Gln Gln Gln His Leu Glu Gln Leu Leu Met Asp Leu
            20                  25                  30

Gln Glu Leu Leu Ser Arg Met Glu Asp Ser Arg Asn Leu Arg Leu Pro
        35                  40                  45

Arg Met Leu Thr Phe Lys Phe Tyr Leu Pro Glu Gln Ala Thr Glu Leu
    50                  55                  60

Lys Asp Leu Gln Cys Leu Glu Asp Glu Leu Pro Leu Arg Gln Val
65                  70                  75                  80

Leu Asp Leu Thr Gln Ser Lys Ser Phe Gln Leu Glu Asp Ala Glu Asn
                85                  90                  95

Phe Ile Ser Asn Ile Arg Val Thr Val Val Lys Leu Lys Gly Ser Asp
            100                 105                 110

Asn Thr Phe Glu Cys Gln Phe Asp Asp Glu Pro Ala Thr Val Val Asp
        115                 120                 125

Phe Leu Arg Arg Trp Ile Ala Phe Cys Gln Ser Ile Ile Ser Thr Ser
    130                 135                 140

Pro Gln
145

<210> SEQ ID NO 30
<211> LENGTH: 447
<212> TYPE: DNA
<213> ORGANISM: Artificial Sequence
<220> FEATURE:
<223> OTHER INFORMATION: Synthetic:  mIL-2 QQ 6.2-13 (nucleic acid
      sequence)

<400> SEQUENCE: 30
gcacccacct caagctccac ttcaagctct acagcggaag cacaacagca gcagcagcag      60
cagcagcagc agcagcagca cctggagcag ctgttgatgg acctacagga gctcctgagt     120
aggatggagg atcacaggaa cctgagactc cccaggatgc tcaccttcaa attttacttg     180
cccgagcagg ccacagaatt gaaagatctc cagtgcctag aagatgaact gaacctctg     240 cggcaggttc tggatttgac tcaaagcaaa agctttcaat ggaagatgc tgagaatttc     300 atcagcaata tcagagtaac tgttgtaaaa ctaaagggct ctgacaacac atttgagtgc     360
caattcgatg atgagccagc aactgtggtg gactttctga ggagatggat agccttctgt     420
caaagcatca tctcaacaag ccctcag                                         447

<210> SEQ ID NO 31
<211> LENGTH: 149
<212> TYPE: PRT
<213> ORGANISM: Artificial Sequence
<220> FEATURE:
<223> OTHER INFORMATION: Synthetic:  mIL-2 QQ 6.2-13 (amino acid
      sequence)

<400> SEQUENCE: 31

Ala Pro Thr Ser Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asp His Arg Asn Leu

```
                35                  40                  45
Arg Leu Pro Arg Met Leu Thr Phe Lys Phe Tyr Leu Pro Glu Gln Ala
         50                  55                  60

Thr Glu Leu Lys Asp Leu Gln Cys Leu Glu Asp Glu Leu Glu Pro Leu
 65                  70                  75                  80

Arg Gln Val Leu Asp Leu Thr Gln Ser Lys Ser Phe Gln Leu Glu Asp
                 85                  90                  95

Ala Glu Asn Phe Ile Ser Asn Ile Arg Val Thr Val Val Lys Leu Lys
                100                 105                 110

Gly Ser Asp Asn Thr Phe Glu Cys Gln Phe Asp Asp Glu Pro Ala Thr
            115                 120                 125

Val Val Asp Phe Leu Arg Arg Trp Ile Ala Phe Cys Gln Ser Ile Ile
        130                 135                 140

Ser Thr Ser Pro Gln
145

<210> SEQ ID NO 32
<211> LENGTH: 461
<212> TYPE: DNA
<213> ORGANISM: Homo sapiens
<220> FEATURE:
<221> NAME/KEY: misc_feature
<222> LOCATION: (1)..(461)
<223> OTHER INFORMATION: Full length human IL-2 (nucleic acid sequence)

<400> SEQUENCE: 32
atgtacagga tgcaactcct gtcttgcatt gcactaagtc ttgcacttgt cacaaacagt         60
gcacctactt caagttctac aaagaaaaca cagctacaac tggagcattt actgctggat       120
ttacagatga ttttgaatgg aattaataat acaagaatcc caaactcac caggatgctc         180 acatttaagt tttacatgcc caagaaggcc acagaactga acatcttca gtgtctagaa         240 gaagaactca aacctctgga ggaagtgcta aatttagctc aaagcaaaaa ctttcactta        300
agacccaggg acttaatcag caatatcaac gtaaagttc tggaactaaa gggatctgaa         360
acaacattca tgtgtaatat gctgatgaga cagcaaccat gtagaatttt ctgaacagat        420
ggattacctt ttgtcaaagc atcatctcaa cactgacttg a                            461

<210> SEQ ID NO 33
<211> LENGTH: 153
<212> TYPE: PRT
<213> ORGANISM: Homo sapiens
<220> FEATURE:
<221> NAME/KEY: misc_feature
<222> LOCATION: (1)..(153)
<223> OTHER INFORMATION: Full length human IL-2 (amino acid sequence)

<400> SEQUENCE: 33

Met Tyr Arg Met Gln Leu Leu Ser Cys Ile Ala Leu Ser Leu Ala Leu
 1               5                  10                  15

Val Thr Asn Ser Ala Pro Thr Ser Ser Ser Thr Lys Lys Thr Gln Leu
             20                  25                  30

Gln Leu Glu His Leu Leu Leu Asp Leu Gln Met Ile Leu Asn Gly Ile
         35                  40                  45

Asn Asn Tyr Lys Asn Pro Lys Leu Thr Arg Met Leu Thr Phe Lys Phe
     50                  55                  60

Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
```

```
                    85                  90                  95
Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Thr
145                 150
```

<210> SEQ ID NO 34
<211> LENGTH: 401
<212> TYPE: DNA
<213> ORGANISM: Homo sapiens
<220> FEATURE:
<221> NAME/KEY: misc_feature
<222> LOCATION: (1)..(401)
<223> OTHER INFORMATION: Human IL-2 without signal peptide (nucleic acid
      sequence)

<400> SEQUENCE: 34

```
gcacctactt caagttctac aaagaaaaca cagctacaac tggagcattt actgctggat      60
ttacagatga ttttgaatgg aattaataat tacaagaatc ccaaactcac caggatgctc     120
acatttaagt tttacatgcc caagaaggcc acagaactga acatcttca gtgtctagaa      180
gaagaactca aacctctgga ggaagtgcta aatttagctc aaagcaaaaa ctttcactta     240
agacccaggg acttaatcag caatatcaac gtaatagttc tggaactaaa gggatctgaa     300
acaacattca tgtgtaatat gctgatgaga cagcaaccat tgtagaattt ctgaacagat     360
ggattacctt ttgtcaaagc atcatctcaa cactgacttg a                        401
```

<210> SEQ ID NO 35
<211> LENGTH: 133
<212> TYPE: PRT
<213> ORGANISM: Homo sapiens
<220> FEATURE:
<221> NAME/KEY: misc_feature
<222> LOCATION: (1)..(133)
<223> OTHER INFORMATION: Human IL-2 without signal peptide (amino acid
      sequence)

<400> SEQUENCE: 35

```
Ala Pro Thr Ser Ser Ser Thr Lys Lys Thr Gln Leu Gln Leu Glu His
1               5                  10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
```

-continued

130

<210> SEQ ID NO 36
<211> LENGTH: 749
<212> TYPE: PRT
<213> ORGANISM: Homo sapiens
<220> FEATURE:
<221> NAME/KEY: misc_feature
<222> LOCATION: (1)..(749)
<223> OTHER INFORMATION: Human serum albumin (amino acid sequence)

<400> SEQUENCE: 36

```
Met Asp Met Arg Val Pro Ala Gln Leu Leu Gly Leu Leu Leu Leu Trp
1               5                   10                  15

Leu Pro Gly Ala Arg Cys Ala Asp Ala His Lys Ser Glu Val Ala His
                20                  25                  30

Arg Phe Lys Asp Leu Gly Glu Glu Asn Phe Lys Ala Leu Val Leu Ile
            35                  40                  45

Ala Phe Ala Gln Tyr Leu Gln Gln Cys Pro Phe Glu Asp His Val Lys
        50                  55                  60

Leu Val Asn Glu Val Thr Glu Phe Ala Lys Thr Cys Val Ala Asp Glu
65                  70                  75                  80

Ser Ala Glu Asn Cys Asp Lys Ser Leu His Thr Leu Phe Gly Asp Lys
                85                  90                  95

Leu Cys Thr Val Ala Thr Leu Arg Glu Thr Tyr Gly Glu Met Ala Asp
            100                 105                 110

Cys Cys Ala Lys Gln Glu Pro Glu Arg Asn Glu Cys Phe Leu Gln His
        115                 120                 125

Lys Asp Asp Asn Pro Asn Leu Pro Arg Leu Val Arg Pro Glu Val Asp
130                 135                 140

Val Met Cys Thr Ala Phe His Asp Asn Glu Glu Thr Phe Leu Lys Lys
145                 150                 155                 160

Tyr Leu Tyr Glu Ile Ala Arg Arg His Pro Tyr Phe Tyr Ala Pro Glu
                165                 170                 175

Leu Leu Phe Phe Ala Lys Arg Tyr Lys Ala Ala Phe Thr Glu Cys Cys
            180                 185                 190

Gln Ala Ala Asp Lys Ala Ala Cys Leu Leu Pro Lys Leu Asp Glu Leu
        195                 200                 205

Arg Asp Glu Gly Lys Ala Ser Ser Ala Lys Gln Arg Leu Lys Cys Ala
    210                 215                 220

Ser Leu Gln Lys Phe Gly Glu Arg Ala Phe Lys Ala Trp Ala Val Ala
225                 230                 235                 240

Arg Leu Ser Gln Arg Phe Pro Lys Ala Glu Phe Ala Glu Val Ser Lys
                245                 250                 255

Leu Val Thr Asp Leu Thr Lys Val His Thr Glu Cys Cys His Gly Asp
            260                 265                 270

Leu Leu Glu Cys Ala Asp Asp Arg Ala Asp Leu Ala Lys Tyr Ile Cys
        275                 280                 285

Glu Asn Gln Asp Ser Ile Ser Ser Lys Leu Lys Glu Cys Cys Glu Lys
    290                 295                 300

Pro Leu Leu Glu Lys Ser His Cys Ile Ala Glu Val Glu Asn Asp Glu
305                 310                 315                 320

Met Pro Ala Asp Leu Pro Ser Leu Ala Ala Asp Phe Val Glu Ser Lys
                325                 330                 335

Asp Val Cys Lys Asn Tyr Ala Glu Ala Lys Asp Val Phe Leu Gly Met
            340                 345                 350
```

```
Phe Leu Tyr Glu Tyr Ala Arg Arg His Pro Asp Tyr Ser Val Val Leu
            355                 360                 365

Leu Leu Arg Leu Ala Lys Thr Tyr Glu Thr Thr Leu Glu Lys Cys Cys
    370                 375                 380

Ala Ala Ala Asp Pro His Glu Cys Tyr Ala Lys Val Phe Asp Glu Phe
385                 390                 395                 400

Lys Pro Leu Val Glu Glu Pro Gln Asn Leu Ile Lys Gln Asn Cys Glu
                405                 410                 415

Leu Phe Glu Gln Leu Gly Glu Tyr Lys Phe Gln Asn Ala Leu Leu Val
            420                 425                 430

Arg Tyr Thr Lys Lys Val Pro Gln Val Ser Thr Pro Thr Leu Val Glu
        435                 440                 445

Val Ser Arg Asn Leu Gly Lys Val Gly Ser Lys Cys Cys Lys His Pro
    450                 455                 460

Glu Ala Lys Arg Met Pro Cys Ala Glu Asp Tyr Leu Ser Val Val Leu
465                 470                 475                 480

Asn Gln Leu Cys Val Leu His Glu Lys Thr Pro Val Ser Asp Arg Val
                485                 490                 495

Thr Lys Cys Cys Thr Glu Ser Leu Val Asn Arg Arg Pro Cys Phe Ser
            500                 505                 510

Ala Leu Glu Val Asp Glu Thr Tyr Val Pro Lys Glu Phe Asn Ala Glu
        515                 520                 525

Thr Phe Thr Phe His Ala Asp Ile Cys Thr Leu Ser Glu Lys Glu Arg
    530                 535                 540

Gln Ile Lys Lys Gln Thr Ala Leu Val Glu Leu Val Lys His Lys Pro
545                 550                 555                 560

Lys Ala Thr Lys Glu Gln Leu Lys Ala Val Met Asp Asp Phe Ala Ala
                565                 570                 575

Phe Val Glu Lys Cys Cys Lys Ala Asp Asp Lys Glu Thr Cys Phe Ala
            580                 585                 590

Glu Glu Gly Lys Lys Leu Val Ala Ala Ser Gln Ala Ala Leu Gly Leu
        595                 600                 605

Gly Gly Gly Ser Ala Pro Thr Ser Ser Thr Lys Lys Thr Gln Leu
    610                 615                 620

Gln Leu Glu His Leu Leu Leu Asp Leu Gln Met Ile Leu Asn Gly Ile
625                 630                 635                 640

Asn Asn Tyr Lys Asn Pro Lys Leu Thr Arg Met Leu Thr Phe Lys Phe
                645                 650                 655

Tyr Met Pro Lys Lys Ala Thr Glu Leu Lys His Leu Gln Cys Leu Glu
            660                 665                 670

Glu Glu Leu Lys Pro Leu Glu Glu Val Leu Asn Leu Ala Gln Ser Lys
        675                 680                 685

Asn Phe His Leu Arg Pro Arg Asp Leu Ile Ser Asn Ile Asn Val Ile
    690                 695                 700

Val Leu Glu Leu Lys Gly Ser Glu Thr Thr Phe Met Cys Glu Tyr Ala
705                 710                 715                 720

Asp Glu Thr Ala Thr Ile Val Glu Phe Leu Asn Arg Trp Ile Thr Phe
                725                 730                 735

Cys Gln Ser Ile Ile Ser Thr Leu Thr Gly Gly Gly Ser
            740                 745

<210> SEQ ID NO 37
<211> LENGTH: 726
```

```
<212> TYPE: PRT
<213> ORGANISM: Homo sapiens
<220> FEATURE:
<221> NAME/KEY: misc_feature
<222> LOCATION: (1)..(726)
<223> OTHER INFORMATION: Mature HSA (amino acid sequence)

<400> SEQUENCE: 37
```

| Asp | Ala | His | Lys | Ser | Glu | Val | Ala | His | Arg | Phe | Lys | Asp | Leu | Gly | Glu |
|---|---|---|---|---|---|---|---|---|---|---|---|---|---|---|---|
| 1 | | | | 5 | | | | | 10 | | | | | 15 | |

| Glu | Asn | Phe | Lys | Ala | Leu | Val | Leu | Ile | Ala | Phe | Ala | Gln | Tyr | Leu | Gln |
|---|---|---|---|---|---|---|---|---|---|---|---|---|---|---|---|
| | | | 20 | | | | | 25 | | | | | 30 | | |

| Gln | Cys | Pro | Phe | Glu | Asp | His | Val | Lys | Leu | Val | Asn | Glu | Val | Thr | Glu |
|---|---|---|---|---|---|---|---|---|---|---|---|---|---|---|---|
| | | 35 | | | | | 40 | | | | | 45 | | | |

| Phe | Ala | Lys | Thr | Cys | Val | Ala | Asp | Glu | Ser | Ala | Glu | Asn | Cys | Asp | Lys |
|---|---|---|---|---|---|---|---|---|---|---|---|---|---|---|---|
| | 50 | | | | | 55 | | | | | 60 | | | | |

| Ser | Leu | His | Thr | Leu | Phe | Gly | Asp | Lys | Leu | Cys | Thr | Val | Ala | Thr | Leu |
|---|---|---|---|---|---|---|---|---|---|---|---|---|---|---|---|
| 65 | | | | | 70 | | | | | 75 | | | | | 80 |

| Arg | Glu | Thr | Tyr | Gly | Glu | Met | Ala | Asp | Cys | Cys | Ala | Lys | Gln | Glu | Pro |
|---|---|---|---|---|---|---|---|---|---|---|---|---|---|---|---|
| | | | | 85 | | | | | 90 | | | | | 95 | |

| Glu | Arg | Asn | Glu | Cys | Phe | Leu | Gln | His | Lys | Asp | Asp | Asn | Pro | Asn | Leu |
|---|---|---|---|---|---|---|---|---|---|---|---|---|---|---|---|
| | | | 100 | | | | | 105 | | | | | 110 | | |

| Pro | Arg | Leu | Val | Arg | Pro | Glu | Val | Asp | Val | Met | Cys | Thr | Ala | Phe | His |
|---|---|---|---|---|---|---|---|---|---|---|---|---|---|---|---|
| | | 115 | | | | | 120 | | | | | 125 | | | |

| Asp | Asn | Glu | Glu | Thr | Phe | Leu | Lys | Lys | Tyr | Leu | Tyr | Glu | Ile | Ala | Arg |
|---|---|---|---|---|---|---|---|---|---|---|---|---|---|---|---|
| | 130 | | | | | 135 | | | | | 140 | | | | |

| Arg | His | Pro | Tyr | Phe | Tyr | Ala | Pro | Glu | Leu | Leu | Phe | Phe | Ala | Lys | Arg |
|---|---|---|---|---|---|---|---|---|---|---|---|---|---|---|---|
| 145 | | | | | 150 | | | | | 155 | | | | | 160 |

| Tyr | Lys | Ala | Ala | Phe | Thr | Glu | Cys | Cys | Gln | Ala | Ala | Asp | Lys | Ala | Ala |
|---|---|---|---|---|---|---|---|---|---|---|---|---|---|---|---|
| | | | | 165 | | | | | 170 | | | | | 175 | |

| Cys | Leu | Leu | Pro | Lys | Leu | Asp | Glu | Leu | Arg | Asp | Glu | Gly | Lys | Ala | Ser |
|---|---|---|---|---|---|---|---|---|---|---|---|---|---|---|---|
| | | | 180 | | | | | 185 | | | | | 190 | | |

| Ser | Ala | Lys | Gln | Arg | Leu | Lys | Cys | Ala | Ser | Leu | Gln | Lys | Phe | Gly | Glu |
|---|---|---|---|---|---|---|---|---|---|---|---|---|---|---|---|
| | | 195 | | | | | 200 | | | | | 205 | | | |

| Arg | Ala | Phe | Lys | Ala | Trp | Ala | Val | Ala | Arg | Leu | Ser | Gln | Arg | Phe | Pro |
|---|---|---|---|---|---|---|---|---|---|---|---|---|---|---|---|
| 210 | | | | | 215 | | | | | 220 | | | | | |

| Lys | Ala | Glu | Phe | Ala | Glu | Val | Ser | Lys | Leu | Val | Thr | Asp | Leu | Thr | Lys |
|---|---|---|---|---|---|---|---|---|---|---|---|---|---|---|---|
| 225 | | | | | 230 | | | | | 235 | | | | | 240 |

| Val | His | Thr | Glu | Cys | Cys | His | Gly | Asp | Leu | Leu | Glu | Cys | Ala | Asp | Asp |
|---|---|---|---|---|---|---|---|---|---|---|---|---|---|---|---|
| | | | | 245 | | | | | 250 | | | | | 255 | |

| Arg | Ala | Asp | Leu | Ala | Lys | Tyr | Ile | Cys | Glu | Asn | Gln | Asp | Ser | Ile | Ser |
|---|---|---|---|---|---|---|---|---|---|---|---|---|---|---|---|
| | | | 260 | | | | | 265 | | | | | 270 | | |

| Ser | Lys | Leu | Lys | Glu | Cys | Cys | Glu | Lys | Pro | Leu | Leu | Glu | Lys | Ser | His |
|---|---|---|---|---|---|---|---|---|---|---|---|---|---|---|---|
| | | 275 | | | | | 280 | | | | | 285 | | | |

| Cys | Ile | Ala | Glu | Val | Glu | Asn | Asp | Glu | Met | Pro | Ala | Asp | Leu | Pro | Ser |
|---|---|---|---|---|---|---|---|---|---|---|---|---|---|---|---|
| | 290 | | | | | 295 | | | | | 300 | | | | |

| Leu | Ala | Ala | Asp | Phe | Val | Glu | Ser | Lys | Asp | Val | Cys | Lys | Asn | Tyr | Ala |
|---|---|---|---|---|---|---|---|---|---|---|---|---|---|---|---|
| 305 | | | | | 310 | | | | | 315 | | | | | 320 |

| Glu | Ala | Lys | Asp | Val | Phe | Leu | Gly | Met | Phe | Leu | Tyr | Glu | Tyr | Ala | Arg |
|---|---|---|---|---|---|---|---|---|---|---|---|---|---|---|---|
| | | | | 325 | | | | | 330 | | | | | 335 | |

| Arg | His | Pro | Asp | Tyr | Ser | Val | Val | Leu | Leu | Leu | Arg | Leu | Ala | Lys | Thr |
|---|---|---|---|---|---|---|---|---|---|---|---|---|---|---|---|
| | | | 340 | | | | | 345 | | | | | 350 | | |

| Tyr | Glu | Thr | Thr | Leu | Glu | Lys | Cys | Cys | Ala | Ala | Ala | Asp | Pro | His | Glu |
|---|---|---|---|---|---|---|---|---|---|---|---|---|---|---|---|
| | | 355 | | | | | 360 | | | | | 365 | | | |

| Cys | Tyr | Ala | Lys | Val | Phe | Asp | Glu | Phe | Lys | Pro | Leu | Val | Glu | Glu | Pro |
|---|---|---|---|---|---|---|---|---|---|---|---|---|---|---|---|

```
                370                 375                 380
Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Ser Ala Pro Thr
            580                 585                 590

Ser Ser Ser Thr Lys Lys Thr Gln Leu Gln Leu Glu His Leu Leu Leu
        595                 600                 605

Asp Leu Gln Met Ile Leu Asn Gly Ile Asn Asn Tyr Lys Asn Pro Lys
    610                 615                 620

Leu Thr Arg Met Leu Thr Phe Lys Phe Tyr Met Pro Lys Lys Ala Thr
625                 630                 635                 640

Glu Leu Lys His Leu Gln Cys Leu Glu Glu Glu Leu Lys Pro Leu Glu
                645                 650                 655

Glu Val Leu Asn Leu Ala Gln Ser Lys Asn Phe His Leu Arg Pro Arg
            660                 665                 670

Asp Leu Ile Ser Asn Ile Asn Val Ile Val Leu Glu Leu Lys Gly Ser
        675                 680                 685

Glu Thr Thr Phe Met Cys Glu Tyr Ala Asp Glu Thr Ala Thr Ile Val
    690                 695                 700

Glu Phe Leu Asn Arg Trp Ile Thr Phe Cys Gln Ser Ile Ile Ser Thr
705                 710                 715                 720

Leu Thr Gly Gly Gly Ser
                725

<210> SEQ ID NO 38
<211> LENGTH: 2247
<212> TYPE: DNA
<213> ORGANISM: Homo sapiens
<220> FEATURE:
<221> NAME/KEY: misc_feature
<222> LOCATION: (1)..(2247)
<223> OTHER INFORMATION: Human serum albumin (nucleic acid sequence)

<400> SEQUENCE: 38
```

```
atggatatgc gggtgcctgc tcagctgctg ggactgctgc tgctgtggct gcctggggct    60
agatgcgccg atgctcacaa aagcgaagtc gcacacaggt tcaaagatct gggggaggaa   120
aactttaagg ctctggtgct gattgcattc gcccagtacc tgcagcagtg cccctttgag   180
gaccacgtga aactggtcaa cgaagtgact gagttcgcca agacctgcgt ggccgacgaa   240
tctgctgaga attgtgataa aagtctgcat actctgtttg gggataagct gtgtacagtg   300
gccactctgc gagaaaccta tggagagatg cagactgct gtgccaaaca ggaacccgag    360
cggaacgaat gcttcctgca gcataaggac gataacccca atctgcctcg cctggtgcga   420
cctgaggtgg acgtcatgtg tacagccttc acgataatg aggaaacttt tctgaagaaa    480
tacctgtacg aaatcgctcg gagacatcct tacttttatg caccagagct gctgttcttt   540
gccaaacgct acaaggccgc tttcaccgag tgctgtcagg cagccgataa agctgcatgc   600
ctgctgccta agctggacga actgagggat gagggcaagg ccagctccgc taaacagcgc   660
ctgaagtgtg ctagcctgca gaaattcggg gagcgagcct tcaaggcttg ggcagtggca   720
cggctgagtc agagattccc aaaggcagaa tttgccgagg tctcaaaact ggtgaccgac   780
ctgacaaagg tgcacaccga atgctgtcat ggcgacctgc tggagtgcgc cgacgatcga   840
gctgatctgg caaagtatat ttgtgagaac caggactcca tctctagtaa gctgaaagaa   900
tgctgtgaga aaccactgct ggaaaagtct cactgcattg ccgaagtgga aacgacgag    960
atgccagctg atctgccctc actggccgct gacttcgtcg aaagcaaaga tgtgtgtaag  1020
aattacgctg aggcaaagga tgtgttcctg ggaatgtttc tgtacgagta tgccaggcgc  1080
cacccagact actccgtggt cctgctgctg aggctggcta aacatatga accacactg    1140
gagaagtgct gtgcagccgc tgatccccat gaatgctatg ccaaagtctt cgacgagttt  1200
aagcccctgg tggaggaacc tcagaacctg atcaaacaga attgtgaact gtttgagcag  1260
ctgggcgagt acaagttcca gaacgccctg ctggtgcgct ataccaagaa agtcccacag  1320
gtgtccacac ccactctggt ggaggtgagc cggaatctgg gcaaagtggg gagtaaatgc  1380
tgtaagcacc ctgaagccaa gaggatgcca tgcgctgagg attacctgag tgtggtcctg  1440
aatcagctgt gtgtcctgca tgaaaaaaca cctgtcagcg accgggtgac aaagtgctgt  1500
actgagtcac tggtgaaccg acggccctgc tttagcgccc tggaagtcga tgagacttat  1560
gtgcctaaag agttcaacgc tgagaccttc acatttcacg cagacatttg taccctgagc  1620
gaaaaggaga gacagatcaa gaaacagaca gccctggtcg aactggtgaa gcataaaccc  1680
aaggccacaa aagagcagct gaaggctgtc atggacgatt tcgcagcctt tgtggaaaaa  1740
tgctgtaagg cagacgataa ggagacttgc tttgccgagg aaggaaagaa actggtggct  1800
gcatcccagg cagctctggg actggaggga ggatctgccc ctaccttcaag ctccactaag  1860
aaaacccagc tgcagctgga gcacctgctg ctggacctgc agatgattct gaacgggatc  1920
aacaattaca aaaatccaaa gctgacccgg atgctgacat tcaagtttta tatgcccaag  1980
aaagccacag agctgaaaca cctgcagtgc ctggaggaag agctgaagcc tctggaagag  2040
gtgctgaacc tggcccagag caagaatttc catctgagac caagggatct gatctccaac  2100
attaatgtga tcgtcctgga actgaaggga tctgagacta cctttatgtg cgaatacgct  2160
gacgagactg caaccattgt ggagttcctg aacagatgga tcaccttctg ccagtccatc  2220
atttctactc tgacaggcgg ggggagc                                        2247
```

<210> SEQ ID NO 39

```
<211> LENGTH: 28
<212> TYPE: PRT
<213> ORGANISM: Artificial Sequence
<220> FEATURE:
<223> OTHER INFORMATION: Synthetic:  EETI-II from Knottin Database

<400> SEQUENCE: 39

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly
            20                  25

<210> SEQ ID NO 40
<211> LENGTH: 47
<212> TYPE: PRT
<213> ORGANISM: Artificial Sequence
<220> FEATURE:
<223> OTHER INFORMATION: Synthetic:  AgRP from Knottin Database

<400> SEQUENCE: 40

Gly Cys Val Arg Leu His Glu Ser Cys Leu Gly Gln Gln Val Pro Cys
1               5                   10                  15

Cys Asp Pro Cys Ala Thr Cys Tyr Cys Arg Phe Phe Asn Ala Phe Cys
            20                  25                  30

Tyr Cys Arg Lys Leu Gly Thr Ala Met Asn Pro Cys Ser Arg Thr
        35                  40                  45

<210> SEQ ID NO 41
<211> LENGTH: 48
<212> TYPE: PRT
<213> ORGANISM: Artificial Sequence
<220> FEATURE:
<223> OTHER INFORMATION: Synthetic:  Omega agatoxin from Knottin
      Database

<400> SEQUENCE: 41

Glu Asp Asn Cys Ile Ala Glu Asp Tyr Gly Lys Cys Thr Trp Gly Gly
1               5                   10                  15

Thr Lys Cys Cys Arg Gly Arg Pro Cys Arg Cys Ser Met Ile Gly Thr
            20                  25                  30

Asn Cys Glu Cys Thr Pro Arg Leu Ile Met Glu Gly Leu Ser Phe Ala
        35                  40                  45

<210> SEQ ID NO 42
<211> LENGTH: 33
<212> TYPE: PRT
<213> ORGANISM: Artificial Sequence
<220> FEATURE:
<223> OTHER INFORMATION: Synthetic:  EETI-II Library
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: Xaa can be any naturally occurring amino acid

<400> SEQUENCE: 42

Gly Cys Xaa Xaa Xaa Arg Gly Asp Xaa Xaa Xaa Xaa Xaa Cys Lys Gln
1               5                   10                  15

Asp Ser Asp Cys Leu Ala Gly Cys Val Cys Gly Pro Asn Gly Phe Cys
            20                  25                  30

Gly
```

<210> SEQ ID NO 43
<211> LENGTH: 33
<212> TYPE: PRT
<213> ORGANISM: Artificial Sequence
<220> FEATURE:
<223> OTHER INFORMATION: Synthetic: EETI-II K15S Mutation Library
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: Xaa can be any naturally occurring amino acid

<400> SEQUENCE: 43

Gly Cys Xaa Xaa Xaa Arg Gly Asp Xaa Xaa Xaa Xaa Xaa Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 44
<211> LENGTH: 822
<212> TYPE: DNA
<213> ORGANISM: Artificial Sequence
<220> FEATURE:
<223> OTHER INFORMATION: Synthetic: 2.5F-(K15S) mIgG2aFc Nucleic Acid
      Sequence

<400> SEQUENCE: 44
ggttgtccaa gaccaagagg tgataatcca ccattgactt gttctcaaga ttctgattgt      60
ttggctggtt gtgtttgtgg tccaaatggt ttttgtggtg gtcgactaga gcccagagtg    120
cccataacac agaaccctg tcctccactc aaagagtgtc ccccatgcgc agctccagac     180
ctcttgggtg gaccatccgt cttcatcttc cctccaaaga tcaaggatgt actcatgatc    240
tccctgagcc ccatggtcac atgtgtggtg gtggatgtga gcgaggatga cccagacgtc    300
cagatcagct ggtttgtgaa caacgtggaa gtacacacag ctcagacaca aacccataga    360
gaggattaca acagtactct ccgggtggtc agtgcccctcc ccatccagca ccaggactgg    420
atgagtggca aggagttcaa atgcaaggtc aacaacagag ccctcccatc ccccatcgag    480
aaaaccatct caaacccag ggccagta agagctccac aggtatatgt cttgcctcca       540
ccagcagaag agatgactaa gaaagagttc agtctgacct gcatgatcac aggcttctta    600
cctgccgaaa ttgctgtgga ctggaccagc aatgggcgta cagagcaaaa ctacaagaac    660
accgcaacag tcctggactc tgatggttct tacttcatgt acagcaagct cagagtacaa    720
aagagcactt gggaaagagg aagtcttttc gcctgctcag tggtccacga gggtctgcac    780
aatcacctta cgactaagac catctcccgg tctctgggta aa                        822

<210> SEQ ID NO 45
<211> LENGTH: 271
<212> TYPE: PRT
<213> ORGANISM: Artificial Sequence
<220> FEATURE:
<223> OTHER INFORMATION: Synthetic: 2.5F-(K15S) mIgG2aFc Amino Acid
      Sequence

<400> SEQUENCE: 45

Gly Cys Pro Arg Pro Arg Gly Asp Asn Pro Pro Leu Thr Cys Ser Gln
1               5                   10                  15

```
Asp Ser Asp Cys Leu Ala Gly Cys Val Cys Gly Pro Asn Gly Phe Cys
         20                  25                  30

Gly Glu Pro Arg Val Pro Ile Thr Gln Asn Pro Cys Pro Pro Leu Lys
         35                  40                  45

Glu Cys Pro Pro Cys Ala Ala Pro Asp Leu Leu Gly Gly Pro Ser Val
 50                  55                  60

Phe Ile Phe Pro Pro Lys Ile Lys Asp Val Leu Met Ile Ser Leu Ser
 65                  70                  75                  80

Pro Met Val Thr Cys Val Val Val Asp Val Ser Glu Asp Asp Pro Asp
                 85                  90                  95

Val Gln Ile Ser Trp Phe Val Asn Asn Val Glu Val His Thr Ala Gln
             100                 105                 110

Thr Gln Thr His Arg Glu Asp Tyr Asn Ser Thr Leu Arg Val Val Ser
         115                 120                 125

Ala Leu Pro Ile Gln His Gln Asp Trp Met Ser Gly Lys Glu Phe Lys
 130                 135                 140

Cys Lys Val Asn Asn Arg Ala Leu Pro Ser Pro Ile Glu Lys Thr Ile
145                 150                 155                 160

Ser Lys Pro Arg Gly Pro Val Arg Ala Pro Gln Val Tyr Val Leu Pro
                 165                 170                 175

Pro Pro Ala Glu Glu Met Thr Lys Lys Glu Phe Ser Leu Thr Cys Met
             180                 185                 190

Ile Thr Gly Phe Leu Pro Ala Glu Ile Ala Val Asp Trp Thr Ser Asn
         195                 200                 205

Gly Arg Thr Glu Gln Asn Tyr Lys Asn Thr Ala Thr Val Leu Asp Ser
 210                 215                 220

Asp Gly Ser Tyr Phe Met Tyr Ser Lys Leu Arg Val Gln Lys Ser Thr
225                 230                 235                 240

Trp Glu Arg Gly Ser Leu Phe Ala Cys Ser Val Val His Glu Gly Leu
                 245                 250                 255

His Asn His Leu Thr Thr Lys Thr Ile Ser Arg Ser Leu Gly Lys
             260                 265                 270
```

<210> SEQ ID NO 46
<211> LENGTH: 822
<212> TYPE: DNA
<213> ORGANISM: Artificial Sequence
<220> FEATURE:
<223> OTHER INFORMATION: Synthetic: 2.5D- (K15S) mIgG2aFc Nucleic Acid
      Sequence

<400> SEQUENCE: 46

```
ggttgtccac aaggcagagg tgattgggct ccaacttctt gttctcaaga ttctgattgt     60
ttggctggtt gtgtttgtgg tccaaatggt ttttgtggtg gtcgactaga gcccagagtg    120
cccataacac agaaccctg tcctccactc aaagagtgtc ccccatgcgc agctccagac    180
ctcttgggtg gaccatccgt cttcatcttc cctccaaaga tcaaggatgt actcatgatc    240
tccctgagcc ccatggtcac atgtgtggtg gtggatgtga gcgaggatga cccagacgtc    300
cagatcagct ggtttgtgaa caacgtggaa gtacacacag ctcagacaca aacccataga    360
gaggattaca cagtactct ccgggtggtc agtgccctcc ccatccagca ccaggactgg    420
atgagtggca aggagttcaa atgcaaggtc aacaacagag ccctcccatc ccccatcgag    480
aaaaccatct caaacccag agggccagta agagctccac aggtatatgt cttgcctcca    540
ccagcagaag agatgactaa gaaagagttc agtctgacct gcatgatcac aggcttctta    600
```

```
cctgccgaaa ttgctgtgga ctggaccagc aatgggcgta cagagcaaaa ctacaagaac      660
accgcaacag tcctggactc tgatggttct tacttcatgt acagcaagct cagagtacaa      720
aagagcactt gggaaagagg aagtctttc gcctgctcag tggtccacga gggtctgcac      780 aatcaccta cgactaagac catctcccgg tctctgggta aa                          822
```

<210> SEQ ID NO 47
<211> LENGTH: 271
<212> TYPE: PRT
<213> ORGANISM: Artificial Sequence
<220> FEATURE:
<223> OTHER INFORMATION: Synthetic: 2.5D- (K15S) mIgG2aFc Amino Acid Sequence

<400> SEQUENCE: 47

```
Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
            20                  25                  30

Gly Glu Pro Arg Val Pro Ile Thr Gln Asn Pro Cys Pro Pro Leu Lys
        35                  40                  45

Glu Cys Pro Pro Cys Ala Ala Pro Asp Leu Leu Gly Gly Pro Ser Val
    50                  55                  60

Phe Ile Phe Pro Pro Lys Ile Lys Asp Val Leu Met Ile Ser Leu Ser
65                  70                  75                  80

Pro Met Val Thr Cys Val Val Asp Val Ser Glu Asp Asp Pro Asp
                85                  90                  95

Val Gln Ile Ser Trp Phe Val Asn Val Glu Val His Thr Ala Gln
            100                 105                 110

Thr Gln Thr His Arg Glu Asp Tyr Asn Ser Thr Leu Arg Val Val Ser
        115                 120                 125

Ala Leu Pro Ile Gln His Gln Asp Trp Met Ser Gly Lys Glu Phe Lys
    130                 135                 140

Cys Lys Val Asn Asn Arg Ala Leu Pro Ser Pro Ile Glu Lys Thr Ile
145                 150                 155                 160

Ser Lys Pro Arg Gly Pro Val Arg Ala Pro Gln Val Tyr Val Leu Pro
                165                 170                 175

Pro Pro Ala Glu Glu Met Thr Lys Lys Glu Phe Ser Leu Thr Cys Met
            180                 185                 190

Ile Thr Gly Phe Leu Pro Ala Glu Ile Ala Val Asp Trp Thr Ser Asn
        195                 200                 205

Gly Arg Thr Glu Gln Asn Tyr Lys Asn Thr Ala Thr Val Leu Asp Ser
    210                 215                 220

Asp Gly Ser Tyr Phe Met Tyr Ser Lys Leu Arg Val Gln Lys Ser Thr
225                 230                 235                 240

Trp Glu Arg Gly Ser Leu Phe Ala Cys Ser Val Val His Glu Gly Leu
                245                 250                 255

His Asn His Leu Thr Thr Lys Thr Ile Ser Arg Ser Leu Gly Lys
            260                 265                 270
```

<210> SEQ ID NO 48
<211> LENGTH: 265
<212> TYPE: PRT
<213> ORGANISM: Artificial Sequence
<220> FEATURE:
<223> OTHER INFORMATION: Synthetic: 2.5F- (K15S) hIgG1Fc Amino Acid Sequence

<400> SEQUENCE: 48

```
Gly Cys Pro Arg Pro Arg Gly Asp Asn Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Glu Pro Lys Ser Cys Asp Lys Thr His Thr Cys Pro Pro Cys Pro
        35                  40                  45

Ala Pro Glu Leu Leu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Glu Glu Met
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys
            260                 265
```

<210> SEQ ID NO 49
<211> LENGTH: 260
<212> TYPE: PRT
<213> ORGANISM: Artificial Sequence
<220> FEATURE:
<223> OTHER INFORMATION: Synthetic: 2.5F- (K15S) hIgG1Fc Fc Upper Hinge Deletion (DEPKSC) Amino Acid Sequence

<400> SEQUENCE: 49

```
Gly Cys Pro Arg Pro Arg Gly Asp Asn Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Asp Lys Thr His Thr Cys Pro Pro Cys Pro Ala Pro Glu Leu Leu
        35                  40                  45

Gly Gly Pro Ser Val Phe Leu Phe Pro Pro Lys Pro Lys Asp Thr Leu
    50                  55                  60

Met Ile Ser Arg Thr Pro Glu Val Thr Cys Val Val Val Asp Val Ser
65                  70                  75                  80
```

His Glu Asp Pro Glu Val Lys Phe Asn Trp Tyr Val Asp Gly Val Glu
                85                  90                  95

Val His Asn Ala Lys Thr Lys Pro Arg Glu Glu Gln Tyr Asn Ser Thr
        100                 105                 110

Tyr Arg Val Val Ser Val Leu Thr Val Leu His Gln Asp Trp Leu Asn
    115                 120                 125

Gly Lys Glu Tyr Lys Cys Lys Val Ser Asn Lys Ala Leu Pro Ala Pro
130                 135                 140

Ile Glu Lys Thr Ile Ser Lys Ala Lys Gly Gln Pro Arg Glu Pro Gln
145                 150                 155                 160

Val Tyr Thr Leu Pro Pro Ser Arg Glu Glu Met Thr Lys Asn Gln Val
                165                 170                 175

Ser Leu Thr Cys Leu Val Lys Gly Phe Tyr Pro Ser Asp Ile Ala Val
            180                 185                 190

Glu Trp Glu Ser Asn Gly Gln Pro Glu Asn Asn Tyr Lys Thr Thr Pro
        195                 200                 205

Pro Val Leu Asp Ser Asp Gly Ser Phe Phe Leu Tyr Ser Lys Leu Thr
    210                 215                 220

Val Asp Lys Ser Arg Trp Gln Gln Gly Asn Val Phe Ser Cys Ser Val
225                 230                 235                 240

Met His Glu Ala Leu His Asn His Tyr Thr Gln Lys Ser Leu Ser Leu
                245                 250                 255

Ser Pro Gly Lys
            260

<210> SEQ ID NO 50
<211> LENGTH: 265
<212> TYPE: PRT
<213> ORGANISM: Artificial Sequence
<220> FEATURE:
<223> OTHER INFORMATION: Synthetic: 2.5D- (K15S) hIgG1Fc Amino Acid
      Sequence

<400> SEQUENCE: 50

Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
            20                  25                  30

Gly Glu Pro Lys Ser Cys Asp Lys Thr His Thr Cys Pro Pro Cys Pro
        35                  40                  45

Ala Pro Glu Leu Leu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Glu Glu Met
                165                 170                 175

```
Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
            195                 200                 205

Tyr Lys Thr Thr Pro Pro Val Leu Asp Ser Asp Gly Ser Phe Phe Leu
            210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys
            260                 265

<210> SEQ ID NO 51
<211> LENGTH: 260
<212> TYPE: PRT
<213> ORGANISM: Artificial Sequence
<220> FEATURE:
<223> OTHER INFORMATION: Synthetic: 2.5D- (K15S) hIgG1Fc Fc Upper
      Hinge Deletion (DEPKSC) Amino Acid Sequence

<400> SEQUENCE: 51

Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
                20                  25                  30

Gly Asp Lys Thr His Thr Cys Pro Pro Cys Pro Ala Pro Glu Leu Leu
            35                  40                  45

Gly Gly Pro Ser Val Phe Leu Phe Pro Pro Lys Pro Lys Asp Thr Leu
        50                  55                  60

Met Ile Ser Arg Thr Pro Glu Val Thr Cys Val Val Asp Val Ser
65                  70                  75                  80

His Glu Asp Pro Glu Val Lys Phe Asn Trp Tyr Val Asp Gly Val Glu
                85                  90                  95

Val His Asn Ala Lys Thr Lys Pro Arg Glu Glu Gln Tyr Asn Ser Thr
            100                 105                 110

Tyr Arg Val Val Ser Val Leu Thr Val Leu His Gln Asp Trp Leu Asn
        115                 120                 125

Gly Lys Glu Tyr Lys Cys Lys Val Ser Asn Lys Ala Leu Pro Ala Pro
    130                 135                 140

Ile Glu Lys Thr Ile Ser Lys Ala Lys Gly Gln Pro Arg Glu Pro Gln
145                 150                 155                 160

Val Tyr Thr Leu Pro Pro Ser Arg Glu Glu Met Thr Lys Asn Gln Val
                165                 170                 175

Ser Leu Thr Cys Leu Val Lys Gly Phe Tyr Pro Ser Asp Ile Ala Val
            180                 185                 190

Glu Trp Glu Ser Asn Gly Gln Pro Glu Asn Asn Tyr Lys Thr Thr Pro
        195                 200                 205

Pro Val Leu Asp Ser Asp Gly Ser Phe Phe Leu Tyr Ser Lys Leu Thr
    210                 215                 220

Val Asp Lys Ser Arg Trp Gln Gln Gly Asn Val Phe Ser Cys Ser Val
225                 230                 235                 240

Met His Glu Ala Leu His Asn His Tyr Thr Gln Lys Ser Leu Ser Leu
                245                 250                 255

Ser Pro Gly Lys
```

<210> SEQ ID NO 52
<211> LENGTH: 287
<212> TYPE: PRT
<213> ORGANISM: Homo sapiens
<220> FEATURE:
<221> NAME/KEY: misc_feature
<222> LOCATION: (1)..(287)
<223> OTHER INFORMATION: hPD-1 amino acid sequence

<400> SEQUENCE: 52

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Pro Trp Asn
            20                  25                  30

Pro Pro Thr Phe Phe Pro Ala Leu Leu Val Val Thr Glu Gly Asp Asn
        35                  40                  45

Ala Thr Phe Thr Cys Ser Phe Ser Asn Thr Ser Glu Ser Phe Val Leu
    50                  55                  60

Asn Trp Tyr Arg Met Ser Pro Ser Asn Gln Thr Asp Lys Leu Ala Ala
65                  70                  75                  80

Phe Pro Glu Asp Arg Ser Gln Pro Gly Gln Asp Cys Arg Phe Arg Val
                85                  90                  95

Thr Gln Leu Pro Asn Gly Arg Asp Phe His Met Ser Val Val Arg Ala
            100                 105                 110

Arg Arg Asn Asp Ser Gly Thr Tyr Leu Cys Gly Ala Ile Ser Leu Ala
        115                 120                 125

Pro Lys Ala Gln Ile Lys Glu Ser Leu Arg Ala Glu Leu Arg Val Thr
    130                 135                 140

Glu Arg Arg Ala Glu Val Pro Thr Ala His Pro Ser Pro Ser Pro Arg
145                 150                 155                 160

Pro Ala Gly Gln Phe Gln Thr Leu Val Val Gly Val Val Gly Gly Leu
                165                 170                 175

Leu Gly Ser Leu Val Leu Leu Val Trp Val Leu Ala Val Ile Cys Ser
            180                 185                 190

Arg Ala Ala Arg Gly Thr Ile Gly Ala Arg Arg Thr Gly Gln Pro Leu
        195                 200                 205

Lys Glu Asp Pro Ser Ala Val Pro Val Phe Ser Val Asp Tyr Gly Glu
    210                 215                 220

Leu Asp Phe Gln Trp Arg Glu Lys Thr Pro Glu Pro Pro Val Pro Cys
225                 230                 235                 240

Val Pro Glu Gln Thr Glu Tyr Ala Thr Ile Val Phe Pro Ser Gly Met
                245                 250                 255

Gly Thr Ser Ser Pro Ala Arg Arg Gly Ser Ala Asp Gly Pro Arg Ser
            260                 265                 270

Ala Gln Pro Leu Arg Pro Glu Asp Gly His Cys Ser Trp Pro Leu
        275                 280                 285

<210> SEQ ID NO 53
<211> LENGTH: 290
<212> TYPE: PRT
<213> ORGANISM: Homo sapiens
<220> FEATURE:
<221> NAME/KEY: misc_feature
<222> LOCATION: (1)..(290)
<223> OTHER INFORMATION: hPD-L-1 amino acid sequence

<400> SEQUENCE: 53

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
290

<210> SEQ ID NO 54
<211> LENGTH: 223
<212> TYPE: PRT
<213> ORGANISM: Homo sapiens
<220> FEATURE:
<221> NAME/KEY: misc_feature
<222> LOCATION: (1)..(223)
<223> OTHER INFORMATION: hCTLA-4 amino acid sequence

<400> SEQUENCE: 54

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
            35                  40                  45
```

```
Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
210                 215                 220

<210> SEQ ID NO 55
<211> LENGTH: 525
<212> TYPE: PRT
<213> ORGANISM: Homo sapiens
<220> FEATURE:
<221> NAME/KEY: misc_feature
<222> LOCATION: (1)..(525)
<223> OTHER INFORMATION: hLAG3 amino acid sequence

<400> SEQUENCE: 55

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
```

```
                     180                 185                 190
Arg Pro Asp Arg Pro Ala Ser Val His Trp Phe Arg Asn Arg Gly Gln
            195                 200                 205
Gly Arg Val Pro Val Arg Glu Ser Pro His His Leu Ala Glu Ser
        210                 215                 220
Phe Leu Phe Leu Pro Gln Val Ser Pro Met Asp Ser Gly Pro Trp Gly
225                 230                 235                 240
Cys Ile Leu Thr Tyr Arg Asp Gly Phe Asn Val Ser Ile Met Tyr Asn
                245                 250                 255
Leu Thr Val Leu Gly Leu Glu Pro Pro Thr Pro Leu Thr Val Tyr Ala
            260                 265                 270
Gly Ala Gly Ser Arg Val Gly Leu Pro Cys Arg Leu Pro Ala Gly Val
        275                 280                 285
Gly Thr Arg Ser Phe Leu Thr Ala Lys Trp Thr Pro Pro Gly Gly Gly
        290                 295                 300
Pro Asp Leu Leu Val Thr Gly Asp Asn Gly Asp Phe Thr Leu Arg Leu
305                 310                 315                 320
Glu Asp Val Ser Gln Ala Gln Ala Gly Thr Tyr Thr Cys His Ile His
                325                 330                 335
Leu Gln Glu Gln Gln Leu Asn Ala Thr Val Thr Leu Ala Ile Ile Thr
                340                 345                 350
Val Thr Pro Lys Ser Phe Gly Ser Pro Gly Ser Leu Gly Lys Leu Leu
            355                 360                 365
Cys Glu Val Thr Pro Val Ser Gly Gln Glu Arg Phe Val Trp Ser Ser
        370                 375                 380
Leu Asp Thr Pro Ser Gln Arg Ser Phe Ser Gly Pro Trp Leu Glu Ala
385                 390                 395                 400
Gln Glu Ala Gln Leu Leu Ser Gln Pro Trp Gln Cys Gln Leu Tyr Gln
                405                 410                 415
Gly Glu Arg Leu Leu Gly Ala Ala Val Tyr Phe Thr Glu Leu Ser Ser
            420                 425                 430
Pro Gly Ala Gln Arg Ser Gly Arg Ala Pro Gly Ala Leu Pro Ala Gly
        435                 440                 445
His Leu Leu Leu Phe Leu Ile Leu Gly Val Leu Ser Leu Leu Leu Leu
        450                 455                 460
Val Thr Gly Ala Phe Gly Phe His Leu Trp Arg Arg Gln Trp Arg Pro
465                 470                 475                 480
Arg Arg Phe Ser Ala Leu Glu Gln Gly Ile His Pro Pro Gln Ala Gln
                485                 490                 495
Ser Lys Ile Glu Glu Leu Glu Gln Glu Pro Glu Pro Glu Pro Glu Pro
            500                 505                 510
Glu Pro Glu Pro Glu Pro Glu Pro Glu Gln Leu
        515                 520                 525

<210> SEQ ID NO 56
<211> LENGTH: 300
<212> TYPE: PRT
<213> ORGANISM: Homo sapiens
<220> FEATURE:
<221> NAME/KEY: misc_feature
<222> LOCATION: (1)..(300)
<223> OTHER INFORMATION: hTIM3 amino acid sequence

<400> SEQUENCE: 56

Met Phe Ser His Leu Pro Phe Asp Cys Val Leu Leu Leu Leu Leu Leu
1               5                   10                  15
```

-continued

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
 50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Gly Ile Tyr Ile Gly Ala Gly Ile
            195                 200                 205

Cys Ala Gly Leu Ala Leu Ala Leu Ile Phe Gly Ala Leu Ile Phe Lys
210                 215                 220

Trp Tyr Ser His Ser Lys Glu Lys Ile Gln Asn Leu Ser Leu Ile Ser
225                 230                 235                 240

Leu Ala Asn Leu Pro Pro Ser Gly Leu Ala Asn Ala Val Ala Glu Gly
                245                 250                 255

Ile Arg Ser Glu Glu Asn Ile Tyr Thr Ile Glu Glu Asn Val Tyr Glu
            260                 265                 270

Val Glu Glu Pro Asn Glu Tyr Tyr Cys Tyr Val Ser Ser Arg Gln Gln
            275                 280                 285

Pro Ser Gln Pro Leu Gly Cys Arg Phe Ala Met Pro
290                 295                 300

<210> SEQ ID NO 57
<211> LENGTH: 532
<212> TYPE: PRT
<213> ORGANISM: Homo sapiens
<220> FEATURE:
<221> NAME/KEY: misc_feature
<222> LOCATION: (1)..(532)
<223> OTHER INFORMATION: hB7-H3 amino acid sequence

<400> SEQUENCE: 57

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Gln Leu Asn Leu
 50                  55                  60

```
Ile Trp Gln Leu Thr Asp Thr Lys Gln Leu Val His Ser Phe Ala Glu
 65                  70                  75                  80

Gly Gln Asp Gln Gly Ser Ala Tyr Ala Asn Arg Thr Ala Leu Phe Pro
                 85                  90                  95

Asp Leu Leu Ala Gln Gly Asn Ala Ser Leu Arg Leu Gln Arg Val Arg
            100                 105                 110

Val Ala Asp Glu Gly Ser Phe Cys Phe Val Ser Ile Arg Asp Phe Gly
        115                 120                 125

Ser Ala Ala Val Ser Leu Gln Val Ala Ala Pro Tyr Ser Lys Pro Ser
    130                 135                 140

Met Thr Leu Glu Pro Asn Lys Asp Leu Arg Pro Gly Asp Thr Val Thr
145                 150                 155                 160

Ile Thr Cys Ser Ser Tyr Gln Gly Tyr Pro Glu Ala Glu Val Phe Trp
                165                 170                 175

Gln Asp Gly Gln Gly Val Pro Leu Thr Gly Asn Val Thr Thr Ser Gln
            180                 185                 190

Met Ala Asn Glu Gln Gly Leu Phe Asp Val His Ser Ile Leu Arg Val
        195                 200                 205

Val Leu Gly Ala Asn Gly Thr Tyr Ser Cys Leu Val Arg Asn Pro Val
    210                 215                 220

Leu Gln Gln Asp Ala His Ser Ser Val Thr Ile Thr Pro Gln Arg Ser
225                 230                 235                 240

Pro Thr Gly Ala Val Glu Val Gln Val Pro Glu Asp Pro Val Val Ala
                245                 250                 255

Leu Val Gly Thr Asp Ala Thr Leu Arg Cys Ser Phe Ser Pro Glu Pro
            260                 265                 270

Gly Phe Ser Leu Ala Gln Leu Asn Leu Ile Trp Gln Leu Thr Asp Thr
        275                 280                 285

Lys Gln Leu Val His Ser Phe Thr Glu Gly Arg Asp Gln Gly Ser Ala
    290                 295                 300

Tyr Ala Asn Arg Thr Ala Leu Phe Pro Asp Leu Ala Gln Gly Asn
305                 310                 315                 320

Ala Ser Leu Arg Leu Gln Arg Val Arg Val Ala Asp Glu Gly Ser Phe
                325                 330                 335

Thr Cys Phe Val Ser Ile Arg Asp Phe Gly Ser Ala Ala Val Ser Leu
            340                 345                 350

Gln Val Ala Ala Pro Tyr Ser Lys Pro Ser Met Thr Leu Glu Pro Asn
        355                 360                 365

Lys Asp Leu Arg Pro Gly Asp Thr Val Thr Ile Thr Cys Ser Ser Tyr
    370                 375                 380

Arg Gly Tyr Pro Glu Ala Glu Val Phe Trp Gln Asp Gly Gln Gly Val
385                 390                 395                 400

Pro Leu Thr Gly Asn Val Thr Thr Ser Gln Met Ala Asn Glu Gln Gly
                405                 410                 415

Leu Phe Asp Val His Ser Val Leu Arg Val Val Leu Gly Ala Asn Gly
            420                 425                 430

Thr Tyr Ser Cys Leu Val Arg Asn Pro Val Leu Gln Gln Asp Ala His
        435                 440                 445

Gly Ser Val Thr Ile Thr Gly Gln Pro Met Thr Phe Pro Pro Glu Ala
    450                 455                 460

Leu Trp Val Thr Val Gly Leu Ser Val Cys Leu Ile Ala Leu Leu Val
465                 470                 475                 480

Ala Leu Ala Phe Val Cys Trp Arg Lys Ile Lys Gln Ser Cys Glu Glu
```

```
                485                 490                 495
Glu Asn Ala Gly Ala Glu Asp Gln Asp Gly Glu Gly Glu Gly Ser Lys
            500                 505                 510

Thr Ala Leu Gln Pro Leu Lys His Ser Asp Ser Lys Glu Asp Asp Gly
        515                 520                 525

Gln Glu Ile Ala
    530

<210> SEQ ID NO 58
<211> LENGTH: 166
<212> TYPE: PRT
<213> ORGANISM: Homo sapiens
<220> FEATURE:
<221> NAME/KEY: misc_feature
<222> LOCATION: (1)..(166)
<223> OTHER INFORMATION: hB7-H4 amino acid sequence

<400> SEQUENCE: 58

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Ala Phe Ser Met Pro Glu Val Asn Val Asp Tyr Asn Ala Ser Ser Glu
        35                  40                  45

Thr Leu Arg Cys Glu Ala Pro Arg Trp Phe Pro Gln Pro Thr Val Val
    50                  55                  60

Trp Ala Ser Gln Val Asp Gln Gly Ala Asn Phe Ser Glu Val Ser Asn
65                  70                  75                  80

Thr Ser Phe Glu Leu Asn Ser Glu Asn Val Thr Met Lys Val Val Ser
                85                  90                  95

Val Leu Tyr Asn Val Thr Ile Asn Asn Thr Tyr Ser Cys Met Ile Glu
            100                 105                 110

Asn Asp Ile Ala Lys Ala Thr Gly Asp Ile Lys Val Thr Glu Ser Glu
        115                 120                 125

Ile Lys Arg Arg Ser His Leu Gln Leu Leu Asn Ser Lys Ala Ser Leu
    130                 135                 140

Cys Val Ser Ser Phe Phe Ala Ile Ser Trp Ala Leu Leu Pro Leu Ser
145                 150                 155                 160

Pro Tyr Leu Met Leu Lys
                165

<210> SEQ ID NO 59
<211> LENGTH: 1425
<212> TYPE: DNA
<213> ORGANISM: Artificial Sequence
<220> FEATURE:
<223> OTHER INFORMATION: Synthetic: Anti-VEGF clone B20-4.1.1 Heavy
      Chain nucleic acid sequence

<400> SEQUENCE: 59
atgggctggt ccctgatcct gctgttcctg gtggctgtgg ccactggcgt gcactctgaa      60
gtgcagctgg tggaatctgg cggcggactg gtgcagcctg gcggatctct gagactgagc     120
tgtgccgcca gcggcttcag catcagcggc agctggatct ctgggtgcg ccaggccct      180 ggaaagggcc tggaatgggt gggagccatc tggcctttg gcggctacac ccactacgcc     240
gacagcgtga aggccggtt taccatcagc gccgacacca gcaagaacac cgcctacctc     300
cagatgaaca gcctgcgggc cgaggacacc gccgtgtact attgtgccag atgggggccac     360
```

```
agcacctccc cctgggccat ggattattgg ggccaggaa ccctcgtgac cgtgtcctct    420
gccaaaacaa cagccccatc ggtctatcca ctggccctg tgtgtggagg tacaactggc    480
tcctcggtga ctctaggatg cctggtcaag ggttatttcc ctgagccagt gaccttgacc    540
tggaactctg gctcactgtc cagtggtgtg cacaccttcc cagctctcct ccaatctggc    600
ctctacaccc tcagcagctc agtgactgta acctcgaaca cctggcccag ccagaccatc    660
acctgcaatg tggcccaccc ggcaagcagc accaaagtgg acaagaaaat tgagcccaga    720
gtgcccataa cacagaaccc ctgtcctcca ctcaaagagt gtccccatg cgcagctcca    780
gacctcttgg gtggaccatc cgtcttcatc ttccctccaa agatcaagga tgtactcatg    840
atctccctga gccccatggt cacatgtgtg gtggtggatg tgagcgagga tgacccagac    900
gtccagatca gctggtttgt gaacaacgtg gaagtacaca cagctcagac acaaacccat    960
agagaggatt acaacagtac tctccgggtg gtcagtgccc tccccatcca gcaccaggac   1020
tggatgagtg gcaaggagtt caaatgcaag gtcaacaaca gagccctccc atccccatc    1080
gagaaaacca tctcaaaacc cagagggcca gtaagagctc acaggtata tgtcttgcct    1140
ccaccagcag aagagatgac taagaaaga ttcagtctga cctgcatgat cacaggcttc   1200
ttacctgccg aaattgctgt ggactggacc agcaatgggc gtacagagca aaactacaag   1260
aacaccgcaa cagtcctgga ctctgatggt tcttacttca tgtacagcaa gctcagagta   1320
caaaagagca cttgggaaag aggaagtctt ttcgcctgct cagtggtcca cgagggtctg   1380
cacaatcacc ttacgactaa gaccatctcc cggtctctgg gtaaa               1425
```

<210> SEQ ID NO 60
<211> LENGTH: 475
<212> TYPE: PRT
<213> ORGANISM: Artificial Sequence
<220> FEATURE:
<223> OTHER INFORMATION: Synthetic: Anti-VEGF clone B20-4.1.1 Heavy
      Chain amino acid sequence

<400> SEQUENCE: 60

```
Met Gly Trp Ser Leu Ile Leu Leu Phe Leu Val Ala Val Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Ile
        35                  40                  45

Ser Gly Ser Trp Ile Phe Trp Val Arg Gln Ala Pro Gly Lys Gly Leu
    50                  55                  60

Glu Trp Val Gly Ala Ile Trp Pro Phe Gly Gly Tyr Thr His Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ala Arg Trp Gly His Ser Thr Ser Pro Trp Ala Met Asp
        115                 120                 125

Tyr Trp Gly Gln Gly Thr Leu Val Thr Val Ser Ala Lys Thr Thr
    130                 135                 140

Ala Pro Ser Val Tyr Pro Leu Ala Pro Val Cys Gly Gly Thr Gly
145                 150                 155                 160

Ser Ser Val Thr Leu Gly Cys Leu Val Lys Gly Tyr Phe Pro Glu Pro
                165                 170                 175
```

```
Val Thr Leu Thr Trp Asn Ser Gly Ser Leu Ser Ser Gly Val His Thr
            180                 185                 190

Phe Pro Ala Leu Leu Gln Ser Gly Leu Tyr Thr Leu Ser Ser Ser Val
        195                 200                 205

Thr Val Thr Ser Asn Thr Trp Pro Ser Gln Thr Ile Thr Cys Asn Val
    210                 215                 220

Ala His Pro Ala Ser Ser Thr Lys Val Asp Lys Lys Ile Glu Pro Arg
225                 230                 235                 240

Val Pro Ile Thr Gln Asn Pro Cys Pro Pro Leu Lys Glu Cys Pro Pro
            245                 250                 255

Cys Ala Ala Pro Asp Leu Leu Gly Gly Pro Ser Val Phe Ile Phe Pro
        260                 265                 270

Pro Lys Ile Lys Asp Val Leu Met Ile Ser Leu Ser Pro Met Val Thr
    275                 280                 285

Cys Val Val Val Asp Val Ser Glu Asp Asp Pro Asp Val Gln Ile Ser
290                 295                 300

Trp Phe Val Asn Asn Val Glu Val His Thr Ala Gln Thr Gln Thr His
305                 310                 315                 320

Arg Glu Asp Tyr Asn Ser Thr Leu Arg Val Val Ser Ala Leu Pro Ile
            325                 330                 335

Gln His Gln Asp Trp Met Ser Gly Lys Glu Phe Lys Cys Lys Val Asn
        340                 345                 350

Asn Arg Ala Leu Pro Ser Pro Ile Glu Lys Thr Ile Ser Lys Pro Arg
    355                 360                 365

Gly Pro Val Arg Ala Pro Gln Val Tyr Val Leu Pro Pro Pro Ala Glu
370                 375                 380

Glu Met Thr Lys Lys Glu Phe Ser Leu Thr Cys Met Ile Thr Gly Phe
385                 390                 395                 400

Leu Pro Ala Glu Ile Ala Val Asp Trp Thr Ser Asn Gly Arg Thr Glu
            405                 410                 415

Gln Asn Tyr Lys Asn Thr Ala Thr Val Leu Asp Ser Asp Gly Ser Tyr
        420                 425                 430

Phe Met Tyr Ser Lys Leu Arg Val Gln Lys Ser Thr Trp Glu Arg Gly
    435                 440                 445

Ser Leu Phe Ala Cys Ser Val Val His Glu Gly Leu His Asn His Leu
450                 455                 460

Thr Thr Lys Thr Ile Ser Arg Ser Leu Gly Lys
465                 470                 475

<210> SEQ ID NO 61
<211> LENGTH: 708
<212> TYPE: DNA
<213> ORGANISM: Artificial Sequence
<220> FEATURE:
<223> OTHER INFORMATION: Synthetic: Anti-VEGF clone B20-4.1.1 Light
      Chain nucleic acid sequence

<400> SEQUENCE: 61
atggacatga gagtgcccgc ccagctgctg ggacttctgc tgctgtggct gccaggcgcc      60
agatgcgaca tccagatgac ccagagcccc agcagcctgt ctgccagcgt gggcgacaga     120
gtgaccatca cctgtagagc tctctcaggg gtgcggacaa gcctggcctg gtatcagcag     180
aagcctggca aggccccaa gctgctgatc tacgatgcca gctctctggc cagcggcgtg     240
cccagcagat tttctggcag cggctccggc accgacttca ccctgacaat cagctccctc     300
```

```
cagcccgagg acttcgccac ctactactgc cagcagagct acaagagccc cctgaccttt      360
ggccagggca ccaaggtgga aatcaagcgg gctgatgctg caccaactgt atccatcttc      420
ccaccatcca gtgagcagtt aacatctgga ggtgcctcag tcgtgtgctt cttgaacaac      480
ttctacccca agacatcaa tgtcaagtgg aagattgatg gcagtgaacg acaaaatggc       540
gtcctgaaca gttggactga tcaggacagc aaagacagca cctacagcat gagcagcacc      600
ctcacgttga ccaaggacga gtatgaacga cataacagct atacctgtga ggccactcac      660
aagacatcaa cttcacccat tgtcaagagc ttcaacagga atgagtgt                   708
```

<210> SEQ ID NO 62
<211> LENGTH: 236
<212> TYPE: PRT
<213> ORGANISM: Artificial Sequence
<220> FEATURE:
<223> OTHER INFORMATION: Synthetic: Anti-VEGF clone B20-4.1.1 Light
      Chain amino acid sequence

<400> SEQUENCE: 62

```
Met Asp Met Arg Val Pro Ala Gln Leu Leu Gly Leu Leu Leu Leu Trp
1               5                   10                  15

Leu Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Val Arg Thr Ser Leu Ala Trp Tyr Gln Gln Lys Pro Gly Lys
    50                  55                  60

Ala Pro Lys Leu Leu Ile Tyr Asp Ala Ser Ser Leu Ala Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ser Tyr Lys Ser Pro Leu Thr Phe Gly Gln Gly Thr Lys Val Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235
```

<210> SEQ ID NO 63
<211> LENGTH: 1413
<212> TYPE: DNA
<213> ORGANISM: Artificial Sequence
<220> FEATURE:
<223> OTHER INFORMATION: Synthetic: Anti-CTLA-4 clone 9D9 Heavy Chain
      nucleic acid sequence -continued

```
<400> SEQUENCE: 63
atgggctggt cccctgatcct gctgttcctg gtggctgtgg ccaccggcgt gcactctgaa      60
gccaagctcc aggaatccgg ccctgtgctc gtgaagcctg gcgcctctgt gaagatgagc     120
tgcaaggcca gcggctacac ctttaccgac tactacatga actgggtcaa gcagagccac     180
ggcaagtctc tggaatggat cggcgtgatc aaccccctaca acggcgacac cagctacaac     240
cagaagttca gggcaaggc caccctgacc gtggacaaga gcagcagcac cgcctacatg       300
gaactgaaca gcctgaccag cgaggacagc gccgtgtact attgcgcccg gtactacggc     360
agttggttcg cctattgggg ccagggcacc ctgatcaccg tgtccacagc caaaacaaca     420
gccccatcgg tctatccact ggcccctgtg tgtggaggta caactggctc ctcggtgact     480
ctaggatgcc tggtcaaggg ttatttccct gagccagtga ccttgacctg gaactctggc     540
tcactgtcca gtggtgtgca caccttccca gctctcctcc aatctggcct ctacaccctc     600
agcagctcag tgactgtaac ctcgaacacc tggcccagcc agaccatcac ctgcaatgtg     660
gcccacccgg caagcagcac caaagtggac aagaaaattg agcccagagt gcccataaca     720
cagaacccct gtcctccact caaagagtgt ccccatgcg cagctccaga cctcttgggt      780
ggaccatccg tcttcatctt ccctccaaag atcaaggatg tactcatgat ctccctgagc     840
cccatggtca catgtgtggt ggtggatgtg agcgaggatg acccagacgt ccagatcagc     900
tggtttgtga caacgtgga agtacacaca gctcagacac aaacccatag agaggattac      960
aacagtactc tccgggtggt cagtgccctc cccatccagc accaggactg gatgagtggc    1020
aaggagttca atgcaaggt caacaacaga gccctcccat cccccatcga aaaaccatc      1080 tcaaaaccca gagggccagt aagagctcca caggtatatg tcttgcctcc accagcagaa    1140
gagatgacta agaaagagtt cagtctgacc tgcatgatca caggcttctt acctgccgaa    1200
attgctgtgg actggaccag caatgggcgt acagagcaaa actacaagaa caccgcaaca    1260
gtcctggact ctgatggttc ttacttcatg tacagcaagc tcagagtaca aaagagcact    1320
tgggaaagag gaagtctttt cgcctgctca gtggtccacg agggtctgca caatcacctt    1380
acgactaaga ccatctcccg gtctctgggt aaa                                    1413
```

<210> SEQ ID NO 64
<211> LENGTH: 471
<212> TYPE: PRT
<213> ORGANISM: Artificial Sequence
<220> FEATURE:
<223> OTHER INFORMATION: Synthetic: Anti-CTLA-4 clone 9D9 Heavy Chain amino acid sequence

<400> SEQUENCE: 64

```
Met Gly Trp Ser Leu Ile Leu Leu Phe Leu Val Ala Val Ala Thr Gly
1               5                   10                  15

Val His Ser Glu Ala Lys Leu Gln Glu Ser Gly Pro Val Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Asn Trp Val Lys Gln Ser His Gly Lys Ser Leu
    50                  55                  60

Glu Trp Ile Gly Val Ile Asn Pro Tyr Asn Gly Asp Thr Ser Tyr Asn
65                  70                  75                  80

Gln Lys Phe Lys Gly Lys Ala Thr Leu Thr Val Asp Lys Ser Ser Ser
                85                  90                  95
```

Thr Ala Tyr Met Glu Leu Asn Ser Leu Thr Ser Glu Asp Ser Ala Val
            100                 105                 110

Tyr Tyr Cys Ala Arg Tyr Tyr Gly Ser Trp Phe Ala Tyr Trp Gly Gln
            115                 120                 125

Gly Thr Leu Ile Thr Val Ser Thr Ala Lys Thr Thr Ala Pro Ser Val
130                 135                 140

Tyr Pro Leu Ala Pro Val Cys Gly Gly Thr Thr Gly Ser Ser Val Thr
145                 150                 155                 160

Leu Gly Cys Leu Val Lys Gly Tyr Phe Pro Glu Pro Val Thr Leu Thr
                165                 170                 175

Trp Asn Ser Gly Ser Leu Ser Ser Gly Val His Thr Phe Pro Ala Leu
            180                 185                 190

Leu Gln Ser Gly Leu Tyr Thr Leu Ser Ser Val Thr Val Thr Ser
            195                 200                 205

Asn Thr Trp Pro Ser Gln Thr Ile Thr Cys Asn Val Ala His Pro Ala
            210                 215                 220

Ser Ser Thr Lys Val Asp Lys Lys Ile Glu Pro Arg Val Pro Ile Thr
225                 230                 235                 240

Gln Asn Pro Cys Pro Pro Leu Lys Glu Cys Pro Pro Cys Ala Ala Pro
                245                 250                 255

Asp Leu Leu Gly Gly Pro Ser Val Phe Ile Phe Pro Pro Lys Ile Lys
            260                 265                 270

Asp Val Leu Met Ile Ser Leu Ser Pro Met Val Thr Cys Val Val Val
            275                 280                 285

Asp Val Ser Glu Asp Asp Pro Asp Val Gln Ile Ser Trp Phe Val Asn
            290                 295                 300

Asn Val Glu Val His Thr Ala Gln Thr Gln Thr His Arg Glu Asp Tyr
305                 310                 315                 320

Asn Ser Thr Leu Arg Val Val Ser Ala Leu Pro Ile Gln His Gln Asp
                325                 330                 335

Trp Met Ser Gly Lys Glu Phe Lys Cys Lys Val Asn Asn Arg Ala Leu
            340                 345                 350

Pro Ser Pro Ile Glu Lys Thr Ile Ser Lys Pro Arg Gly Pro Val Arg
            355                 360                 365

Ala Pro Gln Val Tyr Val Leu Pro Pro Ala Glu Glu Met Thr Lys
370                 375                 380

Lys Glu Phe Ser Leu Thr Cys Met Ile Thr Gly Phe Leu Pro Ala Glu
385                 390                 395                 400

Ile Ala Val Asp Trp Thr Ser Asn Gly Arg Thr Glu Gln Asn Tyr Lys
                405                 410                 415

Asn Thr Ala Thr Val Leu Asp Ser Asp Gly Ser Tyr Phe Met Tyr Ser
            420                 425                 430

Lys Leu Arg Val Gln Lys Ser Thr Trp Glu Arg Gly Ser Leu Phe Ala
            435                 440                 445

Cys Ser Val Val His Glu Gly Leu His Asn His Leu Thr Thr Lys Thr
450                 455                 460

Ile Ser Arg Ser Leu Gly Lys
465                 470

<210> SEQ ID NO 65
<211> LENGTH: 723
<212> TYPE: DNA
<213> ORGANISM: Artificial Sequence
<220> FEATURE:
<223> OTHER INFORMATION: Synthetic: Anti-CTLA-4 clone 9D9 Light Chain nucleic acid sequence

<400> SEQUENCE: 65

```
atggacatga gagtgcccgc ccagctgctg ggacttctgc tgctgtggct gccaggcgcc      60
agatgcgaca tcgtgatgac ccagaccacc ctgagcctgc ctgtgtccct gggagatcag     120
gccagcatca gctgtcggag cagccagagc atcgtgcaca gcaacggcaa cacctacctg     180
gaatggtatc tccagaagcc cggccagagc cccaagctgc tgatctacaa ggtgtccaac     240
cggttcagcg gcgtgcccga cagattttct ggcagcggct ccggcaccga cttcaccctg     300
aagatctccc gggtggaagc cgaggacctg ggcgtgtact actgttttca aggcagccac     360
gtgccctaca ccttcggcgg aggcaccaag ctggaaatca gcgggctga tgctgcacca     420
actgtatcca tcttcccacc atccagtgag cagttaacat ctggaggtgc ctcagtcgtg     480
tgcttcttga caacttcta ccccaaagac atcaatgtca agtggaagat tgatggcagt     540
gaacgacaaa atggcgtcct gaacagttgg actgatcagg acagcaaaga cagcacctac     600
agcatgagca gcaccctcac gttgaccaag gacgagtatg aacgacataa cagctatacc     660
tgtgaggcca ctcacaagac atcaacttca cccattgtca agagcttcaa caggaatgag     720
tgt                                                                   723
```

<210> SEQ ID NO 66
<211> LENGTH: 241
<212> TYPE: PRT
<213> ORGANISM: Artificial Sequence
<220> FEATURE:
<223> OTHER INFORMATION: Synthetic: Anti-CTLA-4 clone 9D9 Light Chain amino acid sequence

<400> SEQUENCE: 66

```
Met Asp Met Arg Val Pro Ala Gln Leu Leu Gly Leu Leu Leu Leu Trp
1               5                   10                  15

Leu Pro Gly Ala Arg Cys Asp Ile Val Met Thr Gln Thr Thr Leu Ser
            20                  25                  30

Leu Pro Val Ser Leu Gly Asp Gln Ala Ser Ile Ser Cys Arg Ser Ser
        35                  40                  45

Gln Ser Ile Val His Ser Asn Gly Asn Thr Tyr Leu Glu Trp Tyr Leu
    50                  55                  60

Gln Lys Pro Gly Gln Ser Pro Lys Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Leu Gly Val
            100                 105                 110

Tyr Tyr Cys Phe Gln Gly Ser His Val Pro Tyr Thr Phe Gly Gly Gly
        115                 120                 125

Thr Lys Leu Glu Ile Lys Arg Ala Asp Ala Ala Pro Thr Val Ser Ile
    130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys Asp Ile Asn Val Lys Trp Lys
                165                 170                 175

Ile Asp Gly Ser Glu Arg Gln Asn Gly Val Leu Asn Ser Trp Thr Asp
            180                 185                 190

Gln Asp Ser Lys Asp Ser Thr Tyr Ser Met Ser Ser Thr Leu Thr Leu
        195                 200                 205
```

```
Thr Lys Asp Glu Tyr Glu Arg His Asn Ser Tyr Thr Cys Glu Ala Thr
    210                 215                 220
His Lys Thr Ser Thr Ser Pro Ile Val Lys Ser Phe Asn Arg Asn Glu
225                 230                 235                 240
Cys

<210> SEQ ID NO 67
<211> LENGTH: 33
<212> TYPE: PRT
<213> ORGANISM: Artificial Sequence
<220> FEATURE:
<223> OTHER INFORMATION: Synthetic:  1.4A, EETI-II

<400> SEQUENCE: 67

Gly Cys Ala Glu Pro Arg Gly Asp Met Pro Trp Thr Trp Cys Lys Gln
1               5                   10                  15
Asp Ser Asp Cys Leu Ala Gly Cys Val Cys Gly Pro Asn Gly Phe Cys
            20                  25                  30
Gly

<210> SEQ ID NO 68
<211> LENGTH: 33
<212> TYPE: PRT
<213> ORGANISM: Artificial Sequence
<220> FEATURE:
<223> OTHER INFORMATION: Synthetic:  1.4B, EETI-II

<400> SEQUENCE: 68

Gly Cys Val Gly Gly Arg Gly Asp Trp Ser Pro Lys Trp Cys Lys Gln
1               5                   10                  15
Asp Ser Asp Cys Pro Ala Gly Cys Val Cys Gly Pro Asn Gly Phe Cys
            20                  25                  30
Gly

<210> SEQ ID NO 69
<211> LENGTH: 33
<212> TYPE: PRT
<213> ORGANISM: Artificial Sequence
<220> FEATURE:
<223> OTHER INFORMATION: Synthetic:  1.4C, EETI-II

<400> SEQUENCE: 69

Gly Cys Ala Glu Leu Arg Gly Asp Arg Ser Tyr Pro Glu Cys Lys Gln
1               5                   10                  15
Asp Ser Asp Cys Leu Ala Gly Cys Val Cys Gly Pro Asn Gly Phe Cys
            20                  25                  30
Gly

<210> SEQ ID NO 70
<211> LENGTH: 33
<212> TYPE: PRT
<213> ORGANISM: Artificial Sequence
<220> FEATURE:
<223> OTHER INFORMATION: Synthetic:  1.4E, EETI-II

<400> SEQUENCE: 70

Gly Cys Arg Leu Pro Arg Gly Asp Val Pro Arg Pro His Cys Lys Gln
1               5                   10                  15
Asp Ser Asp Cys Gln Ala Gly Cys Val Cys Gly Pro Asn Gly Phe Cys
            20                  25                  30
```

Gly

<210> SEQ ID NO 71
<211> LENGTH: 33
<212> TYPE: PRT
<213> ORGANISM: Artificial Sequence
<220> FEATURE:
<223> OTHER INFORMATION: Synthetic: 1.4H, EETI-II

<400> SEQUENCE: 71

Gly Cys Tyr Pro Leu Arg Gly Asp Asn Pro Tyr Ala Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 72
<211> LENGTH: 33
<212> TYPE: PRT
<213> ORGANISM: Artificial Sequence
<220> FEATURE:
<223> OTHER INFORMATION: Synthetic: 1.5B, EETI-II

<400> SEQUENCE: 72

Gly Cys Thr Ile Gly Arg Gly Asp Trp Ala Pro Ser Glu Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 73
<211> LENGTH: 33
<212> TYPE: PRT
<213> ORGANISM: Artificial Sequence
<220> FEATURE:
<223> OTHER INFORMATION: Synthetic: 1.5F, EETI-II

<400> SEQUENCE: 73

Gly Cys His Pro Pro Arg Gly Asp Asn Pro Pro Val Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 74
<211> LENGTH: 33
<212> TYPE: PRT
<213> ORGANISM: Artificial Sequence
<220> FEATURE:
<223> OTHER INFORMATION: Synthetic: 2.3A, EETI-II

<400> SEQUENCE: 74

Gly Cys Pro Glu Pro Arg Gly Asp Asn Pro Pro Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 75
<211> LENGTH: 33
<212> TYPE: PRT
<213> ORGANISM: Artificial Sequence

```
<220> FEATURE:
<223> OTHER INFORMATION: Synthetic: 2.3B, EETI-II

<400> SEQUENCE: 75

Gly Cys Leu Pro Pro Arg Gly Asp Asn Pro Pro Ser Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 76
<211> LENGTH: 33
<212> TYPE: PRT
<213> ORGANISM: Artificial Sequence
<220> FEATURE:
<223> OTHER INFORMATION: Synthetic: 2.3C, EETI-II

<400> SEQUENCE: 76

Gly Cys His Leu Gly Arg Gly Asp Trp Ala Pro Val Gly Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 77
<211> LENGTH: 33
<212> TYPE: PRT
<213> ORGANISM: Artificial Sequence
<220> FEATURE:
<223> OTHER INFORMATION: Synthetic: 2.3D, EETI-II

<400> SEQUENCE: 77

Gly Cys Asn Val Gly Arg Gly Asp Trp Ala Pro Ser Glu Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 78
<211> LENGTH: 33
<212> TYPE: PRT
<213> ORGANISM: Artificial Sequence
<220> FEATURE:
<223> OTHER INFORMATION: Synthetic: 2.3E, EETI-II

<400> SEQUENCE: 78

Gly Cys Phe Pro Gly Arg Gly Asp Trp Ala Pro Ser Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 79
<211> LENGTH: 33
<212> TYPE: PRT
<213> ORGANISM: Artificial Sequence
<220> FEATURE:
<223> OTHER INFORMATION: Synthetic: 2.3F, EETI-II

<400> SEQUENCE: 79

Gly Cys Pro Leu Pro Arg Gly Asp Asn Pro Pro Thr Glu Cys Lys Gln
1               5                   10                  15
```

-continued

Asp Ser Asp Cys Gln Ala Gly Cys Val Cys Gly Pro Asn Gly Phe Cys
            20                  25                  30

Gly

<210> SEQ ID NO 80
<211> LENGTH: 33
<212> TYPE: PRT
<213> ORGANISM: Artificial Sequence
<220> FEATURE:
<223> OTHER INFORMATION: Synthetic: 2.3G, EETI-II

<400> SEQUENCE: 80

Gly Cys Ser Glu Ala Arg Gly Asp Asn Pro Arg Leu Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 81
<211> LENGTH: 32
<212> TYPE: PRT
<213> ORGANISM: Artificial Sequence
<220> FEATURE:
<223> OTHER INFORMATION: Synthetic: 2.3H, EETI-II

<400> SEQUENCE: 81

Gly Cys Leu Leu Gly Arg Gly Asp Trp Ala Pro Glu Ala Cys Lys Gln
1               5                   10                  15

Asp Ser Asp Cys Arg Ala Gly Cys Val Cys Pro Asn Gly Phe Cys Gly
            20                  25                  30

<210> SEQ ID NO 82
<211> LENGTH: 33
<212> TYPE: PRT
<213> ORGANISM: Artificial Sequence
<220> FEATURE:
<223> OTHER INFORMATION: Synthetic: 2.3I, EETI-II

<400> SEQUENCE: 82

Gly Cys His Val Gly Arg Gly Asp Trp Ala Pro Leu Lys Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 83
<211> LENGTH: 33
<212> TYPE: PRT
<213> ORGANISM: Artificial Sequence
<220> FEATURE:
<223> OTHER INFORMATION: Synthetic: 2.3J, EETI-II

<400> SEQUENCE: 83

Gly Cys Val Arg Gly Arg Gly Asp Trp Ala Pro Pro Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 84
<211> LENGTH: 33

```
<212> TYPE: PRT
<213> ORGANISM: Artificial Sequence
<220> FEATURE:
<223> OTHER INFORMATION: Synthetic: 2.4A, EETI-II

<400> SEQUENCE: 84

Gly Cys Leu Gly Gly Arg Gly Asp Trp Ala Pro Pro Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 85
<211> LENGTH: 33
<212> TYPE: PRT
<213> ORGANISM: Artificial Sequence
<220> FEATURE:
<223> OTHER INFORMATION: Synthetic: 2.4C, EETI-II

<400> SEQUENCE: 85

Gly Cys Phe Val Gly Arg Gly Asp Trp Ala Pro Leu Thr Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 86
<211> LENGTH: 33
<212> TYPE: PRT
<213> ORGANISM: Artificial Sequence
<220> FEATURE:
<223> OTHER INFORMATION: Synthetic: 2.4D, EETI-II

<400> SEQUENCE: 86

Gly Cys Pro Val Gly Arg Gly Asp Trp Ser Pro Ala Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 87
<211> LENGTH: 33
<212> TYPE: PRT
<213> ORGANISM: Artificial Sequence
<220> FEATURE:
<223> OTHER INFORMATION: Synthetic: 2.4E, EETI-II

<400> SEQUENCE: 87

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 88
<211> LENGTH: 33
<212> TYPE: PRT
<213> ORGANISM: Artificial Sequence
<220> FEATURE:
<223> OTHER INFORMATION: Synthetic: 2.4F, EETI-II

<400> SEQUENCE: 88
```

```
Gly Cys Tyr Gln Gly Arg Gly Asp Trp Ser Pro Ser Cys Lys Gln
 1               5                  10                  15

Asp Ser Asp Cys Pro Ala Gly Cys Val Cys Gly Pro Asn Gly Phe Cys
            20                  25                  30

Gly
```

<210> SEQ ID NO 89
<211> LENGTH: 33
<212> TYPE: PRT
<213> ORGANISM: Artificial Sequence
<220> FEATURE:
<223> OTHER INFORMATION: Synthetic: 2.4G, EETI-II

<400> SEQUENCE: 89

```
Gly Cys Ala Pro Gly Arg Gly Asp Trp Ala Pro Ser Glu Cys Lys Gln
 1               5                  10                  15

Asp Ser Asp Cys Gln Ala Gly Cys Val Cys Gly Pro Asn Gly Phe Cys
            20                  25                  30

Gly
```

<210> SEQ ID NO 90
<211> LENGTH: 33
<212> TYPE: PRT
<213> ORGANISM: Artificial Sequence
<220> FEATURE:
<223> OTHER INFORMATION: Synthetic: 2.4J, EETI-II

<400> SEQUENCE: 90

```
Gly Cys Val Gln Gly Arg Gly Asp Trp Ser Pro Pro Ser Cys Lys Gln
 1               5                  10                  15

Asp Ser Asp Cys Pro Ala Gly Cys Val Cys Gly Pro Asn Gly Phe Cys
            20                  25                  30

Gly
```

<210> SEQ ID NO 91
<211> LENGTH: 33
<212> TYPE: PRT
<213> ORGANISM: Artificial Sequence
<220> FEATURE:
<223> OTHER INFORMATION: Synthetic: 2.5A, EETI-II

<400> SEQUENCE: 91

```
Gly Cys His Val Gly Arg Gly Asp Trp Ala Pro Glu Glu Cys Lys Gln
 1               5                  10                  15

Asp Ser Asp Cys Gln Ala Gly Cys Val Cys Gly Pro Asn Gly Phe Cys
            20                  25                  30

Gly
```

<210> SEQ ID NO 92
<211> LENGTH: 33
<212> TYPE: PRT
<213> ORGANISM: Artificial Sequence
<220> FEATURE:
<223> OTHER INFORMATION: Synthetic: 2.5C, EETI-II

<400> SEQUENCE: 92

```
Gly Cys Asp Gly Gly Arg Gly Asp Trp Ala Pro Pro Ala Cys Lys Gln
 1               5                  10                  15

Asp Ser Asp Cys Arg Ala Gly Cys Val Cys Gly Pro Asn Gly Phe Cys
            20                  25                  30

Gly
```

<210> SEQ ID NO 93
<211> LENGTH: 33
<212> TYPE: PRT
<213> ORGANISM: Artificial Sequence
<220> FEATURE:
<223> OTHER INFORMATION: Synthetic: 2.5D, EETI-II

<400> SEQUENCE: 93

Gly Cys Pro Gln Gly Arg Gly Asp Trp Ala Pro Thr Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 94
<211> LENGTH: 33
<212> TYPE: PRT
<213> ORGANISM: Artificial Sequence
<220> FEATURE:
<223> OTHER INFORMATION: Synthetic: 2.5F, EETI-II

<400> SEQUENCE: 94

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 95
<211> LENGTH: 33
<212> TYPE: PRT
<213> ORGANISM: Artificial Sequence
<220> FEATURE:
<223> OTHER INFORMATION: Synthetic: 2.5D K15S Mutant, EETI-II

<400> SEQUENCE: 95

Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 96
<211> LENGTH: 33
<212> TYPE: PRT
<213> ORGANISM: Artificial Sequence
<220> FEATURE:
<223> OTHER INFORMATION: Synthetic: 2.5F K15S Mutant, EETI-II

<400> SEQUENCE: 96

Gly Cys Pro Arg Pro Arg Gly Asp Asn Pro Pro Leu Thr Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 97
<211> LENGTH: 33
<212> TYPE: PRT
<213> ORGANISM: Artificial Sequence
<220> FEATURE:

<223> OTHER INFORMATION: Synthetic: 2.5H, EETI-II

<400> SEQUENCE: 97

Gly Cys Pro Gln Gly Arg Gly Asp Trp Ala Pro Glu Trp Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 98
<211> LENGTH: 33
<212> TYPE: PRT
<213> ORGANISM: Artificial Sequence
<220> FEATURE:
<223> OTHER INFORMATION: Synthetic: 2.5J, EETI-II

<400> SEQUENCE: 98

Gly Cys Pro Arg Gly Arg Gly Asp Trp Ser Pro Pro Ala Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 99
<211> LENGTH: 38
<212> TYPE: PRT
<213> ORGANISM: Artificial Sequence
<220> FEATURE:
<223> OTHER INFORMATION: Synthetic: 3A, AgRp

<400> SEQUENCE: 99

Gly Cys Val Arg Leu His Glu Ser Cys Leu Gly Gln Gln Val Pro Cys
1               5                   10                  15

Cys Asp Pro Ala Ala Thr Cys Tyr Cys Val Val Arg Gly Asp Trp Arg
            20                  25                  30

Lys Arg Cys Tyr Cys Arg
        35

<210> SEQ ID NO 100
<211> LENGTH: 38
<212> TYPE: PRT
<213> ORGANISM: Artificial Sequence
<220> FEATURE:
<223> OTHER INFORMATION: Synthetic: 3B, AgRp

<400> SEQUENCE: 100

Gly Cys Val Arg Leu His Glu Ser Cys Leu Gly Gln Gln Val Pro Cys
1               5                   10                  15

Cys Asp Pro Ala Ala Thr Cys Tyr Cys Glu Glu Arg Gly Asp Met Leu
            20                  25                  30

Glu Lys Cys Tyr Cys Arg
        35

<210> SEQ ID NO 101
<211> LENGTH: 38
<212> TYPE: PRT
<213> ORGANISM: Artificial Sequence
<220> FEATURE:
<223> OTHER INFORMATION: Synthetic: 3C, AgRp

<400> SEQUENCE: 101

Gly Cys Val Arg Leu His Glu Ser Cys Leu Gly Gln Gln Val Pro Cys

```
1               5                   10                  15
Cys Asp Pro Ala Ala Thr Cys Tyr Cys Glu Thr Arg Gly Asp Gly Lys
            20                  25                  30

Glu Lys Cys Tyr Cys Arg
        35

<210> SEQ ID NO 102
<211> LENGTH: 38
<212> TYPE: PRT
<213> ORGANISM: Artificial Sequence
<220> FEATURE:
<223> OTHER INFORMATION: Synthetic: 3D, AgRp

<400> SEQUENCE: 102

Gly Cys Val Arg Leu His Glu Ser Cys Leu Gly Gln Gln Val Pro Cys
1               5                   10                  15

Cys Asp Pro Ala Ala Thr Cys Tyr Cys Gln Trp Arg Gly Asp Gly Asp
            20                  25                  30

Val Lys Cys Tyr Cys Arg
        35

<210> SEQ ID NO 103
<211> LENGTH: 38
<212> TYPE: PRT
<213> ORGANISM: Artificial Sequence
<220> FEATURE:
<223> OTHER INFORMATION: Synthetic: 3E, AgRp

<400> SEQUENCE: 103

Gly Cys Val Arg Leu His Glu Ser Cys Leu Gly Gln Gln Val Pro Cys
1               5                   10                  15

Cys Asp Pro Ala Ala Thr Cys Tyr Cys Ser Arg Arg Gly Asp Met Arg
            20                  25                  30

Glu Arg Cys Tyr Cys Arg
        35

<210> SEQ ID NO 104
<211> LENGTH: 38
<212> TYPE: PRT
<213> ORGANISM: Artificial Sequence
<220> FEATURE:
<223> OTHER INFORMATION: Synthetic: 3F, AgRp

<400> SEQUENCE: 104

Gly Cys Val Arg Leu His Glu Ser Cys Leu Gly Gln Gln Val Pro Cys
1               5                   10                  15

Cys Asp Pro Ala Ala Thr Cys Tyr Cys Gln Tyr Arg Gly Asp Gly Met
            20                  25                  30

Lys His Cys Tyr Cys Arg
        35

<210> SEQ ID NO 105
<211> LENGTH: 38
<212> TYPE: PRT
<213> ORGANISM: Artificial Sequence
<220> FEATURE:
<223> OTHER INFORMATION: Synthetic: 3G, AgRp

<400> SEQUENCE: 105

Gly Cys Val Arg Leu His Glu Ser Cys Leu Gly Gln Gln Val Pro Cys
1               5                   10                  15

Cys Asp Pro Ala Ala Thr Cys Tyr Cys Thr Gly Arg Gly Asp Thr Lys
```

```
                    20                  25                  30

Val Leu Cys Tyr Cys Arg
         35

<210> SEQ ID NO 106
<211> LENGTH: 38
<212> TYPE: PRT
<213> ORGANISM: Artificial Sequence
<220> FEATURE:
<223> OTHER INFORMATION: Synthetic:  3H, AgRp

<400> SEQUENCE: 106

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Met Lys
            20                  25                  30

Arg Arg Cys Tyr Cys Arg
         35

<210> SEQ ID NO 107
<211> LENGTH: 38
<212> TYPE: PRT
<213> ORGANISM: Artificial Sequence
<220> FEATURE:
<223> OTHER INFORMATION: Synthetic:  3I, AgRp

<400> SEQUENCE: 107

Gly Cys Val Arg Leu His Glu Ser Cys Leu Gly Gln Gln Val Pro Cys
1               5                   10                  15

Cys Asp Pro Ala Ala Thr Cys Tyr Cys Thr Gly Arg Gly Asp Val Arg
            20                  25                  30

Met Asn Cys Tyr Cys Arg
         35

<210> SEQ ID NO 108
<211> LENGTH: 38
<212> TYPE: PRT
<213> ORGANISM: Artificial Sequence
<220> FEATURE:
<223> OTHER INFORMATION: Synthetic:  3J, AgRp

<400> SEQUENCE: 108

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
            20                  25                  30

Ser Lys Cys Tyr Cys Arg
         35

<210> SEQ ID NO 109
<211> LENGTH: 38
<212> TYPE: PRT
<213> ORGANISM: Artificial Sequence
<220> FEATURE:
<223> OTHER INFORMATION: Synthetic:  4A, AgRp

<400> SEQUENCE: 109

Gly Cys Val Arg Leu His Glu Ser Cys Leu Gly Gln Gln Val Pro Cys
1               5                   10                  15

Cys Asp Pro Ala Ala Thr Cys Tyr Cys Arg Gly Arg Gly Asp Met Arg
            20                  25                  30

Arg Glu Cys Tyr Cys Arg
```

<210> SEQ ID NO 110
<211> LENGTH: 38
<212> TYPE: PRT
<213> ORGANISM: Artificial Sequence
<220> FEATURE:
<223> OTHER INFORMATION: Synthetic: 4B, AgRp

<400> SEQUENCE: 110

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Val Lys
            20                  25                  30

Val Asn Cys Tyr Cys Arg
        35

<210> SEQ ID NO 111
<211> LENGTH: 38
<212> TYPE: PRT
<213> ORGANISM: Artificial Sequence
<220> FEATURE:
<223> OTHER INFORMATION: Synthetic: 4C, AgRp

<400> SEQUENCE: 111

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Glu Lys
            20                  25                  30

Met Ser Cys Tyr Cys Arg
        35

<210> SEQ ID NO 112
<211> LENGTH: 38
<212> TYPE: PRT
<213> ORGANISM: Artificial Sequence
<220> FEATURE:
<223> OTHER INFORMATION: Synthetic: 4D, AgRp

<400> SEQUENCE: 112

Gly Cys Val Arg Leu His Glu Ser Cys Leu Gly Gln Gln Val Pro Cys
1               5                   10                  15

Cys Asp Pro Ala Ala Thr Cys Tyr Cys Val Ser Arg Gly Asp Met Arg
            20                  25                  30

Lys Arg Cys Tyr Cys Arg
        35

<210> SEQ ID NO 113
<211> LENGTH: 38
<212> TYPE: PRT
<213> ORGANISM: Artificial Sequence
<220> FEATURE:
<223> OTHER INFORMATION: Synthetic: 4E, AgRp

<400> SEQUENCE: 113

Gly Cys Val Arg Leu His Glu Ser Cys Leu Gly Gln Gln Val Pro Cys
1               5                   10                  15

Cys Asp Pro Ala Ala Thr Cys Tyr Cys Glu Arg Arg Gly Asp Ser Val
            20                  25                  30

Lys Lys Cys Tyr Cys Arg
        35

-continued

```
<210> SEQ ID NO 114
<211> LENGTH: 38
<212> TYPE: PRT
<213> ORGANISM: Artificial Sequence
<220> FEATURE:
<223> OTHER INFORMATION: Synthetic: 4F, AgRp

<400> SEQUENCE: 114

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Thr Arg
            20                  25                  30

Arg Arg Cys Tyr Cys Arg
        35

<210> SEQ ID NO 115
<211> LENGTH: 38
<212> TYPE: PRT
<213> ORGANISM: Artificial Sequence
<220> FEATURE:
<223> OTHER INFORMATION: Synthetic: 4G, AgRp

<400> SEQUENCE: 115

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Val Val
            20                  25                  30

Arg Arg Cys Tyr Cys Arg
        35

<210> SEQ ID NO 116
<211> LENGTH: 38
<212> TYPE: PRT
<213> ORGANISM: Artificial Sequence
<220> FEATURE:
<223> OTHER INFORMATION: Synthetic: 4H, AgRp

<400> SEQUENCE: 116

Gly Cys Val Arg Leu His Glu Ser Cys Leu Gly Gln Gln Val Pro Cys
1               5                   10                  15

Cys Asp Pro Ala Ala Thr Cys Tyr Cys Lys Gly Arg Gly Asp Asn Lys
            20                  25                  30

Arg Lys Cys Tyr Cys Arg
        35

<210> SEQ ID NO 117
<211> LENGTH: 38
<212> TYPE: PRT
<213> ORGANISM: Artificial Sequence
<220> FEATURE:
<223> OTHER INFORMATION: Synthetic: 4I, AgRp
<220> FEATURE:
<221> NAME/KEY: misc_feature
<222> LOCATION: (21)..(21)
<223> OTHER INFORMATION: Xaa can be any naturally occurring amino acid

<400> SEQUENCE: 117

Gly Cys Val Arg Leu His Glu Ser Cys Leu Gly Gln Gln Val Pro Cys
1               5                   10                  15

Cys Asp Pro Ala Xaa Thr Cys Tyr Cys Lys Gly Arg Gly Asp Val Arg
            20                  25                  30

Arg Val Cys Tyr Cys Arg
        35
```

```
<210> SEQ ID NO 118
<211> LENGTH: 38
<212> TYPE: PRT
<213> ORGANISM: Artificial Sequence
<220> FEATURE:
<223> OTHER INFORMATION: Synthetic:  4J, AgRp

<400> SEQUENCE: 118

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Asn Lys
            20                  25                  30

Val Lys Cys Tyr Cys Arg
        35

<210> SEQ ID NO 119
<211> LENGTH: 38
<212> TYPE: PRT
<213> ORGANISM: Artificial Sequence
<220> FEATURE:
<223> OTHER INFORMATION: Synthetic:  5A, AgRp

<400> SEQUENCE: 119

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Asn Arg
            20                  25                  30

Leu Lys Cys Tyr Cys Arg
        35

<210> SEQ ID NO 120
<211> LENGTH: 38
<212> TYPE: PRT
<213> ORGANISM: Artificial Sequence
<220> FEATURE:
<223> OTHER INFORMATION: Synthetic:  5B, AgRp

<400> SEQUENCE: 120

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
            20                  25                  30

Lys Lys Cys Tyr Cys Arg
        35

<210> SEQ ID NO 121
<211> LENGTH: 38
<212> TYPE: PRT
<213> ORGANISM: Artificial Sequence
<220> FEATURE:
<223> OTHER INFORMATION: Synthetic:  5C, AgRp

<400> SEQUENCE: 121

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Met Arg
            20                  25                  30

Arg Arg Cys Tyr Cys Arg
        35

<210> SEQ ID NO 122
<211> LENGTH: 38
```

-continued

```
<212> TYPE: PRT
<213> ORGANISM: Artificial Sequence
<220> FEATURE:
<223> OTHER INFORMATION: Synthetic: 5D, AgRp

<400> SEQUENCE: 122

Gly Cys Val Arg Leu His Glu Ser Cys Leu Gly Gln Gln Val Pro Cys
1               5                   10                  15

Cys Asp Pro Ala Ala Thr Cys Tyr Cys Gln Gly Arg Gly Asp Gly Asp
            20                  25                  30

Val Lys Cys Tyr Cys Arg
        35

<210> SEQ ID NO 123
<211> LENGTH: 38
<212> TYPE: PRT
<213> ORGANISM: Artificial Sequence
<220> FEATURE:
<223> OTHER INFORMATION: Synthetic: 5E, AgRp

<400> SEQUENCE: 123

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Asn Asp
            20                  25                  30

Leu Val Cys Tyr Cys Arg
        35

<210> SEQ ID NO 124
<211> LENGTH: 38
<212> TYPE: PRT
<213> ORGANISM: Artificial Sequence
<220> FEATURE:
<223> OTHER INFORMATION: Synthetic: 5F, AgRp

<400> SEQUENCE: 124

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
            20                  25                  30

Ile Arg Cys Tyr Cys Arg
        35

<210> SEQ ID NO 125
<211> LENGTH: 38
<212> TYPE: PRT
<213> ORGANISM: Artificial Sequence
<220> FEATURE:
<223> OTHER INFORMATION: Synthetic: 5G, AgRp

<400> SEQUENCE: 125

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Asn Asp
            20                  25                  30

Leu Val Cys Tyr Cys Arg
        35

<210> SEQ ID NO 126
<211> LENGTH: 38
<212> TYPE: PRT
<213> ORGANISM: Artificial Sequence
<220> FEATURE:
```

<223> OTHER INFORMATION: Synthetic: 5H, AgRp

<400> SEQUENCE: 126

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Met Lys
            20                  25                  30

Met Lys Cys Tyr Cys Arg
        35

<210> SEQ ID NO 127
<211> LENGTH: 38
<212> TYPE: PRT
<213> ORGANISM: Artificial Sequence
<220> FEATURE:
<223> OTHER INFORMATION: Synthetic: 5I, AgRp

<400> SEQUENCE: 127

Gly Cys Val Arg Leu His Glu Ser Cys Leu Gly Gln Gln Val Pro Cys
1               5                   10                  15

Cys Asp Pro Ala Ala Thr Cys Tyr Cys Ile Gly Arg Gly Asp Val Arg
            20                  25                  30

Arg Arg Cys Tyr Cys Arg
        35

<210> SEQ ID NO 128
<211> LENGTH: 38
<212> TYPE: PRT
<213> ORGANISM: Artificial Sequence
<220> FEATURE:
<223> OTHER INFORMATION: Synthetic: 5J, AgRp

<400> SEQUENCE: 128

Gly Cys Val Arg Leu His Glu Ser Cys Leu Gly Gln Gln Val Pro Cys
1               5                   10                  15

Cys Asp Pro Ala Ala Thr Cys Tyr Cys Glu Glu Arg Gly Asp Gly Arg
            20                  25                  30

Lys Lys Cys Tyr Cys Arg
        35

<210> SEQ ID NO 129
<211> LENGTH: 38
<212> TYPE: PRT
<213> ORGANISM: Artificial Sequence
<220> FEATURE:
<223> OTHER INFORMATION: Synthetic: 6B, AgRp

<400> SEQUENCE: 129

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Arg Asp
            20                  25                  30

Met Lys Cys Tyr Cys Arg
        35

<210> SEQ ID NO 130
<211> LENGTH: 38
<212> TYPE: PRT
<213> ORGANISM: Artificial Sequence
<220> FEATURE:
<223> OTHER INFORMATION: Synthetic: 6C, AgRp

<400> SEQUENCE: 130

Gly Cys Val Arg Leu His Glu Ser Cys Leu Gly Gln Gln Val Pro Cys
1               5                   10                  15

Cys Asp Pro Ala Ala Thr Cys Tyr Cys Thr Gly Arg Gly Asp Glu Lys
            20                  25                  30

Leu Arg Cys Tyr Cys Arg
        35

<210> SEQ ID NO 131
<211> LENGTH: 38
<212> TYPE: PRT
<213> ORGANISM: Artificial Sequence
<220> FEATURE:
<223> OTHER INFORMATION: Synthetic: 6E, AgRp

<400> SEQUENCE: 131

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Asn
            20                  25                  30

Arg Arg Cys Tyr Cys Arg
        35

<210> SEQ ID NO 132
<211> LENGTH: 38
<212> TYPE: PRT
<213> ORGANISM: Artificial Sequence
<220> FEATURE:
<223> OTHER INFORMATION: Synthetic: 6F, AgRp

<400> SEQUENCE: 132

Gly Cys Val Arg Leu His Glu Ser Cys Leu Gly Gln Gln Val Pro Cys
1               5                   10                  15

Cys Asp Pro Ala Ala Thr Cys Tyr Cys Glu Ser Arg Gly Asp Val Val
            20                  25                  30

Arg Lys Cys Tyr Cys Arg
        35

<210> SEQ ID NO 133
<211> LENGTH: 38
<212> TYPE: PRT
<213> ORGANISM: Artificial Sequence
<220> FEATURE:
<223> OTHER INFORMATION: Synthetic: 7C, AgRp

<400> SEQUENCE: 133

Gly Cys Val Arg Leu His Glu Ser Cys Leu Gly Gln Gln Val Pro Cys
1               5                   10                  15

Cys Asp Pro Ala Ala Thr Cys Tyr Cys Tyr Gly Arg Gly Asp Asn Asp
            20                  25                  30

Leu Arg Cys Tyr Cys Arg
        35

<210> SEQ ID NO 134
<211> LENGTH: 51
<212> TYPE: PRT
<213> ORGANISM: Artificial Sequence
<220> FEATURE:
<223> OTHER INFORMATION: Synthetic: peptide linker

<400> SEQUENCE: 134

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Ser Gly Gly Gly Gly Ser Gly Gly
        35                  40                  45

Gly Gly Ser
    50

<210> SEQ ID NO 135
<211> LENGTH: 16
<212> TYPE: PRT
<213> ORGANISM: Artificial Sequence
<220> FEATURE:
<223> OTHER INFORMATION: Synthetic: peptide linker

<400> SEQUENCE: 135

Ser Gly Gly Gly Gly Ser Gly Gly Gly Gly Ser Gly Gly Gly Gly Ser
1               5                   10                  15

<210> SEQ ID NO 136
<211> LENGTH: 21
<212> TYPE: PRT
<213> ORGANISM: Artificial Sequence
<220> FEATURE:
<223> OTHER INFORMATION: Synthetic: peptide linker

<400> SEQUENCE: 136

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 137
<211> LENGTH: 30
<212> TYPE: PRT
<213> ORGANISM: Artificial Sequence
<220> FEATURE:
<223> OTHER INFORMATION: Synthetic: peptide linker

<400> SEQUENCE: 137

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 138
<211> LENGTH: 24
<212> TYPE: PRT
<213> ORGANISM: Artificial Sequence
<220> FEATURE:
<223> OTHER INFORMATION: Synthetic: peptide linker

<400> SEQUENCE: 138

Gly Gly Gly Ser Gly Gly Gly Ser Gly Gly Gly Ser Gly Gly Gly Ser
1               5                   10                  15

Gly Gly Gly Ser Gly Gly Gly Ser
            20

US 10,166,273 B2

SYNERGISTIC TUMOR TREATMENT WITH ANTIBODIES TARGETING PD-1, PD-L1 OR CTLA4 AND INTEGRIN-BINDING-FC-FUSION PROTEIN

RELATED APPLICATIONS

This application is a 35 U.S.C. 371 national stage filing of International Application No. PCT/US2015/044920, filed on Aug. 12, 2015, which claims priority to U.S. Provisional Patent Application No. 62/036,554, filed Aug. 12, 2014. The contents of the aforementioned applications are hereby incorporated by reference in their entireties.

GOVERNMENT FUNDING

This invention was made with Government support under contract CA174795 awarded by the National Institutes of Health. The Government has certain rights in the invention.

REFERENCE TO THE SEQUENCE LISTING

The instant application contains a Sequence Listing which has been submitted electronically in ASCII format and is hereby incorporated by reference in its entirety. Said ASCII copy, created on Feb. 1, 2017, is named MITN_028US_SL.txt and is 163608 bytes in size.

BACKGROUND OF THE INVENTION

Interleukin-2 (IL-2) is a pleiotropic cytokine that activates and induces the proliferation of T cells and NK cells. Although IL-2 is an FDA approved therapy, systemic IL-2 treatment has significant toxicity and therefore the response rate of patients is less than 25%. Combining extended half-life IL-2 and an antibody against a tumor-specific antigen shows promising results for treatment. However, antibody-based therapies often suffer from the fact that many tumors lack known tumor-associated antigens.

Integrins are a family of extracellular matrix adhesion receptors that regulate a diverse array of cellular functions crucial to the initiation, progression and metastasis of solid tumors. The importance of integrins in tumor progression has made them an appealing target for cancer therapy and allows for the treatment of a variety of cancer types. The integrins present on cancerous cells include $\alpha_v\beta_3$, $\alpha_v\beta_5$, and $\alpha_5\beta_1$. A variety of therapeutics have been developed to target individual integrins associated with cancer, including antibodies, linear peptides, cyclic peptides, and peptidomimetics. However, none have utilized small, structured peptide scaffolds or targeted more than two integrins simultaneously. Additionally, current integrin targeting drugs are given as a monotherapy. Novel combination therapies are needed to more effectively combat various cancers.

SUMMARY OF THE INVENTION

The present invention is based, in part, on the discovery that administration of IL-2 attached to a pharmacokinetic modifying group (hereafter referred to as "extended-pharmacokinetic (PK) IL-2") and an integrin-binding-Fc fusion protein provides synergistic tumor control and prolongs survival relative to monotherapy of either agent alone. The integrin-binding-Fc fusion protein comprises (i) an integrin-binding polypeptide having an integrin-binding loop and a knottin polypeptide scaffold; and (ii) an immunoglobulin Fc domain, wherein the integrin-binding polypeptide is operably linked to the Fc domain. An improved cancer therapy is provided that involves the combined administration of an effective amount of IL-2 and an integrin-binding-Fc fusion protein.

Accordingly, in one aspect, the invention provides a method for treating cancer in a subject comprising administering to the subject an effective amount of interleukin (IL)-2, and an integrin-binding-Fc fusion protein, wherein the integrin-binding-Fc fusion protein comprises (i) an integrin-binding polypeptide comprising an integrin-binding loop and an knottin polypeptide scaffold; and (ii) an immunoglobulin Fc domain, wherein the integrin-binding polypeptide is operably linked to the Fc domain.

In one embodiment of the foregoing aspects, the IL-2 is in the form of an extended-PK IL-2, such as an IL-2 fusion protein. In one embodiment, the fusion protein comprises an IL-2 moiety and a moiety selected from the group consisting of an immunoglobulin fragment, human serum albumin, and Fn3. In another embodiment, the fusion protein comprises an IL-2 moiety operably linked to an immunoglobulin Fc domain. In another embodiment, the fusion protein comprises an IL-2 moiety operably linked to human serum albumin. In another embodiment, the extended-PK IL-2 comprises an IL-2 moiety conjugated to a non-protein polymer. In one embodiment, the non-protein polymer is polyethylene glycol.

In one embodiment of the foregoing aspects, the integrin-binding-Fc fusion protein includes an integrin-binding polypeptide that binds to a tumor associated integrin selected from the group consisting of $\alpha_v\beta_3$, $\alpha_v\beta_5$, and $\alpha_5\beta_1$, or combination thereof. In one embodiment, the integrin-binding polypeptide binds to $\alpha_v\beta_3$, $\alpha_v\beta_5$, and $\alpha_5\beta_1$.

In one embodiment of the foregoing aspects, the integrin-binding polypeptide includes an integrin-binding loop within a knottin polypeptide scaffold. In some embodiments, the knottin polypeptide scaffold comprises at least three cysteine disulfide linkages or crosslinked cysteine residues, and the integrin-binding loop is adjacent cysteine residues of the knottin polypeptide scaffold. In one embodiment, the integrin-binding loop comprises an RGD peptide sequence. In another embodiment, the knottin polypeptide scaffold is derived from a knottin protein selected from the group consisting of EETI-II, AgRP, and agatoxin. In one embodiment, the knottin protein is EETI-II.

In one embodiment of the foregoing aspects, the integrin-binding polypeptide includes an integrin-binding loop comprising an RGD peptide sequence and the knottin polypeptide scaffold is derived from EETI-II.

In one embodiment of the foregoing aspects, the knottin polypeptide scaffold is derived from EETI-II and the integrin-binding loop comprises the sequence, $X_1X_2X_3RGDX_7X_8X_9X_{10}X_{11}$, wherein each X represents any amino acid, wherein the loop is inserted between 2 cysteine residues in the EETI-II sequence and replaces the native EETI-II sequence. In another embodiment, the integrin-binding loop is inserted after the first cysteine in the native EETI-II sequence.

In one embodiment of the foregoing aspects, the integrin-binding polypeptide comprises the amino acid sequence set forth in SEQ ID NO: 42 or 43, wherein $X_1$ is selected from the group consisting of A, V, L, P, F, Y, S, H, D, and N; $X_2$ is selected from the group consisting of G, V, L, P, R, E, and Q; $X_3$ is selected from the group consisting of G, A, and P; $X_7$ is selected from the group consisting of W and N; $X_8$ is selected from the group consisting of A, P, and S; $X_9$ is selected from the group consisting of P and R; $X_{10}$ is selected from the group consisting of A, V, L, P, S, T, and E;

and $X_{11}$ is selected from the group consisting of G, A, W, S, T, K, and E. In a further embodiment, the integrin-binding-Fc fusion comprises an integrin-binding polypeptide, as set forth in SEQ ID NOs: 42 or 43, operably linked to a human IgG Fc domain, as set forth in SEQ ID NOs: 2 or 3.

In one embodiment of the foregoing aspects, the integrin-binding polypeptide comprises an amino acid sequence selected from the amino acid sequences set forth in Table 1. In another embodiment, the integrin-binding polypeptide comprises an amino acid sequence from the group consisting of SEQ ID NOs: 67-133. In a further embodiment, an integrin-binding polypeptide, set forth in Table 1, is operably linked to a human IgG1 Fc domain, set forth in SEQ ID NOs: 2 or 3.

In one embodiment of the foregoing aspects, the integrin-binding polypeptide comprises the amino acid sequence of SEQ ID NO: 93, 94, 95 or 96.

In one embodiment of the foregoing aspects, the Fc domain is a human IgG1 Fc domain.

In one embodiment of the foregoing aspects, the integrin-binding polypeptide is operably linked with or without a linker to the Fc domain. In some embodiments, the integrin-binding polypeptide is linked to the N-terminus or C-terminus of the Fc domain without a linker. In other embodiments, the integrin-binding polypeptide is linked to the N-terminus or C-terminus of the Fc donor with a linker such as a Gly-Ser linker.

In one embodiment of the foregoing aspects, the integrin-binding-Fc fusion protein comprises the amino acid sequence of SEQ ID NO: 48, 49, 50 or 51.

In any of the foregoing aspects, the methods comprise administering IL-2 and the integrin-binding-Fc fusion protein in the form of a pharmaceutical composition with a pharmaceutically acceptable carrier.

In some embodiments, the integrin-binding-Fc fusion protein is in the form of a dimer.

In any of the foregoing aspects, the methods comprise administering IL-2 and the integrin-binding-Fc fusion protein simultaneously or sequentially.

In any of the foregoing aspects, the methods further comprise administering an immune checkpoint blocker, such an antibody or antibody fragment targeting PD-1, PD-L1, CTLA-4, TIM3, LAG3, or a member of the B7 family. In one embodiment, the immune checkpoint blocker is an antibody or antibody fragment thereof targeting PD-1. In another embodiment, the immune checkpoint blocker is an antibody or antibody fragment targeting CTLA4.

In certain embodiments, an antagonist of VEGF is administered in place of an immune checkpoint blocker. In a further embodiment, the antagonist of VEGF is an antibody or antibody fragment thereof that binds VEGF, an antibody or antibody fragment thereof that binds VEGF receptor, a small molecule inhibitor of the VEGF receptor tyrosine kinases, a dominant negative VEGF, or a VEGF receptor.

In one embodiment of the foregoing aspects, the methods comprise administering an integrin-binding-Fc fusion protein and an immune checkpoint blocker, with or without IL-2.

In any of the foregoing aspects, the cancer is selected from the group consisting of melanoma, leukemia, lung cancer, breast cancer, prostate cancer, ovarian cancer, colon cancer, renal cell carcinoma, pancreatic cancer, cervical cancer, and brain cancer. In some embodiments, the cancer is melanoma. In other embodiments, the cancer is brain cancer, such as medullablastoma. In other embodiments, the cancer is colon cancer.

In another aspect, the invention provides a method for inhibiting growth and/or proliferation of tumor cells in a subject comprising administering to the subject an effective amount of an extended-pharmacokinetic (PK) interleukin (IL)-2, and an integrin-binding-Fc fusion protein, wherein the integrin-binding-Fc fusion protein comprises (i) an integrin-binding polypeptide comprising an integrin-binding loop and a knottin polypeptide scaffold; and (ii) an immunoglobulin Fc domain, wherein the integrin-binding polypeptide is operably linked to the Fc domain.

In another aspect, the invention provides a method for inhibiting growth and/or proliferation of tumor cells in a subject comprising administering to the subject an effective amount of an integrin-binding-Fc fusion protein, wherein the integrin-binding-Fc fusion protein comprises (i) an integrin-binding polypeptide comprising an integrin-binding loop and a knottin polypeptide scaffold; and (ii) an immunoglobulin Fc domain, wherein the integrin-binding polypeptide is operably linked to the Fc domain, and an immune checkpoint blocker. In a further embodiment, an effective amount of IL-2 is also administered.

In one embodiment of the foregoing aspect, the immune checkpoint blocker is an antibody or antibody fragment targeting PD-1. In another aspect, the immune checkpoint blocker is an antibody or antibody fragment targeting CTLA-4.

In another aspect, the invention provides a method for inhibiting growth and/or proliferation of tumor cells in a subject comprising administering to the subject an effective amount of an integrin-binding-Fc fusion protein, wherein the integrin-binding-Fc fusion protein comprises (i) an integrin-binding polypeptide comprising an integrin-binding loop and a knottin polypeptide scaffold; and (ii) an immunoglobulin Fc domain, wherein the integrin-binding polypeptide is operably linked to the Fc domain, and an antagonist of VEGF. In certain embodiments, the antagonist of VEGF is an antibody or antibody fragment thereof that binds VEGF, an antibody or antibody fragment thereof that binds VEGF receptor, a small molecule inhibitor of the VEGF receptor tyrosine kinases, a dominant negative VEGF, or a VEGF receptor.

BRIEF DESCRIPTION OF THE DRAWINGS

These and other features, aspects, and advantages of the present invention will become better understood with regard to the following description, and accompanying drawings.

FIG. 1 is adapted from Biochemistry, 40, 15520-15527 (2001) and *J. Biol. Chem.,* 2003, 278:6314-6322.

Figure 3A:
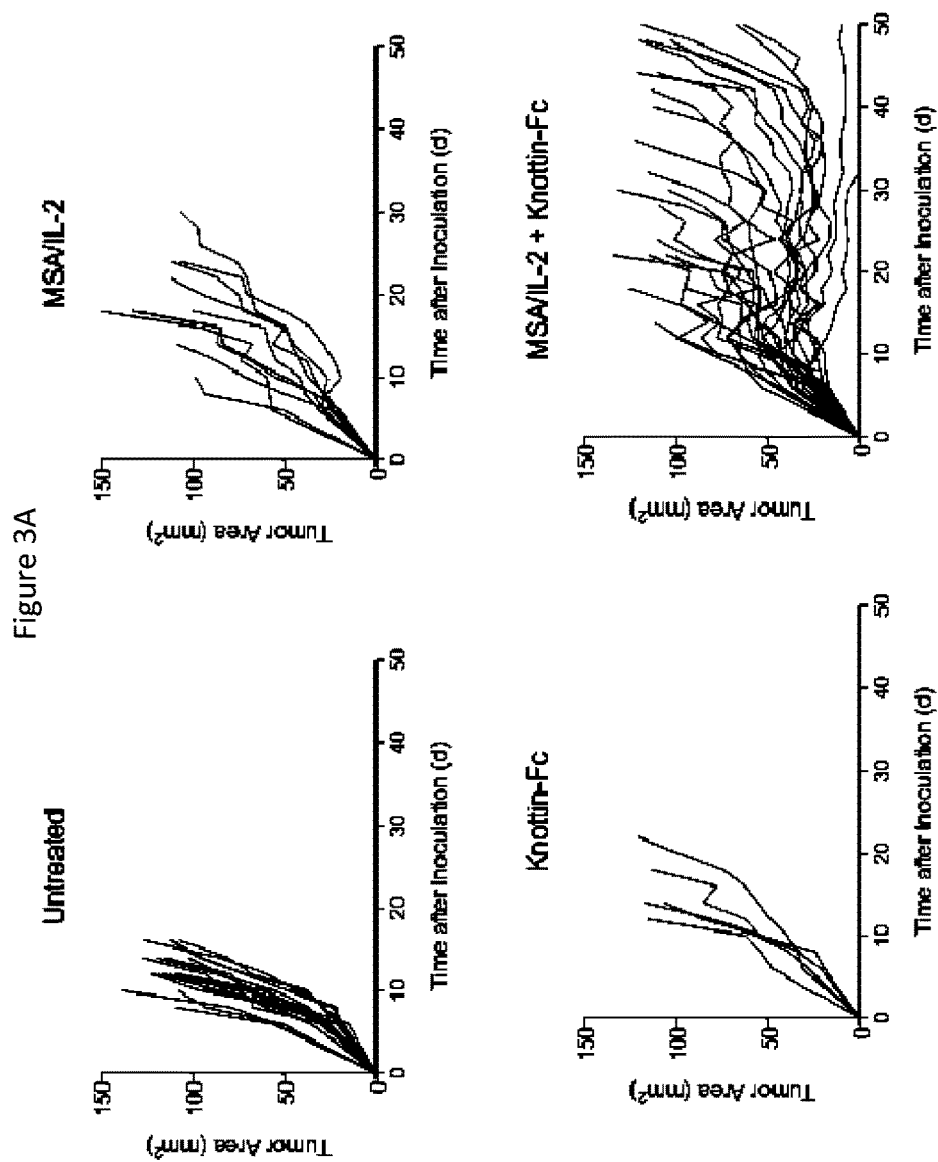
Figure 3B:
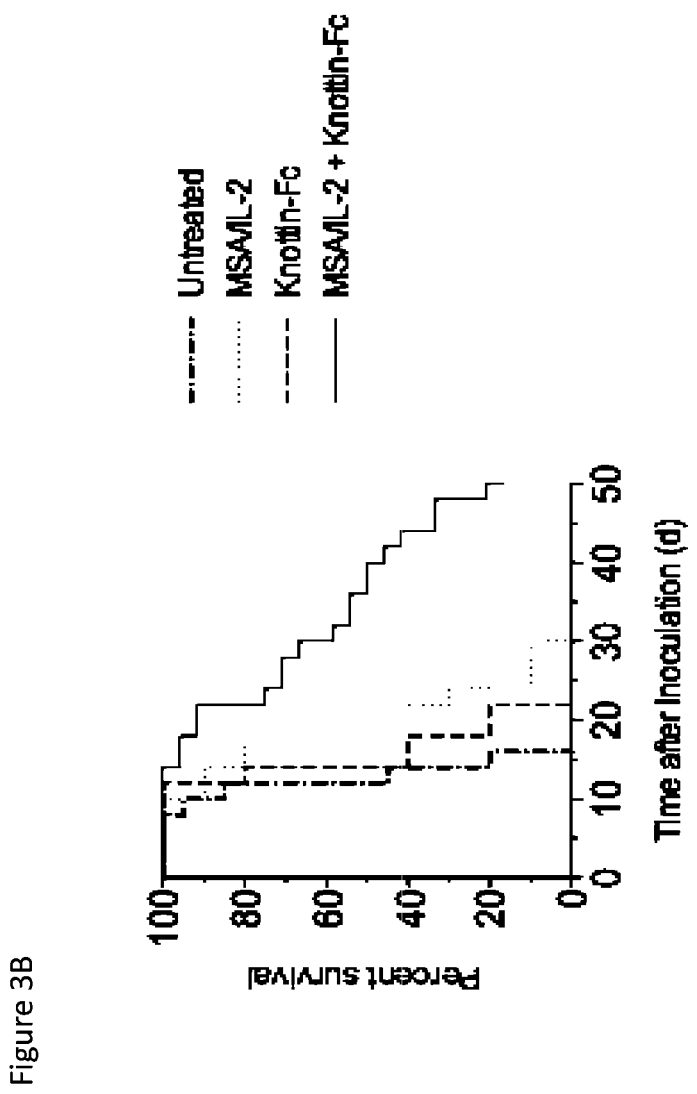

FIGS. 3A and 3B depict synergistic tumor control in established B16F10 melanoma tumors. $1 \times 10^6$ B16F10 cells were injected into the flanks of C57BL/6 mice. 30 µg MSA/IL-2 and/or 500 µg knottin-Fc was administered on day 6 after tumor inoculation, and every 6 days after for a total of four treatments. FIG. 3A) Tumor area graphs for each treatment. FIG. 3B) Kaplan-Meier survival plot.

Figure 4A:
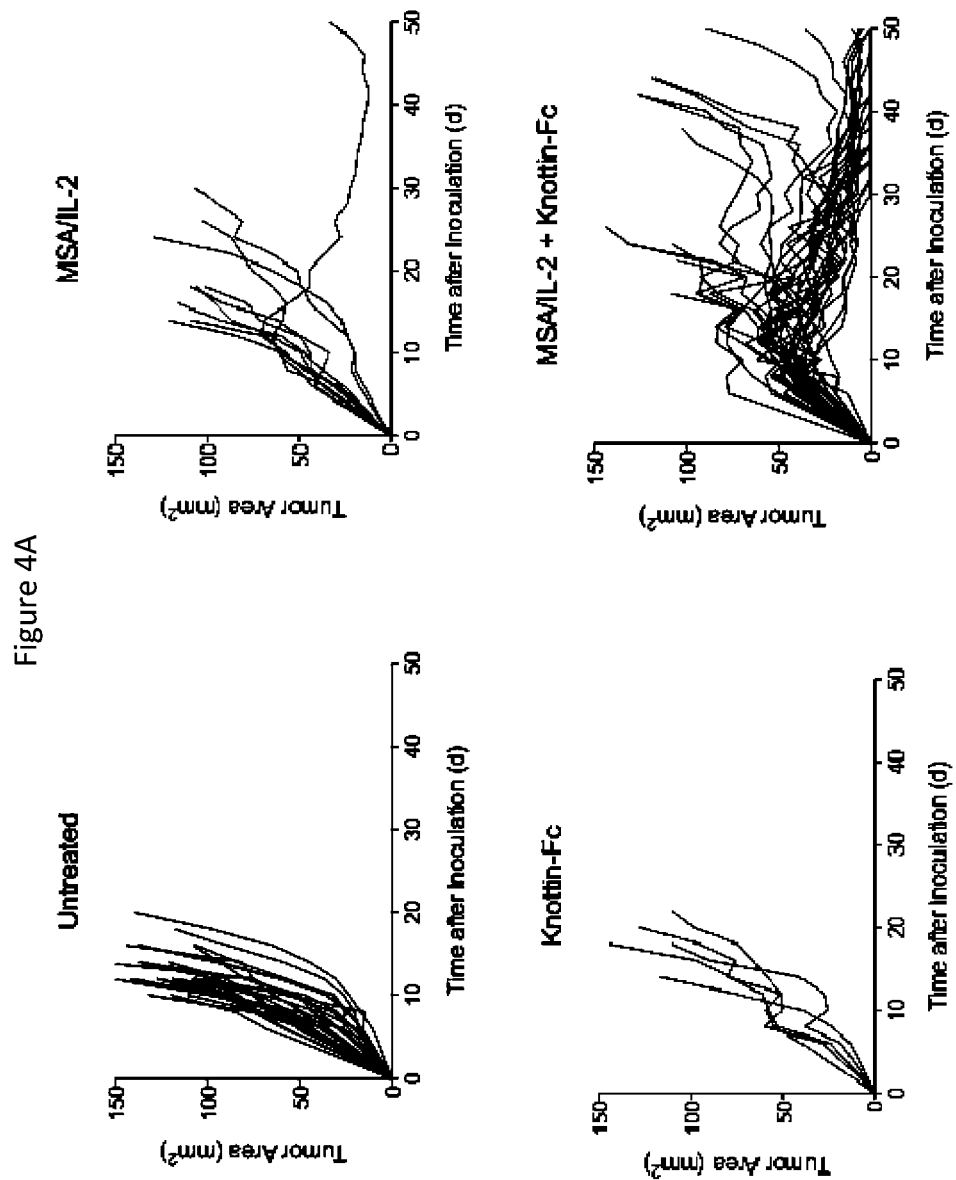
Figure 4B:
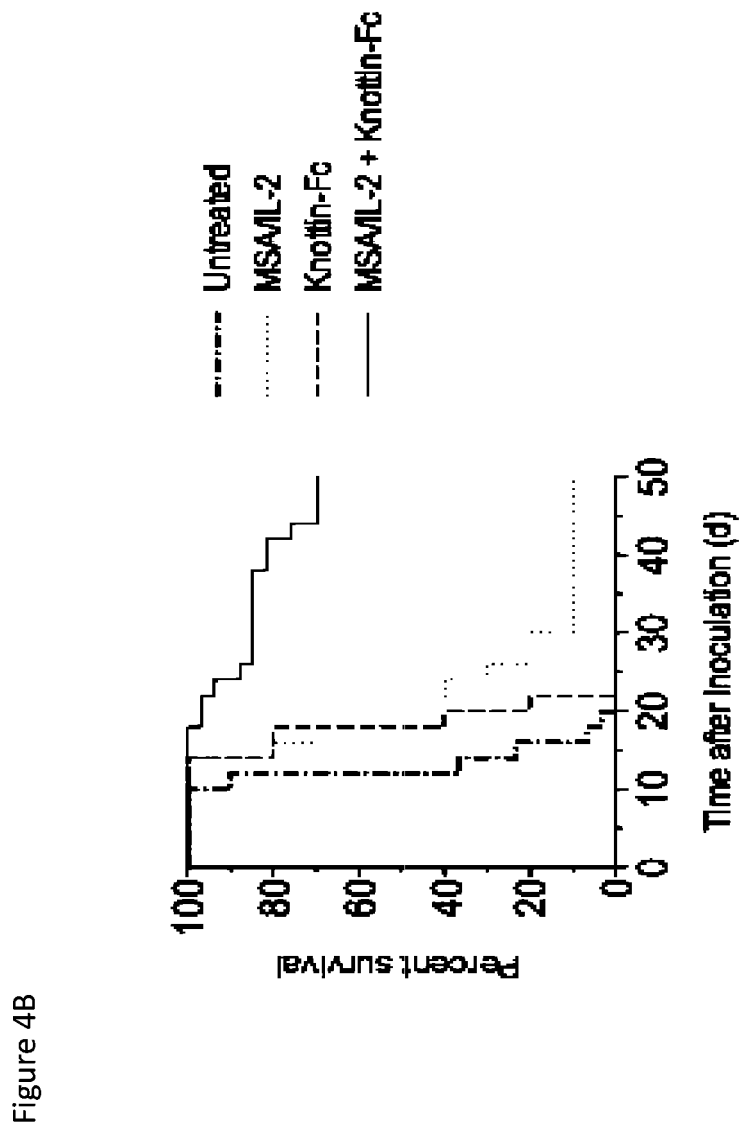

FIGS. 4A and 4B depict synergistic tumor control in established MC38 colon tumors. $1 \times 10^6$ MC38 cells were injected into the flanks of C57BL/6 mice and 30 µg MSA/IL-2 and/or 500 µg knottin-Fc was administered on day 6 after tumor inoculation, and every 6 days after for a total of four treatments. FIG. 4A) Tumor area graphs for each treatment. FIG. 4B) Kaplan-Meier survival plot.

Figure 5A:
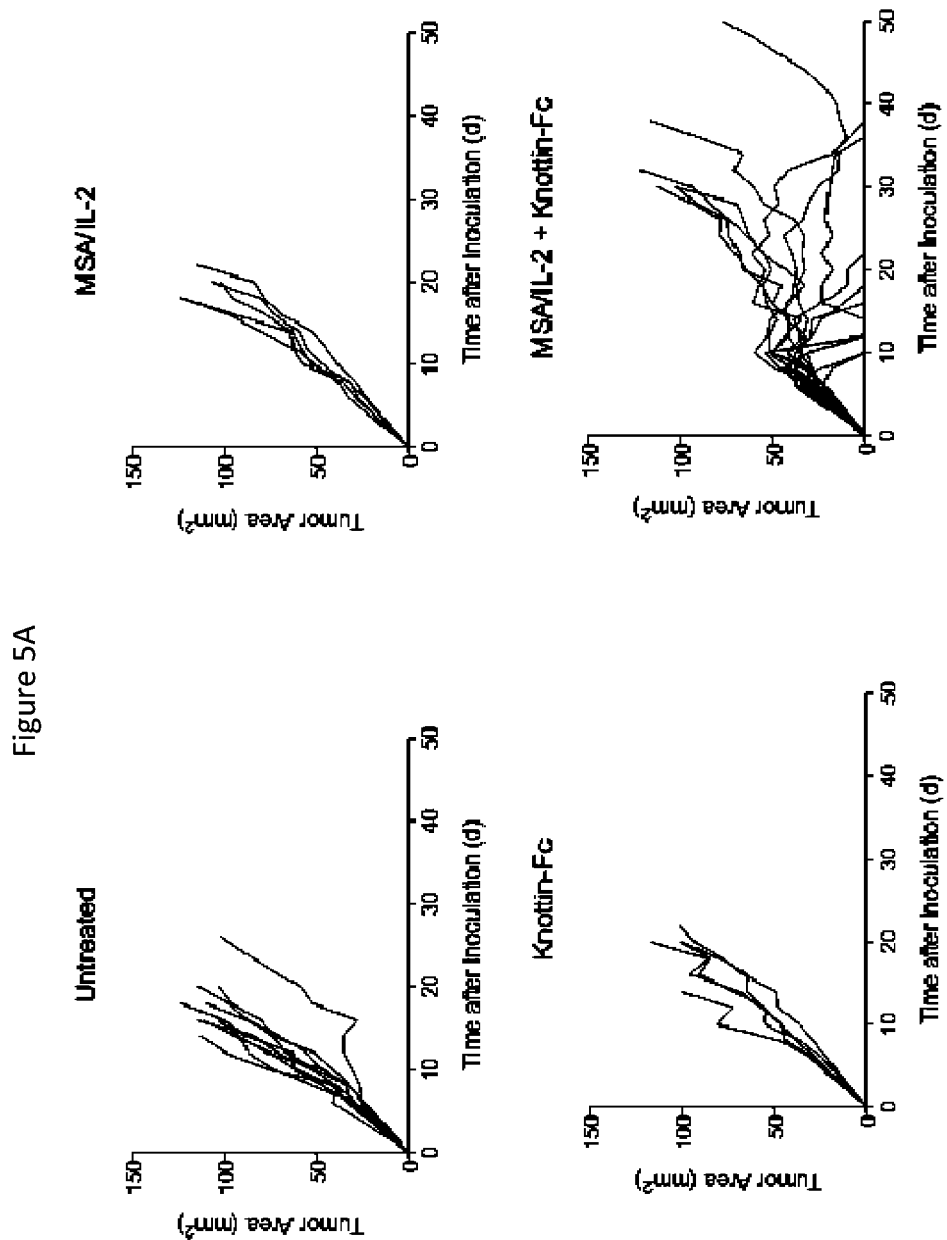
Figure 5B:
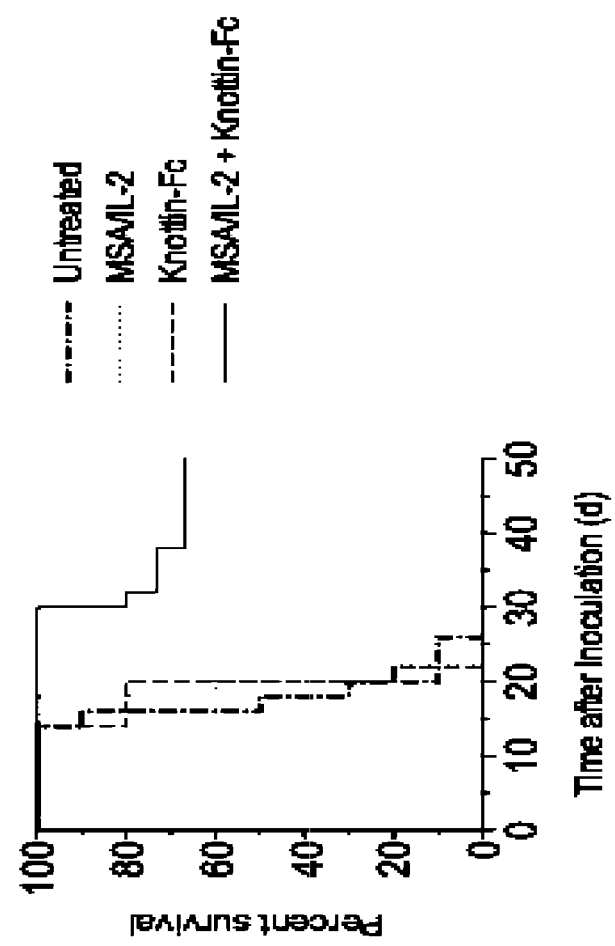

FIGS. 5A and 5B depict synergistic tumor control in established Ag104A fibrosarcoma tumors. $1 \times 10^6$ Ag104A cells were injected into the flanks of C3H/HeN mice. 12.5 µg MSA/IL-2 and/or 500 µg knottin-Fc was administered on day 6 after tumor inoculation, and every 6 days after for a total of four treatments. FIG. 5A) Tumor area graphs for each treatment. FIG. 5B) Kaplan-Meier survival plot.

Figure 6A:
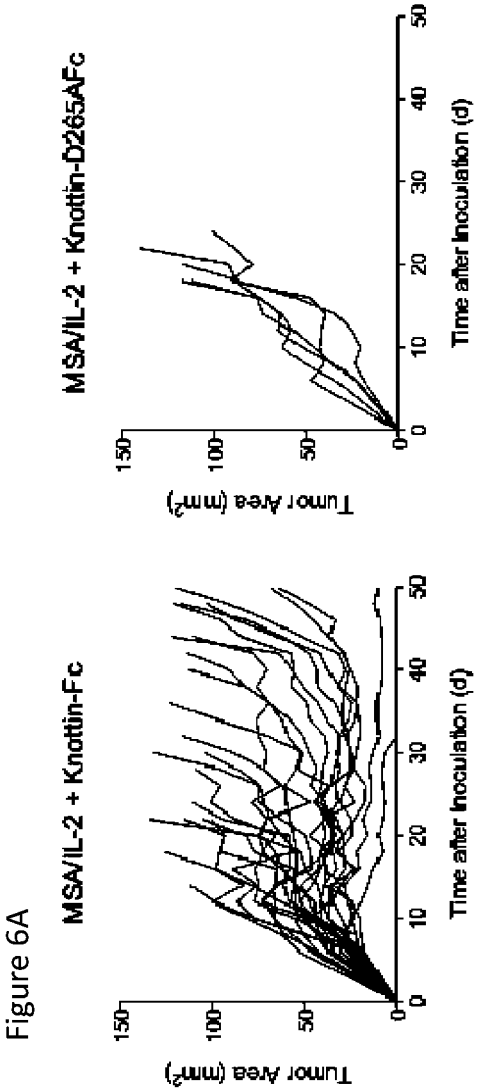
Figure 6B:
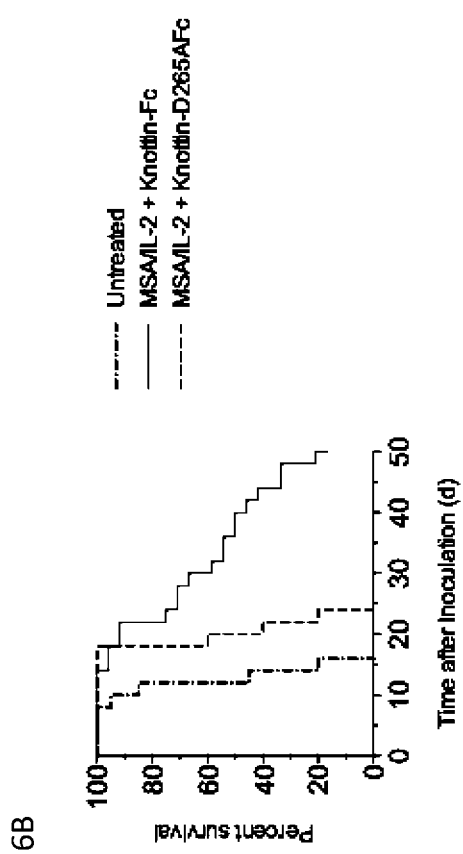

FIGS. 6A and 6B depict synergistic tumor control in established B16F10 melanoma tumors. $1 \times 10^6$ B16F10 cells were injected into the flanks of C57BL/6 mice. 30 µg MSA/IL-2 was and 500 µg knottin-Fc or knottin-Fc D265A was administered on day 6 after tumor inoculation and every day after for a total of four treatments. FIG. 6A) Tumor area graphs for each treatment. FIG. 6B) Kaplan-Meier survival plot.

Figure 7A:
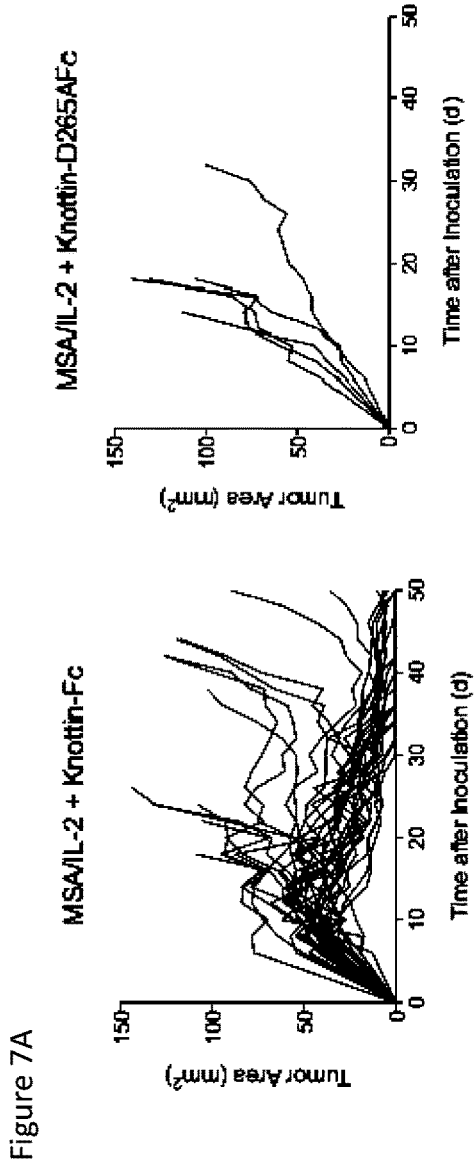
Figure 7B:
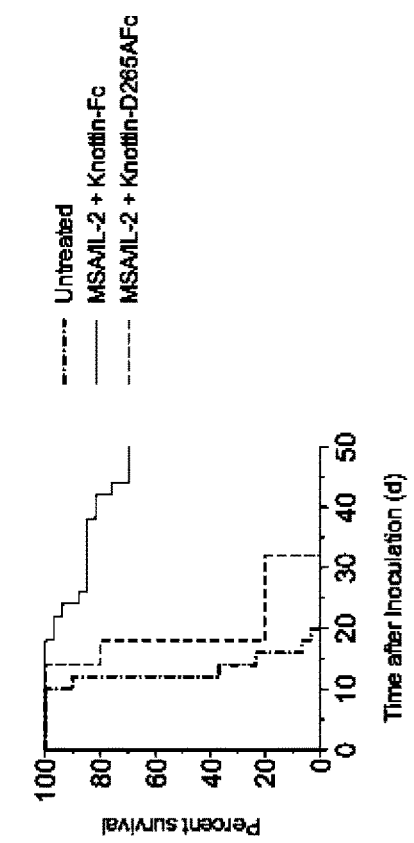

FIGS. 7A and 7B depict synergistic tumor control in established MC38 tumors. $1 \times 10^6$ MC38 cells were injected into the flanks of C57BL/6 mice and 30 µg MSA/IL-2 and 500 µg knottin-Fc or knottin-Fc D265A was administered on day 6 after tumor inoculation and every 6 days after for a total of four treatments. FIG. 7A) Tumor area graphs for each treatment. FIG. 7B) Kaplan-Meier survival plot.

Figure 8A:
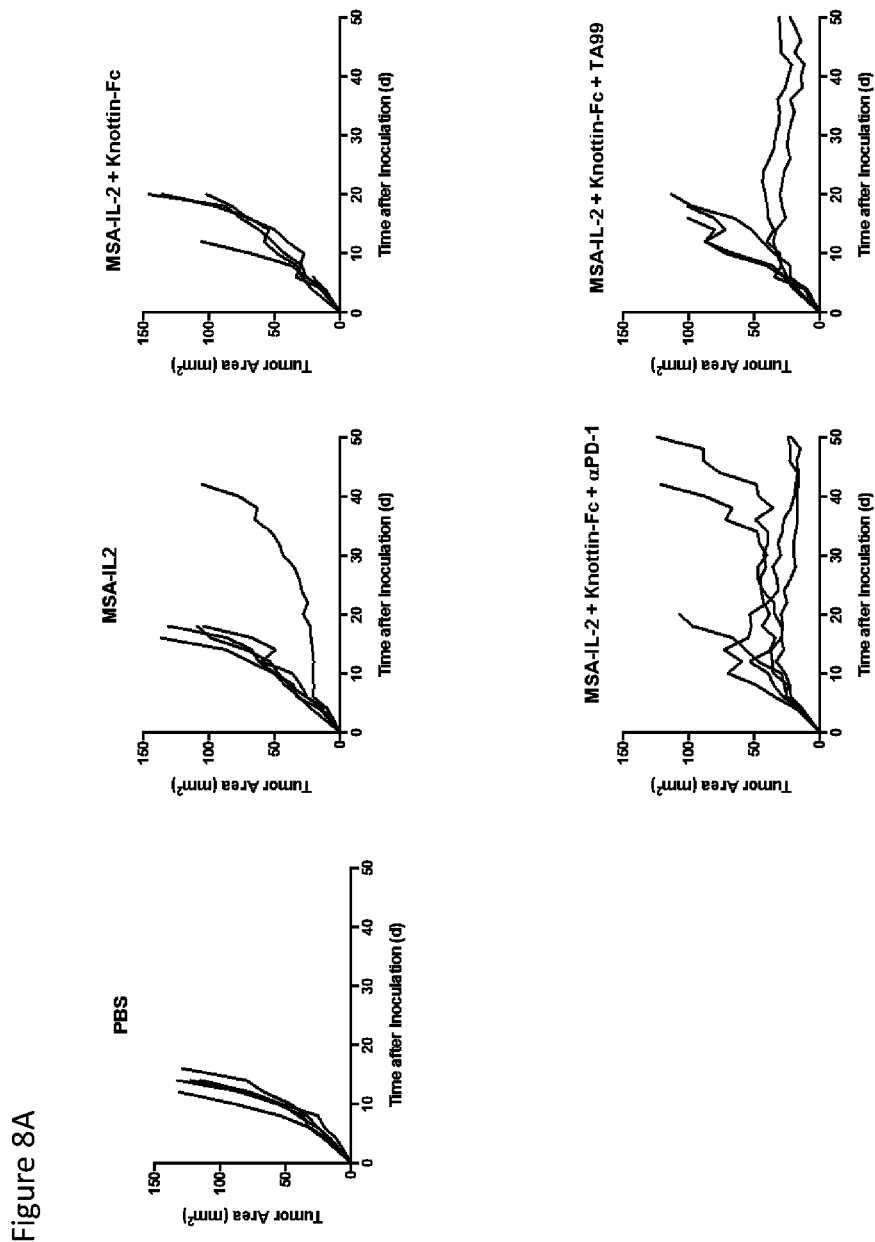
Figure 8B:
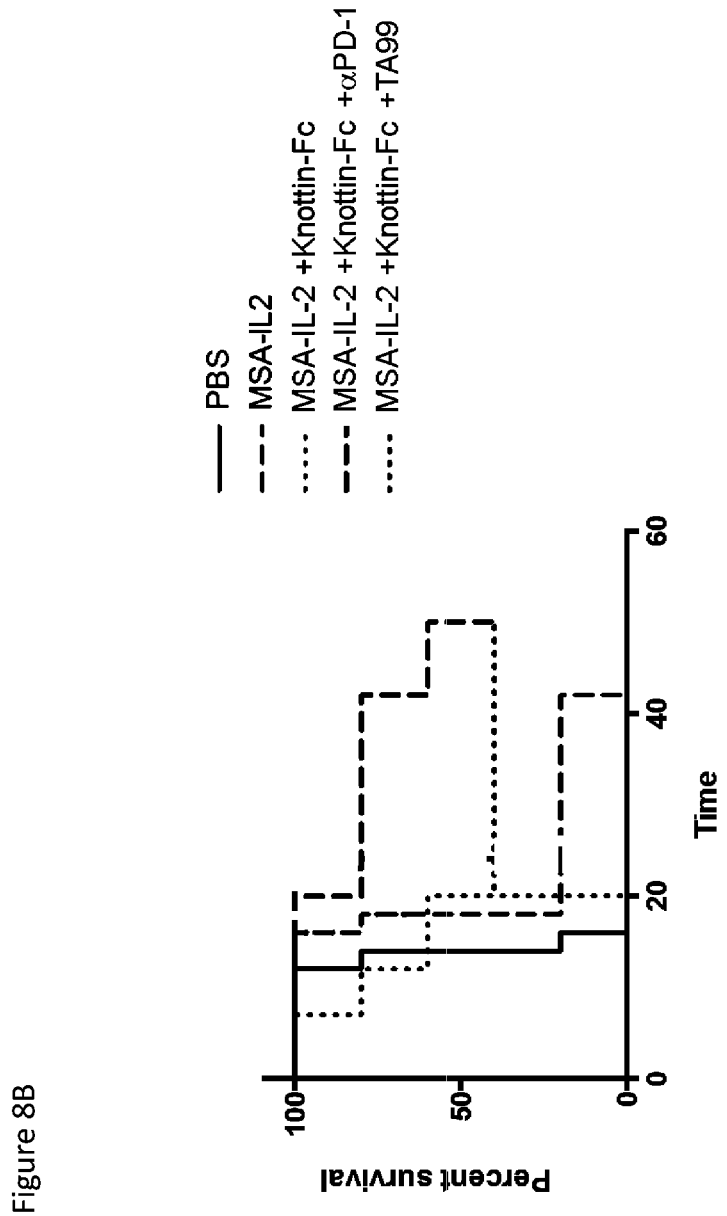

FIGS. 8A and 8B depict synergistic tumor control with an antibody in established B16F10 tumors. $1 \times 10^6$ B16F10 cells were injected into the flanks of C57BL/6 mice. 30 µg MSA/IL-2 was administered every 6 days beginning on day 6 after tumor inoculation for a total of 5 treatments. 200 µg knottin-Fc was administered daily from days 6-30 after tumor inoculation. Antibodies against TYRP-1 (TA99) were administered at 100 µg per mouse every 6 days starting on day 6 after tumor inoculation. Antibodies against PD-1 (for immune checkpoint blockade) were administered at 200 µg per mouse every 6 days starting on day 6 after tumor inoculation. FIG. 8A) Tumor area graphs for each treatment. FIG. 8B) Kaplan-Meier survival plot.

Figure 9A:
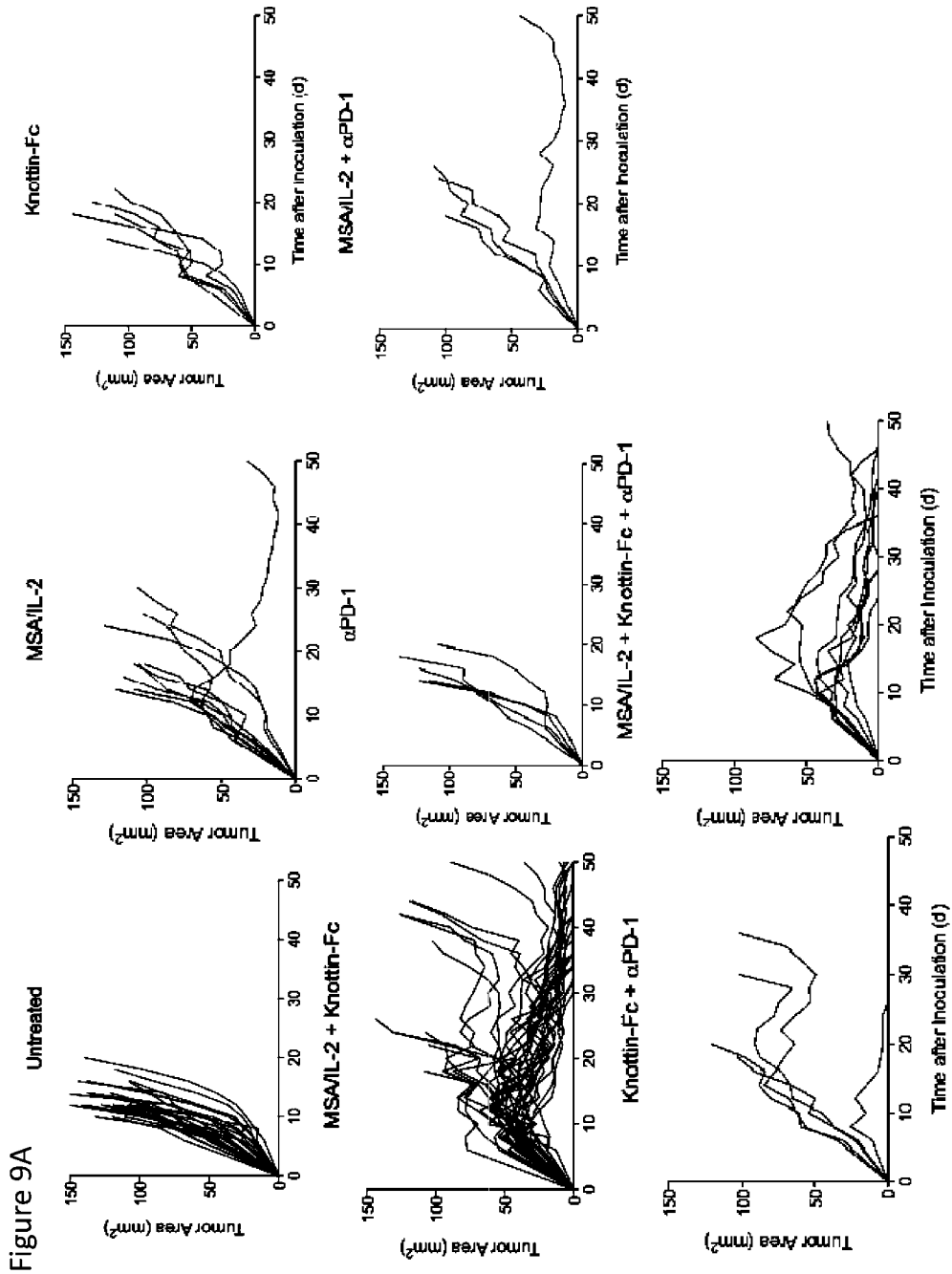

FIGS. 9A and 9B depict synergistic tumor control with an antibody in established MC38 tumors. $1 \times 10^6$ MC38 cells were injected into the flanks of C57BL/6 mice. 30 µg MSA/IL-2, 500 µg knottin-Fc, and/or 200 µg anti-PD-1 antibody was administered on day 6 after tumor inoculation and every 6 days after for a total of four treatments. FIG. 9A) Tumor area graphs for each treatment. FIG. 9B) Kaplan-Meier survival plot.

Figure 10:
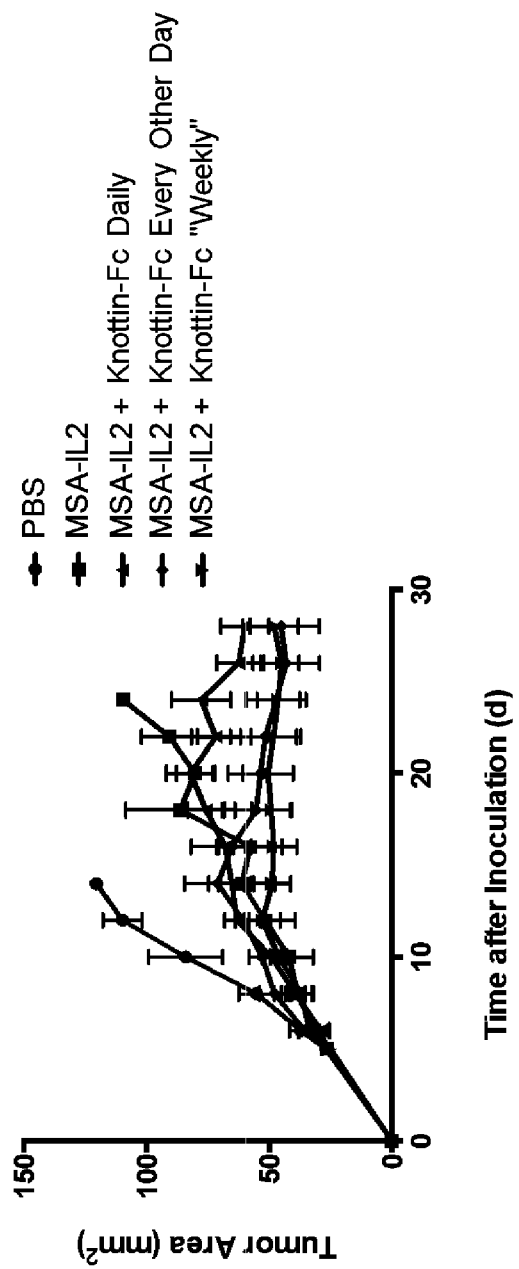

FIG. 10 is a line graph depicting tumor growth control comparing dosing schedules of knottin-Fc with MSA-IL-2 in the B16F10 tumor model. 30 µg MSA/IL-2 was administered on days 6, 12, 18 and 24 after tumor inoculation. 200 µg knottin-Fc was administered daily or every other day starting 6 days after tumor inoculation. 500 µg knottin-Fc was administered for the weekly regiment on the same days as MSA/IL-2. Mean tumor area is plotted with 5 mice per group and error bars represent SEM.

Figure 11:
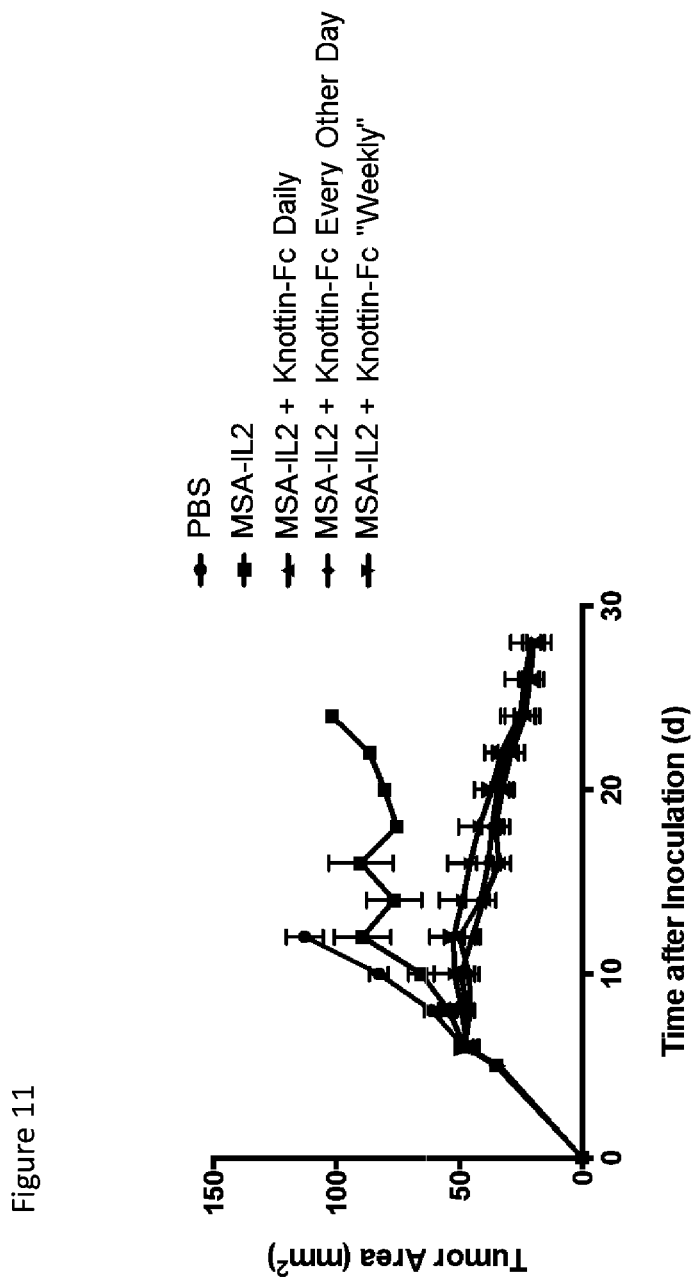

FIG. 11 is a line graph depicting tumor growth control comparing dosing schedules of knottin-Fc with MSA/IL-2 in the MC38 tumor model. 30 µg MSA/IL-2 was administered on days 6, 12, 18 and 24 after tumor inoculation. 200 µg knottin-Fc was administered daily or every other day starting 6 days after tumor inoculation. 500 µg knottin-Fc was administered for the weekly regiment on the same days as MSA/IL-2. Mean tumor area is plotted with 5 mice per group and error bars represent SEM.

Figure 12:
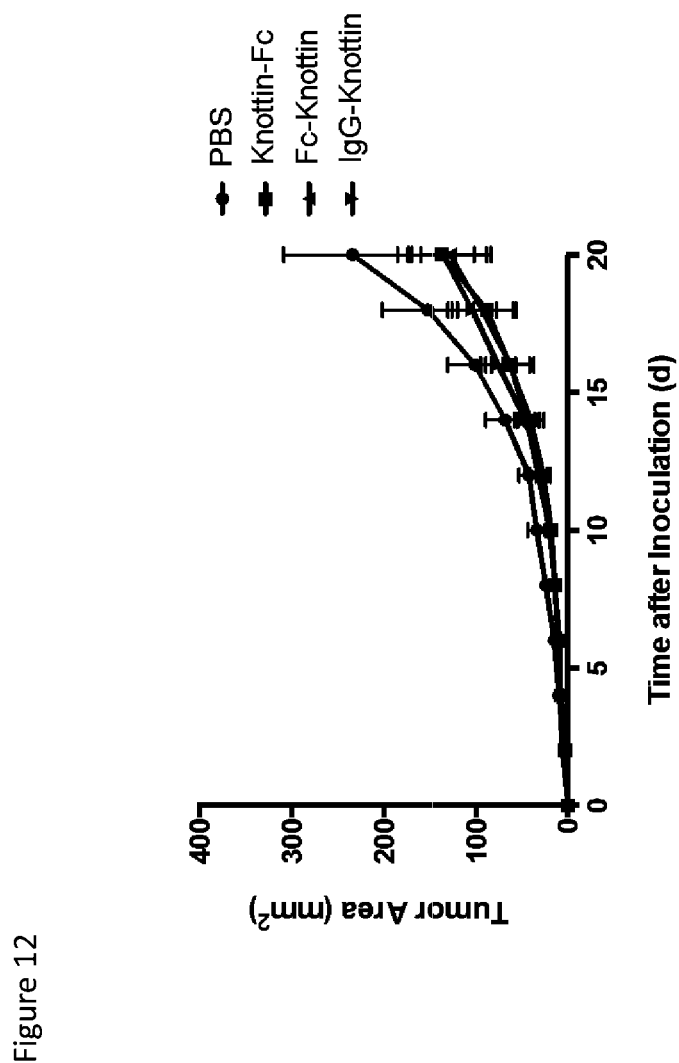

FIG. 12 is a line graph depicting tumor control in subcutaneous B16F10 tumors. Fc was either fused to the N-terminus (knottin-Fc) or C-terminus (Fc-knottin) to compare efficacies of fusion placement. Additionally, knottin was fused to the heavy chain of an irrelevant IgG on the C-terminus (IgG-knottin). Mice were treated with 80 µg knottin-Fc or Fc-knottin or 200 µg IgG-knottin every two days starting immediately after tumor inoculation.

Figure 13:
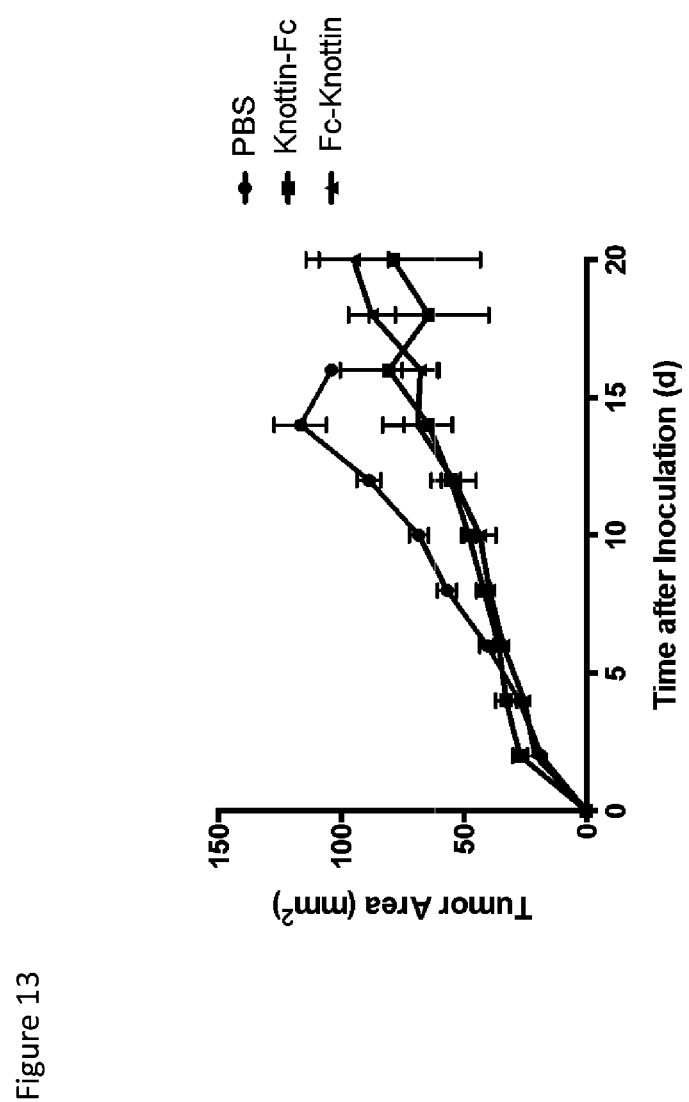

FIG. 13 is a line graph depicting tumor control in subcutaneous MC38 tumors. Fc was either fused to the N-terminus (knottin-Fc) or C-terminus (Fc-knottin) to compare efficacies of fusion placement. Additionally, knottin was fused to the heavy chain of an irrelevant IgG on the C-terminus (IgG-knottin). Mice were treated with 200 µg knottin-Fc or Fc-knottin every two days starting immediately after tumor inoculation.

Figure 14A:
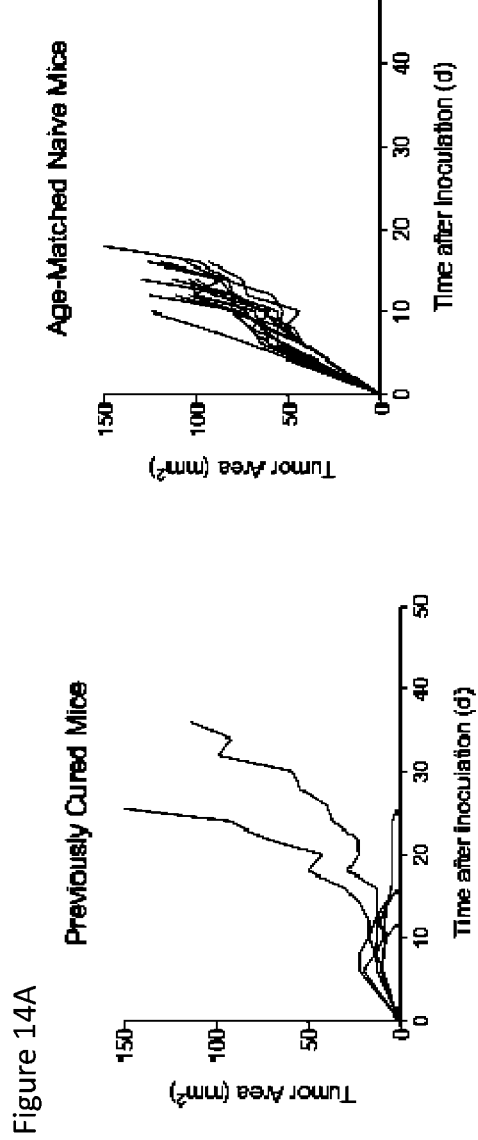
Figure 14B:
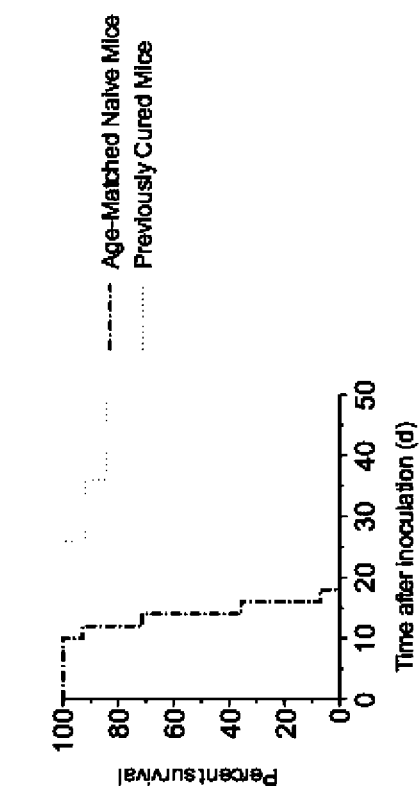

FIGS. 14A and 14B depict tumor control after secondary tumor challenge with MC38 tumors cells. Previously cured mice (treated with MSA/IL-2 and knottin-Fc) and age-matched naïve mice were inoculated with $1 \times 10^6$ MC38 tumor cells in the opposite flank 16-20 weeks after the initial tumor inoculation. No further treatment was administered. FIG. 14A) Tumor area graphs for previously cured mice and age-matched naïve mice following secondary tumor challenge. FIG. 14B) Kaplan-Meier plot of mice subjected to secondary tumor challenge.

Figures 15A, 15B:
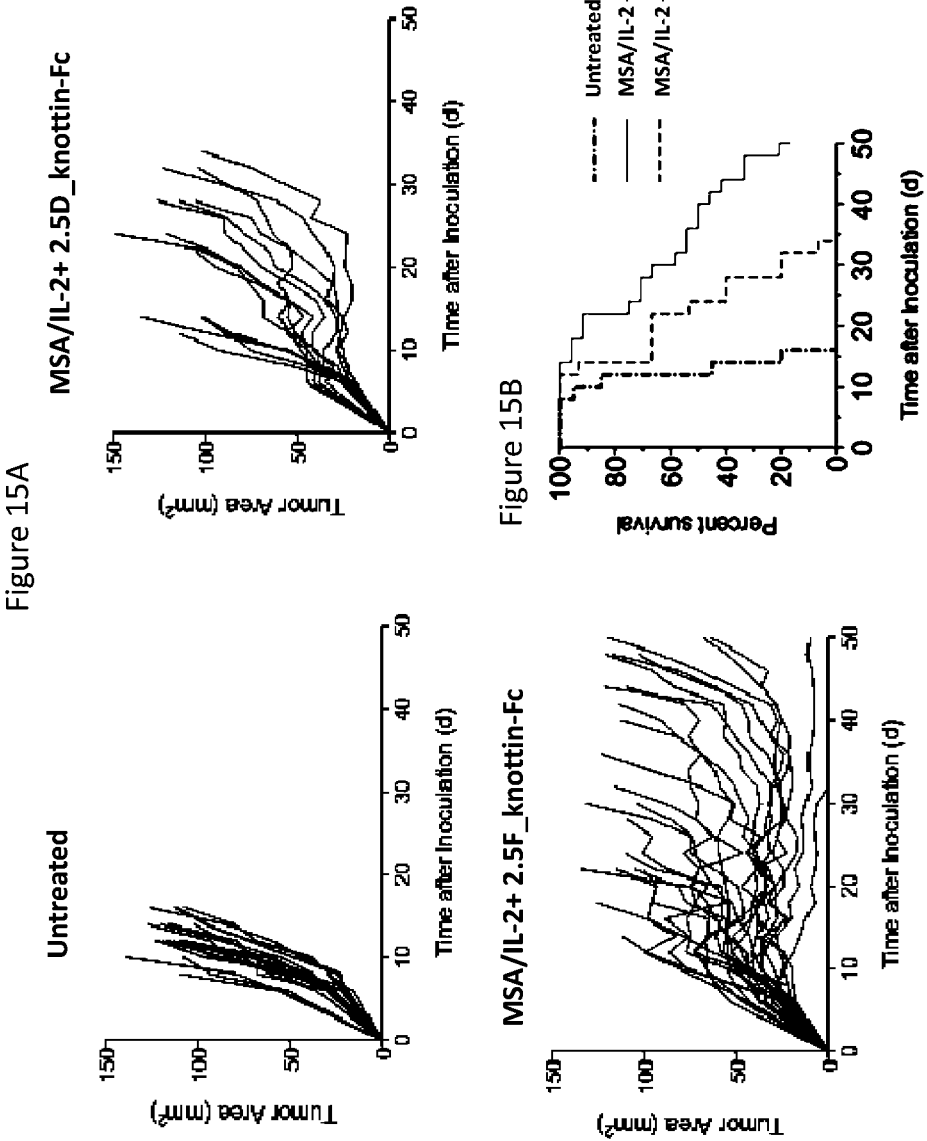

FIGS. 15A and 15B depict synergistic tumor control in established B16F10 melanoma tumors. $1 \times 10^6$ B16F10 cells were injected into the flanks of C57BL/6 mice. 30 µg MSA/IL-2, 500 µg knottin-Fc that targets 3 integrins ("2.5F_knottin-Fc"), and/or knottin-Fc that targets 2 integrins ("2.5D_knottin-Fc"), was administered on day 6 after tumor inoculation, and every 6 days after for a total of four treatments. FIG. 15A) Tumor area graphs for each treatment. FIG. 15B) Kaplan-Meier survival plot.

FIGS. 16A and 16B depict synergistic tumor control in established MC38 tumors. $1 \times 10^6$ MC38 cells were injected into the flanks of C57BL/6 mice. 30 µg MSA/IL-2, 500 µg knottin-Fc that targets 3 integrins ("2.5F_knottin-Fc"), and/or knottin-Fc that targets 2 integrins ("2.5D_knottin-Fc"), was administered on day 6 after tumor inoculation, and every 6 days after for a total of four treatments. FIG. 16A) Tumor area graphs for each treatment. FIG. 16B) Kaplan-Meier survival plot.

FIGS. 17A and 17B depict synergistic tumor control in established Ag104A angiosarcoma tumors. $1 \times 10^6$ Ag104A cells were injected into the flanks of C3H/HeN mice. 30 µg MSA/IL-2, 500 µg knottin-Fc that targets 3 integrins ("2.5F_knottin-Fc"), and/or knottin-Fc that targets 2 integrins ("2.5D_knottin-Fc") was administered on day 6 after tumor inoculation, and every 6 days after for a total of four treatments. FIG. 17A) Tumor area graphs for each treatment. FIG. 17B) Kaplan-Meier survival plot.

Figure 18A:
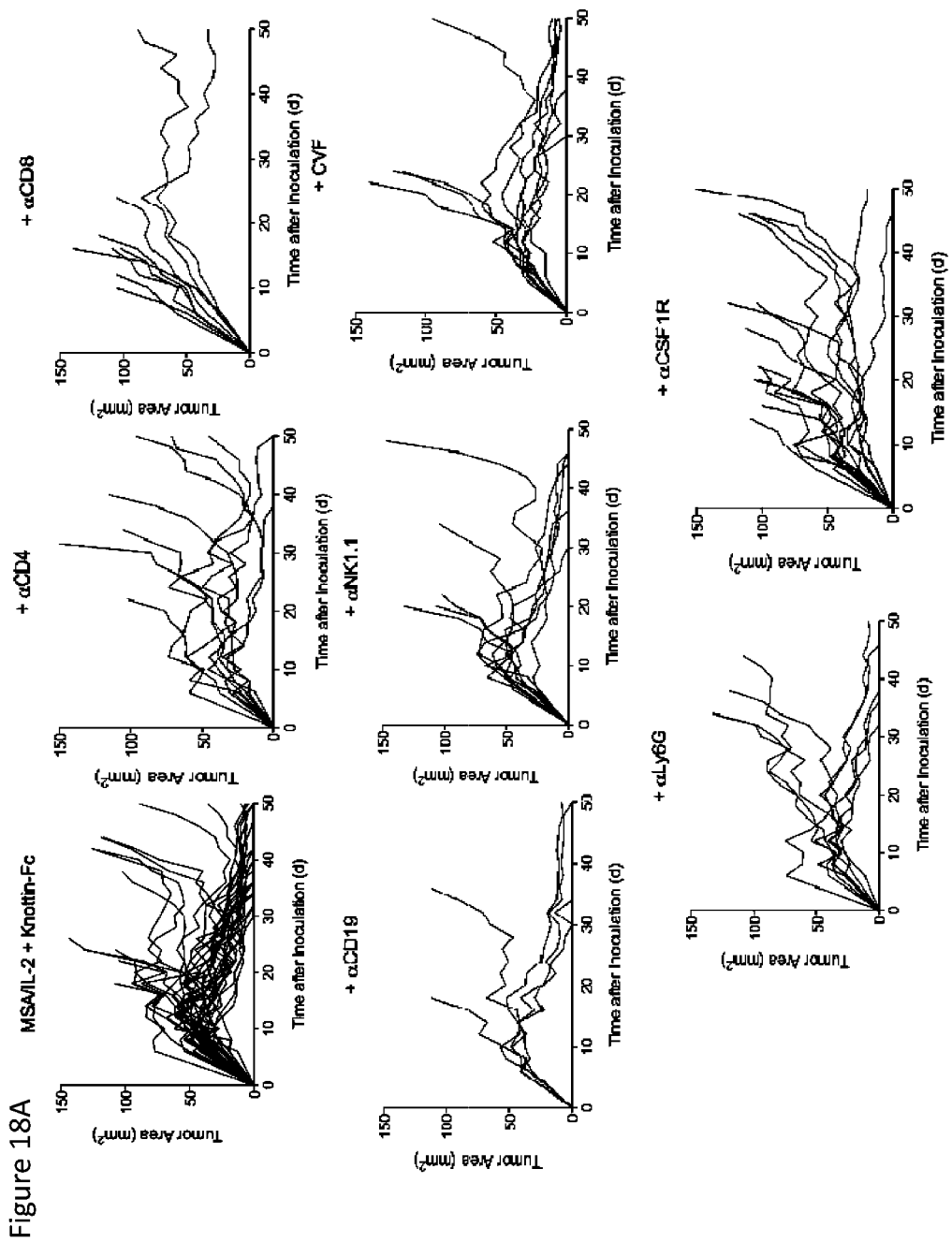
Figure 18B:
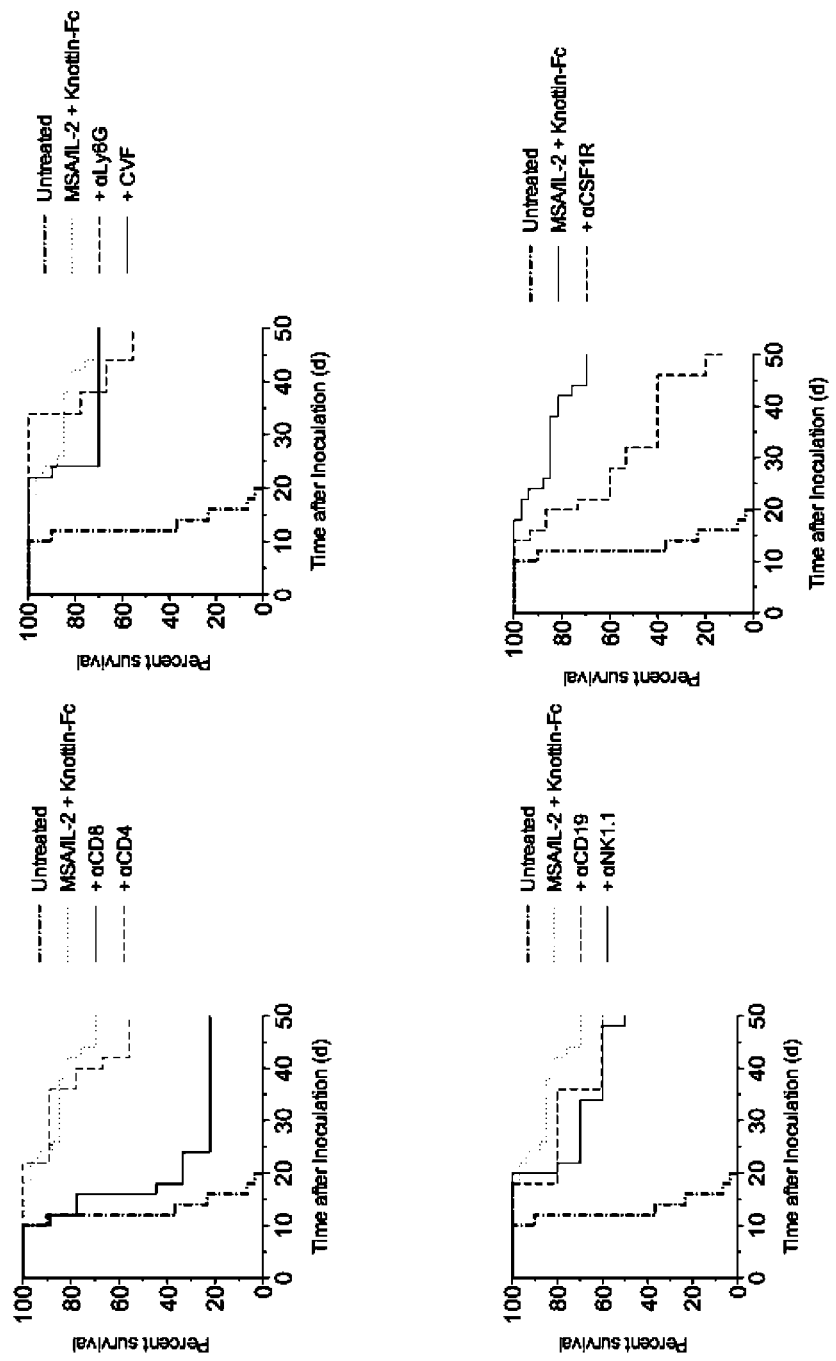

FIGS. 18A and 18B depict the effect of immune cell depletions on survival of mice with established MC38 tumors treated with knottin-Fc and MSA/IL-2. 1×10$^6$ MC38 cells were injected into the flanks of C57BL/6 mice. 30 µg MSA/IL-2 and 500 µg knottin-Fc was administered on day 6 after tumor inoculation, and every 6 days after for a total of four treatments. 400 µg anti-CD8, anti-CD4, anti-NK1.1, anti-Ly6G or anti-CD19 antibodies were dosed every four days for a total of six treatments starting on day 4 after tumor inoculation. 300 µg anti-CSF-1R was dosed every two days for a total of eleven treatments starting on day 5 of tumor inoculation. 30 µg cobra venom factor (CVF) was administered every 6 days for a total of 4 treatments starting on day 5 after tumor inoculation. FIG. 18A) Tumor area graphs for each treatment. FIG. 18B) Kaplan-Meier survival plots.

Figure 19A:
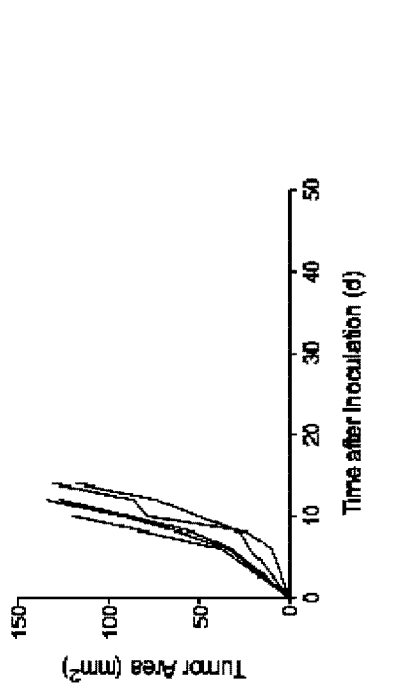
Figure 19B:
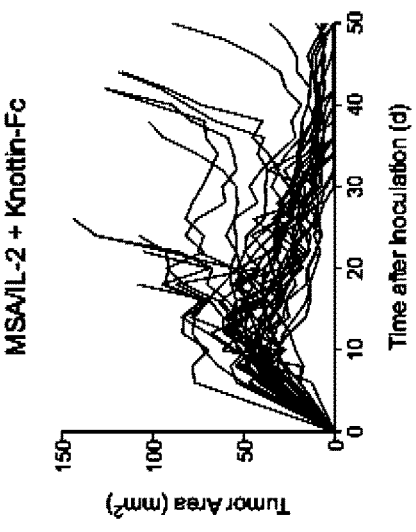
Figure 19B:
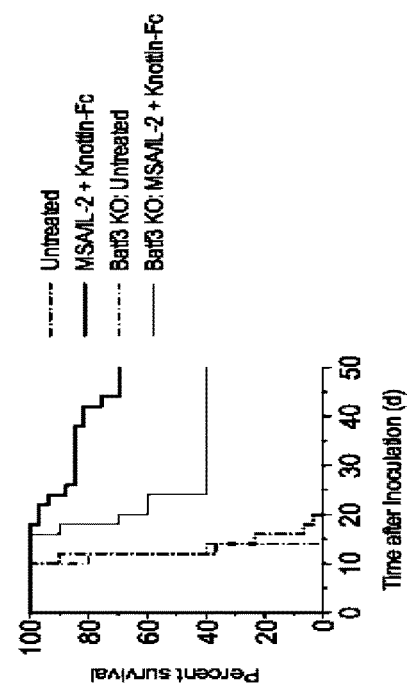
Figure 19B:
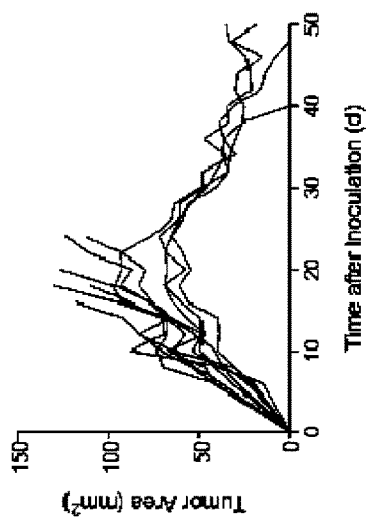

FIGS. 19A and 19B depict the effect of dendritic cell depletion on survival of mice with established MC38 tumors. 1×10$^6$ MC38 cells were injected into the flanks of C57BL/6 mice or Batf3−/− mice. 30 µg MSA/IL-2 and 500 µg knottin-Fc was administered on day 6 after tumor inoculation, and every 6 days after for a total of four treatments. FIG. 19A) Tumor area graphs for each treatment. FIG. 19B) Kaplan-Meier survival plot.

FIGS. 20A and 20B depict the role of IFNγ in the efficacy of treatment with MSA/IL-2 and knottin-Fc in mice with established MC38 tumors. 1×10$^6$ MC38 cells were injected into the flanks of C57BL/6 mice. 30 µg MSA/IL-2 and 500 µg knottin-Fc was administered on day 6 after tumor inoculation, and every 6 days after for a total of four treatments. 200 µg anti-IFNγ antibody was administered every two days for a total of eleven treatments starting on day 5 after tumor inoculation. FIG. 20A) Tumor area graphs for each treatment. FIG. 20B) Kaplan-Meier survival plot.

Figure 21A:
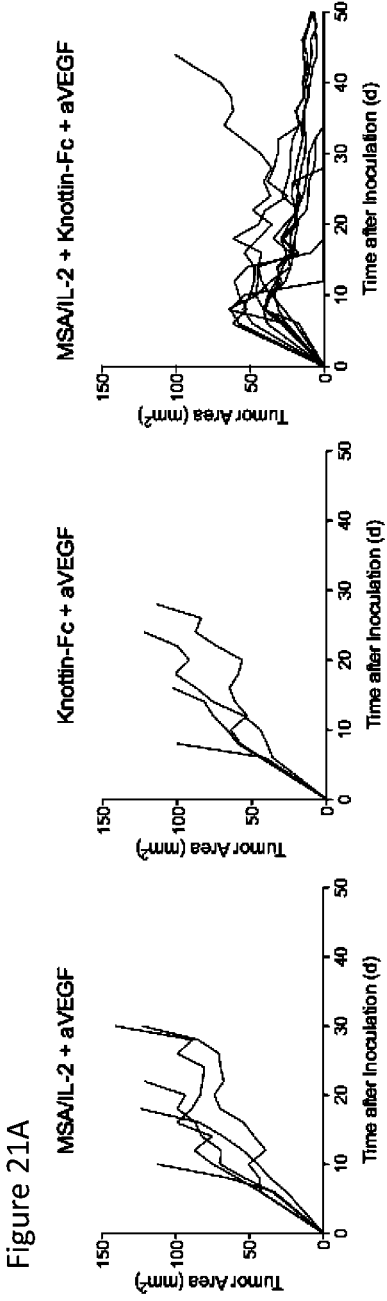
Figure 21B:
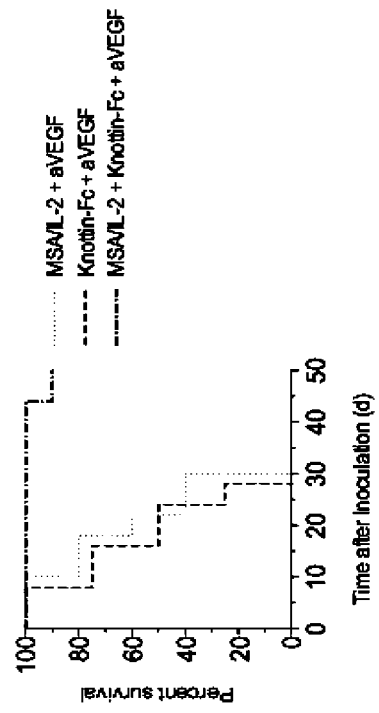

FIGS. 21A and 21B depict synergistic tumor control in established MC38 tumors. 1×10$^6$ MC38 cells were injected into the flanks of C57BL/6 mice. 30 µg MSA/IL-2, 500 µg knottin-Fc, and/or 200 µg anti-VEGF antibody was administered on day 6 after tumor inoculation, and every 6 days after for a total for 4 treatments. FIG. 21A) Tumor area graphs for each treatment. FIG. 21B) Kaplan-Meier survival plot.

Figure 22:
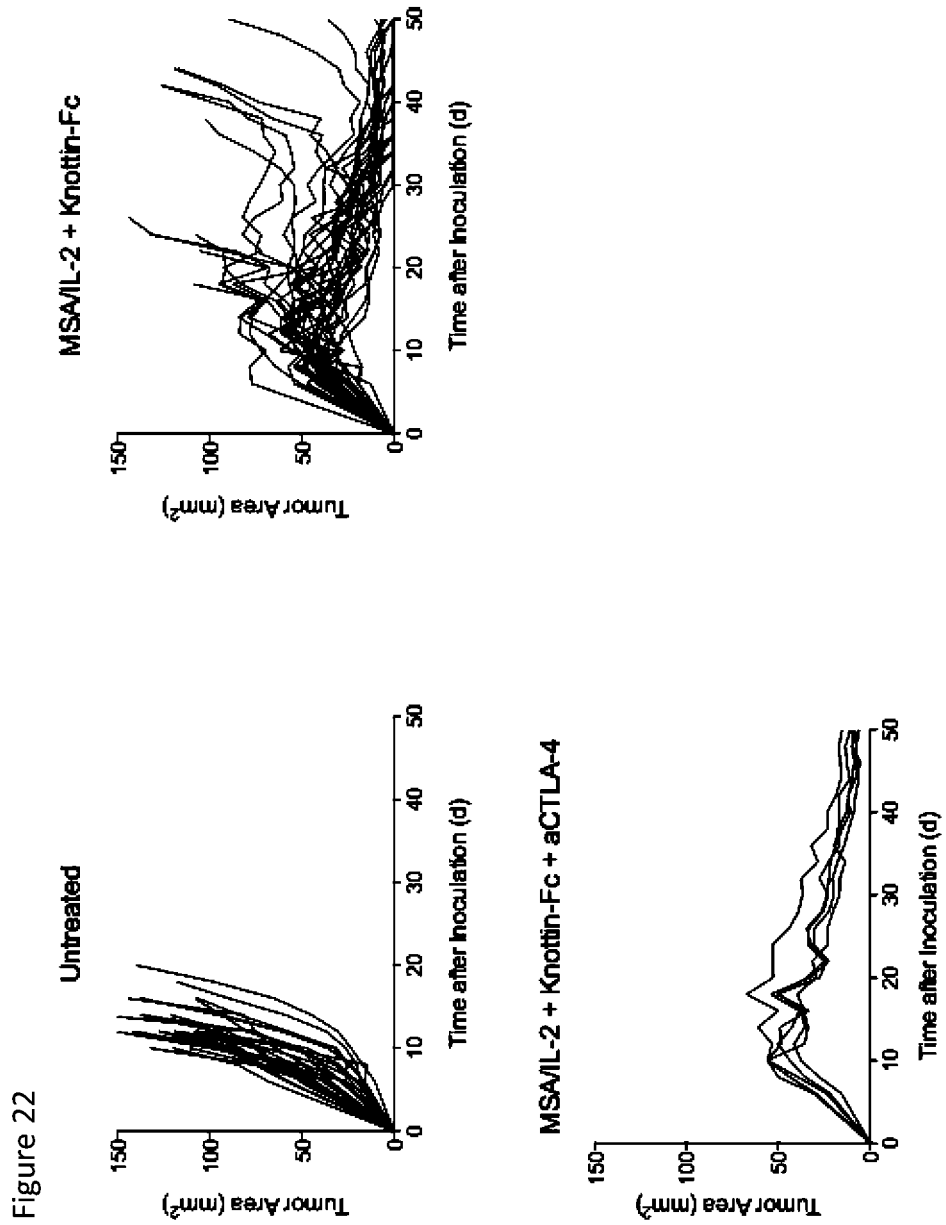

FIG. 22 shows tumor area graphs depicting synergistic tumor control in established MC38 tumors. 1×10$^6$ MC38 cells were injected into the flanks of C57BL/6 mice. 30 µg MSA/IL-2, 500 µg knottin-Fc, and/or 200 µg anti-CTLA-4 antibody was administered on day 6 after tumor inoculation, and every 6 days after for a total for 4 treatments.

FIGS. 23A and 23B depict the synergistic tumor control in established B16F10 tumors. 1×10$^6$ B16F10 cells were injected into the flanks of C57BL/6 mice. 30 µg MSA/IL-2, 500 µg knottin-Fc, 200 µg anti-VEGF antibody and/or 200 µg anti-CTLA-4 antibody was administered on day 6 after tumor inoculation, and every 6 days after for a total for 4 treatments. FIG. 23A) Tumor area graphs for each treatment. FIG. 23B). Kaplan-Meier survival plots

DETAILED DESCRIPTION OF THE INVENTION

Definitions

Terms used in the claims and specification are defined as set forth below unless otherwise specified. In the case of direct conflict with a term used in a parent provisional patent application, the term used in the instant specification shall control.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups {e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions," can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al. Biol. Chem. 260: 2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene. Polynucleotides used herein can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, "interleukin (IL)-2," refers to a pleiotropic cytokine that activates and induces proliferation of T cells and natural killer (NK) cells. IL-2 signals by binding its receptor, IL-2R, which is comprised of alpha, beta, and gamma subunits. IL-2 signaling stimulates proliferation of antigen-activated T cells.

As used herein, the term "PK" is an acronym for "pharmacokinetic" and encompasses properties of a compound including, by way of example, absorption, distribution, metabolism, and elimination by a subject. As used herein, an "extended-PK group" refers to a protein, peptide, or moiety that increases the circulation half-life of a biologically active molecule when fused to or administered together with the biologically active molecule. Examples of an extended-PK group include PEG, human serum albumin (HSA) binders (as disclosed in U.S. Publication Nos. 2005/0287153 and 2007/0003549, PCT Publication Nos. WO 2009/083804 and WO 2009/133208, and SABA molecules as described in US2012/094909), human serum albumin, Fc or Fc fragments and variants thereof, and sugars (e.g., sialic acid). Other exemplary extended-PK groups are disclosed in Kontermann et al., Current Opinion in Biotechnology 2011; 22:868-876, which is herein incorporated by reference in its entirety. As used herein, an "extended-PK IL-2" refers to an IL-2 moiety in combination with an extended-PK group. In one embodiment, the extended-PK IL-2 is a fusion protein in which an IL-2 moiety is linked or fused to an extended-PK group. An exemplary fusion protein is an HSA/IL-2 fusion in which one or more IL-2 moieties are linked to HSA.

The term "extended-PK IL-2" is also intended to encompass IL-2 mutants with mutations in one or more amino acid residues that enhance the affinity of IL-2 for one or more of its receptors, for example, CD25. In one embodiment, the IL-2 moiety of extended-PK IL-2 is wild-type IL-2. In another embodiment, the IL-2 moiety is a mutant IL-2 which exhibits greater affinity for CD25 than wild-type IL-2. When a particular type of extended-PK group is indicated, such as HSA-IL-2, it should be understood that this encompasses both HSA or MSA fused to a wild-type IL-2 moiety or HSA or MSA fused to a mutant IL-2 moiety.

In certain aspects, the extended-PK IL-2 or knottin-Fc described can employ one or more "linker domains," such as polypeptide linkers. As used herein, the term "linker" or "linker domain" refers to a sequence which connects two or more domains (e.g., the PK moiety and IL-2) in a linear sequence. As used herein, the term "polypeptide linker" refers to a peptide or polypeptide sequence (e.g., a synthetic peptide or polypeptide sequence) which connects two or more domains in a linear amino sequence of a polypeptide chain. For example, polypeptide linkers may be used to connect an IL-2 moiety or an integrin binding polypeptide to an Fc domain or other PK-extender such as HSA. In some embodiments, such polypeptide linkers can provide flexibility to the polypeptide molecule. Exemplary linkers include Gly-Ser linkers.

As used herein, the terms "linked," "fused", or "fusion" are used interchangeably. These terms refer to the joining together of two or more elements or components or domains, by whatever means including chemical conjugation or recombinant means. Methods of chemical conjugation (e.g., using heterobifunctional crosslinking agents) are known in the art.

The term "integrin" means a transmembrane heterodimeric protein important for cell adhesion. Integrins comprise an α and β subunit. These proteins bind to extracellular matrix components (e.g., fibronectin, collagen, laminin, etc.) and respond by inducing signaling cascades. Integrins bind to extracellular matrix components by recognition of the RGD motif. Certain integrins are found on the surface of tumor cells and therefore make promising therapeutic targets. In certain embodiments, the integrins being targeted are $\alpha_v\beta_3$, $\alpha_v\beta_5$, and $\alpha_5\beta_1$, individually or in combination.

The term "integrin-binding polypeptide" refers to a polypeptide which includes an integrin-binding domain or loop within a knottin polypeptide scaffold. The integrin binding domain or loop includes at least one RGD peptide. In certain embodiments, the RGD peptide is recognized by $\alpha_v\beta_3$, $\alpha_v\beta_5$, or $\alpha_5\beta_1$. In certain embodiments the RGD peptide binds to a combination of $\alpha_v\beta_3$, $\alpha_v\beta_5$, and/or $\alpha_5\beta_1$. These specific integrins are found on tumor cells and their vasculature and are therefore the targets of interest.

The term "loop domain" refers to an amino acid subsequence within a peptide chain that has no ordered secondary structure, and resides generally on the surface of the peptide. The term "loop" is understood in the art as referring to secondary structures that are not ordered as in the form of an alpha helix, beta sheet, etc.

The term "integrin-binding loop" refers to a primary sequence of about 9-13 amino acids which is typically created ab initio through experimental methods such as directed molecular evolution to bind to integrins. In certain embodiments, the integrin-binding loop includes an RGD peptide sequence, or the like, placed between amino acids which are particular to the scaffold and the binding specificity desired. The RGD-containing peptide or like (RYD, etc) is generally not simply taken from a natural binding sequence of a known protein. The integrin-binding loop is preferably inserted within a knottin polypeptide scaffold between cysteine residues, and the length of the loop adjusted for optimal integrin-binding depending on the three-dimensional spacing between cysteine residues. For example, if the flanking cysteine residues in the knottin scaffold are linked to each other, the optimal loop may be shorter than if the flanking cysteine residues are linked to cysteine residues separated in primary sequence. Otherwise, particular amino acid substitutions can be introduced to constrain a longer RGD-containing loop into an optimal conformation for high affinity integrin binding. The knottin polypeptide scaffolds used herein may contain certain modifications made to truncate the native knottin, or to remove a loop or unnecessary cysteine residue or disulfide bond.

Incorporation of integrin-binding sequences into a molecular (e.g., knottin polypeptide) scaffold provides a framework for ligand presentation that is more rigid and stable than linear or cyclic peptide loops. In addition, the conformational flexibility of small peptides in solution is high, and results in large entropic penalties upon binding.

Incorporation of an integrin-binding sequence into a knottin polypeptide scaffold provides conformational constraints that are required for high affinity integrin binding. Furthermore, the scaffold provides a platform to carry out protein engineering studies such as affinity or stability maturation.

As used herein, the term "knottin protein" refers to a structural family of small proteins, typically 25-40 amino acids, which bind to a range of molecular targets like proteins, sugars and lipids. Their three-dimensional structure is essentially defined by a peculiar arrangement of three to five disulfide bonds. A characteristic knotted topology with one disulfide bridge crossing the macro-cycle limited by the two other intra-chain disulfide bonds, which was found in several different microproteins with the same cystine network, lent its name to this class of biomolecules. Although their secondary structure content is generally low, the knottins share a small triple-stranded antiparallel β-sheet, which is stabilized by the disulfide bond framework. Biochemically well-defined members of the knottin family, also called cystine knot proteins, include the trypsin inhibitor EETI-II from *Ecballium elaterium* seeds, the neuronal N-type Ca2+ channel blocker ω-conotoxin from the venom of the predatory cone snail *Conus geographus*, agouti-related protein (AgRP, See Millhauser et al., "Loops and Links: Structural Insights into the Remarkable Function of the Agouti-Related Protein," Ann. N.Y. Acad. Sci., Jun. 1, 2003; 994(1): 27-35), the omega agatoxin family, etc. A suitable agatoxin sequence [SEQ ID NO: 41] is given in U.S. Pat. No. 8,536,301, having a common inventor with the present application. Other agatoxin sequences suitable for use in the methods disclosed herein include, Omega-agatoxin-Aa4b (GenBank Accession number P37045) and Omega-agatoxin-Aa3b (GenBank Accession number P81744). Other knottin sequences suitable for use in the methods disclosed herein include, knottin [*Bemisia tabaci*] (GenBank Accession number FJ601218.1), Omega-lycotoxin (Genbank Accession number P85079), mu-O conotoxin MrVIA=voltage-gated sodium channel blocker (Genbank Accession number AAB34917) and *Momordica cochinchinensis* Trypsin Inhibitor I (MCoTI-I) or II (McoTI-II) (Uniprot Accession numbers P82408 and P82409 respectively).

Knottin proteins have a characteristic disulfide linked structure. This structure is also illustrated in Gelly et al., "The KNOTTIN website and database: a new information system dedicated to the knottin scaffold," Nucleic Acids Research, 2004, Vol. 32, Database issue D156-D159. A triple-stranded β-sheet is present in many knottins. The spacing between cysteine residues is important, as is the molecular topology and conformation of the integrin-binding loop.

The term "molecular scaffold" means a polymer having a predefined three-dimensional structure, into which an integrin-binding loop is incorporated, such as an RGD peptide sequence as described herein. The term "molecular scaffold" has an art-recognized meaning (in other contexts), which is also intended here. For example, a review by Skerra, "Engineered protein scaffolds for molecular recognition," *J. Mol. Recognit.* 2000; 13:167-187 describes the following scaffolds: single domains of antibodies of the immunoglobulin superfamily, protease inhibitors, helix-bundle proteins, disulfide-knotted peptides and lipocalins. Guidance is given for the selection of an appropriate molecular scaffold.

The term "knottin polypeptide scaffold" refers to a knottin protein suitable for use as a molecular scaffold, as described herein. Characteristics of a desirable knottin polypeptide scaffold for engineering include 1) high stability in vitro and in vivo, 2) the ability to replace amino acid regions of the scaffold with other sequences without disrupting the overall fold, 3) the ability to create multifunctional or bispecific targeting by engineering separate regions of the molecule, and 4) a small size to allow for chemical synthesis and incorporation of non-natural amino acids if desired. Scaffolds derived from human proteins are favored for therapeutic applications to reduce toxicity or immunogenicity concerns, but are not always a strict requirement. Other scaffolds that have been used for protein design include fibronectin (Koide et al., 1998), lipocalin (Beste et al., 1999), cytotoxic T lymphocyte-associated antigen 4 (CTLA-4) (Hufton et al., 2000), and tendamistat (McConnell and Hoess, 1995; Li et al., 2003). While these scaffolds have proved to be useful frameworks for protein engineering, molecular scaffolds such as knottins have distinct advantages: their small size and high stability.

As used herein, the term "EETI" means Protein Data Bank Entry (PDB) 2ETI. Its entry in the Knottin database is EETI-II. It has the sequence:

```
                                    (SEQ ID NO: 39)
       GC PRILMRCKQDSDCLAGCVCGPNGFCG.
```

As used herein, the term "AgRP" means PDB entry 1HYK. Its entry in the Knottin database is SwissProt AGRP_HUMAN, where the full-length sequence of 129 amino acids may be found. It comprises the sequence beginning at amino acid 87. An additional G is added to this construct. It also includes a C105A mutation described in Jackson, et al. 2002 Biochemistry, 41, 7565.

```
                                              (SEQ ID NO: 40)
GCVRLHESCLGQQVPCCDPCATCYC RFFNAF CYCR-KLGTAMNPCSRT
```

The bold and underlined portion, from loop 4, is replaced by the RGD sequences described herein. Loops 1 and 3 are shown between brackets below:

```
GC[VRLHES]CLGQQVPCC[DPCAT]CYCRFFNAFCYCR-
KLGTAMNPCSRT
```

As used herein, "integrin-binding-Fc fusion" is used interchangeably with "knottin-Fc" and refers to an integrin-binding polypeptide that includes an integrin-binding amino acid sequence within a knottin polypeptide scaffold and is operably linked to an Fc domain. In certain embodiments, the Fc domain is fused to the N-terminus of the integrin-binding polypeptide. In certain embodiments, the Fc domain is fused to the C-terminus of the integrin binding polypeptide. In some embodiments, the Fc domain is operably linked to the integrin-binding polypeptide via a linker.

As used herein, the term "Fc region" refers to the portion of a native immunoglobulin formed by the respective Fc domains (or Fc moieties) of its two heavy chains. As used herein, the term "Fc domain" refers to a portion of a single immunoglobulin (Ig) heavy chain wherein the Fc domain does not comprise an Fv domain. As such, an Fc domain can also be referred to as "Ig" or "IgG." In certain embodiments, an Fc domain begins in the hinge region just upstream of the papain cleavage site and ends at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In other embodiments, an Fc domain comprises a complete Fc domain (i.e., a hinge domain, a CH2 domain, and a CH3 domain). In one embodiment, an Fc domain comprises a hinge domain (or portion thereof) fused to a CH3 domain (or portion thereof). In another embodiment, an Fc domain comprises a CH2 domain (or portion thereof) fused to a CH3 domain (or portion thereof). In another embodiment, an Fc domain consists of a CH3 domain or portion thereof. In another embodiment, an Fc domain consists of a hinge domain (or portion thereof) and a CH3 domain (or portion thereof). In another embodiment, an Fc domain consists of a CH2 domain (or portion thereof) and a CH3 domain. In another embodiment, an Fc domain consists of a hinge domain (or portion thereof) and a CH2 domain (or portion thereof). In one embodiment, an Fc domain lacks at least a portion of a CH2 domain (e.g., all or part of a CH2 domain). An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. A human IgG1 constant region can be found at Uniprot P01857 and in Table 2 (i.e., SEQ ID NO: 1) The Fc domain of human IgG1 can be found in Table 2 (i.e., SEQ ID NO: 2). The Fc domain of human IgG1 with a deletion of the upper hinge region can be found in Table 2 (i.e., SEQ ID NO: 3). The Fc domain encompasses native Fc and Fc variant molecules. As with Fc variants and native Fc's, the term Fc domain includes molecules in monomeric or multimeric (e.g., dimeric) form, whether digested from whole antibody or produced by other means. The assignment of amino acid residue numbers to an Fc domain is in accordance with the definitions of Kabat. See, e.g., Sequences of Proteins of Immunological Interest (Table of Contents, Introduction and Constant Region Sequences sections), 5$^{th}$ edition, Bethesda, Md.:NIH vol. 1:647-723 (1991); Kabat et al., "Introduction" Sequences of Proteins of Immunological Interest, US Dept of Health and Human Services, NIH, 5$^{th}$ edition, Bethesda, Md. vol. 1:xiii-xcvi (1991); Chothia & Lesk, J. Mol. Biol. 196:901-917 (1987); Chothia et al., Nature 342:878-883 (1989), each of which is herein incorporated by reference for all purposes.

As set forth herein, it will be understood by one of ordinary skill in the art that any Fc domain may be modified such that it varies in amino acid sequence from the native Fc domain of a naturally occurring immunoglobulin molecule. In certain exemplary embodiments, the Fc domain has increased effector function (e.g., FcγR binding).

The Fc domains of a polypeptide of the invention may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants, in the context of IL-2 or a knottin protein, necessarily have less than 100% sequence identity or similarity with the starting IL-2 or knottin protein. In a preferred embodiment, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In one embodiment, there is one amino acid difference between a starting polypeptide sequence and the sequence derived therefrom. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity.

In one embodiment, a polypeptide comprising IL-2 or a variant thereof, for use in extended-PK IL-2 consists of, consists essentially of, or comprises an amino acid sequence selected from SEQ ID Nos: 5, 7, 9, 11, 13, 15, 17, 19, 21, 23, 25, 27, 29, 31, 33, and 35. In an embodiment, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from SEQ ID Nos: 5, 7, 9, 11, 13, 15, 17, 19, 21, 23, 25, 27, 29, 31, 33, and 35. In an embodiment, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from SEQ ID Nos: 5, 7, 9, 11, 13, 15, 17, 19, 21, 23, 25, 27, 29, 31, 33, and 35. In an embodiment, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from SEQ ID Nos: 5, 7, 9, 11, 13, 15, 17, 19, 21, 23, 25, 27, 29, 31, 33, and 35.

In an embodiment, the peptides are encoded by a nucleotide sequence. Nucleotide sequences can be useful for a number of applications, including: cloning, gene therapy, protein expression and purification, mutation introduction, DNA vaccination of a host in need thereof, antibody generation for, e.g., passive immunization, PCR, primer and probe generation, and the like. In an embodiment, the nucleotide sequence of the invention comprises, consists of, or consists essentially of, a nucleotide sequence of IL-2, or a variant thereof, selected from SEQ ID Nos: 4, 6, 8, 10, 12, 14, 16, 18, 20, 22, 24, 26, 28, 30, 32, and 34. In an embodiment, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence set forth in SEQ ID Nos: 4, 6, 8, 10, 12, 14, 16, 18, 20, 22, 24, 26, 28, 30, 32, and 34. In an embodiment, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence set forth in SEQ ID Nos: 4, 6, 8, 10, 12, 14, 16, 18, 20, 22, 24, 26, 28, 30, 32, and 34. In an embodiment, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence set forth in SEQ ID Nos: 4, 6, 8, 10, 12, 14, 16, 18, 20, 22, 24, 26, 28, 30, 32, and 34.

In one embodiment, a polypeptide comprising integrin-binding peptide or a variant thereof, consists of, consists essentially of, or comprises an amino acid sequence selected from SEQ ID Nos: 67-133. In an embodiment, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from SEQ ID Nos: 67-133. In an embodiment, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from SEQ ID Nos: 67-133. In an embodiment, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from SEQ ID Nos: 67-133.

It will also be understood by one of ordinary skill in the art that the extended-PK IL-2 or a knottin-Fc fusion used herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The polypeptides described herein (e.g., IL-2, extended-PK IL-2, PK moieties, knottin, Fc, knottin-Fc, and the like) may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagines, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of a coding sequence, such as by saturation mutagenesis, and the resultant mutants can be incorporated into binding polypeptides of the invention and screened for their ability to bind to the desired target.

The "Programmed Death-1 (PD-1)" receptor refers to an immuno-inhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. AAC51773 (SEQ ID NO: 52).

"Programmed Death Ligand-1 (PD-L1)" is one of two cell surface glycoprotein ligands for PD-1 (the other being PD-L2) that downregulates T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7 (SEQ ID NO: 53).

"Cytotoxic T Lymphocyte Associated Antigen-4 (CTLA-4)" is a T cell surface molecule and is a member of the immunoglobulin superfamily. This protein downregulates the immune system by binding to CD80 and CD86. The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. P16410 (SEQ ID NO: 54):

"Lymphocyte Activation Gene-3 (LAG3)" is an inhibitory receptor associated with inhibition of lymphocyte activity by binding to MHC class II molecules. This receptor enhances the function of Treg cells and inhibits CD8+ effector T cell function. The term "LAG3" as used herein includes human LAG3 (hLAG3), variants, isoforms, and species homologs of hLAG3, and analogs having at least one common epitope. The complete hLAG3 sequence can be found under GenBank Accession No. P18627 (SEQ ID NO: 55).

"T Cell Membrane Protein-3 (TIM3)" is an inhibitory receptor involved in the inhibition of lymphocyte activity by inhibition of $T_H1$ cells responses. Its ligand is galectin 9, which is upregulated in various types of cancers. The term "TIM3" as used herein includes human TIM3 (hTIM3), variants, isoforms, and species homologs of hTIM3, and analogs having at least one common epitope. The complete hTIM3 sequence can be found under GenBank Accession No. Q8TDQo (SEQ ID NO: 56).

The "B7 family" refers to inhibitory ligands with undefined receptors. The B7 family encompasses B7-H3 and B7-H4, both upregulated on tumor cells and tumor infiltrating cells. The complete hB7-H3 and hB7-H4 sequence can be found under GenBank Accession Nos. Q5ZPR3 and AAZ17406 (SEQ ID Nos: 57 and 58) respectively.

"Vascular Endothelial Growth Factor (VEGF)" is a secreted disulfide-linked homodimer that selectively stimulates endothelial cells to proliferate, migrate, and produce matrix-degrading enzymes, all of which are processes required for the formation of new vessels. In addition to being the only known endothelial cell specific mitogen, VEGF is unique among angiogenic growth factors in its ability to induce a transient increase in blood vessel permeability to macromolecules. The term "VEGF" or "VEGF-A" is used to refer to the 165-amino acid human vascular endothelial cell growth factor and related 121-, 145-, 189-, and 206-amino acid human vascular endothelial cell growth factors, as described by, e.g., Leung et al. Science, 246: 1306 (1989), and Houck et al. Mol. Endocrin., 5: 1806 (1991), together with the naturally occurring allelic and processed forms thereof. VEGF-A is part of a gene family including VEGF-B, VEGF-C, VEGF-D, VEGF-E, VEGF-F, and P1GF. VEGF-A primarily binds to two high affinity receptor tyrosine kinases, VEGFR-1 (Flt-1) and VEGFR-2 (Flk-1/KDR), the latter being the major transmitter of vascular endothelial cell mitogenic signals of VEGF-A.

As used herein, "immune checkpoint" refers to co-stimulatory and inhibitory signals that regulate the amplitude and quality of T cell receptor recognition of an antigen. In certain embodiments, the immune checkpoint is an inhibitory signal. In certain embodiments, the inhibitory signal is the interaction between PD-1 and PD-L1. In certain embodiments, the inhibitory signal is the interaction between CTLA-4 and CD80 or CD86 to displace CD28 binding. In certain embodiments the inhibitory signal is the interaction between LAG3 and MHC class II molecules. In certain embodiments, the inhibitory signal is the interaction between TIM3 and galectin 9.

As used herein, "immune checkpoint blocker" refers to a molecule that reduces, inhibits, interferes with or modulates one or more checkpoint proteins. In certain embodiments, the immune checkpoint blocker prevents inhibitory signals associated with the immune checkpoint. In certain embodiments, the immune checkpoint blocker is an antibody, or fragment thereof, that disrupts inhibitory signaling associated with the immune checkpoint. In certain embodiments, the immune checkpoint blocker is a small molecule that disrupts inhibitory signaling. In certain embodiments, the immune checkpoint blocker is an antibody, fragment thereof, or antibody mimic, that prevents the interaction between checkpoint blocker proteins, e.g., an antibody, or fragment thereof, that prevents the interaction between PD-1 and PD-L1. In certain embodiments, the immune checkpoint blocker is an antibody, or fragment thereof, that prevents the interaction between CTLA-4 and CD80 or CD86. In certain embodiments, the immune checkpoint blocker is an antibody, or fragment thereof, that prevents the interaction between LAG3 and MHC class II molecules. In certain embodiments the, the immune checkpoint blocker is an antibody, or fragment thereof, that prevents the interaction between TIM3 and galectin 9. The checkpoint blocker may also be in the form of the soluble form of the molecules (or mutation thereof) themselves, e.g., a soluble PD-L1 or PD-L1 fusion.

The term "ameliorating" refers to any therapeutically beneficial result in the treatment of a disease state, e.g., cancer, including prophylaxis, lessening in the severity or progression, remission, or cure thereof.

The term "in vivo" refers to processes that occur in a living organism.

The term "mammal" or "subject" or "patient" as used herein includes both humans and non-humans and include but is not limited to humans, non-human primates, canines, felines, murines, bovines, equines, and porcines.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As used herein, the term "gly-ser polypeptide linker" refers to a peptide that consists of glycine and serine residues. An exemplary gly-ser polypeptide linker comprises the amino acid sequence Ser(Gly$_4$Ser)n (SEQ ID NO: 134). In one embodiment, n=1. In one embodiment, n=2. In another embodiment, n=3, i.e., Ser(Gly$_4$Ser)3 (SEQ ID NO: 135). In another embodiment, n=4, i.e., Ser(Gly$_4$Ser)4 (SEQ ID NO: 136). In another embodiment, n=5. In yet another embodiment, n=6. In another embodiment, n=7. In yet another embodiment, n=8. In another embodiment, n=9. In yet another embodiment, n=10. Another exemplary gly-ser polypeptide linker comprises the amino acid sequence (Gly$_4$Ser)n (SEQ ID NO: 137). In one embodiment, n=1. In one embodiment, n=2. In a preferred embodiment, n=3. In another embodiment, n=4. In another embodiment, n=5. In yet another embodiment, n=6. Another exemplary gly-ser polypeptide linker comprises the amino acid sequence (Gly$_3$Ser)n (SEQ ID NO: 138). In one embodiment, n=1. In one embodiment, n=2. In a preferred embodiment, n=3. In another embodiment, n=4. In another embodiment, n=5. In yet another embodiment, n=6.

As used herein, "half-life" refers to the time taken for the serum or plasma concentration of a polypeptide to reduce by 50%, in vivo, for example due to degradation and/or clearance or sequestration by natural mechanisms. The extended-PK IL-2 used herein is stabilized in vivo and its half-life increased by, e.g., fusion to HSA, MSA or Fc, through PEGylation, or by binding to serum albumin molecules (e.g., human serum albumin) which resist degradation and/or clearance or sequestration. The half-life can be determined in any manner known per se, such as by pharmacokinetic analysis. Suitable techniques will be clear to the person skilled in the art, and may for example generally involve the steps of suitably administering a suitable dose of the amino acid sequence or compound of the invention to a subject;

collecting blood samples or other samples from said subject at regular intervals; determining the level or concentration of the amino acid sequence or compound of the invention in said blood sample; and calculating, from (a plot of) the data thus obtained, the time until the level or concentration of the amino acid sequence or compound of the invention has been reduced by 50% compared to the initial level upon dosing. Further details are provided in, e.g., standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, $2^{nd}$ Rev. Edition, Marcel Dekker (1982).

As used herein, a "small molecule" is a molecule with a molecular weight below about 500 Daltons.

As used herein, "therapeutic protein" refers to any polypeptide, protein, protein variant, fusion protein and/or fragment thereof which may be administered to a subject as a medicament. An exemplary therapeutic protein is an interleukin, e.g., IL-7.

As used herein, "synergy" or "synergistic effect" with regard to an effect produced by two or more individual components refers to a phenomenon in which the total effect produced by these components, when utilized in combination, is greater than the sum of the individual effects of each component acting alone.

The term "sufficient amount" or "amount sufficient to" means an amount sufficient to produce a desired effect, e.g., an amount sufficient to reduce the size of a tumor.

The term "therapeutically effective amount" is an amount that is effective to ameliorate a symptom of a disease. A therapeutically effective amount can be a "prophylactically effective amount" as prophylaxis can be considered therapy.

As used herein, "combination therapy" embraces administration of each agent or therapy in a sequential manner in a regiment that will provide beneficial effects of the combination and co-administration of these agents or therapies in a substantially simultaneous manner. Combination therapy also includes combinations where individual elements may be administered at different times and/or by different routes but which act in combination to provide a beneficial effect by co-action or pharmacokinetic and pharmacodynamics effect of each agent or tumor treatment approaches of the combination therapy.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

It must be noted that, as used in the specification and the appended claims, the singular forms "a," "an" and "the" include plural referents unless the context clearly dictates otherwise.

Various aspects described herein are described in further detail in the following subsections.

IL-2 and Extended-PK IL-2

Interleukin-2 (IL-2) is a cytokine that induces proliferation of antigen-activated T cells and stimulates natural killer (NK) cells. The biological activity of IL-2 is mediated through a multi-subunit IL-2 receptor complex (IL-2R) of three polypeptide subunits that span the cell membrane: p55 (IL-2Ra, the alpha subunit, also known as CD25 in humans), p75 (IL-2Rβ, the beta subunit, also known as CD 122 in humans) and p64 (IL-2Ry, the gamma subunit, also known as CD 132 in humans). T cell response to IL-2 depends on a variety of factors, including: (1) the concentration of IL-2; (2) the number of IL-2R molecules on the cell surface; and (3) the number of IL-2R occupied by IL-2 (i.e., the affinity of the binding interaction between IL-2 and IL-2R (Smith, "Cell Growth Signal Transduction is Quantal" In Receptor Activation by Antigens, Cytokines, Hormones, and Growth Factors 766:263-271, 1995)). The IL-2:IL-2R complex is internalized upon ligand binding and the different components undergo differential sorting. IL-2Ra is recycled to the cell surface, while IL-2 associated with the IL-2:IL-2Rpγ complex is routed to the lysosome and degraded. When administered as an intravenous (i.v.) bolus, IL-2 has a rapid systemic clearance (an initial clearance phase with a half-life of 12.9 minutes followed by a slower clearance phase with a half-life of 85 minutes) (Konrad et al., Cancer Res. 50:2009-2017, 1990).

Thus, in some embodiments, IL-2 therapy, such as systemic IL-2, is administered to a subject in an effective amount in combination with an integrin-binding-Fc fusion protein, and optionally an immune checkpoint blocker.

However, outcomes of systemic IL-2 administration in cancer patients are far from ideal. While 15 to 20 percent of patients respond objectively to high-dose IL-2, the great majority do not, and many suffer severe, life-threatening side effects, including nausea, confusion, hypotension, and septic shock. The severe toxicity associated with IL-2 treatment is largely attributable to the activity of natural killer (NK) cells. NK cells express the intermediate-affinity receptor, IL-2Rpγ$_c$, and thus are stimulated at nanomolar concentrations of IL-2, which do in fact result in patient sera during high-dose IL-2 therapy. Attempts to reduce serum concentration, and hence selectively stimulate IL-2RaPγ$_c$-bearing cells, by reducing dose and adjusting dosing regimen have been attempted, and while less toxic, such treatments were also less efficacious. Given the toxicity issues associated with high dose IL-2 cancer therapy, numerous groups have attempted to improve anti-cancer efficacy of IL-2 by simultaneously administering therapeutic antibodies. Yet, such efforts have been largely unsuccessful, yielding no additional or limited clinical benefit compared to IL-2 therapy alone. Accordingly, novel IL-2 therapies are needed to more effectively combat various cancers.

Applicants recently discovered that the ability of IL-2 to control tumors in various cancer models could be substantially increased by attaching IL-2 to a pharmacokinetic modifying group. The resulting molecule, hereafter referred to as "extended-pharmacokinetic (PK) IL-2," has a prolonged circulation half-life relative to free IL-2. The prolonged circulation half-life of extended-PK IL-2 permits in vivo serum IL-2 concentrations to be maintained within a therapeutic range, leading to the enhanced activation of many types of immune cells, including T cells. Because of its favorable pharmacokinetic profile, extended-PK IL-2 can be dosed less frequently and for longer periods of time when compared with unmodified IL-2. Extended-PK IL-2 is described in detail in International Patent Application NO. PCT/US2013/042057, filed May 21, 2013, and claiming the benefit of priority to U.S. Provisional Patent Application No. 61/650,277, filed May 22, 2012. The entire contents of the foregoing applications are incorporated by reference herein.

A. IL-2 and Mutants Thereof

In certain embodiments, an effective amount of human IL-2 is administered systemically. In some embodiments, an effective amount of an extended-PK IL-2 is administered systemically. In one embodiment, the IL-2 is a human recombinant IL-2 such as Proleukin® (aldesleukin). Proleukin® is a human recombinant interleukin-2 product produced in *E. coli*. Proleukin® differs from the native interleukin-2 in the following ways: a) it is not glycosylated; b) it has no N-terminal alanine; and c) it has serine substituted for cysteine at amino acid positions 125. Proleukin® exists as biogicially active, non-covalently bound microaggregates with an average size of 27 recombinant interleukin-2 molecules. Proleukin® (aldesleukin) is administered by intravenous infusion. In some aspects, the IL-2 portion of the extended-PK IL-2 is wild-type IL-2 (e.g., human IL-2 in its precursor form (SEQ ID NO: 33) or mature IL-2 (SEQ ID NO: 35)).

In certain embodiments, the extended-PK IL-2 is mutated such that it has an altered affinity (e.g., a higher affinity) for the IL-2R alpha receptor compared with unmodified IL-2.

Site-directed mutagenesis can be used to isolate IL-2 mutants that exhibit high affinity binding to CD25, i.e., IL-2Rα, as compared to wild-type IL-2. Increasing the affinity of IL-2 for IL-2Rα at the cell surface will increase receptor occupancy within a limited range of IL-2 concentration, as well as raise the local concentration of IL-2 at the cell surface.

In certain embodiments, the invention features IL-2 mutants, which may be, but are not necessarily, substantially purified and which can function as high affinity CD25 binders. IL-2 is a T cell growth factor that induces proliferation of antigen-activated T cells and stimulation of NK cells. Exemplary IL-2 mutants which are high affinity binders include those described in WO2013/177187A2 (herein incorporated by reference in its entirety), such as those with amino acid sequences set forth in SEQ ID Nos: 7, 23, 25, 27, 29, and 31. Further exemplary IL-2 mutants with increased affinity for CD25 are disclosed in U.S. Pat. No. 7,569,215, the contents of which are incorporated herein by reference. In one embodiment, the IL-2 mutant does not bind to CD25, e.g., those with amino acid sequences set forth in SEQ ID Nos: 9 and 11.

IL-2 mutants include an amino acid sequence that is at least 80% identical to SEQ ID NO: 33 that bind CD25. For example, an IL-2 mutant can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) that increases the affinity for the alpha subunit of the IL-2 receptor relative to wild-type IL-2. It should be understood that mutations identified in mouse IL-2 may be made at corresponding residues in full length human IL-2 (nucleic acid sequence (accession: NM000586) of SEQ ID NO: 32; amino acid sequence (accession: P60568) of SEQ ID NO: 33) or human IL-2 without the signal peptide (nucleic acid sequence of SEQ ID NO: 34; amino acid sequence of SEQ ID NO: 35). Accordingly, in certain embodiments, the IL-2 moiety of the extended-PK IL-2 is human IL-2. In other embodiments, the IL-2 moiety of the extended-PK IL-2 is a mutant human IL-2.

IL-2 mutants can be at least or about 50%, at least or about 65%, at least or about 70%, at least or about 80%, at least or about 85%, at least or about 87%, at least or about 90%, at least or about 95%, at least or about 97%, at least or about 98%, or at least or about 99% identical in amino acid sequence to wild-type IL-2 (in its precursor form or, preferably, the mature form). The mutation can consist of a change in the number or content of amino acid residues. For example, the IL-2 mutants can have a greater or a lesser number of amino acid residues than wild-type IL-2. Alternatively, or in addition, IL-2 mutants can contain a substitution of one or more amino acid residues that are present in the wild-type IL-2.

By way of illustration, a polypeptide that includes an amino acid sequence that is at least 95% identical to a reference amino acid sequence of SEQ ID NO: 33 is a polypeptide that includes a sequence that is identical to the reference sequence except for the inclusion of up to five alterations of the reference amino acid of SEQ ID NO: 33. For example, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino (N—) or carboxy (C—) terminal positions of the reference amino acid sequence or anywhere between those terminal positions, interspersed either individually among residues in the reference sequence or in one or more contiguous groups within the reference sequence.

The substituted amino acid residue(s) can be, but are not necessarily, conservative substitutions, which typically include substitutions within the following groups: glycine, alanine; valine, isoleucine, leucine; aspartic acid, glutamic acid; asparagines, glutamine; serine, threonine; lysine, arginine; and phenylalanine, tyrosine. These mutations can be at amino acid residues that contact IL-2Rα.

In general, the polypeptides used in the practice of the instant invention will be synthetic, or produced by expression of a recombinant nucleic acid molecule. In the event the polypeptide is an extended-PK IL-2 (e.g., a fusion protein containing at least IL-2 and a heterologous polypeptide, such as a hexa-histidine tag or hemagglutinin tag or an Fc region or human serum albumin), it can be encoded by a hybrid nucleic acid molecule containing one sequence that encodes IL-2 and a second sequence that encodes all or part of the heterologous polypeptide.

The techniques that are required to make IL-2 mutants are routine in the art, and can be performed without resort to undue experimentation by one of ordinary skill in the art. For example, a mutation that consists of a substitution of one or more of the amino acid residues in IL-2 can be created using a PCR-assisted mutagenesis technique (e.g., as known in the art and/or described herein for the creation of IL-2 mutants). Mutations that consist of deletions or additions of amino acid residues to an IL-2 polypeptide can also be made with standard recombinant techniques. In the event of a deletion or addition, the nucleic acid molecule encoding IL-2 is simply digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

In addition to generating IL-2 mutants via expression of nucleic acid molecules that have been altered by recombinant molecular biological techniques, IL-2 mutants can be chemically synthesized. Chemically synthesized polypeptides are routinely generated by those of skill in the art.

As noted above, IL-2 can also be prepared as fusion or chimeric polypeptides that include IL-2 and a heterologous polypeptide (i.e., a polypeptide that is not IL-2). The heterologous polypeptide can increase the circulating half-life of the chimeric polypeptide in vivo, and may, therefore, further enhance the properties of IL-2. As discussed in further detail infra, the polypeptide that increases the circulating half-life may be serum albumin, such as human or mouse serum albumin.

In other embodiments, the chimeric polypeptide can include IL-2 and a polypeptide that functions as an antigenic tag, such as a FLAG sequence. FLAG sequences are recognized by biotinylated, highly specific, anti-FLAG antibodies, as described herein (see also Blanar et al., Science 256: 1014, 1992; LeClair et al., Proc. Natl. Acad. Sci. USA 89:8145, 1992). In certain embodiments, the chimeric polypeptide further comprises a C-terminal c-myc epitope tag.

Chimeric polypeptides can be constructed using no more than conventional molecular biological techniques, which are well within the ability of those of ordinary skill in the art to perform.

a. Nucleic Acid Molecules Encoding IL-2

IL-2, either alone or as a part of a chimeric polypeptide, such as those described herein, can be obtained by expression of a nucleic acid molecule. Thus, nucleic acid molecules encoding polypeptides containing IL-2 or an IL-2 mutant are considered within the scope of the invention, such as those with nucleic acid sequences set forth in SEQ ID Nos: 4, 6, 8, 10, 12, 14, 16, 18, 20, 22, 24, 26, 28, 30, 32, and 34. Just as IL-2 mutants can be described in terms of their identity with wild-type IL-2, the nucleic acid molecules encoding them will necessarily have a certain identity with those that encode wild-type IL-2. For example, the nucleic acid molecule encoding an IL-2 mutant can be at least 50%, at least 65%, preferably at least 75%, more preferably at least 85%, and most preferably at least 95% (e.g., 99%) identical to the nucleic acid encoding full length wild-type IL-2 (e.g., SEQ ID NO: 32 or wild-type IL-2 without the signal peptide (e.g., SEQ ID NO: 34).

The nucleic acid molecules of the invention can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The isolated nucleic acid molecules can include fragments not found as such in the natural state. Thus, the invention encompasses use of recombinant molecules, such as those in which a nucleic acid sequence (for example, a sequence encoding an IL-2 mutant) is incorporated into a vector (e.g., a plasmid or viral vector) or into the genome of a heterologous cell (or the genome of a homologous cell, at a position other than the natural chromosomal location).

As described above, IL-2 mutants of the invention may exist as a part of a chimeric polypeptide. In addition to, or in place of, the heterologous polypeptides described above, a nucleic acid molecule of the invention can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-hosphotransferase (HPH), thymidine kinase (TK), lacz (encoding β-galactosidase), and xanthine guanine phosphoribosyl transferase (XGPRT). As with many of the standard procedures associated with the practice of the invention, skilled artisans will be aware of additional useful reagents, for example, of additional sequences that can serve the function of a marker or reporter.

The nucleic acid molecules of the invention can be obtained by introducing a mutation into IL-2-encoding DNA obtained from any biological cell, such as the cell of a mammal. Thus, the nucleic acids used herein (and the polypeptides they encode) can be those of a mouse, rat, guinea pig, cow, sheep, horse, pig, rabbit, monkey, baboon, dog, or cat. Typically, the nucleic acid molecules will be those of a human.

B. Extended-PK Groups

As described supra, IL-2 or mutant IL-2 is fused to an extended-PK group, which increases circulation half-life. Non-limiting examples of extended-PK groups are described infra. It should be understood that other PK groups that increase the circulation half-life of IL-2, or variants thereof, are also applicable to extended-PK IL-2.

In certain embodiments, the serum half-life of extended-PK IL-2 is increased relative to IL-2 alone (i.e., IL-2 not fused to an extended-PK group). In certain embodiments, the serum half-life of extended-PK IL-2 is at least 20, 40, 60, 80, 100, 120, 150, 180, 200, 400, 600, 800, or 1000% longer relative to the serum half-life of IL-2 alone. In other embodiments, the serum half-life of the extended-PK IL-2 is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of IL-2 alone. In certain embodiments, the serum half-life of the extended-PK IL-2 is at least 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

a. Serum Albumin and Serum Albumin Binding Proteins

In certain embodiments, the extended-PK group is a serum albumin, or fragments thereof. Methods of fusing serum albumin to proteins are disclosed in, e.g., US2010/0144599, US2007/0048282, and US2011/0020345, which are herein incorporated by reference in their entirety. In certain embodiments, the extended-PK group is HSA, or variants or fragments thereof, such as those disclosed in U.S. Pat. No. 5,876,969, WO 2011/124718, WO 2013/075066, and WO 2011/0514789.

In certain embodiments, the extended-PK group is a serum albumin binding protein such as those described in US2005/0287153, US2007/0003549, US2007/0178082, US2007/0269422, US2010/0113339, WO2009/083804, and WO2009/133208, which are herein incorporated by reference in their entirety.

b. PEGylation

In certain embodiments, an extended-PK IL-2 used herein includes a polyethylene glycol (PEG) domain. PEGylation is well known in the art to confer increased circulation half-life to proteins. Methods of PEGylation are well known and disclosed in, e.g., U.S. Pat. No. 7,610,156, U.S. Pat. No. 7,847,062, all of which are hereby incorporated by reference.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_{n-1}$CH$_2$CH$_2$OH, where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462, both of which are hereby incorporated by reference. One form of PEGs includes two PEG side-chains (PEG2) linked via the primary amino groups of a lysine (Monfardini et al., Bioconjugate Chem 1995; 6:62-9).

In one embodiment, pegylated IL-2 is produced by site-directed pegylation, particularly by conjugation of PEG to a cysteine moiety at the N- or C-terminus. A PEG moiety may also be attached by other chemistry, including by conjugation to amines.

PEG conjugation to peptides or proteins generally involves the activation of PEG and coupling of the activated PEG-intermediates directly to target proteins/peptides or to a linker, which is subsequently activated and coupled to target proteins/peptides (see Abuchowski et al., JBC 1977; 252:3571 and JBC 1977; 252:3582, and Harris et. al., in: Poly(ethylene glycol) Chemistry: Biotechnical and Biomedical Applications; (J. M. Harris ed.) Plenum Press: New York, 1992; Chap. 21 and 22).

A variety of molecular mass forms of PEG can be selected, e.g., from about 1,000 Daltons (Da) to 100,000 Da (n is 20 to 2300), for conjugating to IL-2. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

One skilled in the art can select a suitable molecular mass for PEG, e.g., based on how the pegylated IL-2 will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 1993; 10:91-114.

In one embodiment of the invention, PEG molecules may be activated to react with amino groups on IL-2 such as with lysines (Bencham C. O. et al., Anal. Biochem., 131, 25 (1983); Veronese, F. M. et al., Appl. Biochem., 11, 141 (1985); Zalipsky, S. et al., Polymeric Drugs and Drug Delivery Systems, adrs 9-110 ACS Symposium Series 469 (1999); Zalipsky, S. et al., Europ. Polym. J., 19, 1177-1183 (1983); Delgado, C. et al., Biotechnology and Applied Biochemistry, 12, 119-128 (1990)).

In one embodiment, carbonate esters of PEG are used to form the PEG-IL-2 conjugates. N,N'-disuccinimidylcarbonate (DSC) may be used in the reaction with PEG to form active mixed PEG-succinimidyl carbonate that may be subsequently reacted with a nucleophilic group of a linker or an amino group of IL-2 (see U.S. Pat. No. 5,281,698 and U.S. Pat. No. 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382,657), respectively.

Pegylation of IL-2 can be performed according to the methods of the state of the art, for example by reaction of IL-2 with electrophilically active PEGs (Shearwater Corp., USA, www.shearwatercorp.com). Preferred PEG reagents are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C, et al., Bioconjugate Chem. 6 (1995) 62-69).

In another embodiment, PEG molecules may be coupled to sulfhydryl groups on IL-2 (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. No. 6,610,281 and U.S. Pat. No. 5,766,897 describe exemplary reactive PEG species that may be coupled to sulfhydryl groups.

In certain embodiments where PEG molecules are conjugated to cysteine residues on IL-2 the cysteine residues are native to IL-2 whereas in other embodiments, one or more cysteine residues are engineered into IL-2. Mutations may be introduced into the coding sequence of IL-2 to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein.

In another embodiment, pegylated IL-2 comprise one or more PEG molecules covalently attached to a linker.

In one embodiment, IL-2 is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, Bioconjug Chem. 2004; 15(5): 1005-1009.

Monopegylation of IL-2 can also be achieved according to the general methods described in WO 94/01451. WO 94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

The ratio of IL-2 to activated PEG in the conjugation reaction can be from about 1:0.5 to 1:50, between from about 1:1 to 1:30, or from about 1:5 to 1:15. Various aqueous buffers can be used to catalyze the covalent addition of PEG to IL-2, or variants thereof. In one embodiment, the pH of a buffer used is from about 7.0 to 9.0. In another embodiment, the pH is in a slightly basic range, e.g., from about 7.5 to 8.5. Buffers having a pKa close to neutral pH range may be used, e.g., phosphate buffer.

Conventional separation and purification techniques known in the art can be used to purify PEGylated IL-2, such as size exclusion (e.g. gel filtration) and ion exchange chromatography. Products may also be separated using SDS-PAGE. Products that may be separated include mono-, di-, tri-poly- and un-pegylated IL-2 as well as free PEG. The percentage of mono-PEG conjugates can be controlled by pooling broader fractions around the elution peak to increase the percentage of mono-PEG in the composition.

In one embodiment, PEGylated IL-2 of the invention contains one, two or more PEG moieties. In one embodiment, the PEG moiety(ies) are bound to an amino acid residue which is on the surface of the protein and/or away from the surface that contacts CD25. In one embodiment, the combined or total molecular mass of PEG in PEG-IL-2 is from about 3,000 Da to 60,000 Da, optionally from about 10,000 Da to 36,000 Da. In one embodiment, PEG in pegylated IL-2 is a substantially linear, straight-chain PEG.

In one embodiment, PEGylated IL-2 of the invention will preferably retain at least 25%, 50%, 60%, 70%, 80%, 85%, 90%, 95% or 100% of the biological activity associated with the unmodified protein. In one embodiment, biological activity refers to the ability to bind CD25. The serum clearance rate of PEG-modified IL-2 may be decreased by about 10%, 20%, 30%, 40%, 50%, 60%, 70%, 80%, or even 90%, relative to the clearance rate of the unmodified IL-2. PEG-modified IL-2 may have a circulation half-life which is enhanced relative to the half-life of unmodified IL-2. The half-life of PEG-IL-2, or variants thereof, may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of unmodified IL-2. In certain embodiments, the protein half-life is determined in vitro, such as in a buffered saline solution or in serum. In other embodiments, the protein half-life is an in vivo circulation half-life, such as the half-life of the protein in the serum or other bodily fluid of an animal.

c. Other Extended-PK Groups

In certain embodiments, the extended-PK group is transferrin, as disclosed in U.S. Pat. No. 7,176,278 and U.S. Pat. No. 8,158,579, which are herein incorporated by reference in their entirety.

In certain embodiments, the extended-PK group is a serum immunoglobulin binding protein such as those disclosed in US2007/0178082, which is herein incorporated by reference in its entirety.

In certain embodiments, the extended-PK group is a fibronectin (Fn)-based scaffold domain protein that binds to serum albumin, such as those disclosed in US2012/0094909, which is herein incorporated by reference in its entirety. Methods of making fibronectin-based scaffold domain proteins are also disclosed in US2012/0094909. A non-limiting example of a Fn3-based extended-PK group is Fn3(HSA), i.e., a Fn3 protein that binds to human serum albumin.

d. Fc Domains

In certain embodiments, an extended-PK IL-2 includes an Fc domain, as described in WO2013177187. The Fc domain does not contain a variable region that binds to antigen. Fc domains useful for producing the extended-PK IL-2 described herein may be obtained from a number of different sources. In certain embodiments, an Fc domain of the extended-PK IL-2 is derived from a human immunoglobulin. In a certain embodiment, the Fc domain is from a human IgG1 constant region (SEQ ID NO: 1). The Fc domain of human IgG1 is set forth in SEQ ID NO: 2. In certain embodiments, the Fc domain of human IgG1 does not have the upper hinge region (SEQ ID NO: 3). It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the Fc domain or portion thereof may be derived from any immunoglobulin class, including IgM, IgG, IgD, IgA, and IgE, and any immunoglobulin isotype, including IgG1, IgG2, IgG3, and IgG4.

In some aspects, an extended-PK IL-2 includes a mutant Fc domain. In some aspects, an extended-PK IL-2 includes a mutant, IgG1 Fc domain. In some aspects, a mutant Fc domain comprises one or more mutations in the hinge, CH2, and/or CH3 domains. In some aspects, a mutant Fc domain includes a D265A mutation.

In one embodiment, the extended-PK IL-2 of the invention lacks one or more constant region domains of a complete Fc region, i.e., they are partially or entirely deleted. In certain embodiments, the extended-PK IL-2 of the invention will lack an entire CH2 domain. In certain embodiments, the extended-PK IL-2 of the invention comprise CH2 domain-deleted Fc regions derived from a vector (e.g., from IDEC Pharmaceuticals, San Diego) encoding an IgG1 human constant region domain (see, e.g., WO02/060955A2 and WO02/096948A2). This exemplary vector is engineered to delete the CH2 domain and provide a synthetic vector expressing a domain-deleted IgG1 constant region. It will be noted that these exemplary constructs are preferably engineered to fuse a binding CH3 domain directly to a hinge region of the respective Fc domain.

Integrin-Binding-Fc Fusion Proteins

Integrins are a family of extracellular matrix adhesion receptors that regulate a diverse array of cellular functions crucial to the initiation, progression and metastasis of solid tumors. The importance of integrins in tumor progression has made them an appealing target for cancer therapy and allows for the treatment of a variety of cancer types. The integrins present on cancerous cells include $\alpha_v\beta_3$, $\alpha_v\beta_5$, and $\alpha_5\beta_1$.

Knottin proteins are small compact peptides that have high thermal and proteolytic stability and are tolerant to mutagenesis, making them good molecular scaffolds. These peptides contain at least 3 disulfide bonds that form a "knot"

core. They also contain several loops exposed to the surface, allowing these loops to bind targets. These loops can be engineered to bind specific targets with high affinity, making them a useful tool for therapy.

The present invention involves the use of a knottin polypeptide scaffold engineered with an RGD sequence capable of binding integrins, fused to an Fc donor, which confers a therapeutic benefit (also referred to as "knottin-Fc"). As described supra, Fc fragments have been added to proteins and/or therapeutics to extend half-life. In the context of knottin-Fc as used herein, the effector function of Fc contributes to the treatment of a variety of cancers when used in conjunction with systemic IL-2, such as extended-PK IL-2. In certain embodiments, a knottin-Fc that binds two integrins simultaneously is used (2.5D, SEQ ID NO: 93 or 95). In certain embodiments, a knottin-Fc that binds three integrins simultaneously, reflected in Table 1, is used (2.5F, SEQ ID NO: 94 or 96).

A. Methods of Engineering Knottin Polypeptide Scaffolds

Knottin polypeptide scaffolds are used to insert an integrin-binding sequence, preferably in the form of a loop, to confer specific integrin binding. Integrin-binding is preferably engineered into a knottin polypeptide scaffold by inserting an integrin-binding peptide sequence, such as an RGD peptide. In some embodiments, insertion of an integrin-binding peptide sequence results in replacement of portion of the native knottin protein. For example, in one embodiment an RGD peptide sequence is inserted into a native solvent exposed loop by replacing all or a portion of the loop with an RGD-containing peptide sequence (e.g., 5-12 amino acid sequence) that has been selected for binding to one or more integrins. The solvent-exposed loop (i.e., on the surface) will generally be anchored by disulfide-linked cysteine residues in the native knottin protein sequence. The integrin-binding replacement amino acid sequence can be obtained by randomizing codons in the loop portion, expressing the engineered peptide, and selecting the mutants with the highest binding to the predetermined ligand. This selection step may be repeated several times, taking the tightest binding proteins from the previous step and re-randomizing the loops.

Integrin-binding polypeptides may be modified in a number of ways. For example, the polypeptide may be further cross-linked internally, or may be cross-linked to each other, or the RGD loops may be grafted onto other cross linked molecular scaffolds. There are a number of commercially available crosslinking reagents for preparing protein or peptide bioconjugates. Many of these crosslinkers allow dimeric homo- or heteroconjugation of biological molecules through free amine or sulfhydryl groups in protein side chains. More recently, other crosslinking methods involving coupling through carbohydrate groups with hydrazide moieties have been developed. These reagents have offered convenient, facile, crosslinking strategies for researchers with little or no chemistry experience in preparing bioconjugates.

The EETI-II knottin protein (SEQ ID NO: 39) contains a disulfide knotted topology and possesses multiple solvent-exposed loops that are amenable to mutagenesis. Preferred embodiments use EETI-II as the molecular scaffold.

Another example of a knottin protein which can be used as a molecular scaffold is AgRP or agatoxin. The amino acid sequences of AgRP (SEQ ID NO: 40) and agatoxin (SEQ ID NO: 41) differ but their structure is identical. Exemplary AgRP knottins are found in Table 1.

Additional AgRP engineered knottins can be made as described in the above-referenced US 2009/0257952 to Cochran et al. (the contents of which are incorporated herein by reference). AgRP knottin fusions can be prepared using AgRP loops 1, 2 and 3, as well as loop 4 as exemplified above.

The present polypeptides may be produced by recombinant DNA or may be synthesized in solid phase using a peptide synthesizer, which has been done for the peptides of all three scaffolds described herein. They may further be capped at their N-termini by reaction with fluorescein isothiocyanate (FITC) or other labels, and, still further, may be synthesized with amino acid residues selected for additional crosslinking reactions. TentaGel S RAM Fmoc resin (Advanced ChemTech) may be used to give a C-terminal amide upon cleavage. B-alanine is used as the N-terminal amino acid to prevent thiazolidone formation and release of fluorescein during peptide deprotection (Hermanson, 1996). Peptides are cleaved from the resin and side-chains are deprotected with 8% trifluoroacetic acid, 2% triisopropylsilane, 5% dithiothreitol, and the final product is recovered by ether precipitation.

Peptides are purified by reverse phase HPLC using an acetonitrile gradient in 0.1% trifluoroacetic acid and a C4 or C18 column (Vydac) and verified using matrix-assisted laser desorption/ionization time-of-flight mass spectrometry (MALDI-TOF) or electrospray ionization-mass spectrometry (ESI-MS).

When the present peptides are produced by recombinant DNA, expression vectors encoding the selected peptide are transformed into a suitable host. The host should be selected to ensure proper peptide folding and disulfide bond formation as described above. Certain peptides, such as EETI-II, can fold properly when expressed in prokaryotic hosts such as bacteria.

Dimeric, trimeric, and tetrameric complexes of the present peptides can be formed through genetic engineering of the above sequences or by reaction of the synthetic crosslinkers with engineered peptides carrying an introduced cysteine residue, for example on the C-terminus of the peptide. These oligomeric peptide complexes can be purified by gel filtration. Oligomers of the present peptides can be prepared by preparing vectors encoding multiple peptide sequences end-to-end. Also, multimers may be prepared by complexing the peptides, such as, e.g., described in U.S. Pat. No. 6,265,539. There, an active HIV peptide is prepared in multimer form by altering the amino-terminal residue of the peptide so that it is peptide-bonded to a spacer peptide that contains an amino-terminal lysyl residue and one to about five amino acid residues such as glycyl residues to form a composite polypeptide. Alternatively, each peptide is synthesized to contain a cysteine (Cys) residue at each of its amino- and carboxy-termini. The resulting di-cysteine-terminated (di-Cys) peptide is then oxidized to polymerize the di-Cys peptide monomers into a polymer or cyclic peptide multimer. Multimers may also be prepared by solid phase peptide synthesis utilizing a lysine core matrix. The present peptides may also be prepared as nanoparticles. See, "Multivalent Effects of RGD Peptides Obtained by Nanoparticle Display," Montet, et al., J. Med. Chem.; 2006; 49(20) pp 6087-6093. EETI dimerization may be carried out with the present EETI-II peptides according to the EETI-II dimerization paper: "Grafting of thrombopoietin-mimetic peptides into cystine knot miniproteins yields high-affinity thrombopoietin antagonist and agonists," Krause, et al., FEBS Journal; 2006; 274 pp 86-95. This is further described in PCT application No. PCT/US2013/065610, herein incorporated by reference.

Synergistic sites on fibronectin and other adhesion proteins have been identified for enhanced integrin binding (Ruoslahti, 1996; Koivunen et al., 1994; Aota et al., 1994; Healy et al., 1995). The ability to incorporate different integrin-specific motifs into one soluble molecule would have an important impact on therapeutic development. Crosslinkers with heterofunctional specificity may be used for creating integrin-binding proteins with synergistic binding effects. In addition, these same crosslinkers could easily be used to create bispecific targeting molecules, or as vehicles for delivery of radionuclides or toxic agents for therapeutic applications.

B. Integrin-Binding Peptides

The integrin-binding polypeptides for use in Fc fusions include an integrin-binding loop (e.g., RGD peptide sequence) and a knottin polypeptide scaffold. Such integrin-binding polypeptides are described in U.S. Pat. No. 8,536,301, the contents of which are incorporated herein by reference. As described in U.S. Pat. No. 8,536,301, integrin-binding polypeptides may be varied in the non-RGD residues to a certain degree without affecting binding specificity and potency. For example, if three of the eleven residues were varied, one would have about 70% identity to 2.5D. Table 1 shows exemplary integrin-binding polypeptides within the scope of the invention, and their specific knottin polypeptide scaffold (e.g., EETI-II or AgRP). Preferred integrin-binding polypeptides for use in Fc fusions are peptides 2.5D and 2.5F.

In certain embodiments, the integrin-binding polypeptide binds to $\alpha_v\beta_3$, $\alpha_v\beta_5$, or $\alpha_5\beta_1$ separately.

In certain embodiments, the integrin-binding polypeptide binds to $\alpha_v\beta_3$ and $\alpha_v\beta_5$ simultaneously.

In certain embodiments, the integrin-binding polypeptide binds to $\alpha_v\beta_3$, $\alpha_v\beta_5$, and $\alpha_5\beta_1$ simultaneously.

In certain embodiments, the integrin-binding loop is within an engineered EETI-II scaffold. In certain embodiments, the lysine in position 15 of the EETI-II scaffold is replaced with a serine. In certain embodiments, the integrin-binding polypeptide comprises the amino acid sequence set forth in SEQ ID NO: 42 or 43, wherein $X_1$ is selected from the group consisting of A, V, L, P, F, Y, S, H, D, and N; $X_2$ is selected from the group consisting of G, V, L, P, R, E, and Q; $X_3$ is selected from the group consisting of G, A, and P; $X_7$ is selected from the group consisting of W and N; $X_8$ is selected from the group consisting of A, P, and S; $X_9$ is selected from the group consisting of P and R; $X_{10}$ is selected from the group consisting of A, V, L, P, S, T, and E; and $X_{11}$ is selected from the group consisting of G, A, W, S, T, K, and E. In a further embodiment, the integrin-binding-Fc fusion comprises an integrin-binding polypeptide, as set forth in SEQ ID Nos: 42 or 43, operably linked to a human IgG Fc domain, as set forth in SEQ ID Nos: 2 or 3.

In certain embodiments, the integrin-binding loop is within an engineered AgRP or agatoxin scaffold.

In certain embodiments, the integrin-binding polypeptide is 2.5D and 2.5F, disclosed in Table 1. Any of the integrin-binding polypeptides in Table 1 can be used in Fc fusion as described herein.

TABLE 1

Integrin Binding Knottin Sequences

| SEQ ID NO | Peptide Identifier | Scaffold | Sequenc(RGD motif is underlined with flanking residues) |
|---|---|---|---|
| 67 | 1.4A | EETI-II | GCAEPRGDMPWTWCKQDSDCLAGCVCGPNGFCG |
| 68 | 1.4B | EETI-II | GCVGGRGDWSPKWCKQDSDCPAGCVCGPNGFCG |
| 69 | 1.4C | EETI-II | GCAELRGDRSYPECKQDSDCLAGCVCGPNGFCG |
| 70 | 1.4E | EETI-II | GCRLPRGDVPRPHCKQDSDCQAGCVCGPNGFCG |
| 71 | 1.4H | EETI-II | GCYPLRGDNPYAACKQDSDCRAGCVCGPNGFCG |
| 72 | 1.5B | EETI-II | GCTIGRGDWAPSECKQDSDCLAGCVCGPNGFCG |
| 73 | 1.5F | EETI-II | GCHPPRGDNPPVTCKQDSDCLAGCVCGPNGFCG |
| 74 | 2.3A | EETI-II | GCPEPRGDNPPPSCKQDSDCRAGCVCGPNGFCG |
| 75 | 2.3B | EETI-II | GCLPPRGDNPPPSCKQDSDCQAGCVCGPNGFCG |
| 76 | 2.3C | EETI-II | GCHLGRGDWAPVGCKQDSDCPAGCVCGPNGFCG |
| 77 | 2.3D | EETI-II | GCNVGRGDWAPSECKQDSDCPAGCVCGPNGFCG |
| 78 | 2.3E | EETI-II | GCFPGRGDWAPSSCKQDSDCRAGCVCGPNGFCG |
| 79 | 2.3F | EETI-II | GCPLPRGDNPPTECKQDSDCQAGCVCGPNGFCG |
| 80 | 2.3G | EETI-II | GCSEARGDNPRLSCKQDSDCRAGCVCGPNGFCG |
| 81 | 2.3H | EETI-II | GCLLGRGDWAPEACKQDSDCRAGCVCPNGFCG |
| 82 | 2.3I | EETI-II | GCHVGRGDWAPLKCKQDSDCQAGCVCGPNGFCG |
| 83 | 2.3J | EETI-II | GCVRGRGDWAPPSCKQDSDCPAGCVCGPNGFCG |
| 84 | 2.4A | EETI-II | GCLGGRGDWAPPACKQDSDCRAGCVCGPNGFCG |
| 85 | 2.4C | EETI-II | GCFVGRGDWAPLTCKQDSDCQAGCVCGPNGFCG |

TABLE 1-continued

Integrin Binding Knottin Sequences

| SEQ ID NO | Peptide Identifier | Scaffold | Sequenc(RGD motif is underlined with flanking residues) |
|---|---|---|---|
| 86 | 2.4D | EETI-II | GCPVGRGDWSPASCKQDSDCRAGCVCGPNGFCG |
| 87 | 2.4E | EETI-II | GCPRPRGDNPPLTCKQDSDCLAGCVCGPNGFCG |
| 88 | 2.4F | EETI-II | GCYQGRGDWSPSSCKQDSDCPAGCVCGPNGFCG |
| 89 | 2.4G | EETI-II | GCAPGRGDWAPSECKQDSDCQAGCVCGPNGFCG |
| 90 | 2.4J | EETI-II | GCVQGRGDWSPPSCKQDSDCPAGCVCGPNGFCG |
| 91 | 2.5A | EETI-II | GCHVGRGDWAPEECKQDSDCQAGCVCGPNGFCG |
| 92 | 2.5C | EETI-II | GCDGGRGDWAPPACKQDSDCRAGCVCGPNGFCG |
| 93 | 2.5D | EETI-II | GCPQGRGDWAPTSCKQDSDCRAGCVCGPNGFCG |
| 94 | 2.5F | EETI-II | GCPRPRGDNPPLTCKQDSDCLAGCVCGPNGFCG |
| 95 | 2.5D K15S Mutant | EETI-II | GCPQGRGDWAPTSCSQDSDCLAGCVCGPNGFCG |
| 96 | 2.5F K15S Mutant | EETI-II | GCPRPRGDNPPLTCSQDSDCLAGCVCGPNGFCG |
| 97 | 2.5H | EETI-II | GCPQGRGDWAPEWCKQDSDCPAGCVCGPNGFCG |
| 98 | 2.5J | EETI-II | GCPRGRGDWSPPACKQDSDCQAGCVCGPNGFCG |
| 99 | 3A | AgRp | GCVRLHESCLGQQVPCCDPAATCYCVVRGDWRKRCYCR |
| 100 | 3B | AgRp | GCVRLHESCLGQQVPCCDPAATCYCEERGDMLEKCYCR |
| 101 | 3C | AgRp | GCVRLHESCLGQQVPCCDPAATCYCETRGDGKEKCYCR |
| 102 | 3D | AgRp | GCVRLHESCLGQQVPCCDPAATCYCQWRGDGDVKCYCR |
| 103 | 3E | AgRp | GCVRLHESCLGQQVPCCDPAATCYCSRRGDMRERCYCR |
| 104 | 3F | AgRp | GCVRLHESCLGQQVPCCDPAATCYCQYRGDMKHCYCR |
| 105 | 3G | AgRp | GCVRLHESCLGQQVPCCDPAATCYCTGRGDTKVLCYCR |
| 106 | 3H | AgRp | GCVRLHESCLGQQVPCCDPAATCYCVERGDMKRRCYCR |
| 107 | 3I | AgRp | GCVRLHESCLGQQVPCCDPAATCYCTGRGDVRMNCYCR |
| 108 | 3J | AgRp | GCVRLHESCLGQQVPCCDPAATCYCVERGDMSKCYCR |
| 109 | 4A | AgRp | GCVRLHESCLGQQVPCCDPAATCYCRGRGDMRRECYCR |
| 110 | 4B | AgRp | GCVRLHESCLGQQVPCCDPAATCYCEGRGDVKVNCYCR |
| 111 | 4C | AgRp | GCVRLHESCLGQQVPCCDPAATCYCVGRGDEKMSCYCR |
| 112 | 4D | AgRp | GCVRLHESCLGQQVPCCDPAATCYCVSRGDMRKRCYCR |
| 113 | 4E | AgRp | GCVRLHESCLGQQVPCCDPAATCYCERRGDSVKKCYCR |
| 114 | 4F | AgRp | GCVRLHESCLGQQVPCCDPAATCYCEGRGDTRRRCYCR |
| 115 | 4G | AgRp | GCVRLHESCLGQQVPCCDPAATCYCEGRGDVVRRCYCR |
| 116 | 4H | AgRp | GCVRLHESCLGQQVPCCDPAATCYCKGRGDNKRKCYCR |
| 117 | 4I | AgRp | GCVRLHESCLGQQVPCCDPAXTCYCKGRGDVRRVCYCR |
| 118 | 4J | AgRp | GCVRLHESCLGQQVPCCDPAATCYCVGRGDNKVKCYCR |
| 119 | 5A | AgRp | GCVRLHESCLGQQVPCCDPAATCYCVGRGDNRLKCYCR |
| 120 | 5B | AgRp | GCVRLHESCLGQQVPCCDPAATCYCVERGDGMKKCYCR |
| 121 | 5C | AgRp | GCVRLHESCLGQQVPCCDPAATCYCEGRGDMRRRCYCR |
| 122 | 5D | AgRp | GCVRLHESCLGQQVPCCDPAATCYCQGRGDGDVKCYCR |

TABLE 1-continued

Integrin Binding Knottin Sequences

| SEQ ID NO | Peptide Identifier | Scaffold | Sequenc(RGD motif is underlined with flanking residues) |
|---|---|---|---|
| 123 | 5E | AgRp | GCVRLHESCLGQQVPCCDPAATCYCSGRGDNDLVCYCR |
| 124 | 5F | AgRp | GCVRLHESCLGQQVPCCDPAATCYCVERGDGMIRCYCR |
| 125 | 5G | AgRp | GCVRLHESCLGQQVPCCDPAATCYCSGRGDNDLVCYCR |
| 126 | 5H | AgRp | GCVRLHESCLGQQVPCCDPAATCYCEGRGDMKMKCYCR |
| 127 | 5I | AgRp | GCVRLHESCLGQQVPCCDPAATCYCIGRGDVRRRCYCR |
| 128 | 5J | AgRp | GCVRLHESCLGQQVPCCDPAATCYCEERGDGRKKCYCR |
| 129 | 6B | AgRp | GCVRLHESCLGQQVPCCDPAATCYCEGRGDRDMKCYCR |
| 130 | 6C | AgRp | GCVRLHESCLGQQVPCCDPAATCYCTGRGDEKLRCYCR |
| 131 | 6E | AgRp | GCVRLHESCLGQQVPCCDPAATCYCVERGDGNRRCYCR |
| 132 | 6F | AgRp | GCVRLHESCLGQQVPCCDPAATCYCESRGDVVRKCYCR |
| 133 | 7C | AgRp | GCVRLHESCLGQQVPCCDPAATCYCYGRGDNDLRCYCR |

The present polypeptides target $\alpha_v\beta_3$, $\alpha_v\beta_5$, and in some cases $\alpha_5\beta_1$ integrin receptors. They do not bind to other integrins tested, such as $\alpha_{iib}\beta_3$, where there was little to no affinity. Thus, these engineered integrin-binding polypeptides have broad diagnostic and therapeutic applications in a variety of human cancers that specifically overexpress the above named integrins. As described below, these polypeptides bind with high affinity to both detergent-solubilized and tumor cell surface integrin receptors.

The $\alpha_v\beta_3$ (and $\alpha_v\beta_5$) integrins are also highly expressed on many tumor cells including osteosarcomas, neuroblastomas, carcinomas of the lung, breast, prostate, and bladder, glioblastomas, and invasive melanomas The $\alpha_v\beta_3$ integrin has been shown to be expressed on tumor cells and/or the vasculature of breast, ovarian, prostate, and colon carcinomas, but not on normal adult tissues or blood vessels. Also, the $\alpha_5\beta_1$ integrin has been shown to be expressed on tumor cells and/or the vasculature of breast, ovarian, prostate, and colon carcinomas, but not on normal adult tissue or blood vessels. The present, small, conformationally-constrained polypeptides (about 33 amino acids) are so constrained by intramolecular bonds. For example, EETI-II has three disulfide linkages. This will make it more stable in vivo. These peptides target $\alpha_v$ integrins alone, or both $\alpha_v$ and $\alpha_5\beta_1$ integrins. Until now, it is believed that the development of a single agent that can bind $\alpha_v\beta_3$, $\alpha_v\beta_5$, and $\alpha_5\beta_1$ integrins with high affinity and specificity has not been achieved. Since all three of these integrins are expressed on tumors and are involved in mediating angiogenesis and metastasis, a broad spectrum targeting agent (i.e., $\alpha_v\beta_3$, $\alpha_v\beta_3$, and $\alpha_5\beta_1$) will likely be more effective for diagnostic and therapeutic applications.

The present engineered knottin-Fc fusions have several advantages over previously identified integrin-targeting compounds. They possess a compact, disulfide-bonded core that confers proteolytic resistance and exceptional in vivo stability.

Our studies indicate the half-life of integrin-binding-Fc fusion protein in mouse serum to be greater than 90 hours. Their larger size (~3-4 kDa) and enhanced affinity compared to RGD-based cyclic peptides confer enhanced pharmacokinetics and biodistribution for molecular imaging and therapeutic applications. These knottin-Fc proteins are small enough to allow for chemical synthesis and site-specific conjugation of imaging probes, radioisotopes, or chemotherapeutic agents. Furthermore, they can easily be chemically modified to further improve in vivo properties if necessary.

C. Knottin-Fc Fusion

The knottin-Fc fusions described herein and in U.S. Patent Application No. 2014/0073518, herein incorporated by reference in its entirety, combine an engineered integrin-binding polypeptide (within a knottin scaffold) and an Fc domain or antibody like construct capable of binding FcγR and inducing ADCC.

The Fc portion of an antibody is formed by the two carboxy terminal domains of the two heavy chains that make up an immunoglobin molecule. The IgG molecule contains 2 heavy chains (~50 kDa each) and 2 light chains (~25 kDa each). The general structure of all antibodies is very similar, a small region at the tip of the protein is extremely variable, allowing millions of antibodies with slightly different tip structures to exist. This region is known as the hypervariable region (Fab). The other fragment contains no antigen-binding activity but was originally observed to crystallize readily, and for this reason was named the Fc fragment, for Fragment crystallizable. This fragment corresponds to the paired $CH_2$ and $CH_3$ domains and is the part of the antibody molecule that interacts with effector molecules and cells. The functional differences between heavy-chain isotypes lie mainly in the Fc fragment. The hinge region that links the Fc and Fab portions of the antibody molecule is in reality a flexible tether, allowing independent movement of the two Fab arms, rather than a rigid hinge. This has been demonstrated by electron microscopy of antibodies bound to haptens. Thus the present fusion proteins can be made to contain two knottin peptides, one on each arm of the antibody fragment.

The Fc portion varies between antibody classes (and subclasses) but is identical within that class. The C-terminal end of the heavy chain forms the Fc region. The Fc region plays an important role as a receptor binding portion. The Fc portion of antibodies will bind to Fc receptors in two different ways. For example, after IgG and IgM bind to a pathogen by their Fab portion their Fc portions can bind to receptors on phagocytic cells (like macrophages) inducing phagocytosis.

The present knottin-Fc fusions can be implemented such that the Fc portion is used to provide dual binding capability, and/or for half-life extension, for improving expression levels, etc. The Fc fragment in the knottin-Fc can be, for example, from murine IgG2a or human IgG1. Linkers can be optionally used to connect the knottin to the Fc portion. Preferably, the linkers do not affect the binding affinity of the knottin-Fc to integrins or Fc receptors. A variety of Fc domain gene sequences (e.g., mouse and human constant region gene sequences) are available in the form of publicly accessible deposits.

a. Fc-Domains

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g., hinge, CH2, and/or CH3 sequences, or portions thereof) can be derived from these sequences using art recognized techniques. The genetic material obtained using any of the foregoing methods may then be altered or synthesized to obtain polypeptides used herein. It will further be appreciated that alleles, variants and mutations of constant region DNA sequences are suitable for use in the methods disclosed herein.

Knottin-Fc suitable for use in the methods disclosed herein may comprise one or more Fc domains (e.g., 2, 3, 4, 5, 6, 7, 8, 9, 10, or more Fc domains). In one embodiment, the Fc domains may be of different types. In one embodiment, at least one Fc domain present in a knottin-Fc comprises a hinge domain or portion thereof. In another embodiment, a knottin-Fc comprises at least one Fc domain which comprises at least one CH2 domain or portion thereof. In another embodiment, a knottin-Fc comprises at least one Fc domain which comprises at least one CH3 domain or portion thereof. In another embodiment, a knottin-Fc comprises at least one Fc domain which comprises at least one CH4 domain or portion thereof. In another embodiment, a knottin-Fc comprises at least one Fc domain which comprises at least one hinge domain or portion thereof and at least one CH2 domain or portion thereof (e.g, in the hinge-CH2 orientation). In another embodiment, a knottin-Fc comprises at least one Fc domain which comprises at least one CH2 domain or portion thereof and at least one CH3 domain or portion thereof (e.g, in the CH2-CH3 orientation). In another embodiment, a knottin-Fc comprises at least one Fc domain comprising at least one hinge domain or portion thereof, at least one CH2 domain or portion thereof, and least one CH3 domain or portion thereof, for example in the orientation hinge-CH2-CH3, hinge-CH3-CH2, or CH2-CH3-hinge.

In certain embodiments, a knottin-Fc comprises at least one complete Fc region derived from one or more immunoglobulin heavy chains (e.g., an Fc domain including hinge, CH2, and CH3 domains, although these need not be derived from the same antibody). In other embodiments a knottin-Fc comprises at least two complete Fc domains derived from one or more immunoglobulin heavy chains. In certain embodiments, the complete Fc domain is derived from a human IgG immunoglobulin heavy chain (e.g., human IgG1).

In another embodiment, a knottin-Fc comprises at least one Fc domain comprising a complete CH3 domain. In another embodiment, a knottin-Fc comprises at least one Fc domain comprising a complete CH2 domain. In another embodiment, a knottin-Fc comprises at least one Fc domain comprising at least a CH3 domain, and at least one of a hinge region, and a CH2 domain. In one embodiment, a knottin-Fc comprises at least one Fc domain comprising a hinge and a CH3 domain. In another embodiment, a knottin-Fc comprises at least one Fc domain comprising a hinge, a CH2, and a CH3 domain. In certain embodiments, the Fc domain is derived from a human IgG immunoglobulin heavy chain (e.g., human IgG1). In certain embodiments, a human IgG1 Fc domain is used with a hinge region mutation, substitution, or deletion to remove or substitute one or more hinge region cysteine residues.

The constant region domains or portions thereof making up an Fc domain of a knottin-Fc may be derived from different immunoglobulin molecules. For example, a polypeptide used in the invention may comprise a CH2 domain or portion thereof derived from an IgG1 molecule and a CH3 region or portion thereof derived from an IgG3 molecule. In another example, a knottin-Fc can comprise an Fc domain comprising a hinge domain derived, in part, from an IgG1 molecule and, in part, from an IgG3 molecule. As set forth herein, it will be understood by one of ordinary skill in the art that an Fc domain may be altered such that it varies in amino acid sequence from a naturally occurring antibody molecule.

In other constructs it may be desirable to provide a peptide spacer between one or more constituent Fc domains. For example, a peptide spacer may be placed between a hinge region and a CH2 domain and/or between a CH2 and a CH3 domain. For example, compatible constructs could be expressed wherein the CH2 domain has been deleted and the remaining CH3 domain (synthetic or unsynthetic) is joined to the hinge region with a 1-20, 1-10, or 1-5 amino acid peptide spacer. Such a peptide spacer may be added, for instance, to ensure that the regulatory elements of the constant region domain remain free and accessible or that the hinge region remains flexible. Preferably, any linker peptide compatible with the instant invention will be relatively non-immunogenic and not prevent proper folding of the Fc.

b. Changes to Fc Amino Acids

In certain embodiments, an Fc domain is altered or modified, e.g., by amino acid mutation (e.g., addition, deletion, or substitution). As used herein, the term "Fc domain variant" refers to an Fc domain having at least one amino acid modification, such as an amino acid substitution, as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region.

In certain embodiments, the hinge region of human IgG1 Fc domain is altered by an amino acid substitution or deletion to mutate or remove one or more of three hinge region cysteine residues (located at residues 220, 226, and 229 by EU numbering). In some aspects, the upper hinge region is deleted to remove a cysteine that pairs with the light chain. For example, amino acids "EPKSC" in the upper hinge region are deleted, as set forth in SEQ ID NO: 3. In other aspects, one or more of three hinge region cysteines is mutated (e.g., to serine). In certain embodiments, cysteine 220 is mutated to serine.

In certain embodiments, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

In certain embodiments, a knottin-Fc fusion comprises an Fc variant comprising more than one amino acid substitution. The knottin-Fc fusion used in the methods described herein may comprise, for example, 2, 3, 4, 5, 6, 7, 8, 9, 10 or more amino acid substitutions. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, or 25 amino acid positions or more.

In certain embodiments, a knottin-Fc fusion comprises an amino acid substitution to an Fc domain which alters the antigen-independent effector functions of the polypeptide, in particular the circulating half-life of the polypeptide.

In one embodiment, the knottin-Fc exhibits enhanced binding to an activating FcγR (e.g. Fcγ1, Fcγ1a, or FcγRIIIa). Exemplary amino acid substitutions which altered FcR or complement binding activity are disclosed in International PCT Publication No. WO 2005/063815 which is incorporated by reference herein. In certain embodiments the Fc region contains at least one of the following mutations: S239D, S239E, L261A, H268D, S298A, A330H, A330L, I332D, I332E, I332Q, K334V, A378F, A378K, A378W, A378Y, H435S, or H435G. In certain embodiments, the Fc region contains at least one of the following mutations: S239D, S239E, I332D or I332E or H268D. In certain embodiments, the Fc region contains at least one of the following mutations: I332D or I332E or H268D.

The knottin-Fc used herein may also comprise an amino acid substitution which alters the glycosylation of the knottin-Fc. For example, the Fc domain of the knottin-Fc may comprise an Fc domain having a mutation leading to reduced glycosylation (e.g., N- or O-linked glycosylation) or may comprise an altered glycoform of the wild-type Fc domain (e.g., a low fucose or fucose-free glycan). In another embodiment, the knottin-Fc has an amino acid substitution near or within a glycosylation motif, for example, an N-linked glycosylation motif that contains the amino acid sequence NXT or NXS. Exemplary amino acid substitutions which reduce or alter glycosylation are disclosed in WO05/018572 and US2007/0111281, which are incorporated by reference herein. In other embodiments, the knottin-Fc used herein comprises at least one Fc domain having engineered cysteine residue or analog thereof which is located at the solvent-exposed surface. In certain embodiments, the knottin-Fc used herein comprises an Fc domain comprising at least one engineered free cysteine residue or analog thereof that is substantially free of disulfide bonding with a second cysteine residue. Any of the above engineered cysteine residues or analogs thereof may subsequently be conjugated to a functional domain using art-recognized techniques (e.g., conjugated with a thiol-reactive heterobifunctional linker).

In one embodiment, the knottin-Fc used herein may comprise a genetically fused Fc domain having two or more of its constituent Fc domains independently selected from the Fc domains described herein. In one embodiment, the Fc domains are the same. In another embodiment, at least two of the Fc domains are different. For example, the Fc domains of the knottin-Fc used herein comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc domains of the knottin-Fc used herein may differ in sequence at one or more amino acid positions. For example, at least two of the Fc domains may differ at about 5 amino acid positions (e.g., 1, 2, 3, 4, or 5 amino acid positions), about 10 positions, about 15 positions, about 20 positions, about 30 positions, about 40 positions, or about 50 positions).

Immune Checkpoint Blocker

In certain embodiments, immune checkpoint blockers are used in combination with other therapeutic agents described herein (e.g., extended-PK IL-2 and integrin-binding-Fc fusion protein). T cell activation and effector functions are balanced by co-stimulatory and inhibitory signals, referred to as "immune checkpoints." Inhibitory ligands and receptors that regulate T cell effector functions are overexpressed on tumor cells. Subsequently, agonists of co-stimulatory receptors or antagonists of inhibitory signals, result in the amplification of antigen-specific T cell responses. In contrast to therapeutic antibodies which target tumor cells directly, immune checkpoint blockers enhance endogenous anti-tumor activity. In certain embodiments, the immune checkpoint blocker suitable for use in the methods disclosed herein, is an antagonist of inhibitory signals, e.g., an antibody which targets, for example, PD-1, PD-L1, CTLA-4, LAG3, B7-H3, B7-H4, and TIM3. These ligands and receptors are reviewed in Pardoll, D., Nature. 12: 252-264, 2012.

Disclosed herein are methods for treating a subject afflicted with diseases such as cancer, which methods comprise administering to the subject a composition comprising a therapeutically effective amount of a molecule which blocks the immune checkpoint, and an integrin-binding-Fc fusion protein. In certain embodiments, the methods for treating a subject afflicted with diseases such as cancer, which methods comprise administering to the subject a composition comprising a therapeutically effective amount of a molecule which blocks the immune checkpoint, an integrin-binding-Fc fusion protein, and IL-2 (e.g., extended-PK IL-2). In certain embodiments, the immune checkpoint blocker is an antibody or an antigen-binding portion thereof, that disrupts or inhibits signaling from an inhibitory immunoregulator. In certain embodiments, the immune checkpoint blocker is a small molecule that disrupts or inhibits signaling from an inhibitory immunoregulator.

In certain embodiments, the inhibitory immunoregulator (immune checkpoint blocker) is a component of the PD-1/PD-L1 signaling pathway. Accordingly, certain embodiments provide methods for immunotherapy of a subject afflicted with cancer, which methods comprise administering to the subject a therapeutically effective amount of an antibody or an antigen-binding portion thereof that disrupts the interaction between the PD-1 receptor and its ligand, PD-L1. Antibodies known in the art which bind to PD-1 and disrupt the interaction between the PD-1 and its ligand, PD-L1, and stimulates an anti-tumor immune response, are suitable for use in the methods disclosed herein. In certain embodiments, the antibody or antigen-binding portion thereof binds specifically to PD-1. For example, antibodies that target PD-1 include, e.g., nivolumab (BMS-936558, Bristol-Myers Squibb) and pembrolizumab (lambrolizumab, MK03475, Merck). Other suitable antibodies for use in the methods disclosed herein are anti-PD-1 antibodies disclosed in U.S. Pat. No. 8,008,449, herein incorporated by reference. In certain embodiments, the antibody or antigen-binding portion thereof binds specifically to PD-L1 and inhibits its interaction with PD-1, thereby increasing immune activity. Antibodies known in the art which bind to PD-L1 and disrupt the interaction between the PD-1 and PD-L1, and stimulates an anti-tumor immune response, are suitable for use in the methods disclosed herein. For example, antibodies that target PD-L1 and are in clinical trials, include BMS-936559 (Bristol-Myers Squibb) and MPDL3280A (Genetech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, are suitable for use in the methods disclosed herein.

In certain embodiments, the inhibitory immunoregulator is a component of the CTLA-4 signaling pathway. Accordingly, certain embodiments provide methods for immunotherapy of a subject afflicted with cancer, which methods comprise administering to the subject a therapeutically effective amount of an antibody or an antigen-binding portion thereof that targets CTLA-4 and disrupts its interaction with CD80 and CD86. Exemplary antibodies that target CTLA-4 include ipilimumab (MDX-010, MDX-101, Bristol-Myers Squibb), which is FDA approved, and tremelimumab (ticilimumab, CP-675, 206, Pfizer), currently undergoing human trials. Other suitable antibodies that target CTLA-4 are disclosed in WO 2012/120125, U.S. Pat. No. 6,984,720, No. 6,682,7368, and U.S. Patent Applications 2002/0039581, 2002/0086014, and 2005/0201994, herein incorporated by reference. It will be understood by one of ordinary skill that any antibody which binds to CTLA-4, disrupts its interaction with CD80 and CD86, and stimulates an anti-tumor immune response, are suitable for use in the methods disclosed herein.

In certain embodiments, the inhibitory immunoregulator is a component of the LAG3 (lymphocyte activation gene 3) signaling pathway. Accordingly, certain embodiments provide methods for immunotherapy of a subject afflicted with cancer, which methods comprise administering to the subject a therapeutically effective amount of an antibody or an antigen-binding portion thereof that targets LAG3 and disrupts its interaction with MHC class II molecules. An exemplary antibody that targets LAG3 is IMP321 (Immutep), currently undergoing human trials. Other suitable antibodies that target LAG3 are disclosed in U.S. Patent Application 2011/0150892, herein incorporated by reference. It will be understood by one of ordinary skill that any antibody which binds to LAG3, disrupts its interaction with MHC class II molecules, and stimulates an anti-tumor immune response, are suitable for use in the methods disclosed herein.

In certain embodiments, the inhibitory immunoregulator is a component of the B7 family signaling pathway. In certain embodiments, the B7 family members are B7-H3 and B7-H4. Accordingly, certain embodiments provide methods for immunotherapy of a subject afflicted with cancer, which methods comprise administering to the subject a therapeutically effective amount of an antibody or an antigen-binding portion thereof that targets B7-H3 or -H4. The B7 family does not have any defined receptors but these ligands are upregulated on tumor cells or tumor-infiltrating cells. Preclinical mouse models have shown that blockade of these ligands can enhance anti-tumor immunity. An exemplary antibody that targets B7-H3 is MGA271 (Macrogenics), currently undergoing human trials. Other suitable antibodies that target B7 family members are disclosed in U.S. Patent Application 2013/0149236, herein incorporated by reference. It will be understood by one of ordinary skill that any antibody which binds to B7-H3 or H4, and stimulates an anti-tumor immune response, are suitable for use in the methods disclosed herein.

In certain embodiments, the inhibitory immunoregulator is a component of the TIM3 (T cell membrane protein 3) signaling pathway. Accordingly, certain embodiments provide methods for immunotherapy of a subject afflicted with cancer, which methods comprise administering to the subject a therapeutically effective amount of an antibody or an antigen-binding portion thereof that targets TIM3 and disrupts its interaction with galectin 9. Suitable antibodies that target TIM3 are disclosed in U.S. Patent Application 2013/0022623, herein incorporated by reference. It will be understood by one of ordinary skill that any antibody which binds to TIM3, disrupts its interaction with galectin 9, and stimulates an anti-tumor immune response, are suitable for use in the methods disclosed herein.

It should be understood that antibodies targeting immune checkpoints suitable for use in the methods disclosed herein are not limited to those described supra. Moreover, it will be understood by one of ordinary skill in the art that other immune checkpoint targets can also be targeted by antagonists or antibodies in the methods described herein, provided that the targeting results in the stimulation of an anti-tumor immune response as reflected in, e.g., an increase in T cell proliferation, enhanced T cell activation, and/or increased cytokine production (e.g., IFN-γ, IL-2).

Alternatives to Immune Checkpoint Blockers

In certain embodiments, an antagonist of vascular endothelial growth factor (VEGF) is used in place of an immune checkpoint blocker. VEGF has recently been demonstrated to play a role in immune suppression (Liang, W.-C. et al. *J. Biol. Chem.* (2006) Vol 281: 951-961; Voron, T. et al. *Front Oncol* (2014) Vol. 4: Article 70; Terme, M. et al., *Clin Dev Immunol* (2012) Vol. 2012: Article ID 492920; Kandalaft, E. et al., *Curr Top Microbiol Immunol* (2011) Vol 344: 129-48), therefore blocking its activity would enhance the immune response, similar to that of an immune checkpoint blocker. A "VEGF antagonist" refers to a molecule capable of neutralizing, blocking, inhibiting, abrogating, reducing or interfering with VEGF activities including its binding to one or more VEGF receptors. Non-limiting examples of VEGF antagonists include anti-VEGF antibodies and antigen-binding fragments thereof, receptor molecules and derivatives which bind specifically to VEGF thereby sequestering its binding to one or more receptors (e.g., a VEGF receptor), anti-VEGF receptor antibodies, VEGF receptor antagonists such as small molecule inhibitors of the VEGFR tyrosine kinases, or a dominant negative VEGF.

In certain embodiments, the VEGF antagonist is an antibody. An "anti-VEGF antibody" is an antibody that binds to VEGF with sufficient affinity and specificity. Non-limiting examples of anti-VEGF antibodies are described in U.S. Pat. Nos. 6,884,879, 7,060,269, 6,582,959, 6,703,030, 6,054,297, US Patent Application Nos. 2006009360, 20050186208, 20030206899, 20030190317, 20030203409, 20050112126, and PCT Publication Nos. WO 98/45332, 96/30046, 94/10202, 05/044853, 13/181452. The contents of these patents and patent applications are herein incorporated by reference. In certain embodiments the VEGF antibody is bevacizumab (Avastin® Genentech/Roche) or ranibizumab (Lucentis® Genentech/Roche).

In certain embodiments, the VEGF antagonist binds to the VEGF receptor. VEGF receptors, or fragments thereof, that specifically bind to VEGF can be used to bind to and sequester the VEGF protein, thereby preventing it from activating downstream signaling. In certain embodiments, the VEGF receptor, or VEGF binding fragment thereof, is a soluble VEGF receptor, such as sFlt-1. The soluble form of the receptor exerts an inhibitory effect on the biological activity of VEGF by binding to VEGF, thereby preventing it from binding to its natural receptors present on the surface of target cells. Non-limiting examples of VEGF antagonists which bind the VEGF receptor are disclosed in PCT Application Nos. 97/44453, 05/000895 and U.S. Patent Application No. 20140057851. In certain embodiments the VEGF antagonist is a polypeptide with a bifunctional single-chain antagonistic human VEGF variant comprising a modified VEGF wherein the modified VEGF comprises a loop with an integrin-recognition RGD sequence, as described in U.S. Pat. No. 8,741,839, herein incorporated by reference.

Linkers

In certain embodiments, the extended-PK group is optionally fused to IL-2 via a linker. In certain embodiments, an integrin-binding polypeptide is fused to an Fc fragment via a linker. Suitable linkers are well known in the art, such as those disclosed in, e.g., US2010/0210511 US2010/0179094, and US2012/0094909, which are herein incorporated by reference in its entirety. Exemplary linkers include gly-ser polypeptide linkers, glycine-proline polypeptide linkers, and proline-alanine polypeptide linkers. In a certain embodiment, the linker is a gly-ser polypeptide linker, i.e., a peptide that consists of glycine and serine residues.

Exemplary gly-ser polypeptide linkers comprise the amino acid sequence Ser(Gly$_4$Ser)n (SEQ ID NO: 134). In one embodiment, n=1. In one embodiment, n=2. In another embodiment, n=3, i.e., Ser(Gly$_4$Ser)3 (SEQ ID NO: 135). In another embodiment, n=4, i.e., Ser(Gly$_4$Ser)4 (SEQ ID NO: 136). In another embodiment, n=5. In yet another embodiment, n=6. In another embodiment, n=7. In yet another embodiment, n=8. In another embodiment, n=9. In yet another embodiment, n=10. Another exemplary gly-ser polypeptide linker comprises (Gly$_4$Ser)n (SEQ ID NO: 137). In one embodiment, n=1. In one embodiment, n=2. In a certain embodiment, n=3. In another embodiment, n=4. In another embodiment, n=5. In yet another embodiment, n=6. Another exemplary gly-ser polypeptide linker comprises (Gly$_3$Ser)n (SEQ ID NO: 138). In one embodiment, n=1. In one embodiment, n=2. In a certain embodiment, n=3. In another embodiment, n=4. In another embodiment, n=5. In yet another embodiment, n=6.

Other Therapeutic Agents

The integrin-binding-Fc fusion protein suitable for use in the methods disclosed herein, can be used in conjunction with one or more therapeutic agents. In one embodiment, the therapeutic agent is a therapeutic antibody. In another embodiment, the therapeutic agent is a therapeutic protein. In another embodiment, the therapeutic agent is a small molecule. In another embodiment, the therapeutic agent is an antigen. In another embodiment, the therapeutic agent is a population of cells.

Engineered Fusion Molecules

Also provided herein are engineered molecules that comprise two or more of IL-2, and an antibody (e.g., a therapeutic antibody, an immune checkpoint blocker, or an antibody that antagonizes VEGF) or antibody fragment described herein. Such engineered molecules can effectively reduce the number of components to be administered to a subject (e.g., a cancer patient) in the methods described herein. In some embodiments, the antibody or antibody fragment serves as the scaffold for conjugation with other components (e.g., IL-2).

Accordingly, in certain embodiments, the engineered molecule comprises IL-2 and an antibody or antibody fragment. In a particular embodiment, the antibody for use in the engineered protein is a bispecific antibody, wherein one component is a therapeutic antibody and the other component is an antibody that binds to an immune checkpoint blocker or an antibody that antagonizes VEGF activity. Methods for generating bispecific antibodies are known in the art.

Accordingly, in certain embodiments, the engineered molecule comprises IL-2 and a bispecific antibody which binds to a therapeutic target and an immune checkpoint blocker or an antibody that antagonizes VEGF.

In certain embodiments, the IL-2 component for use in the engineered protein is an IL-2 lacking a pharmacokinetic moiety (i.e., a non-extended-PK IL-2). In other embodiments, the IL-2 comprises a pharmacokinetic moiety (an extended-PK IL-2).

In certain embodiments, the components of the engineered molecule are conjugated to the antibody or bispecific antibody with or without a linker. Suitable linkers for conjugation are described herein and extensively described in the art.

Regions to which polypeptide-based components (e.g., IL-2) of the engineered molecule can be fused, with or without a linker, to the antibody are generally known in the art, and include, for example, the C-terminus of the antibody heavy chain, and the C-terminus of the antibody light chain.

In certain embodiments, components of the engineered molecule do not interfere with the function of the other components. By way of example, when the engineered protein comprises a therapeutic antibody and IL-2, the IL-2 will be fused to the therapeutic antibody in a manner such that the antibody retains its antigen-binding function, and IL-2 retains the ability to interact with its receptor. The methods described herein, e.g., in the Examples, can be used to determine whether components of the engineered protein retain their respective functions.

Methods of Making Polypeptides

In some aspects, the polypeptides described herein (e.g., IL-2, such as extended-PK IL-2, and knottin-Fc) are made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The methods of making polypeptides also include a vector capable of expressing the peptides in an appropriate host. The vector comprises the DNA molecule that codes for the peptides operatively linked to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins ($3^{rd}$ ed.) 2: 105-253; and Erickson et al. (1976), The Proteins ($3^{rd}$ ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

Expression of Polypeptides

The nucleic acid molecules described above can be contained within a vector that is capable of directing their expression in, for example, a cell that has been transduced with the vector. Accordingly, in addition to extended-PK IL-2 and knottin-Fc mutants, expression vectors containing a nucleic acid molecule encoding an extended-PK IL-2 or knottin-Fc mutant and cells transfected with these vectors are among the certain embodiments.

Vectors suitable for use include T7-based vectors for use in bacteria (see, for example, Rosenberg et al., Gene 56: 125, 1987), the pMSXND expression vector for use in mammalian cells (Lee and Nathans, J. Biol. Chem. 263:3521, 1988), and baculovirus-derived vectors (for example the expression vector pBacPAKS from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance ($neo^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes an extended-PK IL-2 or knottin-Fc mutant are also features of the invention. A cell of the invention is a transfected cell, i.e., a cell into which a nucleic acid molecule, for example a nucleic acid molecule encoding an extended-PK IL-2 mutant or knottin-Fc, has been introduced by means of recombinant DNA techniques. The progeny of such a cell are also considered within the scope of the invention.

The precise components of the expression system are not critical. For example, an extended-PK IL-2 or knottin-Fc mutant can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., as therapeutic agents, as described herein.

Pharmaceutical Compositions and Modes of Administration

In certain embodiments, IL-2 is administered together (simultaneously or sequentially) with a knottin-Fc. In certain embodiments, IL-2 is administered prior to the administration of a knottin-Fc. In certain embodiments, IL-2 is administered concurrently with the administration of a knottin-Fc. In certain embodiments, IL-2 is administered subsequent to the administration of a knottin-Fc. In certain embodiments, the IL-2 and a knottin-Fc are administered simultaneously. In other embodiments, the IL-2 and a knottin-Fc are administered sequentially. In yet other embodiments, the IL-2 and a knottin-Fc are administered within one, two, or three days of each other.

In certain embodiments, IL-2 and knottin-Fc are administered with an immune checkpoint blocker. In certain embodiments the immune checkpoint blocker is an anti-PD-1 antibody. In certain embodiments, the immune checkpoint blocker is an anti-CTLA-4 antibody. In certain embodiments, an antagonist of VEGF is used in place of an immune checkpoint blocker.

Pharmaceutical compositions of the invention can be administered in combination therapy, i.e., combined with other agents. Agents include, but are not limited to, in vitro synthetically prepared chemical compositions, antibodies, antigen binding regions, and combinations and conjugates thereof. In certain embodiments, an agent can act as an agonist, antagonist, allosteric modulator, or toxin.

In certain embodiments, the invention provides for separate pharmaceutical compositions comprising extended-PK IL-2 with a pharmaceutically acceptable diluent, carrier, solubilizer, emulsifier, preservative and/or adjuvant, and another pharmaceutical composition comprising a knottin-Fc with a pharmaceutically acceptable diluent, carrier, solubilizer, emulsifier, preservative and/or adjuvant. In certain embodiments, the invention further provides for a separate pharmaceutical composition comprising an immune checkpoint blocker (or an antagonist of VEGF) with a pharmaceutically acceptable diluent, carrier, solubilizer, emulsifier, preservative and/or adjuvant. In certain embodiments, the pharmaceutical compositions comprise both extended-PK IL-2 and knottin-Fc with a pharmaceutically acceptable diluents, carrier, solubilizer, emulsifier, preservative and/or adjuvant. In certain embodiments, the pharmaceutical composition comprises extended-PK IL-2, knottin-Fc, and an immune checkpoint blocker (or an antagonist of VEGF) with a pharmaceutically acceptable diluents, carrier, solubilizer, emulsifier, preservative and/or adjuvant.

In certain embodiments, the invention provides for pharmaceutical compositions comprising extended-PK IL-2, together with a pharmaceutically acceptable diluent, carrier, solubilizer, emulsifier, preservative and/or adjuvant, and another pharmaceutical composition comprises a knottin-Fc, together with a pharmaceutically acceptable diluent, carrier, solubilizer, emulsifier, preservative and/or adjuvant. In certain embodiments, the invention provides for pharmaceutical compositions comprising an immune checkpoint blocker, together with a pharmaceutically acceptable diluent, carrier, solubilizer, emulsifier, preservative and/or adjuvant. In certain embodiments, each of the agents, e.g., extended-PK IL-2, a knottin-Fc, and optionally an immune checkpoint blocker (or an antagonist of VEGF), can be formulated as separate compositions. In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18$^{th}$ Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of extended-PK IL-2, a knottin-Fc, and optionally an immune checkpoint blocker (or an antagonist of VEGF).

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising extended-PK IL-2, a knottin-Fc, and optionally an immune checkpoint blocker (or an antagonist of VEGF), can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising extended-PK IL-2, a knottin-Fc, and optionally an immune checkpoint blocker (or an antagonist of VEGF), can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired extended-PK IL-2, a knottin-Fc, and optionally an immune checkpoint blocker (or an antagonist of VEGF), in a pharmaceutically acceptable vehicle. In certain embodiments, a vehicle for parenteral injection is sterile distilled water in which extended-PK IL-2, a knottin-Fc, and optionally an immune checkpoint blocker (or an antagonist of VEGF), are formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, extended-PK IL-2, a knottin-Fc, and optionally an immune checkpoint blocker (or an antagonist of VEGF), can be formulated as a dry powder for inhalation. In certain embodiments, an inhalation solution comprising extended-PK IL-2, a knottin-Fc, and optionally an immune checkpoint blocker (or an antagonist of VEGF), can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, extended-PK IL-2, a knottin-Fc, and optionally an immune checkpoint blocker (or an antagonist of VEGF), that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of extended-PK IL-2, a knottin-Fc, and optionally an immune checkpoint blocker (or an antagonist of VEGF). In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of extended-PK IL-2, a knottin-Fc, and optionally an immune checkpoint blocker (or an antagonist of VEGF), in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving extended-PK IL-2, a knottin-Fc, and optionally an immune checkpoint blocker (or an antagonist of VEGF), in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising extended-PK IL-2 and/or one or more pharmaceutical compositions comprising a knottin-Fc, and optionally an immune checkpoint blocker (or an antagonist of VEGF), to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which extended-PK IL-2, a knottin-Fc, and optionally an immune checkpoint blocker (or an antagonist of VEGF), are being used, the route of administration, and the size (body weight, body surface or organ size) and/or condition (the age and general health) of the patient. In certain embodiments, the clinician can titer the dosage and modify the route of administration to obtain the optimal therapeutic effect. In certain embodiments, a typical dosage of extended-PK IL-2 and a knottin-Fc can each range from about 0.1 µg/kg to up to about 100 mg/kg or more, depending on the factors mentioned above. In certain embodiments, the dosage can range from 0.1 µg/kg up to about 100 mg/kg; or 1 µg/kg up to about 100 mg/kg; or 5 µg/kg up to about 100 mg/kg.

In certain embodiments, a typical dosage for an immune checkpoint blocker can range from about 0.1 mg/kg to up to about 300 mg/kg or more, depending on the factors mentioned above. In certain embodiments, the dosage can range from 1 mg/kg up to about 300 mg/kg; or 5 mg/kg up to about 300 mg/kg; or 10 mg/kg up to about 300 mg/kg.

In certain embodiments, the frequency of dosing will take into account the pharmacokinetic parameters of extended-PK IL-2, a knottin-Fc, and optionally an immune checkpoint blocker (or an antagonist of VEGF), in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data. As described in the Examples below, dosing can occur daily, every other day, or weekly, all with similar anti-tumor responses.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising extended-PK IL-2, a knottin-Fc, and optionally an immune checkpoint blocker (or an antagonist of VEGF), in an ex vivo manner. In such instances, cells, tissues and/or organs that have been removed from the patient are exposed to a pharmaceutical composition comprising extended-PK IL-2, a knottin-Fc, and optionally an immune checkpoint blocker (or an antagonist of VEGF), after which the cells, tissues and/or organs are subsequently implanted back into the patient.

In certain embodiments, extended-PK IL-2, a knottin-Fc, and optionally an immune checkpoint blocker (or an antagonist of VEGF), can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Methods of Treatment

The extended-PK IL-2, a knottin-Fc, and optionally an immune checkpoint blocker (or an antagonist of VEGF), and/or nucleic acids expressing them, described herein, are useful for treating a disorder associated with abnormal apoptosis or a differentiative process (e.g., cellular proliferative disorders or cellular differentiative disorders, such as cancer). Non-limiting examples of cancers that are amenable to treatment with the methods of the present invention are described below.

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. Accordingly, the compositions used herein, comprising, e.g., extended-PK IL-2, a knottin-Fc, and optionally an immune checkpoint blocker (or an antagonist of VEGF), can be administered to a patient who has cancer.

As used herein, we may use the terms "cancer" (or "cancerous"), "hyperproliferative," and "neoplastic" to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The mutant IL-2 polypeptides can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macro globulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

It will be appreciated by those skilled in the art that amounts for each of the extended-PK IL-2, a knottin-Fc, and optionally an immune checkpoint blocker (or an antagonist of VEGF), that are sufficient to reduce tumor growth and size, or a therapeutically effective amount, will vary not only on the particular compounds or compositions selected, but also with the route of administration, the nature of the condition being treated, and the age and condition of the patient, and will ultimately be at the discretion of the patient's physician or pharmacist. The length of time during which the compounds used in the instant method will be given varies on an individual basis.

It will be appreciated by those skilled in the art that the B16 melanoma model used herein is a generalized model for solid tumors. That is, efficacy of treatments in this model is also predictive of efficacy of the treatments in other non-melanoma solid tumors. For example, as described in Baird et al. (J Immunology 2013; 190:469-78; Epub Dec. 7, 2012), efficacy of cps, a parasite strain that induces an adaptive immune response, in mediating anti-tumor immunity against B16F10 tumors was found to be generalizable to other solid tumors, including models of lung carcinoma and ovarian cancer. In another example, results from a line of research into VEGF targeting lymphocytes also shows that results in B16F10 tumors were generalizable to the other tumor types studied (Chinnasamy et al., *JCI* 2010; 120:3953-68; Chinnasamy et al., *Clin Cancer Res* 2012; 18:1672-83). In yet another example, immunotherapy involving LAG-3 and PD-1 led to reduced tumor burden, with generalizable results in a fibrosarcoma and colon adenocarcinoma cell lines (Woo et al., *Cancer Res* 2012; 72:917-27).

In certain embodiments, the extended-PK IL-2, knottin-Fc, and optional immune checkpoint blocker (or an antagonist of VEGF), are used to treat cancer.

In certain embodiments, the extended-PK IL-2, knottin-Fc, and optional immune checkpoint blocker (or an antagonist of VEGF) are used to treat melanoma, leukemia, lung cancer, breast cancer, prostate cancer, ovarian cancer, colon cancer, renal carcinoma, and brain cancer.

In certain embodiments, the extended-PK IL-2, knottin-Fc and optional immune checkpoint blocker (or an antagonist of VEGF) inhibit growth and/or proliferation of tumor cells.

In certain embodiments, the extended-PK IL-2, knottin-Fc, and optional immune checkpoint blocker (or an antagonist of VEGF) reduce tumor size.

In certain embodiments, the extended-PK IL-2, knottin-Fc, and optional immune checkpoint blocker (or an antagonist of VEGF) inhibit metastases of a primary tumor.

In certain embodiments, knottin-Fc and an immune checkpoint blocker (or an antagonist of VEGF), with or without IL-2, inhibit growth and/or proliferation of tumor cells.

In certain embodiments, knottin-Fc and an immune checkpoint blocker (or an antagonist of VEGF), with or without IL-2, reduce tumor size. In certain embodiments, knottin-Fc and an immune checkpoint blocker, with or without IL-2, inhibit metastases of a primary tumor.

It will be appreciated by those skilled in the art that reference herein to treatment extends to prophylaxis as well as the treatment of the noted cancers and symptoms.

Kits

A kit can include extended-PK IL-2, a knottin-Fc, and optionally an immune checkpoint blocker (or an antagonist of VEGF), as disclosed herein, and instructions for use. The kits may comprise, in a suitable container, extended-PK IL-2, an integrin binding knottin-Fc, an optional immune checkpoint blocker (or an antagonist of VEGF), one or more controls, and various buffers, reagents, enzymes and other standard ingredients well known in the art. Certain embodiments include a kit with extended-PK IL-2, knottin-Fc, and optional immune checkpoint blocker (or an antagonist of VEGF) in the same vial. In certain embodiments, a kit includes extended-PK IL-2, knottin-Fc, and optional immune checkpoint blocker (or an antagonist of VEGF) in separate vials.

The container can include at least one vial, well, test tube, flask, bottle, syringe, or other container means, into which extended-PK IL-2, a knottin-Fc, and optionally an immune checkpoint blocker (or an antagonist of VEGF) may be placed, and in some instances, suitably aliquoted. Where an additional component is provided, the kit can contain additional containers into which this component may be placed. The kits can also include a means for containing extended-PK IL-2, a knottin-Fc, and optionally an immune checkpoint blocker (or an antagonist of VEGF) and any other reagent containers in close confinement for commercial sale. Such containers may include injection or blow-molded plastic containers into which the desired vials are retained. Containers and/or kits can include labeling with instructions for use and/or warnings.

The present disclosure is further illustrated by the following examples, which should not be construed as further limiting. The contents of all figures and all references, Genbank sequences, patents and published patent applications cited throughout this application are expressly incorporated herein by reference. In particular, the disclosures of PCT publication WO 13/177187, U.S. Pat. No. 8,536,301, and U.S. Patent Publication No. 2014/0073518 are expressly incorporated herein by reference.

EXAMPLES

Below are examples of specific embodiments for carrying out the methods described herein. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for. The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* ($2^{nd}$ Edition, 1989); *Methods In Enzymology* (S. Colowick and N. Kaplan eds., Academic Press, Inc.); *Remington's Pharmaceutical Sciences*, $18^{th}$ Edition (Easton, Pa.: Mack Publishing Company, 1990); Carey and Sundberg *Advanced Organic Chemistry* $3^{rd}$ Ed. (Plenum Press) Vols A and B (1992).

Moreover, while the examples below employ extended-PK IL-2 of mouse origin (i.e., both the extended-PK group (mouse serum albumin) and IL-2 are of mouse origin) and mouse Fc fused to an integrin-binding knottin, it should be understood that corresponding human extended-PK IL-2 (i.e., human serum albumin (HSA) and human IL-2, and variants thereof) and integrin-binding-human-Fc (i.e., Fc from human IgG1 fused to knottin) can be readily generated by those of ordinary skill in the art using methods described supra, and used in the methods disclosed herein.

Example 1

Knottin-Fc Treatment is as Effective as TA99 Treatment in B16F10 Tumors

To address the lack of general tumor-associated antigens, a knottin-Fc protein was engineered. The knottin-Fc protein comprises two parts: 1) an engineered cystine knot (knottin) peptide that binds with high affinity to tumor-associated $\alpha_v\beta_3$, $\alpha_v\beta_5$, and $\alpha_5\beta_1$ integrin receptors (specifically 2.5F, SEQ ID NO: 94 or 96), and 2) an antibody Fc domain that mediates immune effector functions in vivo. The knottin-Fc used is 2.5F with a K15S substitution, fused to a mouse IgG2a Fc domain, SEQ ID NO: 45, unless stated otherwise.

To determine the effects of the knottin-Fc on tumor growth, $2.5 \times 10^5$ B16F10 murine melanoma cells were injected into the flanks of C57BL/6 mice subcutaneously. Prophylactic treatment was done with 80 µg knottin-Fc, 80 µg knottin-D265A (The D265A mutation in the murine IgG2a Fc domain eliminates binding to FcγR and complement), or 200 µg TA99, administered intraperitoneally every two days, starting on the day of tumor inoculation, for a total of ten treatments. TA99 is an antibody which binds to TYRP-1, (an antigen found on melanoma cells) and inhibits melanoma tumor growth.

Figure 1:
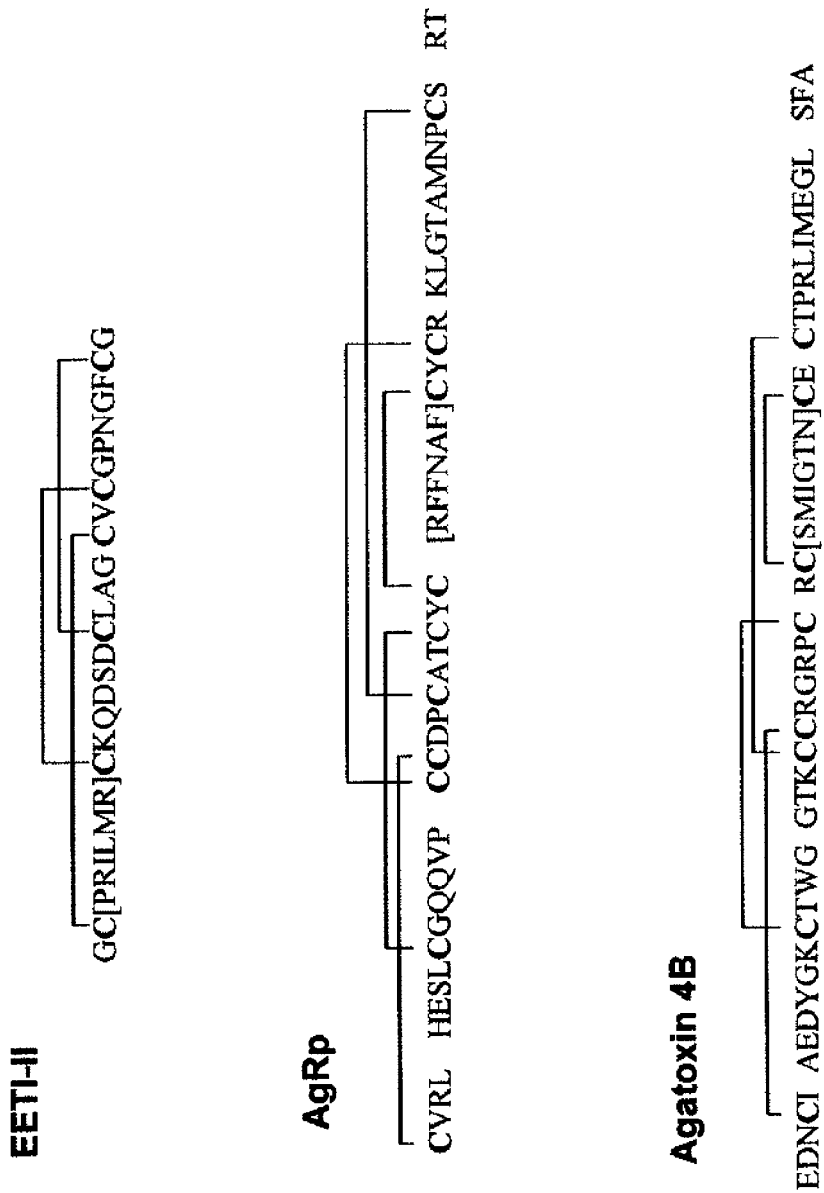
FIG. 1 shows the positions of the Cys-Cys disulfide linkages in the sequences of knottin proteins EETI-II (SEQ ID NO: 39), AgRP (SEQ ID NO: 40) and omega agatoxin 4B (SEQ ID NO: 41). Cysteine residues can be seen to be immediately flanking the RGD mimic loops, which, in the present engineered peptides, are between the brackets. For example, in AgRP, it can be seen that the cysteines flanking the RGD sequence will be linked to each other, whereas in EETI they are not. The size of the grafted sequence will depend on the molecular framework structure, such that shorter loops will be preferred in cases where they are in the framework adjacent to linked cysteines. Disulfide linkages for other knottin proteins are set forth in the knottin database.
Figure 2:
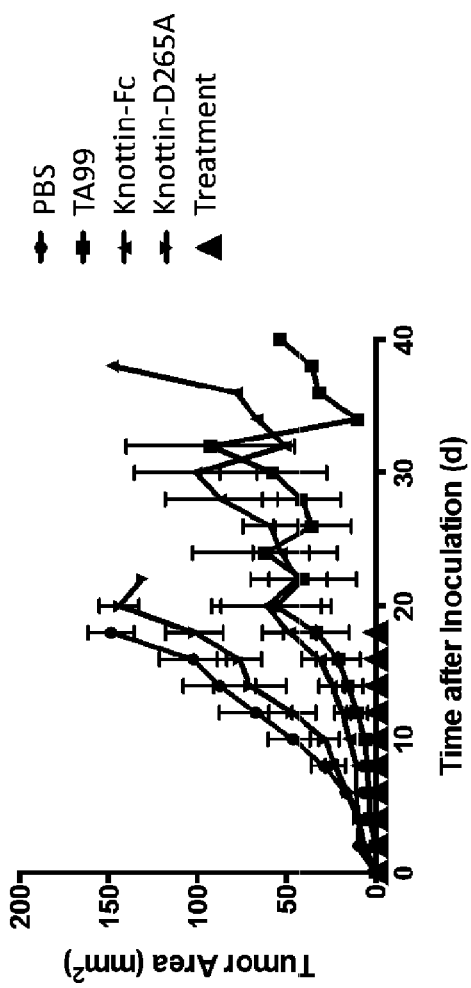
FIG. 2 is a graph comparing tumor control with TA99 and integrin binding knottin-Fc (SEQ ID NO: 45) in subcutaneous B16F10 melanoma tumors. TA99 is an antibody against TYRP-1, an antigen that is overexpressed on melanoma cells. Tumors were established by injecting 2.5×10$^5$ B16F10 cells into the flanks of C57BL/6 mice. Starting on the day of tumor inoculation and every 2 days after, 80 µg knottin-Fc, 80 µg knottin-Fc D265A, or 200 µg TA99 was administered. Error bars represent standard error of the mean (SEM).

Tumor area was measured and plotted (FIG. 2). Tumor area was measured using calipers. The longest dimension of the tumor in any direction was measured first, followed by the measurement of the longest perpendicular dimension. The two values were then multiplied to quantify tumor area in square millimeters.

Both the TA99 treatment and the knottin-Fc treatment controlled tumor growth to a similar extent. The failure of knottin-D265A to prevent tumor growth indicates that tumor control by knottin-Fc is mediated by the effector function of Fc.

Example 2

Knottin-Fc and Extended-PK IL-2 Synergistically Control Tumor Growth of B16F10 Tumors A therapeutic study was conducted to examine the effect of adding MSA/IL-2 to knottin-Fc treatment. Tumors were established by injecting C57BL/6 mice subcutaneously with $1 \times 10^6$ B16F10 murine melanoma cells. 30 µg MSA/IL-2 and/or 500 µg knottin-Fc was administered intraperitoneally on day 6 after tumor inoculation and every 6 days after that for 4 treatments total.

Tumor area was measured and plotted (FIG. 3A). While MSA/IL-2 and knottin-Fc alone had no effect on tumor growth, the combination of MSA/IL-2 and knottin-Fc effectively controlled tumor growth. A Kaplan-Meier survival plot revealed that the combination of MSA/IL-2 and knottin-Fc extended the survival of these mice, whereas monotherapies had no significant effect (FIG. 3B).

Example 3

Knottin-Fc and Extended-PK IL-2 Synergistically Control Tumor Growth of MC38 Tumors A separate therapeutic study was conducted to examine the effect of MSA/IL-2 on knottin-Fc efficacy in a tumor type that has no reported targetable antigens. $1 \times 10^6$ MC38 murine colon carcinoma cells were injected into the flanks of C57BL/6 mice. 6 days after tumor inoculation and every 6 days after for a total of 4 treatments, 30 µg MSA-IL-2 and/or 500 µg knottin-Fc was administered intraperitoneally.

Tumor growth was controlled with the combination of MSA/IL-2 and knottin-Fc, but not when each component was administered as a monotherapy (FIG. 4A). A Kaplan-Meier survival plot shows an increase in survival in the mice treated with the combination of MSA/IL-2 and knottin-Fc compared to when each component was administered as a monotherapy (FIG. 4B).

Example 4

Knottin-Fc and Extended-PK IL-2 Synergistically Control Tumor Growth of Ag104A Tumors An additional study was conducted to examine the effects of MSA/IL-2 on knottin-Fc efficacy in a different tumor type. Ag104A fibrosarcoma tumors were established by injecting $1.0 \times 10^6$ Ag104A cells into the flanks of C3H/HeN mice. Starting six days after tumor inoculation and every 6 days after, 30 µg MSA/IL-2 and/or 500 µg knottin-Fc was administered intraperitoneally.

Tumor growth was controlled with the combination of MSA/IL-2 and knottin-Fc, but not when each component was administered as a monotherapy (FIG. 5A). A Kaplan-Meier survival plot shows an increase in survival in mice treated with the combination of MSA/IL-2 and knottin-Fc compared to when each component was administered alone (FIG. 5B).

Example 5

Effector Function is Required for Synergistic Tumor Control

The results of Example 1 indicate that effector function is required for tumor control by knottin-Fc. To determine the role of effector function in tumor control by synergistic treatment with MSA/IL-2, a further study was conducted using both B16F10 and MC38 cells. $1 \times 10^6$ B16F10 cells (FIGS. 6A and 6B) or MC38 cells (FIGS. 7A and 7B) were injected into the flanks of C57BL/6 mice. 30 µg MSA-IL-2 was administered intraperitoneally on day 6 after tumor inoculation and every 6 days after that for 4 treatments total. 500 µg knottin-Fc or knottin-D265AFc (the D265A mutation in the murine IgG2a Fc domain eliminates binding to FcγR and complement) was administered intraperitoneally on day 6 after tumor inoculation and every six days thereafter for a total of 4 treatments.

Individual tumor size measurements (FIGS. 6A and 7A) and survival plots (FIGS. 6B and 7B) indicate that tumor control by knottin-Fc requires the effector function of Fc.

Example 6

Therapeutic Antibody and Immune Checkpoint Blocker Enhance the Efficacy of Knottin-Fc and Extended-PK IL-2 in B16F10 Tumors To determine the effect of antibodies on knottin-Fc and extended-PK IL-2 synergistic tumor control, an additional study was carried out using B16F10 cells. $1 \times 10^6$ B16F10 cells were injected into the flanks of C57BL/6 mice. 30 µg MSA/IL-2 was administered every 6 days beginning on day 6 after tumor inoculation for a total of 5 treatments and 200 µg knottin-Fc was administered daily from days 6-30 after tumor inoculation. Antibodies against TYRP-1 (TA99) were administered at 100 µg per mouse every 6 days starting on day 6 after B16F10 tumor inoculation. Antibodies against PD-1 were administered at 200 µg per mouse every 6 days starting on day 6 after tumor inoculation.

Individual tumor size measurements (FIG. 8A) and a survival plot (FIG. 8B) indicate that antibodies enhanced tumor control via knottin-Fc and MSA/IL-2. However, this is only effective if the antibody targets an antigen present on the tumor cells. Combining knottin-Fc and MSA/IL-2 with a therapeutic antibody or immune checkpoint blocker increased the efficacy of tumor control and survival improvement.

Example 7

Immune Checkpoint Blocker Enhances the Efficacy of Knottin-Fc and Extended-PK IL-2 in MC38 Tumors To determine the effect of antibodies on knottin-Fc and extended-PK IL-2 synergistic tumor control, an additional study was carried out using MC38 cells. $1 \times 10^6$ MC38 cells were injected into the flanks of C57BL/6 mice. 30 µg MSA/IL-2 and 500 µg knottin-Fc were administered every 6 days beginning on day 6 after tumor inoculation for a total of 4 treatments. Antibodies against PD-1 were administered at 200 µg per mouse every 6 days starting on day 6 after tumor inoculation.

Individual tumor size measurements (FIG. 9A) and survival plots (FIG. 9B) indicate that antibodies enhanced tumor control via knottin-Fc and MSA/IL-2. However, this is only effective if the antibody targets an antigen present on the tumor cells. The most effective treatment was to combine knottin-Fc and MSA/IL-2 with an immune checkpoint blockade (anti-PD-1) antibody.

Example 8

Knottin-Fc is Effective when Administered Every Other Day or Weekly

To determine the minimum dosing requirement for an anti-tumor response, the B16F10 melanoma and MC38 colon carcinoma tumor models were used and knottin-Fc was administered daily, every other day, or weekly. $1 \times 10^6$ B16F10 cells (FIG. 10) or $1 \times 10^6$ MC38 cells (FIG. 11) were injected into the flanks of C57BL/6 mice. 30 µg of MSA/IL-2 was administered on days 6, 12, 18, and 24 after tumor inoculation. 200 µg of knottin-Fc was administered daily or every other day starting on day 6 and ending on day 28. 500 µg of knottin-Fc was administered on days 6, 12, 18, and 24 for the weekly regimen. In both models, administration of knottin-Fc in conjunction with MSA/IL-2 every other day or every 6 days was equivalent to daily administration.

Example 9

Knottin-Fc and Fc-Knottin Constructs Control Tumor Growth

The determine the optimal placement of Fc fused to knottin for an anti-tumor response, Fc was fused to either the N-terminus (Knottin-Fc) or the C-terminus (Fc-Knottin). $2.5 \times 10^5$ B16F10 melanoma cells were injected into the flanks of C57BL/6 mice. 80 µg of knottin-Fc, 80 µg of Fc-knottin, or 200 µg of IgG-knottin was administered immediately after tumor inoculation and every two days after, for a total of 10 treatments. Tumor area was measured (FIG. 12). There was essentially no difference in efficacy between the different knottin-Fc fusion proteins.

To validate this finding, another mouse tumor model was utilized. $1 \times 10^6$ MC38 colon carcinoma cells were injected into the flanks of albino C57BL/6 mice. 200 µg of knottin-Fc or Fc-knottin were administered immediately after tumor inoculation and every two days after, for a total of 10 treatments. Tumor area was measured (FIG. 13). There was essentially no difference in efficacy between knottin-Fc and Fc-knottin. The results from both of these mouse tumor models indicate that the placement of Fc in the knottin-Fc fusion protein does not affect efficacy for an anti-tumor response.

To determine optimal integrin-binding-knottin-Fc constructs, a fusion protein was made containing a (Gly4Ser)3 linker in between the knottin and the Fc domain. No difference in integrin binding affinity to U87MG glioblastoma cells were observed compared to integrin-binding-knottin-Fc containing no linker (data not shown).

Example 10

Knottin-Fc and IL-2 Combination Protects Against Secondary Tumor Challenge

To determine if the combination of knottin-Fc and MSA/IL-2 could protect treated mice from a secondary challenge, the MC38 tumor model was used. $1 \times 10^6$ MC38 cells were injected into the flanks of C57BL/6 mice and both 30 µg MSA/IL-2 and 500 µg knottin-Fc were administered every 6 days beginning on day 6 after tumor inoculation for a total of 4 treatments. 16-20 weeks after the initial tumor inoculation, previously cured mice or age-matched naïve mice were inoculated with $1 \times 10^6$ MC38 cells in the opposite flank. No further treatment was administered.

Individual tumor size measurements (FIG. 14A) and survival plot (FIG. 14B) indicate that knottin-Fc and MSA/IL-2 protect previously treated mice against secondary tumor challenge, demonstrating a potent and sustained immune response against the tumors.

Example 11

Knottin-Fc Targeting all Three Integrins Most Effectively Controls Tumor Growth

To assess the efficacy of a knottin-Fc that targets all three integrins (i.e., αvβ3, αvβ5, and α5β1, "2.5F_knottin-Fc" SEQ ID NO: 45) compared to a knottin-Fc that targets only two integrins (i.e., αvβ3 and αvβ5, "2.5D_knottin-Fc" SEQ ID NO: 47) in controlling tumor growth, an experiment was conducted using three different tumors models (i.e., B16F10, MC38, and Ag104A). $1 \times 10^6$ B16F10 (FIGS. 15A and 15B) or MC38 cells (FIGS. 16A and 16B) were injected into the flanks of C57BL/6 mice. $1.0 \times 10^6$ Ag104A cells (FIGS. 17A and 17B) were injected into the flanks of C3H/HeN mice. 30 μg MSA/IL-2, 500 μg 2.5F_knottin-Fc and/or 2.5D_knottin-Fc were administered every 6 days beginning on day 6 after tumor inoculation for a total of 4 treatments.

Individual tumor size measurements (FIGS. 15A, 16A and 17A) and survival plots (FIGS. 15B, 16B and 17B) indicate that a knottin-Fc that targets all three integrins more effectively controls tumor growth than a knottin-Fc that only targets two integrins.

Example 12

Immune Cell Populations Important for Survival in Tumor-Bearing Mice

To assess the role of various immune cell populations in the improved survival of mice with MC38 tumors treated with knottin-Fc and MSA/IL-2, depletion experiments were conducted. 400 μg anti-CD8, anti-CD4, anti-NK1.1, anti-Ly6G or anti-CD19 antibodies were administered every four days for a total of six treatments starting on day 4 after tumor inoculation. 300 μg anti-CSF-1R antibody was administered every two days for a total of eleven treatments starting on day 4 of tumor inoculation. 30 μg cobra venom factor (CVF) was administered every 6 days for a total of 4 treatments starting on day 5 after tumor inoculation. Anti-CD8 depletes CD8+ T cells, anti-CD4 depletes CD4+ T cells, anti-NK1.1 depletes natural killer cells, anti-Ly6G depletes neutrophils, anti-CD19 depletes B cells, and anti-CSF-1R depletes tissue-resident/tumor-resident macrophages. CVF inhibits complement activity.

Individual tumor size measurements (FIG. 18A) and survival plots (FIG. 18B) indicate that CD8+ T cells and macrophages are particularly important for the synergistic effect of knottin-Fc and MSA/IL-2 on tumor control.

In addition to the immune cell depletions, Batf3-/- mice were used to evaluate the role of cross-presenting CD8+ dendritic cells. Batf3-/- mice lack the function of the basic leucine zipper transcription factor, ATF-like 3. Deletion of Batf3 has been shown to prevent the development of CD8+ dendritic cells, which are important for the cross-presentation of exogenous antigen on MHC Class I.

Tumor areas of treated C57BL/6 (i.e. "control") and Batf3-/- mice were measured and plotted (FIG. 19A), and demonstrated less tumor control in Batf3-/- mice treated with MSA/IL-2 and knottin-Fc. A Kaplan-Meier survival plot was also generated, and revealed a significant decrease in survival in Batf3-/- mice treated with knottin-Fc and MSA/IL-2 compared to C57BL/6 mice (FIG. 19B). This indicated that cross-presentation by dendritic cells may be a factor that contributes to the efficacy of the combination therapy on controlling the growth of MC38 tumors.

Since CD8+ T cells were found to be critical for efficacy of the knottin-Fc and MSA-IL-2 combination, and IFNγ was previously reported to be important in the efficacy of MSA-IL-2 and therapeutic antibody combinations (Zhu et al., *Cancer Cell* (2015) Vol 27: 489-501), the role of IFNγ was investigated in the MC38 tumor model. $1 \times 10^6$ MC38 were injected into the flanks of C57BL/6 mice. 30 μg MSA/IL-2 and 500 μg knottin-Fc were administered every 6 days beginning on day 6 after tumor inoculation for a total of 4 treatments. 200 μg of anti-INFγ antibody was administered every two days for a total of eleven treatments starting on day 5 after rumor inoculation.

As shown in FIGS. 20A and 20B, IFNγ depletion did not significantly affect tumor control or survival of mice with MC38 tumors.

Example 13

Antagonizing Immune Suppression Improves Survival of Tumor-Bearing Mice

To determine whether the efficacy of tumor control could be enhanced by inhibiting suppressors of the immune system, an antagonist of vascular endothelial growth factor (VEGF) or cytotoxic T-lymphocyte-associated protein 4 (CTLA-4) was administered in mice with MC38 or B16F10 tumors. $1 \times 10^6$ MC38 cells (FIGS. 21A, 21B and 22) or B16F10 (FIGS. 23A and 23B) were injected into the flanks of C57BL/6 mice. 30 μg MSA/IL-2, 500 μg knottin-Fc, and 200 μg anti-VEGF antibody or anti-CTLA-4 antibody were administered every 6 days beginning on day 6 after tumor inoculation for a total of 4 treatments.

Synthetic genes, encoding the heavy (VH) and light (VL) chain variable regions of anti-VEGF (clone B20-4.1.1) (Bagri et al., *Clin. Cancer Res.* (2010) Vol 16: 3887-900) and anti-CTLA-4 (9D9) (Selby et al., *Cancer Immunol. Res.* (2013) Vol 1:32-42) antibodies, were codon-optimized for expression in mammalian cells (GeneArt, Life Technologies). B20-4.1.1 antibody constructs were generated by PCR-amplification of DNA inserts encoding for VH and VL regions and cloned via Gibson assembly into separate gWiz expression vectors (Genlantis) containing a CMV promoter, a kanamycin antibiotic resistance gene and the DNA sequence encoding for either murine IgG2a heavy-chain (CH1, CH2 and CH3) or light-chain (CL) constant regions (see below Sequence 1 and 2 for B20-4.1.1). The 9D9 antibody construct was generated by PCR-amplification of DNA inserts encoding the VH and VL regions and sub-cloned into a double cassette p2MPT expression vector (EPFL Protein expression core facility, http://pecf.epfl.ch), containing a CMV promoter, an ampicillin antibiotic resistance gene and both murine IgG2a heavy-chain (CH1, CH2 and CH3) or light-chain (CL) constant regions, via the restriction sites NotI/BamHI and EcoRI/XbaI, respectively. All constructs were verified by DNA sequencing (Macrogen).

Anti-VEGF antibody B20-4.1.1 was expressed in transiently transfected human embryonic kidney (HEK293-F) cells using the Free-Style 293 Expression System (Life Technologies) as described previously (Zhu et al., *Cancer Cell* (2015) Vol 27: 489-501). Antibody 9D9 was expressed in transiently transfected Chinese hamster ovary (CHO)

cells and provided by EPFL Protein expression core facility (http://pecf.epfl.ch). After 7 days of expression, cells were removed by centrifugation (15,000×g for 30 min at 4° C.) and filtration (0.22 μm PES membranes filter) and the proteins in the supernatant purified by protein A chromatography according to the manufacturer's instructions (GE Healthcare). Eluted antibodies were further desalted and purified on a HiLoad Superdex 200 10/600 size exclusion column (GE Healthcare) connected to an AKTApurifier system and equilibrated with buffer PBS 1X pH 7.4. The purified antibodies were concentrated using a 30000 NMWL Amicon Ultra centrifugal filter device (Millipore) at 4000 g and 4° C. and quantified by measuring absorbance at 280 nm using a NanoDrop 2000 spectrophotometer (Thermo Scientific). Molecular weights were confirmed by reducing and non-reducing SDS/PAGE. Purity was evaluated by FPLC. Protein samples were analyzed by SDS-PAGE under denaturing and reducing conditions using NuPAGE 4-12% Bis-Tris Gels (Life Technologies) in MOPS buffer followed by Coomassie staining. Native size and oligomerization state of antibodies after concentration were also analyzed by size-exclusion chromatography with a Superdex 200 10/300 GL column (GE Healthcare) connected to an AKTApurifier system and equilibrated with buffer PBS 1X pH 7.4.

Tumor area was measured and plotted (FIGS. 21A, 22 and 23A) and survival plots were generated (FIGS. 21B and 23B). The triple combinations (i.e., MSA/IL-2+knottin-Fc+anti-VEGF and MSA/IL-2+knottin-Fc+anti-CTLA-4) significantly controlled tumor growth and improved survival compared to the double combinations (i.e., MSA/IL-2+anti-VEGF and knottin-Fc+anti-VEGF or MSA/IL-2+anti-CTLA-4 and knottin-Fc+anti-CTLA-4). This is similar to the results observed when adding an anti-PD-1 antibody to the combination of MSA/IL-2 and knottin-Fc, which indicated that other suppressors of the immune system could be inhibited to improve the efficacy of the combination of MSA/IL-2+knottin-Fc. The improved therapeutic efficacy by addition of an anti-VEGF antibody was also observed in RENCA (renal adenocarcinoma) and LLC (Lewis lung carcinoma) tumor models (data not shown).

EQUIVALENTS

Those skilled in the art will recognize or be able to ascertain, using no more than routine experimentation, many equivalents of the specific embodiments described herein described herein. Such equivalents are intended to be encompassed by the following claims.

TABLE 2

Sequence Summary

| SEQ ID NO | Description | Sequence |
|---|---|---|
| 1 | Human IgG1 constant region (amino acid sequence) | ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCDKTHTCPPC PAPELLGGPSVFLEPPKPKDTLMISRTP EVTCVVVDVSHEDPEVKFNWYVDGVEVH NAKTKPREEQYNSTYRVVSVLTVLHQDW LNGKEYKCKVSNKALPAPIEKTISKAKG QPREPQVYTLPPSRDELTKNQVSLTCLV KGFYPSDIAVEWESNGQPENNYKTTPPV LDSDGSFFLYSKLTVDKSRWQQGNVFSC SVMHEALHNHYTQKSLSLSPGK |

TABLE 2-continued

Sequence Summary

| SEQ ID NO | Description | Sequence |
|---|---|---|
| 2 | Human IgG1 Fc domain (amino acid sequence) | EPKSCDKTHTCPPCPAPELLGGPSVFLE PPKPKDTLMISRTPEVTCVVVDVSHEDP EVKFNWYVDGVEVHNAKTKPREEQYNST YRVVSVLTVLHQDWLNGKEYKCKVSNKA LPAPIEKTISKAKGQPREPQVYTLPPSR DELTKNQVSLTCLVKGFYPSDIAVEWES NGQPENNYKTTPPVLDSDGSFFLYSKLT VDKSRWQQGNVFSCSVMHEALHNHYTQK SLSLSPGK |
| 3 | Human IgG1 Fc domain (amino acid sequence) Deletion (ΔEPKSC) Upper Hinge | DKTHTCPPCPAPELLGGPSVFLEPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSRDELTK NQVSLTCLVKGFYPSDIAVEWESNGQPE NNYKTTPPVLDSDGSFELYSKLTVDKSR WQQGNVESCSVMHEALHNHYTQKSLSLS PGK |
| 4 | Mouse IL-2 (nucleic acid sequence) | GCACCCACTTCAAGCTCCACTTCAAGCT CTACAGCGGAAGCACAGCAGCAGCAGCA GCAGCAGCAGCAGCAGCAGCAGCACCTG GAGCAGCTGTTGATGGACCTACAGGAGC TCCTGAGCAGGATGGAGAATTACAGGAA CCTGAAACTCCCCAGGATGCTCACCTTC AAATTTTACTTGCCCAAGCAGGCCACAG AATTGAAAGATCTTCAGTGCCTAGAAGA TGAACTTGGACCTCTGCGGCATGTTCTG GATTTGACTCAAAGCAAAAGCTTTCAAT TGGAAGATGCTGAGAATTTCATCAGCAA TATCAGAGTAACTGTTGTAAAACTAAAG GGCTCTGACAACACATTTGAGTGCCAAT TCGATGATGAGTCAGCAACTGTGGTGGA CTTTCTGAGGAGATGGATAGCCTTCTGT CAAAGCATCATCTCAACAAGCCCTCAA |
| 5 | Mouse IL-2 (amino acid sequence) | APTSSSTSSSTAEAQQQQQQQQQQQHL EQLLMDLQELLSRMENYRNLKLPRMLTF KFYLPKQATELKDLQCLEDELGPLRHVL DLTQSKSFQLEDAENFISNIRVTVVKLK GSDNTFECQFDDESATVVDFLRRWIAFC QSIISTSPQ |
| 6 | QQ6210 (nucleic acid sequence) | GCACCCACTTCAAGCTCCACTTCAAGCT CTACAGCGGAAGCACAACAGCAGCAGCA GCAGCAGCAGCAGCAGCAGCAGCACCTG GAGCAGCTGTTGATGGACCTACAGGAAC TCCTGAGTAGGATGGAGGATCACAGGAA CCTGAGACTCCCCAGGATGCTCACCTTC AAATTTTACTTGCCCGAGCAGGCCACAG AATTGGAAGATCTTCAGTGCCTAGAAGA TGAACTTGAACCACTGCGGCAAGTTCTG GATTTGACTCAAAGCAAAAGCTTTCAAT TGGAAGATGCTGAGAATTTCATCAGCAA TATCAGAGTAACTGTTGTAAAACTAAAG GGCTCTGACAACACATTTGAGTGCCAAT TCGACGATGAGCCAGCAACTGTGGTGGA CTTTCTGAGGAGATGGATAGCCTTCTGT CAAAGCATCATCTCAACAAGCCCTCAA |
| 7 | QQ6210 (amino acid sequence) | APTSSSTSSSTAEAQQQQQQQQQQQHL EQLLMDLQELLSRMEDHRNLRLPRMLTF KFYLPEQATELEDLQCLEDELEPLRQVL DLTQSKSFQLEDAENFISNIRVTVVKLK GSDNTFECQFDDEPATVVDFLRRWIAFC QSIISTSPQ |
| 8 | E76A (nucleic acid sequence) | GCACCCACTTCAAGCTCCACTTCAAGCT CTACAGCGGAAGCACAGCAGCAGCAGCA GCAGCAGCAGCAGCAGCAGCAGCACCTG GAGCAGCTGTTGATGGACCTACAGGAGC TCCTGAGCAGGATGGAGAATTACAGGAA CCTGAAACTCCCCAGGATGCTCACCTTC |

TABLE 2-continued

Sequence Summary

| SEQ ID NO | Description | Sequence |
|---|---|---|
| | | AAATTTTACTTGCCCAAGCAGGCCACAG AATTGAAAGATCTTCAGTGCCTAGAAGA TGCTCTTGGACCTCTGCGGCATGTTCTG GATTTGACTCAAAGCAAAAGCTTTCAAT TGGAAGATGCTGAGAATTTCATCAGCAA TATCAGAGTAACTGTTGTAAAACTAAAG GGCTCTGACAACACATTTGAGTGCCAAT TCGATGATGAGTCAGCAACTGTGGTGGA CTTTCTGAGGAGATGGATAGCCTTCTGT CAAAGCATCATCTCAACAAGCCCTCAA |
| 9 | E76A (amino acid sequence) | APTSSSTSSSTAEAQQQQQQQQQQQQHL EQLLMDLQELLSRMENYRNLKLPRMTF KFYLPKQATELKDLQCLEDALGPLRHVL DLTQSKSFQLEDAENFISNIRVTVVKLK GSDNTFECQFDDESATVVDFLRRWIAFC QSIISTSPQ |
| 10 | E76G (nucleic acid sequence) | GCACCCACTTCAAGCTCCACTTCAAGCT CTACAGCGGAAGCACAGCAGCAGCAGCA GCAGCAGCAGCAGCAGCAGCAGCACCTG GAGCAGCTGTTGATGGACCTACAGGAGC TCCTGAGCAGGATGGAGAATTACAGGAA CCTGAAACTCCCCAGGATGCTCACCTTC AAATTTTACTTGCCCAAGCAGGCCACAG AATTGAAAGATCTTCAGTGCCTAGAAGA TGGTCTTGGACCTCTGCGGCATGTTCTG GATTTGACTCAAAGCAAAAGCTTTCAAT TGGAAGATGCTGAGAATTTCATCAGCAA TATCAGAGTAACTGTTGTAAAACTAAAG GGCTCTGACAACACATTTGAGTGCCAAT TCGATGATGAGTCAGCAACTGTGGTGGA CTTTCTGAGGAGATGGATAGCCTTCTGT CAAAGCATCATCTCAACAAGCCCTCAA |
| 11 | E76G (amino acid sequence) | APTSSSTSSSTAEAQQQQQQQQQQQQHL EQLLMDLQELLSRMENYRNLKLPRMTF KFYLPKQATELKDLQCLEDGLGPLRHVL DLTQSKSFQLEDAENFISNIRVTVVKLK GSDNTFECQFDDESATVVDFLRRWIAFC QSIISTSPQ |
| 12 | D265A Fc/Flag (nucleic acid sequence) (C-terminal flag tag is underlined) | ATGAGGGTCCCCGCTCAGCTCCTGGGGC TCCTGCTGCTCTGGCTCCCAGGTGCACG ATGTGAGCCCAGAGTGCCCATAACACAG AACCCCTGTCCTCCACTCAAAGAGTGTC CCCCATGCGCAGCTCCAGACCTCTTGGG TGGACCATCCGTCTTCATCTTCCCTCCA AAGATCAAGGATGTACTCATGATCTCCC TGAGCCCCATGGTCACATGTGTGGTGGT GGCCGTGAGCGAGGATGACCCAGACGTC CAGATCAGCTGGTTTGTGAACAACGTGG AAGTACACACAGCTCAGACACAAACCCA TAGAGAGGATTACAACAGTACTCTCCGG GTGGTCAGTGCCCTCCCCATCCAGCACC AGGACTGGATGAGTGGCAAGGAGTTCAA ATGCAAGGTCAACAACAGAGCCCTCCCA TCCCCCATCGAGAAACCATCTCAAAAC CCAGAGGGCCAGTAAGAGCTCCACAGGT ATATGTCTTGCCTCCACCAGCAGAAGAG ATGACTAAGAAAGAGTTCAGTCTGACCT GCATGATCACAGGCTTCTTACCTGCCGA AATTGCTGTGGACTGGACCAGCAATGGG CGTACAGAGCAAAACTACAAGAACACCG CAACAGTCCTGGACTCTGATGGTTCTTA CTTCATGTACAGCAAGCTCAGAGTACAA AAGAGCACTTGGGAAAGAGGAAGTCTTT TCGCCTGCTCAGTGGTCCACGAGGGTCT GCACAATCACCTTACGACTAAGACCATC TCCCGGTCTCTGGGTAAAGGTGGCGGAT CTGACTACAAGGACGACGATGACAAGTG ATAA |
| 13 | D265A Fc/Flag (amino acid sequence) (C-terminal flag tag is underlined) | MRVPAQLLGLLLLWLPGARCEPRVPITQ NPCPPLKECPPCAAPDLLGGPSVFIFPP KIKDVLMISLSPMVTCVVVAVSEDDPDV QISWFVNNVEVHTAQTQTHREDYNSTLR VVSALPIQHQDWMSGKEFKCKVNNRALP SPIEKTISKPRGPVRAPQVYVLPPPAEE MTKKEFSLTCMITGFLPAEIAVDWTSNG RTEQNYKNTATVLDSDGSYFMYSKLRVQ KSTWERGSLFACSVVHEGLHNHLTTKTI SRSLGKGGGS<u>DYKDDDDK</u> |
| 14 | D265A Fc/wt mIL-2 (nucleic acid sequence) (C-terminal 6x his tag is underlined) | ATGAGGGTCCCCGCTCAGCTCCTGGGGC TCCTGCTGCTCTGGCTCCCAGGTGCACG ATGTGAGCCCAGAGTGCCCATAACACAG AACCCCTGTCCTCCACTCAAAGAGTGTC CCCCATGCGCAGCTCCAGACCTCTTGGG TGGACCATCCGTCTTCATCTTCCCTCCA AAGATCAAGGATGTACTCATGATCTCCC TGAGCCCCATGGTCACATGTGTGGTGGT GGCCGTGAGCGAGGATGACCCAGACGTC CAGATCAGCTGGTTTGTGAACAACGTGG AAGTACACACAGCTCAGACACAAACCCA TAGAGAGGATTACAACAGTACTCTCCGG GTGGTCAGTGCCCTCCCCATCCAGCACC AGGACTGGATGAGTGGCAAGGAGTTCAA ATGCAAGGTCAACAACAGAGCCCTCCCA TCCCCCATCGAGAAACCATCTCAAAAC CCAGAGGGCCAGTAAGAGCTCCACAGGT ATATGTCTTGCCTCCACCAGCAGAAGAG ATGACTAAGAAAGAGTTCAGTCTGACCT GCATGATCACAGGCTTCTTACCTGCCGA AATTGCTGTGGACTGGACCAGCAATGGG CGTACAGAGCAAAACTACAAGAACACCG CAACAGTCCTGGACTCTGATGGTTCTTA CTTCATGTACAGCAAGCTCAGAGTACAA AAGAGCACTTGGGAAAGAGGAAGTCTTT TCGCCTGCTCAGTGGTCCACGAGGGTCT GCACAATCACCTTACGACTAAGACCATC TCCCGGTCTCTGGGTAAAGGAGGGGGCT CCGCACCCACTTCAAGCTCCACTTCAAG CTCTACAGCGGAAGCACAGCAGCAGCAG CAGCAGCAGCAGCAGCAGCAGCAGCACC TGGAGCAGCTGTTGATGGACCTACAGGA GCTCCTGAGCAGGATGGAGAATTACAGG AACCTGAAACTCCCCAGGATGCTCACCT TCAAATTTTACTTGCCCAAGCAGGCCAC AGAATTGAAAGATCTTCAGTGCCTAGAA GATGAACTTGGACCTCTGCGGCATGTTC TGGATTTGACTCAAAGCAAAAGCTTTCA ATTGGAAGATGCTGAGAATTTCATCAGC AATATCAGAGTAACTGTTGTAAAACTAA AGGGCTCTGACAACACATTTGAGTGCCA ATTCGATGATGAGTCAGCAACTGTGGTG GACTTTCTGAGGAGATGGATAGCCTTCT GTCAAAGCATCATCTCAACAAGCCCTCA A<u>CACCATCACCACCATCACTGATAA</u> |
| 15 | D265A Fc/wt mIL-2 (amino acid sequence) (C-terminal 6x his tag is underlined) | MRVPAQLLGLLLLWLPGARCEPRVPITQ NPCPPLKECPPCAAPDLLGGPSVFIFPP KIKDVLMISLSPMVTCVVVAVSEDDPDV QISWFVNNVEVHTAQTQTHREDYNSTLR VVSALPIQHQDWMSGKEFKCKVNNRALP SPIEKTISKPRGPVRAPQVYVLPPPAEE MTKKEFSLTCMITGFLPAEIAVDWTSNG RTEQNYKNTATVLDSDGSYFMYSKLRVQ KSTWERGSLFACSVVHEGLHNHLTTKTI SRSLGKGGGSAPTSSSTSSSTAEAQQQQ QQQQQQQQHLEQLLMDLQELLSRMENYR NLKLPRMTFKFYLPKQATELKDLQCLE DELGPLRHVLDLTQSKSFQLEDAENFIS NIRVTVVKLKGSDNTFECQFDDESATVV DFLRRWIAFCQSIISTSPQ<u>HHHHHH</u>** |

| SEQ ID NO | Description | Sequence |
|---|---|---|
| 16 | D265A Fc/ QQ6210 (nucleic acid sequence) (C-terminal 6x his tag is underlined) | ATGAGGGTCCCCGCTCAGCTCCTGGGGC TCCTGCTGCTCTGGCTCCCAGGTGCACG ATGTGAGCCCAGAGTGCCCATAACACAG AACCCCTGTCCTCCACTCAAAGAGTGTC CCCCATGCGCAGCTCCAGACCTCTTGGG TGGACCATCCGTCTTCATCTTCCCTCCA AAGATCAAGGATGTACTCATGATCTCCC TGAGCCCCATGGTCACATGTGTGGTGGT GGCCGTGAGCGAGGATGACCCAGACGTC CAGATCAGCTGGTTTGTGAACAACGTGG AAGTACACAGCTCAGACACAAACCCA TAGAGAGGATTACAACAGTACTCTCCGG GTGGTCAGTGCCCTCCCCATCCAGCACC AGGACTGGATGAGTGGCAAGGAGTTCAA ATGCAAGGTCAACAACAGAGCCCTCCCA TCCCCCATCGAGAAACCATCTCAAAAC CCAGAGGGCCAGTAAGAGCTCCACAGGT ATATGTCTTGCCTCCACCAGCAGAAGAG ATGACTAAGAAAGAGTTCAGTCTGACCT GCATGATCACAGGCTTCTTACCTGCCGA AATTGCTGTGGACTGGACCAGCAATGGG CGTACAGAGCAAAACTACAAGAACACCG CAACAGTCCTGGACTCTGATGGTTCTTA CTTCATGTACAGCAAGCTCAGAGTACAA AAGAGCACTTGGGAAGAGGAAGTCTTT TCGCCTGCTCAGTGGTCCACGAGGGTCT GCACAATCACCTTACGACTAAGACCATC TCCCGGTCTCTGGGTAAAGGAGGGGGCT CCGCACCCACTTCAAGCTCCACTTCAAG CTCTACAGCGGAAGCACAACAGCAGCAG CAGCAGCAGCAGCAGCAGCAGCAGCACC TGGAGCAGCTGTTGATGGACCTACAGGA ACTCCTGAGTAGGATGGAGGATCACAGG AACCTGAGACTCCCCAGGATGCTCACCT TCAAATTTTACTTGCCCAAGCAGGCCAC AGAATTGGAAGATCTTCAGTGCCTAGAA GATGAACTTGAACCACTGCGGCAAGTTC TGGATTTGACTCAAAGCAAAAGCTTTCA ATTGGAAGATGCTGAGAATTTCATCAGC AATATCAGAGTAACTGTTGTAAAACTAA AGGGCTCTGACAACACATTTGAGTGCCA ATTCGACGATGAGCCAGCAACTGTGGTG GACTTTCTGAGGAGATGGATAGCCTTCT GTCAAAGCATCATCTCAACAAGCCCTCA ACACCATCACCACCATCACTGATAA |
| 17 | D265A Fc/ QQ6210 (amino acid sequence) (C-terminal 6x his tag is underlined) | MRVPAQLLGLLLLWLPGARCEPRVPITQ NPCPPLKECPPCAAPDLLGGPSVFIFPP KIKDVLMISLSPMVTCVVVAVSEDDPDV QISWFVNNVEVHTAQTQTHREDYNSTLR VVSALPIQHQDWMSGKEFKCKVNNRALP SPIEKTISKPRGPVRAPQVYVLPPPAEE MTKKEFSLTCMITGFLPAEIAVDWTSNG RTEQNYKNTATVLDSDGSYFMYSKLRVQ KSTWERGSLFACSVVHEGLHNHLTTKTI SRSLGKGGGSAPTSSSTSSSTAEAQQQQ QQQQQQQQHLEQLLMDLQELLSRMEDHR NLRLPRMLTFKFYLPEQATELEDLQCLE DELEPLRQVLDLTQSKSFQLEDAENFIS NIRVTVVKLKGSDNTFECQFDDEPATVV DFLRRWIAFCQSIISTSPQHHHHHH |
| 18 | D265A Fc/ E76A (nucleic acid sequence) (C-terminal 6x his tag is underlined) | ATGAGGGTCCCCGCTCAGCTCCTGGGGC TCCTGCTGCTCTGGCTCCCAGGTGCACG ATGTGAGCCCAGAGTGCCCATAACACAG AACCCCTGTCCTCCACTCAAAGAGTGTC CCCCATGCGCAGCTCCAGACCTCTTGGG TGGACCATCCGTCTTCATCTTCCCTCCA AAGATCAAGGATGTACTCATGATCTCCC TGAGCCCCATGGTCACATGTGTGGTGGT GGCCGTGAGCGAGGATGACCCAGACGTC CAGATCAGCTGGTTTGTGAACAACGTGG AAGTACACAGCTCAGACACAAACCCA TAGAGAGGATTACAACAGTACTCTCCGG GTGGTCAGTGCCCTCCCCATCCAGCACC AGGACTGGATGAGTGGCAAGGAGTTCAA ATGCAAGGTCAACAACAGAGCCCTCCCA TCCCCCATCGAGAAACCATCTCAAAAC CCAGAGGGCCAGTAAGAGCTCCACAGGT ATATGTCTTGCCTCCACCAGCAGAAGAG ATGACTAAGAAAGAGTTCAGTCTGACCT GCATGATCACAGGCTTCTTACCTGCCGA AATTGCTGTGGACTGGACCAGCAATGGG CGTACAGAGCAAAACTACAAGAACACCG CAACAGTCCTGGACTCTGATGGTTCTTA CTTCATGTACAGCAAGCTCAGAGTACAA AAGAGCACTTGGGAAGAGGAAGTCTTT TCGCCTGCTCAGTGGTCCACGAGGGTCT GCACAATCACCTTACGACTAAGACCATC TCCCGGTCTCTGGGTAAAGGAGGGGGCT CCGCACCCACTTCAAGCTCCACTTCAAG CTCTACAGCGGAAGCACAACAGCAGCAG CAGCAGCAGCAGCAGCAGCAGCAGCACC TGGAGCAGCTGTTGATGGACCTACAGGA GCTCCTGAGCAGGATGGAGAATTACAGG AACCTGAAACTCCCCAGGATGCTCACCT TCAAATTTTACTTGCCCAAGCAGGCCAC AGAATTGAAAGATCTTCAGTGCCTAGAA GATGCTCTTGGACCTCTGCGGCATGTTC TGGATTTGACTCAAAGCAAAAGCTTTCA ATTGGAAGATGCTGAGAATTTCATCAGC AATATCAGAGTAACTGTTGTAAAACTAA AGGGCTCTGACAACACATTTGAGTGCCA ATTCGACGATGAGTCAGCAACTGTGGTG GACTTTCTGAGGAGATGGATAGCCTTCT GTCAAAGCATCATCTCAACAAGCCCTCA ACACCATCACCACCATCACTGATAA |
| 19 | D265A Fc/ E76A (amino acid sequence) (C-terminal 6x his tag is underlined) | MRVPAQLLGLLLLWLPGARCEPRVPITQ NPCPPLKECPPCAAPDLLGGPSVFIFPP KIKDVLMISLSPMVTCVVVAVSEDDPDV QISWFVNNVEVHTAQTQTHREDYNSTLR VVSALPIQHQDWMSGKEFKCKVNNRALP SPIEKTISKPRGPVRAPQVYVLPPPAEE MTKKEFSLTCMITGFLPAEIAVDWTSNG RTEQNYKNTATVLDSDGSYFMYSKLRVQ KSTWERGSLFACSVVHEGLHNHLTTKTI SRSLGKGGGSAPTSSSTSSSTAEAQQQQ QQQQQQQQHLEQLLMDLQELLSRMENYR NLKLPRMLTFKFYLPKQATELKDLQCLE DALGPLRHVLDLTQSKSFQLEDAENFIS NIRVTVVKLKGSDNTFECQFDDESATVV DFLRRWIAFCQSIISTSPQHHHHHH |
| 20 | D265A Fc/ E76G (nucleic acid sequence) (C-terminal 6x his tag is underlined) | ATGAGGGTCCCCGCTCAGCTCCTGGGGC TCCTGCTGCTCTGGCTCCCAGGTGCACG ATGTGAGCCCAGAGTGCCCATAACACAG AACCCCTGTCCTCCACTCAAAGAGTGTC CCCCATGCGCAGCTCCAGACCTCTTGGG TGGACCATCCGTCTTCATCTTCCCTCCA AAGATCAAGGATGTACTCATGATCTCCC TGAGCCCCATGGTCACATGTGTGGTGGT GGCCGTGAGCGAGGATGACCCAGACGTC CAGATCAGCTGGTTTGTGAACAACGTGG AAGTACACAGCTCAGACACAAACCCA TAGAGAGGATTACAACAGTACTCTCCGG GTGGTCAGTGCCCTCCCCATCCAGCACC AGGACTGGATGAGTGGCAAGGAGTTCAA ATGCAAGGTCAACAACAGAGCCCTCCCA TCCCCCATCGAGAAACCATCTCAAAAC CCAGAGGGCCAGTAAGAGCTCCACAGGT ATATGTCTTGCCTCCACCAGCAGAAGAG ATGACTAAGAAAGAGTTCAGTCTGACCT GCATGATCACAGGCTTCTTACCTGCCGA AATTGCTGTGGACTGGACCAGCAATGGG CGTACAGAGCAAAACTACAAGAACACCG CAACAGTCCTGGACTCTGATGGTTCTTA |

TABLE 2-continued

Sequence Summary

| SEQ ID NO | Description | Sequence |
|---|---|---|
| | | CTTCATGTACAGCAAGCTCAGAGTACAA |
| | | AAGAGCACTTGGGAAAGAGGAAGTCTTT |
| | | TCGCCTGCTCAGTGGTCCACGAGGGTCT |
| | | GCACAATCACCTTACGACTAAGACCATC |
| | | TCCCGGTCTCTGGGTAAAGGAGGGGCT |
| | | CCGCACCCACTTCAAGCTCCACTTCAAG |
| | | CTCTACAGCGGAAGCACAGCAGCAGCAG |
| | | CAGCAGCAGCAGCAGCAGCAGCAGCACC |
| | | TGGAGCAGCTGTTGATGGACCTACAGGA |
| | | GCTCCTGAGCAGGATGGAGAATTACAGG |
| | | AACCTGAAACTCCCCAGGATGCTCACCT |
| | | TCAAATTTTACTTGCCCAAGCAGGCCAC |
| | | AGAATTGAAAGATCTTCAGTGCCTAGAA |
| | | GATGGTCTTGGACCTCTGCGGCATGTTC |
| | | TGGATTTGACTCAAAGCAAAAGCTTTCA |
| | | ATTGGAAGATGCTGAGAATTTCATCAGC |
| | | AATATCAGAGTAACTGTTGTAAAACTAA |
| | | AGGGCTCTGACAACACATTTGAGTGCCA |
| | | ATTCGATGATGAGTCAGCAACTGTGGTG |
| | | GACTTTCTGAGGAGATGGATAGCCTTCT |
| | | GTCAAAGCATCATCTCAACAAGCCCTCA |
| | | <u>ACACCATCACCACCATCACT</u>GATAA |
| 21 | D265A Fc/E76G (amino acid sequence) (C-terminal 6x his tag is underlined) | MRVPAQLLGLLLLWLPGARCEPRVPITQ NPCPPLKECPPCAAPDLLGGPSVFIFPP KIKDVLMISLSPMVTCVVVAVSEDDPDV QISWFVNNVEVHTAQTQTHREDYNSTLR VVSALPIQHQDWMSGKEFKCKVNNRALP SPIEKTISKPRGPVRAPQVYVLPPPAEE MTKKEFSLTCMITGFLPAEIAVDWTSNG RTEQNYKNTATVLDSDGSYFMYSKLRVQ KSTWERGSLFACSVVHEGLHNHLTTKTI SRSLGKGGGSAPTSSSTSSSTAEAQQQQ QQQQQQQQQHLEQLLMDLQELLSRMENYR NLKLPRMLTFKFYLPKQATELKDLQCLE DGLGPLRHVLDLTQSKSFQLEDAENFIS NIRVTVVKLKGSDNTFECQFDDESATVV DFLRRWIAFCQSIISTSPQ<u>HHHHHH</u> |
| 22 | mIL-2 QQ 6.2-4 (nucleic acid sequence) | GCACCCACCTCAAGCTCCACTTCAAGCT CTACAGCGGAAGCACAACAGCAGCAGCA GCAGCAGCAGCAGCAGCAGCAGCACCTG GAGCAGCTGTTGATGGACCTACAGGAGC TCCTGAGCAGGATGGAGGATTACAGGAA CCTGAGACTCCCCAGGATGCTCACCTTC AAATTTTACTTGCCCAAGCAGGCCACAG AATTGGAAGATCTTCAGTGCCTAGAAGA TGAACTTGAACCTCTGCGGCAAGTTCTG GATTTGACTCAAAGCAAAAGCTTTCAAT TGGAAGATGCTGAGAATTTCATCAGCAA TATCAGAGTAACTGTTGTAAAACTAAAG GGCTCTGACAACACATTTGAGTGCCAAT TCGATGATGAGCCAGCAACTGTGGTGGG CTTTCTGAGGAGATGGATAGCCTTCTGT CAAAGCATCATCTCAACGAGCCCTCAA |
| 23 | mIL-2 QQ 6.2-4 (ammo acid sequence) | APTSSSTSSSTAEAQQQQQQQQQQQHL EQLLMDLQELLSRMEDSRNLRLPRMTF KFYLPKQATELEDLQCLEDELEPLRQVL DLTQSKSFQLEDAENFISNIRVTVVKLK GSDNTFECQFDDEPATVVGFLRRWIAFC QSIISTSPQ |
| 24 | mIL-2 QQ 6.2-8 (nucleic acid sequence) | GCACCCACCTCAAGCTCCACTTCAAGCT CTACAGCGGAAGCACAACAGCAGCAGCA GCAGCAGCAGCACCTGGAGCAGCTGTTG ATGGACCTACAGGAGCTCCTGAGTAGGA TGGAGGATCACAGGAACCTGAGACTCCC CAGGATGCTCACCTTCAAATTTTACTTG CCCAAGCAGGCCACAGAATTGGAAGATC TTCAGTGCCTAGAAGATGAACTTGAACC TCTGCGGCAAGTTCTGGATTTGACTCAA AGCAAAAGCTTTCAATTGGAAGATGCTG AGAATTTCATCAGCAATATCAGAGTAAC TGTTGTAAAACTAAAGGGCTCTGACAAC ACATTTGAGTGCCAATTCGATGATGAGC CAGCAACTGTGGTGGACTTTCTGAGGAG ATGGATAGCCTTCTGTCAAAGCATCATC TCAACAAGCCCTCGA |
| 25 | mIL-2 QQ 6.2-8 (amino acid sequence) | APTSSSTSSSTAEAQQQQQQQQQHLEQLL MDLQELLSRMEDHRNLRLPRMLTFKFYL PKQATELEDLQCLEDELEPLRQVLDLTQ SKSFQLEDAENFISNIRVTVVKLKGSDN TFECQFDDEPATVVDFLRRWIAFCQSII STSPR |
| 26 | mIL-2 QQ 6.2-10 (nucleic acid sequence) | GCACCCACCTCAAGCTCCACTTCAAGCT CTACAGCGGAAGCACAACAGCAGCAGCA GCAGCAGCAGCAGCAGCAGCAGCACCTG GAGCAGCTGTTGATGGACCTACAGGAAC TCCTGAGTAGGATGGAGGATCACAGGAA CCTGAGACTCCCCAGGATGCTCACCTTC AAATTTTACTTGCCCGAGCAGGCCACAG AATTGGAAGATCTTCAGTGCCTAGAAGA TGAACTTGAACCACTGCGGCAAGTTCTG GATTTGACTCAAAGCAAAAGCTTTCAAT TGGAAGATGCTGAGAATTTCATCAGCAA TATCAGAGTAACTGTTGTAAAACTAAAG GGCTCTGACAACACATTTGAGTGCCAAT TCGACGATGAGCCAGCAACTGTGGTGGA CTTTCTGAGGAGATGGATAGCCTTCTGT CAAAGCATCATCTCAACAAGCCCTCAG |
| 27 | mIL-2 QQ 6.2-10 (amino acid sequence) | APTSSSTSSSTAEAQQQQQQQQQQQHL EQLLMDLQELLSRMEDHRNLRLPRMLTF KFYLPEQATELEDLQCLEDELEPLRQVL DLTQSKSFQLEDAENFISNIRVTVVKLK GSDNTFECQFDDEPATVVDFLRRWIAFC QSIISTSPQ |
| 28 | mIL-2 QQ 6.2-11 (nucleic acid sequence) | GCACCCACCTCAAGCTCCACTTCAAGCT CTACAGCGGAAGCACAACAGCAGCAGCA GCAGCAGCAGCACCTGGAGCAGCTGCTG TTGATGGACCTACAGGAGCTCCTGAGCA GGATGGAGGATTCCAGGAACCTGAGACT CCCCAGAATGCTCACCTTCAAATTTTAC TTGCCCGAGCAGGCCACAGAATTGAAAG ATCTCCAGTGCCTAGAAGATGAACTTGA ACCTCTGCGGCAAGTTCTGGATTTGACT CAAAGCAAAAGCTTTCAATTGGAAGATG CTGAGAATTTCATCAGCAATATCAGAGT AACTGTTGTAAAACTAAAGGGCTCTGAC AACACATTTGAGTGCCAATTCGACGATG AGCCAGCAACTGTGGTGGACTTTCTGAG GAGATGGATAGCCTTCTGTCAAAGCATC ATCTCAACAAGCCCTCAG |
| 29 | mIL-2 QQ 6.2-11 (amino acid sequence) | APTSSSTSSSTAEAQQQQQQQQQHLEQL LMDLQELLSRMEDSRNLRLPRMLTFKFY LPEQATELKDLQCLEDELEPLRQVLDLT QSKSFQLEDAENFISNIRVTVVKLKGSD NTFECQFDDEPATVVDFLRRWIAFCQSI ISTSPQ |
| 30 | mIL-2 QQ 6.2-13 (nucleic acid sequence) | GCACCCACCTCAAGCTCCACTTCAAGCT CTACAGCGGAAGCACAACAGCAGCAGCA GCAGCAGCAGCAGCAGCAGCAGCACCTG GAGCAGCTGTTGATGGACCTACAGGAGC TCCTGAGTAGGATGGAGGATCACAGGAA CCTGAGACTCCCCAGGATGCTCACCTTC AAATTTTACTTGCCCGAGCAGGCCACAG AATTGAAAGATCTCCAGTGCCTAGAAGA TGAACTTGAACCTCTGCGGCAGGTTCTG GATTTGACTCAAAGCAAAAGCTTTCAAT TGGAAGATGCTGAGAATTTCATCAGCAA TATCAGAGTAACTGTTGTAAAACTAAAG GGCTCTGACAACACATTTGAGTGCCAAT |

TABLE 2-continued

Sequence Summary

| SEQ ID NO | Description | Sequence |
|---|---|---|
| | | TCGATGATGAGCCAGCAACTGTGGTGGA CTTTCTGAGGAGATGGATAGCCTTCTGT CAAAGCATCATCTCAACAAGCCCTCAG |
| 31 | mIL-2 QQ 6.2-13 (amino acid sequence) | APTSSSTSSSTAEAQQQQQQQQQQQQHL EQLLMDLQELLSRMEDHRNLRLPRMLTF KFYLPEQATELKDLQCLEDELEPLRQVL DLTQSKSFQLEDAENFISNIRVTVVKLK GSDNTFECQFDDEPATVVDFLRRWIAFC QSIISTSPQ |
| 32 | Full length human IL-2 (nucleic acid sequence) | ATGTACAGGATGCAACTCCTGTCTTGCA TTGCACTAAGTCTTGCACTTGTCACAAA CAGTGCACCTACTTCAAGTTCTACAAAG AAAACACAGCTACAACTGGAGCATTTAC TGCTGGATTTACAGATGATTTTGAATGG AATTAATAATTACAAGAATCCCAAACTC ACCAGGATGCTCACATTTAAGTTTTACA TGCCCAAGAAGGCCACAGAACTGAAACA TCTTCAGTGTCTAGAAGAAGAACTCAAA CCTCTGGAGGAAGTGCTAAATTTAGCTC AAAGCAAAAACTTTCACTTAAGACCCAG GGACTTAATCAGCAATATCAACGTAATA GTTCTGGAACTAAAGGGATCTGAAACAA CATTCATGTGTAATATGCTGATGAGACA GCAACCATTGTAGAATTTCTGAACAGAT GGATTACCTTTTGTCAAAGCATCATCTC AACACTGACTTGA |
| 33 | Full length human IL-2 (amino acid sequence) | MYRMQLLSCIALSLALVTNSAPTSSSTK KTQLQLEHLLLDLQMILNGINNYKNPKL TRMLTFKFYMPKKATELKHLQCLEEELK PLEEVLNLAQSKNFHLRPRDLISNINVI VLELKGSETTFMCEYADETATIVEFLNR WITFCQSIISTLT |
| 34 | Human IL-2 without signal peptide (nucleic acid sequence) | GCACCTACTTCAAGTTCTACAAAGAAAA CACAGCTACAACTGGAGCATTTACTGCT GGATTTACAGATGATTTTGAATGGAATT AATAATTACAAGAATCCCAAACTCACCA GGATGCTCACATTTAAGTTTTACATGCC CAAGAAGGCCACAGAACTGAAACATCTT CAGTGTCTAGAAGAAGAACTCAAACCTC TGGAGGAAGTGCTAAATTTAGCTCAAAG CAAAAACTTTCACTTAAGACCCAGGGAC TTAATCAGCAATATCAACGTAATAGTTC TGGAACTAAAGGGATCTGAAACAACATT CATGTGTAATATGCTGATGAGACAGCAA CCATTGTAGAATTTCTGAACAGATGGAT TACCTTTTGTCAAAGCATCATCTCAACA CTGACTTGA |
| 35 | Human IL-2 without signal peptide (amino acid sequence) | APTSSSTKKTQLQLEHLLLDLQMILNGI NNYKNPKLTRMLTFKFYMPKKATELKHL QCLEEELKPLEEVLNLAQSKNFHLRPRD LISNINVIVLELKGSETTFMCEYADETA TIVEFLNRWITFCQSIISTLT |
| 36 | Human serum albumin (amino acid sequence) | MDMRVPAQLLGLLLLWLPGARCADAHKS EVAHRFKDLGEENFKALVLIAFAQYLQQ CPFEDHVKLVNEVTEFAKTCVADESAEN CDKSLHTLFGDKLCTVATLRETYGEMAD CCAKQEPERNECFLQHKDDNPNLRVR PEVDVMCTAFHDNEETFLKKYLYEIARR HPYFYAPELLFFAKRYKAAFTECCQAAD KAACLLPKLDELRDEGKASSAKQRLKCA SLQKFGERAFKAWAVARLSQRFPKAEFA EVSKLVTDLTKVHTECCHGDLLECADDR ADLAKYICENQDSISSKLKECCEKPLLE KSHCIAEVENDEMPADLPSLAADFVESK DVCKNYAEAKDVFLGMFLYEYARRHPDY SVVLLLRLAKTYETTLEKCCAAADPHEC YAKVFDEFKPLVEEPQNLIKQNCELFEQ LGEYKFQNALLVRYTKKVPQVSTPTLVE VSRNLGKVGSKCCKHPEAKRMPCAEDYL SVVLNQLCVLHEKTPVSDRVTKCCTESL VNRRPCFSALEVDETYVPKEFNAETFTF HADICTLSEKERQIKKQTALVELVKHKP KATKEQLKAVMDDFAAFVEKCCKADDKE TCFAEEGKKLVAASQAALGLGGGSAPTS SSTKKTQLQLEHLLLDLQMILNGINNYK NPKLTRMLTFKFYMPKKATELKHLQCLE EELKPLEEVLNLAQSKNFHLRPRDLISN INVIVLELKGSETTFMCEYADETATIVE FLNRWITFCQSIISTLTGGGS |
| 37 | Mature HSA (amino acid sequence) | DAHKSEVAHRFKDLGEENFKALVLIAFA QYLQQCPFEDHVKLVNEVTEFAKTCVAD ESAENCDKSLHTLFGDKLCTVATLRETY GEMADCCAKQEPERNECFLQHKDDNPNL PRLVRPEVDVMCTAFHDNEETFLKKYLY EIARRHPYFYAPELLFFAKRYKAAFTEC CQAADKAACLLPKLDELRDEGKASSAKQ RLKCASLQKFGERAFKAWAVARLSQRFP KAEFAEVSKLVTDLTKVHTECCHGDLLE CADDRADLAKYICENQDSISSKLKECCE KPLLEKSHCIAEVENDEMPADLPSLAAD FVESKDVCKNYAEAKDVFLGMFLYEYAR RHPDYSVVLLLRLAKTYETTLEKCCAAA DPHECYAKVFDEFKPLVEEPQNLIKQNC ELFEQLGEYKFQNALLVRYTKKVPQVST PTLVEVSRNLGKVGSKCCKHPEAKRMPC AEDYLSVVLNQLCVLHEKTPVSDRVTKC CTESLVNRRPCFSALEVDETYVPKEFNA ETFTFHADICTLSEKERQIKKQTALVEL VKHKPKATKEQLKAVMDDFAAFVEKCCK ADDKETCFAEEGKKLVAASQAALGLGGG SAPTSSSTKKTQLQLEHLLLDLQMILNG INNYKNPKLTRMLTFKFYMPKKATELKH LQCLEEELKPLEEVLNLAQSKNFHLRPR DLISNINVIVLELKGSETTFMCEYADET ATIVEFLNRWITFCQSIISTLTGGGS |
| 38 | Human serum albumin (nucleic acid sequence) | ATGGATATGCGGGTGCCTGCTCAGCTGC TGGGACTGCTGCTGCTGTGGCTGCCTGG GGCTAGATGCGCCGATGCTCACAAAAGC GAAGTCGCACACAGGTTCAAAGATCTGG GGGAGGAAAACTTTAAGGCTCTGGTGCT GATTGCATTCGCCCAGTACCTGCAGCAG TGCCCCTTTGAGGACCACGTGAAACTGG TCAACGAAGTGACTGAGTTCGCCAAGAC CTGCGTGGCCGACGAATCTGCTGAGAAT TGTGATAAAAGTCTGCATACTCTGTTTG GGGATAAGCTGTGTACAGTGGCCACTCT GCGAGAAACCTATGGAGAGATGGCAGAC TGCTGTGCCAAACAGGAACCCGAGCGGA ACGAATGCTTCCTGCAGCATAAGGACGA TAACCCCAATCTGCCTCGCCTGGTGCGA CCTGAGGTGGACGTCATGTGTACAGCCT TCCACGATAATGAGGAAACTTTTCTGAA GAAATACCTGTACGAAATCGCTCGGAGA CATCCTTACTTTTATGCACCAGAGCTGC TGTTCTTTGCCAAACGCTACAAGGCCGC TTTCACCGAGTGCTGTCAGGCAGCCGAT AAAGCTGCATGCCTGCTGCCTAAGCTGG ACGAACTGAGGGATGAGGGCAAGGCCAG CTCCGCTAAACAGCGCCTGAAGTGTGCT AGCCTGCAGAAATTCGGAGAGCGAGCCT TCAAGGCTTGGGCAGTGGCACGGCTGAG TCAGAGATTCCCAAAGGCAGAATTTGCC GAGGTCTCAAAACTGGTGACCGACCTGA CAAAGGTGCACACCGAATGCTGTCATGG CGACCTGCTGGAGTGCGCCGACGATCGA GCTGATCTGGCAAAGTATATTTGTGAGA ACCAGGACTCCATCTCTAGTAAGCTGAA AGAATGCTGTGAGAAACCACTGCTGGAA AAGTCTCACTGCATTGCCGAAGTGGAGA |

TABLE 2-continued

Sequence Summary

| SEQ ID NO | Description | Sequence |
|---|---|---|
| | | ACGACGAGATGCCAGCTGATCTGCCCTC ACTGGCCGCTGACTTCGTCGAAAGCAAA GATGTGTGTAAGAATTACGCTGAGGCAA AGGATGTGTTCCTGGGAATGTTTCTGTA CGAGTATGCCAGGCGCCACCCAGACTAC TCCGTGGTCCTGCTGCTGAGGCTGGCTA AAACATATGAAACCACACTGGAGAAGTG CTGTGCAGCCGCTGATCCCCATGAATGC TATGCCAAAGTCTTCGACGAGTTTAAGC CCCTGGTGGAGGAACCTCAGAACCTGAT CAAACAGAATTGTGAACTGTTTGAGCAG CTGGGCGAGTACAAGTTCCAGAACGCCC TGCTGGTGCGCTATACCAAGAAAGTCCC ACAGGTGTCCACACCCACTCTGGTGGAG GTGAGCCGGAATCTGGGCAAAGTGGGGA GTAAATGCTGTAAGCACCCTGAAGCCAA GAGGATGCCATGCGCTGAGGATTACCTG AGTGTGGTCCTGAATCAGCTGTGTGTCC TGCAGTAAAAAACACCTGTCAGCGACCG GGTGACAAAGTGCTGTACTGAGTCACTG GTGAACCGACGGCCCTGCTTTAGCGCCC TGGAAGTCGATGAGACTTATGTGCCTAA AGAGTTCAACGCTGAGACCTTCACATTT CACGCAGACATTTGTACCCTGAGCGAAA AGGAGAGACAGATCAAGAAACAGACAGC CCTGGTCGAACTGGTGAAGCATAAACCC AAGGCCACAAAAGAGCAGCTGAAGGCTG TCATGGACGATTTCGCAGCCTTTGTGGA AAAATGCTGTAAGGCAGACGATAAGGAG ACTTGCTTTGCCGAGGAAGGAAAGAAAC TGGTGGCTGCATCCCAGGCAGCTCTGGG ACTGGGAGGAGGATCTGCCCCTACCTCA AGCTCCACTAAGAAACCCAGCTGCAGC TGGAGCACCTGCTGCTGGACCTGCAGAT GATTCTGAACGGGATCAACAATTACAAA AATCCAAAGCTGACCCGGATGCTGACAT TCAAGTTTTATATGCCCAAGAAAGCCAC AGAGCTGAAACACCTGCAGTGCCTGGAG GAAGAGCTGAAGCCTCTGGAAGAGGTGC TGAACCTGGCCCAGAGCAAGAATTTCCA TCTGAGACCAAGGGATCTGATCTCCAAC ATTAATGTGATCGTCCTGGAACTGAAGG GATCTGAGACTACCTTTATGTGCGAATA CGCTGACGAGACTGCAACCATTGTGGAG TTCCTGAACAGATGGATCACCTTCTGCC AGTCCATCATTTCTACTCTGACAGGCGG GGGGAGC |
| 39 | EETI-II from Knottin Database | GCPRILMRCKQDSDCLAGCVCGPNGFCG |
| 40 | AgRP from Knottin Database "-" indicates where mini protein can be formed | GCVRLHESCLGQQVPCCDPCATCYCRFF NAFCYCR-KLGTAMNPCSRT |
| 41 | Omega agatoxin from Knottin Database "-" indicates where mini protein can be formed | EDN--CIAEDYGKCTWGGTKCCRGRPCR CSMIGTNCECTPRLEVIEGLSFA |
| 42 | EETI-II Library | GCXXXRGDXXXXXCKQDSDCLAGCVCGP NGFCG |
| 43 | EETI-II K15S Mutation Library | GCXXXRGDXXXXXCSQDSDCLAGCVCGP NGFCG |
| 44 | 2.5F-(K15S) mIgG2aFc Nucleic Acid Sequence | GGTTGTCCAAGACCAAGAGGTGATAATC CACCATTGACTTGTTCTCAAGATTCTGA TTGTTTGGCTGGTTGTGTTTGTGGTCCA AATGGTTTTTGTGGTGGTCGACTAGAGC CCAGAGTGCCCATAACACAGAACCCCTG TCCTCCACTCAAAGAGTGTCCCCCATGC GCAGCTCCAGACCTCTTGGGTGGACCAT CCGTCTTCATCTTCCCTCCAAAGATCAA GGATGTACTCATGATCTCCCTGAGCCCC ATGGTCACATGTGTGGTGGTGGATGTGA GCGAGGATGACCCAGACGTCCAGATCAG CTGGTTTGTGAACAACGTGGAAGTACAC ACAGCTCAGACACAAACCCATAGAGAGG ATTACAACAGTACTCTCCGGGTGGTCAG TGCCCTCCCCATCCAGCACCAGGACTGG ATGAGTGGCAAGGAGTTCAAATGCAAGG TCAACAACAGAGCCCTCCCATCCCCCAT CGAGAAAACCATCTCAAAACCCAGAGGG CCAGTAAGAGCTCCACAGGTATATGTCT TGCCTCCACCAGCAGAGAGATGACTAA GAAAGAGTTCAGTCTGACCTGCATGATC ACAGGCTTCTTACCTGCCGAAATTGCTG TGGACTGGACCAGCAATGGGCGTACAGA GCAAAACTACAAGAACACCGCAACAGTC CTGGACTCTGATGGTTCTTACTTCATGT ACAGCAAGCTCAGAGTACAAAAGAGCAC TTGGGAAAGAGGAAGTCTTTTCGCCTGC TCAGTGGTCCACGAGGGTCTGCACAATC ACCTTACGACTAAGACCATCTCCCGGTC TCTGGGTAAA |
| 45 | 2.5F-(K15S) mIgG2aFc Amino Acid Sequence | GCPRPRGDNPPLTCSQDSDCLAGCVCGP NGFCGEPRVPITQNPCPPLKECPPCAAP DLLGGPSVFIFPPKIKDVLMISLSPMVT CVVVDVSEDDPDVQISWFVNNVEVHTAQ TQTHREDYNSTLRVVSALPIQHQDWMSG KEFKCKVNNRALPSPIEKTISKPRGPVR APQVYVLPPPAEEMTKKEFSLTCMITGF LPAEIAVDWTSNGRTEQNYKNTATVLDS DGSYFMYSKLRVQKSTWERGSLFACSVV HEGLHNHLTTKTISRSLGK |
| 46 | 2.5D-(K15S) mIgG2aFc Nucleic Acid Sequence | GGTTGTCCACAAGGCAGAGGTGATTGGG CTCCAACTTCTTGTTCTCAAGATTCTGA TTGTTTGGCTGGTTGTGTTTGTGGTCCA AATGGTTTTTGTGGTGGTCGACTAGAGC CCAGAGTGCCCATAACACAGAACCCCTG TCCTCCACTCAAAGAGTGTCCCCCATGC GCAGCTCCAGACCTCTTGGGTGGACCAT CCGTCTTCATCTTCCCTCCAAAGATCAA GGATGTACTCATGATCTCCCTGAGCCCC ATGGTCACATGTGTGGTGGTGGATGTGA GCGAGGATGACCCAGACGTCCAGATCAG CTGGTTTGTGAACAACGTGGAAGTACAC ACAGCTCAGACACAAACCCATAGAGAGG ATTACAACAGTACTCTCCGGGTGGTCAG TGCCCTCCCCATCCAGCACCAGGACTGG ATGAGTGGCAAGGAGTTCAAATGCAAGG TCAACAACAGAGCCCTCCCATCCCCCAT CGAGAAAACCATCTCAAAACCCAGAGGG CCAGTAAGAGCTCCACAGGTATATGTCT TGCCTCCACCAGCAGAAGAGATGACTAA GAAAGAGTTCAGTCTGACCTGCATGATC ACAGGCTTCTTACCTGCCGAAATTGCTG TGGACTGGACCAGCAATGGGCGTACAGA GCAAAACTACAAGAACACCGCAACAGTC CTGGACTCTGATGGTTCTTACTTCATGT ACAGCAAGCTCAGAGTACAAAAGAGCAC TTGGGAAAGAGGAAGTCTTTTCGCCTGC |

TABLE 2-continued

Sequence Summary

| SEQ ID NO | Description | Sequence |
|---|---|---|
| | | TCAGTGGTCCACGAGGGTCTGCACAATC ACCTTACGACTAAGACCATCTCCCGGTC TCTGGGTAAA |
| 47 | 2.5D-(K15S) mIgG2aFc Amino Acid Sequence | GCPQGRGDWAPTSCSQDSDCLAGCVCGP NGFCGEPRVPITQNPCPPLKECPPCAAP DLLGGPSVFIFPPKIKDVLMISLSPMVT CVVVDVSEDDPDVQISWFVNNVEVHTAQ TQTHREDYNSTLRVVSALPIQHQDWMSG KEFKCKVNNRALPSPIEKTISKPRGPVR APQVYVLPPPAEEMTKKEFSLTCMITGF LPAEIAVDWTSNGRTEQNYKNTATVLDS DGSYFMYSKLRVQKSTWERGSLFACSVV HEGLHNHLTTKTISRSLGK |
| 48 | 2.5F-(K15S) hIgG1Fc Amino Acid Sequence | GCPRPRGDNPPLTCSQDSDCLAGCVCGP NGFCGEPKSCDKTHTCPPCPAPELLGGP SVFLFPPKPKDTLMISRTPEVTCVVVDV SHEDPEVKFNWYVDGVEVHNAKTKPREE QYNSTYRVVSVLTVLHQDWLNGKEYKCK VSNKALPAPIEKTISKAKGQPREPQVYT LPPSREEMTKNQVSLTCLVKGFYPSDIA VEWESNGQPENNYKTTPPVLDSDGSFFL YSKLTVDKSRWQQGNVFSCSVMHEALHN HYTQKSLSLSPGK |
| 49 | 2.5F-(K15S) hIgG1Fc Fc Upper Hinge Deletion (ΔEPKSC) Amino Acid Sequence | GCPRPRGDNPPLTCSQDSDCLAGCVCGP NGFCGDKTHTCPPCPAPELLGGPSVFLE PPKPKDTLMISRTPEVTCVVVDVSHEDP EVKFNWYVDGVEVHNAKTKPREEQYNST YRVVSVLTVLHQDWLNGKEYKCKVSNKA LPAPIEKTISKAKGQPREPQVYTLPPSR EEMTKNQVSLTCLVKGFYPSDIAVEWES NGQPENNYKTTPPVLDSDGSFFLYSKLT VDKSRWQQGNVFSCSVMHEALHNHYTQK SLSLSPGK |
| 50 | 2.5D-(K15S) hIgG1Fc Amino Acid Sequence | GCPQGRGDWAPTSCSQDSDCLAGCVCGP NGFCGEPKSCDKTHTCPPCPAPELLGGP SVFLFPPKPKDTLMISRTPEVTCVVVDV SHEDPEVKFNWYVDGVEVHNAKTKPREE QYNSTYRVVSVLTVLHQDWLNGKEYKCK VSNKALPAPIEKTISKAKGQPREPQVYT LPPSREEMTKNQVSLTCLVKGFYPSDIA VEWESNGQPENNYKTTPPVLDSDGSFFL YSKLTVDKSRWQQGNVFSCSVMHEALHN HYTQKSLSLSPGK |
| 51 | 2.5D-(K15S) hIgG1Fc Fc Upper Hinge Deletion (ΔEPKSC) Amino Acid Sequence | GCPQGRGDWAPTSCSQDSDCLAGCVCGP NGFCGDKTHTCPPCPAPELLGGPSVFLE PPKPKDTLMISRTPEVTCVVVDVSHEDP EVKFNWYVDGVEVHNAKTKPREEQYNST YRVVSVLTVLHQDWLNGKEYKCKVSNKA LPAPIEKTISKAKGQPREPQVYTLPPSR EEMTKNQVSLTCLVKGFYPSDIAVEWES NGQPENNYKTTPPVLDSDGSFFLYSKLT VDKSRWQQGNVFSCSVMHEALHNHYTQK SLSLSPGK |
| 52 | hPD-1 amino acid sequence | MQIPQAPWPVVWAVLQLGWRPGWFLDSP DPWNPPTFFPALLVVTEGDNATFTCSFS NTSESFVLNWYRMSPSNQTDKLAAFPED RSQPGQDCRFRVTQLPNGRDFHMSVVRA RRNDSGTYLCGAISLAPKAQIKESLRAE LRVTERRAEVPTAHPSPSPRPAGQFQTL VVGVVGGLLGSLVLLVWVLAVICSRAAR GTIGARRTGQPLKEDPSAVPVFSVDYGE LDFQWREKTPEPPVPCVPEQTEYATIVF PSGMGTSSPARRGSADGPRSAQPLRPED GHCSWPL |
| 53 | hPD-L-1 amino acid sequence | MRIFAVFIFMTYWHLLNAFTVTVPKDLY VVEYGSNMTIECKFPVEKQLDLAALIVY WEMEDKNIIQFVHGEEDLKVQHSSYRQR ARLLKDQLSLGNAALQITDVKLQDAGVY RCMISYGGADYKRITVKVNAPYNKINQR ILVVDPVTSEHELTCQAEGYPKAEVIWT SSDHQVLSGKTTTTNSKREEKLENVTST LRINTTTNEIFYCTFRRLDPEENHTAEL VIPELPLAHPPNERTHLVILGAILLCLG VALTFIFRLRKGRMMDVKKCGIQDTNSK KQSDTHLEET |
| 54 | hCTLA-4 amino acid sequence | MACLGFQRHKAQLNLATRTWPCTLLFFL LFIPVFCKAMHVAQPAVVLASSRGIASF VCEYASPGKATEVRVTVLRQADSQVTEV CAATYMMGNELTFLDDSICTGTSSGNQV NLTIQGLRAMDTGLYICKVELMYPPPYY LGIGNGTQIYVIDPEPCPDSDFLLWILA AVSSGLFFYSFLLTAVSLSKMLKKRSPL TTGVYVKMPPTEPECEKQFQPYFIPINT |
| 55 | hLAG3 amino acid sequence | MWEAQFLGLLFLQPLWVAPVKPLQPGAE VPVVWAQEGAPAQLPCSPTIPLQDLSLL RRAGVTWQHQPDSGPPAAAPGHPLAPGP HPAAPSSWGPRPRRYTVLSVGPGGLRSG RLPLQPRVQLDERGRQRGDFSLWLRPAR RADAGEYRAAVHLRDRALSCRLRLRLGQ ASMTASPPGSLRASDWVILNCSFSRPDR PASVHWERNRGQGRVPVRESPHHHLAES FLFLPQVSPMDSGPWGCILTYRDGFNVS EVIYNLTVLGLEPPTPLTVYAGAGSRVG LPCRLPAGVGTRSFLTAKWTPPGGGPDL LVTGDNGDFTLRLEDVSQAQAGTYTCHI HLQEQQLNATVTLAIITVTPKSFGSPGS LGKLLCEVTPVSGQERFVWSSLDTPSQR SFSGPWLEAQEAQLLSQPWQCQLYQGER LLGAAVYFTELSSPGAQRSGRAPGALPA GHLLLFLILGVLSLLLLVTGAFGFHLWR RQWRPRRFSALEQGIHPPQAQSKIEELE QEPEPEPEPEPEPEPEPEPEQL |
| 56 | hTIM3 amino acid sequence | MFSHLPFDCVLLLLLLLTRSSEVEYRA EVGQNAYLPCFYTPAAPGNLVPVCWGKG ACPVFECGNVVLRTDERDVNYWTSRYWL NGDFRKGDVSLTIENVTLADSGIYCCRI QIPGIMNDEKFNLKLVIKPAKVTPAPTR QRDFTAAFPRMLTTRGHGPAETQTLGSL PDINLTQISTLANELRDSRLANDLRDSG ATIRGIYIGAGICAGLALALIFGALIFK WYSHSKEKIQNLSLISLANLPPSGLANA VAEGIRSEENIYTIEENVYEVEEPNEYY CYVSSRQQPSQPLGCRFAMP |
| 57 | hB7-H3 amino acid sequence | MLRRRGSPGMGVHVGAALGALWFCLTGA LEVQVPEDPVVALVGTDATLCCSFSPEP GFSLQLNLIWQLTDTKQLVHSFAEGQDQ GSAYANRTALFPDLLAQGNASLRLQRVR VADEGSFCEVSIRDEGSAAVSLQVAAPY SKPSMTLEPNKDLRPGDTVTITCSSYQG YPEAEVFWQDGQGVPLTGNVTTSQMANE QGLFDVHSILRVVLGANGTYSCLVRNPV LQQDAHSSVTITPQRSPTGAVEVQVPED PVVALVGTDATLRCSFSPEPGFSLAQLN LIWQLTDTKQLVHSFTEGRDQGSAYANR TALFPDLLAQGNASLRLQRVRVADEGSF TCFVSIRDEGSAAVSLQVAAPYSKPSMT LEPNKDLRPGDTVTITCSSYRGYPEAEV FWQDGQGVPLTGNVTTSQMANEQGLFDV HSVLRVVLGANGTYSCLVRNPVLQQDAH GSVTITGQPMTFPPEALWVTVGLSVCLI ALLVALAFVCWRKIKQSCEEENAGAEDQ DGEGEGSKTALQPLKHSDSKEDDGQEIA |
| 58 | hB7-H4 amino acid sequence | MASLGQILFWSIISIIIILAGAIALIIG EGISAFSMPEVNVDYNASSETLRCEAPR WFPQPTVVWASQVDQGANFSEVSNTSFE LNSENVTMKVVSVLYNVTINNTYSCMIE |

TABLE 2-continued

Sequence Summary

| SEQ ID NO | Description | Sequence |
|---|---|---|
| | | NDIAKATGDIKVTESEIKRRSHLQLLNS KASLCVSSFFAISWALLPLSPYLMLK |
| 59 | Anti-VEGF clone B20-4.1.1 Heavy Chain nucleic acid sequence | *ATGGGCTGGTCCCTGATCCTGCTGTTCC TGGTGGCTGTGGCCACTGGCGTGCACTC TGAAGTGCAGCTGGTGGAATCTGGCGGC GGACTGGTGCAGCCTGGCGGATCTCTGA GACTGAGCTGTGCCGCCAGCGGCTTCAG CATCAGCGGCAGCTGGATCTTCTGGGTG CGCCAGGCCCCTGGAAAGGGCCTGGAAT GGGTGGGAGCCATCTGGCCTTTTGGCGG CTACACCCACTACGCCGACAGCGTGAAG GGCCGGTTTACCATCAGCGCCGACACCA GCAAGAACACCGCCTACCTCCAGATGAA CAGCCTGCGGCCCGAGGACACCGCCGTG TACTATTGTGCCAGATGGGGCCACAGCA CCTCCCCCTGGGCCATGGATTATTGGGG CCAGGGAACCCTCGTGACCGTGTCCTCT* GCCAAAACAACAGCCCCATCGGTCTATC CACTGGCCCCTGTGTGTGGAGGTACAAC TGGCTCCTCGGTGACTCTAGGATGCCTG GTCAAGGGTTATTTCCCTGAGCCAGTGA CCTTGACCTGGAACTCTGGCTCACTGTC CAGTGGTGTGCACACCTTCCCAGCTCTC CTCCAATCTGGCCTCTACACCCTCAGCA GCTCAGTGACTGTAACCTCGAACACCTG GCCCAGCCAGACCATCACCTGCAATGTG GCCCACCGGCAAGCAGCACCAAAGTGG ACAAGAAAATTGAGCCCAGAGTGCCCAT AACACAGAACCCCTGTCCTCCACTCAAA GAGTGTCCCCATGCGCAGCTCCAGACC TCTTGGGTGGACCATCCGTCTTCATCTT CCCTCCAAAGATCAAGGATGTACTCATG ATCTCCCTGAGCCCCATGGTCACATGTG TGGTGGTGGATGTGAGCGAGGATGACCC AGACGTCCAGATCAGCTGGTTTGTGAAC AACGTGGAAGTACACACAGCTCAGACAC AAACCCATAGAGAGGATTACAACAGTAC TCTCCGGGTGGTCAGTGCCCTCCCCATC CAGCACCAGGACTGCTGGATGGCCAAGG AGTTCAAATGCAAGGTCAACAACAGAGC CCTCCCATCCCCCATCGAGAAAACCATC TCAAAACCCAGAGGGCCAGTAAGAGCTC CACAGGTATATGTCTTGCCTCCACCAGC AGAAGAGATGACTAAGAAAGAGTTCAGT CTGACCTGCATGATCACAGGCTTCTTAC CTGCCGAAATTGCTGTGGACTGGACCAG CAATGGGCGTACAGAGCAAAACTACAAG AACACCGCAACAGTCCTGGACTCTGATG GTTCTTACTTCATGTACAGCAAGCTCAG AGTACAAAGAGACACTTGGGAAAGAGGA AGTCTTTTCGCCTGCTCAGTGGTCCACG AGGGTCTGCACAATCACCTTACGACTAA GACCATCTCCCGGTCTCTGGGTAAA |
| 60 | Anti-VEGF clone B20-4.1.1 Heavy Chain amino acid sequence | *MGWSLILLFLVAVATGVHS*EVQLVESGG GLVQPGGSLRLSCAASGFSISGSWIFWV RQAPGKGLEWVGAIWPFGGYTHYADSVK GRFTISADTSKNTAYLQMNSLRAEDTAV YYCARWGHSTSPWAMDYWGQGTLVTVSS AKTTAPSVYPLAPVCGGTTGSSVTLGCL VKGYFPEPVTLTWNSGSLSSGVHTFPAL LQSGLYTLSSSVTVTSNTWPSQTITCNV AHPASSTKVDKKIEPRVPITQNPCPPLK ECPPCAAPDLLGGPSVFIFPPKIKDVLM ISLSPMVTCVVVDVSEDDPDVQISWFVN NVEVHTAQTQTHREDYNSTLRVVSALPI QHQDWMSGKEFKCKVNNRALPSPIEKTI SKPRGPVRAPQVYVLPPPAEEMTKKEFS LTCMITGFLPAEIAVDWTSNGRTEQNYK NTATVLDSDGSYFMYSKLRVQKSTWERG SLFACSVVHEGLHNHLTTKTISRSLGK |
| 61 | Anti-VEGF clone B20-4.1.1 Light Chain nucleic acid sequence | *ATGGACATGAGAGTGCCCGCCCAGCTGC TGGGACTTCTGCTGCTGTGGCTGCCAGG CGCCAGATGC*GACATCCAGATGACCCAG AGCCCCAGCAGCCTGTCTGCCAGCGTGG GCGACAGAGTGACCATCACCTGTAGAGC CTCTCAGGGCGTGCGGACAAGCCTGGCC TGGTATCAGCAGAAGCCTGGCAAGGCCC CCAAGCTGCTGATCTACGATGCCAGCTC TCTGGCCAGCGGCGTGCCCAGCAGATTT TCTGGCAGCGGCTCCGGCACCGACTTCA CCCTGACAATCAGCTCCCTCCAGCCCGA GGACTTCGCCACCTACTACTGCCAGCAG AGCTACAAGAGCCCCCTGACCTTTGGCC AGGGCACCAAGGTGGAAATCAAGCGGGC TGATGCTGCACCAACTGTATCCATCTTC CCACCATCCAGTGAGCAGTTAACATCTG GAGGTGCCTCAGTCGTGTGCTTCTTGAA CAACTTCTACCCCAAAGACATCAATGTC AAGTGGAAGATTGATGGCAGTGAACGAC AAAATGGCGTCCTGAACAGTTGGACTGA TCAGGACAGCAAAGACAGCACCTACAGC ATGAGCAGCACCCTCACGTTGACCAAGG ACGAGTATGAACGACATAACAGCTATAC CTGTGAGGCCACTCACAAGACATCAACT TCACCCATTGTCAAGAGCTTCAACAGGA ATGAGTGT |
| 62 | Anti-VEGF clone B20-4.1.1 Light Chain amino acid sequence | *MDMRVPAQLLGLLLLWLPGARC*DIQMTQ SPSSLSASVGDRVTITCRASQGVRTSLA WYQQKPGKAPKLLIYDASSLASGVPSRF SGSGSGTDFTLTISSLQPEDFATYYCQQ SYKSPLTFGQGTKVEIKRADAAPTVSIF PPSSEQLTSGGASVVCFLNNFYPKDINV KWKIDGSERQNGVLNSWTDQDSKDSTYS MSSTLTLTKDEYERHNSYTCEATHKTST SPIVKSFNRNEC |
| 63 | Anti-CTLA-4 clone 9D9 Heavy Chain nucleic acid sequence | *ATGGGCTGGTCCCTGATCCTGCTGTTCC TGGTGGCTGTGGCCACCGGCGTGCACTC TGAAGCCAAGCTCCAGGAATCCGGCCCT GTGCTCGTGAAGCCTGGCGCCTCTGTGA AGATGAGCTGCAAGGCCAGCGGCTACAC CTTTACCGACTACTACATGAACTGGGTC AAGCAGAGCCACGGCAAGTCTCTGGAAT GGATCGGCGTGATCAACCCCTACAACGG CGACACCAGCTACAACCAGAAGTTCAAG GGCAAGGCCACCCTGACCGTGGACAAGA GCAGCAGCACCGCCTACATGGAACTGAA CAGCCTGACCAGCGAGGACAGCGCCGTG TACTATTGCGCCCGGTACTACGGCAGTT GGTTCGCCTATTGGGGCCAGGGCACCCT GATCACCGTGTCCACA*GCAAAACAACA GCCCCATCGGTCTATCCACTGGCCCCTG TGTGTGGAGGTACAACTGGCTCCTCGGT GACTCTAGGATGCCTGGTCAAGGGTTAT TTCCCTGAGCCAGTGACCTTGACCTGGA ACTCTGGCTCACTGTCCAGTGGTGTGCA CACCTTCCCAGCTCTCCTCCAATCTGGC CTCTACACCCTCAGCAGCTCAGTGACTG TAACCTCGAACACCTGGCCCAGCCAGAC CATCACCTGCAATGTGGCCCACCCGGCA AGCAGCACCAAAGTGGACAAGAAAATTG AGCCCAGAGTGCCCATAACACAGAACCC CTGTCCTCCACTCAAAGAGTGTCCCCCA TGCGCAGCTCCAGACCTCTTGGGTGGAC CATCCGTCTTCATCTTCCCTCCAAAGAT CAAGGATGTACTCATGATCTCCCTGAGC CCCATGGTCACATGTGTGGTGGTGGATG TGAGCGAGGATGACCCAGACGTCCAGAT CAGCTGGTTTGTGAACAACGTGGAAGTA CACACAGCTCAGACACAAACCCATAGAG AGGATTACAACAGTACTCTCCGGGTGGT CAGTGCCCTCCCCATCCAGCACCAGGAC |

TABLE 2-continued

Sequence Summary

| SEQ ID NO | Description | Sequence |
|---|---|---|
| | | TGGATGAGTGGCAAGGAGTTCAAATGCA AGGTCAACAACAGAGCCCTCCCATCCCC CATCGAGAAAACCATCTCAAAACCCAGA GGGCCAGTAAGAGCTCCACAGGTATATG TCTTGCCTCCACCAGCAGAAGAGATGAC TAAGAAAGAGTTCAGTCTGACCTGCATG ATCACAGGCTTCTTACCTGCCGAAATTG CTGTGGACTGGACCAGCAATGGGCGTAC AGAGCAAAACTACAAGAACACCGCAACA GTCCTGGACTCTGATGGTTCTTACTTCA TGTACAGCAAGCTCAGAGTACAAAAGAG CACTTGGGAAAGAGGAAGTCTTTTCGCC TGCTCAGTGGTCCACGAGGGTCTGCACA ATCACCTTACGACTAAGACCATCTCCCG GTCTCTGGGTAAA |
| 64 | Anti-CTLA-4 clone 9D9 Heavy Chain amino acid sequence | *MGWSLILLFLVAVATGVHS*__EAKLQESGP VLVKPGASVKMSCKASGYTFTDYYMNWV KQSHGKSLEWIGVINPYNGDTSYNQKFK GKATLTVDKSSSTAYMELNSLTSEDSAV YYCARYYGSWFAYWGQGTLITVST__AKTT APSVYPLAPVCGGTTGSSVTLGCLVKGY FPEPVTLTWNSGSLSSGVHTFPALLQSG LYTLSSSVTVTSNTWPSQTITCNVAHPA SSTKVDKKIEPRVPITQNPCPPLKECPP CAAPDLLGGPSVFIFPPKIKDVLMISLS PMVTCVVVDVSEDDPDVQISWFVNNVEV HTAQTQTHREDYNSTLRVVSALPIQHQD WMSGKEFKCKVNNRALPSPIEKTISKPR GPVRAPQVYVLPPPAEEMTKKEFSLTCM ITGFLPAEIAVDWTSNGRTEQNYKNTAT VLDSDGSYFMYSKLRVQKSTWERGSLFA CSVVIIEGLHNHLTTKTISRSLGK |
| 65 | Anti-CTLA-4 clone 9D9 | *ATGGACATGAGAGTGCCCGCCCAGCTGC TGGGACTTCTGCTGCTGTGGCTGCCAGG* |
| | Light Chain nucleic acid sequence | *CGCCAGATGC*__GACATCGTGATGACCCAG ACCACCCTGAGCCTGCCTGTGTCCCTGG GAGATCAGGCCAGCATCAGCTGTCGGAG CAGCCAGAGCATCGTGCACAGCAACGGC AACACCTACCTGGAATGGTATCTCCAGA AGCCCGGCCAGAGCCCCAAGCTGCTGAT CTACAAGGTGTCCAACCGGTTCAGCGGC GTGCCCGACAGATTTTCTGGCAGCGGCT CCGGCACCGACTTCACCCTGAAGATCTC CCGGGTGGAAGCCGAGGACCTGGGCGTG TACTACTGTTTTCAAGGCAGCCACGTGC CCTACACCTTCGGCGGAGGCACCAAGCT GGAAATCAAG__CGGGCTGATGCTGCACCA ACTGTATCCATCTTCCCACCATCCAGTG AGCAGTTAACATCTGGAGGTGCCTCAGT CGTGTGCTTCTTGAACAACTTCTACCCC AAAGACATCAATGTCAAGTGGAAGATTG ATGGCAGTGAACGACAAAATGGCGTCCT GAACAGTTGGACTGATCAGGACAGCAAA GACAGTTACACCTACAGCATGAGCAGCACCC TCACGTTGACCAAGGACGAGTATGAACG ACATAACAGCTATACCTGTGAGGCCACT CACAAGACATCAACTTCACCCATTGTCA AGAGCTTCAACAGGAATGAGTGT |
| 66 | Anti-CTLA-4 clone 9D9 Light Chain amino acid sequence | *MDMRVPAQLLGLLLLWLPGARC*__DIVMTQ TTLSLPVSLGDQASISCRSSQSIVHSNG NTYLEWYLQKPGQSPKLLIYKVSNRFSG VPDRFSGSGSGTDFTLKISRVEAEDLGV YYCFQGSHVPYTEGGGTKLEIK__RADAAP TVSIFPPSSEQLTSGGASVVCFLNNFYP KDINVKWKIDGSERQNGVLNSWTDQDSK DSTYSMSSTLTLTKDEYERHNSYTCEAT HKTSTSPIVKSFNRNEC |

We claim:

1. A method for inhibiting growth and/or proliferation of tumor cells in a subject comprising administering to the subject an effective amount of an integrin-binding-Fc fusion protein, wherein the integrin-binding-Fc fusion protein comprises (i) an integrin-binding polypeptide comprising an integrin-binding loop and a knottin polypeptide scaffold; and (ii) an immunoglobulin Fc domain, wherein the integrin-binding polypeptide is operably linked to the Fc domain, and an immune checkpoint blocker selected from the group consisting of an antibody or antibody fragment targeting PD-1, an antibody or antibody fragment targeting PD-L1, and an antibody or antibody fragment targeting CTLA4.

2. The method of claim 1, wherein the immune checkpoint blocker is an antibody or antibody fragment targeting PD-1.

3. The method of claim 1, wherein the immune checkpoint blocker is an antibody or antibody fragment targeting CTLA4.

4. The method of claim 1, wherein the integrin-binding polypeptide binds to a tumor-associated integrin selected from the group consisting of: αvβ3, αvβ5, α5β1, and any combination thereof.

5. The method of claim 1, wherein the integrin-binding polypeptide binds to αvβ3, αvβ5, and α5β1.

6. The method of claim 1, wherein the knottin polypeptide scaffold comprises at least three cysteine disulfide linkages or crosslinked cysteine residues, and wherein the integrin-binding loop is adjacent to cysteine residues of the knottin polypeptide scaffold.

7. The method of claim 6, wherein the integrin-binding loop comprises an RGD peptide sequence.

8. The method of claim 6, wherein the knottin polypeptide scaffold is derived from a knottin protein selected from the group consisting of: EETI-II, AgRP, and agatoxin.

9. The method of claim 8, wherein the knottin protein is EETI-II.

10. The method of claim 1, wherein the integrin-binding loop comprises an RGD peptide sequence and the knottin polypeptide scaffold is derived from EETI-II.

11. The method of claim 1, wherein the integrin-binding polypeptide comprises the amino acid sequence set forth in SEQ ID NO: 42 or 43, wherein $X_1$ is selected from the group consisting of A, V, L, P, F, Y, S, H, D, and N; $X_2$ is selected from the group consisting of G, V, L, P, R, E, and Q; $X_3$ is selected from the group consisting of G, A, and P; $X_7$ is selected from the group consisting of W and N; $X_8$ is selected from the group consisting of A, P, and S; $X_9$ is selected from the group consisting of P and R; $X_{10}$ is selected from the group consisting of A, V, L, P, S, T, and E; and $X_{11}$ is selected from the group consisting of G, A, W, S, T, K, and E.

12. The method of claim 1, wherein the integrin-binding polypeptide comprises the amino acid sequence set forth in any one of SEQ ID NOs: 67-133.

13. The method of claim 1, wherein the integrin-binding polypeptide comprises the amino acid sequence set forth in SEQ ID NO: 94 or 96.

14. The method of claim 1, wherein the Fc domain is a human IgG1 Fc domain.

15. The method of claim 1, wherein the integrin-binding polypeptide is operably linked with or without a linker to the Fc domain.

16. The method of claim 1, wherein the integrin-binding polypeptide is operably linked to the N-terminus of the Fc domain.

17. The method of claim 1, wherein the integrin-binding polypeptide is operably linked to the C-terminus of the Fc domain.

18. The method of claim 1, wherein the integrin-binding-Fc fusion protein comprises the amino acid sequence of SEQ ID NO: 48, 49, 50, or 51.

19. The method of claim 1, further comprising administering an effective amount of an extended pharmacokinetic interleukin (IL)-2.

20. The method of claim 1, wherein the immune checkpoint blocker is an antibody or antibody fragment targeting PD-L1.

* * * * *